United States Patent
Coleman et al.

(10) Patent No.: US 11,821,019 B2
(45) Date of Patent: *Nov. 21, 2023

(54) BIOLOGICAL PRODUCTION OF MULTI-CARBON COMPOUNDS FROM METHANE

(71) Applicant: INTREXON CORPORATION, Blacksburg, VA (US)

(72) Inventors: William J. Coleman, Redwood City, CA (US); Genevieve M. Vidanes, San Francisco, CA (US); Guillaume Cottarel, Mountain View, CA (US); Sheela Muley, Fremont, CA (US); Roy Kamimura, Daly City, CA (US); Akbar F. Javan, Chapel Hill, NC (US); Jianping Sun, Belmont, CA (US); Eli S. Groban, San Francisco, CA (US)

(73) Assignee: PRECIGEN, INC., Blacksburg, VA (US)

( * ) Notice: Subject to any disclaimer, the term of this patent is extended or adjusted under 35 U.S.C. 154(b) by 240 days.

This patent is subject to a terminal disclaimer.

(21) Appl. No.: 17/103,516

(22) Filed: Nov. 24, 2020

(65) Prior Publication Data

US 2021/0171988 A1 Jun. 10, 2021

Related U.S. Application Data

(60) Continuation of application No. 15/648,920, filed on Jul. 13, 2017, now Pat. No. 10,876,137, which is a continuation of application No. 15/192,290, filed on Jun. 24, 2016, now Pat. No. 9,745,603, which is a division of application No. 14/989,859, filed on Jan. 7, 2016, now Pat. No. 9,399,783, which is a division of application No. 14/206,835, filed on Mar. 12, 2014, now Pat. No. 9,267,158.

(60) Provisional application No. 61/782,830, filed on Mar. 14, 2013.

(51) Int. Cl.
| | |
|---|---|
| C12P 7/16 | (2006.01) |
| C12N 9/04 | (2006.01) |
| C12N 9/10 | (2006.01) |
| C12N 9/88 | (2006.01) |
| C12N 15/52 | (2006.01) |

(52) U.S. Cl.
CPC .............. C12P 7/16 (2013.01); C12N 9/0006 (2013.01); C12N 9/1022 (2013.01); C12N 9/1025 (2013.01); C12N 9/88 (2013.01); C12N 15/52 (2013.01); C12Y 101/01001 (2013.01); C12Y 101/01004 (2013.01); C12Y 101/01086 (2013.01); C12Y 202/01006 (2013.01); C12Y 203/03006 (2013.01); C12Y 401/01072 (2013.01); C12Y 402/01009 (2013.01); C12Y 402/01033 (2013.01); C12Y 403/01019 (2013.01); Y02E 50/10 (2013.01)

(58) Field of Classification Search
None
See application file for complete search history.

(56) References Cited

U.S. PATENT DOCUMENTS

| | | | |
|---|---|---|---|
| 4,594,324 | A | 6/1986 | Dalton et al. |
| 4,982,023 | A | 1/1991 | Han et al. |
| 6,576,449 | B2 | 6/2003 | Clark et al. |
| 6,660,507 | B2 | 12/2003 | Cheng et al. |
| 6,767,744 | B2 | 7/2004 | Koffas et al. |
| 6,818,424 | B2 | 11/2004 | DiCosimo et al. |
| 6,969,595 | B2 | 11/2005 | Brzostowicz et al. |
| 7,026,464 | B2 | 4/2006 | DiCosimo et al. |

(Continued)

FOREIGN PATENT DOCUMENTS

| | | |
|---|---|---|
| EP | 0306466 | 3/1989 |
| EP | 0418187 | 3/1991 |

(Continued)

OTHER PUBLICATIONS

Ward, et al., Genomic Insights into Methanotrophy: The Complete Genome Sequence of Methylococcus Capsulates (Bath) PLoS Biol. vol. 2, Issue 10, e303 (Oct. 2004).

(Continued)

*Primary Examiner* — Suzanne M Noakes
*Assistant Examiner* — Jae W Lee
(74) *Attorney, Agent, or Firm* — THE MARBURY LAW GROUP, PLLC

(57) ABSTRACT

Multi-carbon compounds such as ethanol, n-butanol, sec-butanol, isobutanol, tert-butanol, fatty (or aliphatic long chain) alcohols, fatty acid methyl esters, 2,3-butanediol and the like, are important industrial commodity chemicals with a variety of applications. The present invention provides metabolically engineered host microorganisms which metabolize methane ($CH_4$) as their sole carbon source to produce multi-carbon compounds for use in fuels (e.g., bio-fuel, bio-diesel) and bio-based chemicals. Furthermore, use of the metabolically engineered host microorganisms of the invention (which utilize methane as the sole carbon source) mitigate current industry practices and methods of producing multi-carbon compounds from petroleum or petroleum-derived feedstocks, and ameliorate much of the ongoing depletion of arable food source "farmland" currently being diverted to grow bio-fuel feedstocks, and as such, improve the environmental footprint of future bio-fuel, bio-diesel and bio-based chemical compositions.

19 Claims, 9 Drawing Sheets

Specification includes a Sequence Listing.

(56) References Cited

U.S. PATENT DOCUMENTS

| | | | |
|---|---|---|---|
| 7,851,188 | B2 | 12/2010 | Donaldson et al. |
| 7,910,342 | B2 | 3/2011 | Liao et al. |
| 7,943,362 | B2 | 5/2011 | Frost |
| 7,977,084 | B2 | 7/2011 | Sun et al. |
| 7,993,889 | B1 | 8/2011 | Donaldson et al. |
| 8,017,375 | B2 | 9/2011 | Feldman et al. |
| 8,030,021 | B2 | 10/2011 | Criddle et al. |
| 8,101,808 | B2 | 1/2012 | Evanko et al. |
| 8,158,404 | B2 | 4/2012 | Lies et al. |
| 8,232,089 | B2 | 7/2012 | Urano et al. |
| 8,263,373 | B2 | 9/2012 | Herrema et al. |
| 8,268,599 | B2 | 9/2012 | Schirmer et al. |
| 8,283,143 | B2 | 10/2012 | Hu et al. |
| 8,349,587 | B2 | 1/2013 | Fischer et al. |
| 9,267,158 | B2 * | 2/2016 | Coleman .............. C12N 9/0006 |
| 9,399,783 | B2 * | 7/2016 | Coleman ........ C12Y 101/01086 |
| 9,611,487 | B2 | 4/2017 | Blake et al. |
| 9,745,603 | B2 | 8/2017 | Coleman et al. |
| 10,876,137 | B2 | 12/2020 | Coleman et al. |
| 2006/0057726 | A1 | 3/2006 | Sharpe |
| 2007/0251141 | A1 | 11/2007 | Bist et al. |
| 2009/0263877 | A1 | 10/2009 | Eriksen et al. |
| 2010/0274033 | A1 | 10/2010 | Sanchez-Riera et al. |
| 2011/0301388 | A1 | 12/2011 | Donaldson et al. |
| 2012/0009640 | A1 | 1/2012 | Behrouzian et al. |
| 2013/0344553 | A1 | 12/2013 | Lee |
| 2014/0273128 | A1 | 9/2014 | Coleman et al. |

FOREIGN PATENT DOCUMENTS

| | | |
|---|---|---|
| WO | 200218617 | 3/2002 |
| WO | 2003015534 | 2/2003 |
| WO | 2003016460 | 2/2003 |
| WO | 2004104180 | 12/2004 |
| WO | 2005062867 | 7/2005 |
| WO | 2011019858 | 2/2011 |

OTHER PUBLICATIONS

Anthony, C. and Williams, P., "The structure and mechanism of methanol dehydrogenase," Biochimica et Biophysica Acta 1647:18-23, Elsevier Pub. Co., Netherlands (2003).

Atsumi, S., et al., "Engineering the isobutanol biosynthetic pathway in *Escherichia coli* by comparison of three aldehyde reductase/alcohol dehydrogenase genes," Appl. Microbial Biotechnol 85:651-657, Springer-Verlag GmbH, Germany (2010).

Avalos, J.L., et al., "Compartmentalization of metabolic pathways in yeast mitochondria improves the production of branched-chain alcohols," Nature Biotechnology 31 (4):335-341, Nature Publishing Group, England (2013).

Bastian, S., et al., "Engineered ketol-acid reductoisomerase and alcohol dehydrogenase enable anaerobic 2-methylpropan-1-ol production at theoretical yield in *Escherichia coli*," Metabolic Engineering 13:345-352, Elsevier Inc., United States (2011).

Chistoserdova, L., et al., "A genomic view of methane oxidation by aerobic bacteria and anaerobic archaea," Genome Biology 6: 208. 1-208.6, BioMed Central Ltd., England (2005).

Chistoserdova, L., et al., "The Expanding World of Methyltrophic Metabolism," Ann. Rev Microbiol 63:477-499, Annual Reviews, United States (2009).

Chistoserdova, L., "Modularity of methylotrophy, revisited," Environmental Microbiology 13(10):2603-2622, Society for Applied Microbiology and Blackwell, Publishing Ltd., England (2011).

Culpepper, M.A. and Rosenzweig, A.C., "Architecture and active site of particulate methane monooxygenase," Grit Rev Mol Biol 47(6):483-492, CRC Press, England (2012).

Duan, Y., et al., "De novo Biosynthesis of Biodiesel by *Escherichia coli* in Optimized Fed-Batch Cultivation," PLOS ONE 6(5): 1-7, Public Library of Science, U.S.A. (2011).

Dunfield, P.F., et al., "*Methylocella silvestris* sp. nov . . . , a novel methanotroph isolated from an acidic forest cambisol," International Journal of Systemic and Evolutionary Microbiology 53: 1231-1239, IUMS, England (2003).

Energy Policy Act of 2005, Pub. L. No. 109-58, 119 Stal. 594 (2005).

Gellissen, G., et al., "New yeast expression platforms based on methylotrophic Hansenula polymorpha and Pichia pastoris and on dimorphic Arxula adeninivorans and Yarrowia lipolytica—A comparison," FEMS Yeast Research 5: 1 079-1 096, Elsevier Science B.V., Netherlands (2005).

Hakemian, A.S. and Rosenzweig, A.C., "The Biochemistry of Methane Oxidation," Annu Rev Biochem 76:223.241, Annual Reviews, United States (2007).

Hanson, R.S., and Hanson, T.E., "Methanotrophic Bacteria," Microbiological Reviews 60(2):439-471, American Society for Microbiology, United States (1996).

Jaeger, W.K. and Egelkraut, T.M., "Biofuel Economics in a Setting of Multiple Objectives & Unintended Consequences," Renewable and Sustainable Energy Reviews 15(9):4320-4333, Elsevier Ltd., England (2011).

Jang, Y.- S. et al., "Enhanced Butanol Production Obtained by Reinforcing the Direct Butanol-Forming Route in Clostridium acetobutylicum," mBio 3(5):e00314-12, American Society for Microbiology, United States (2012).

Kidnay, A.J. and Parris, W.R., Fundamentals of Natural Gas Processing, Faulkner, L.L., ed., Taylor and Francis Group, LLC, England (2006).

Kim, S., et al., "Cellulosic ethanol production using a yeast consortium displaying a minicellulosome and β-glucosidase," Microbial Cell Factories 12:14, BioMed Central Ltd., England (2013).

Klett, T. R. et al., "An Evaluation of the USGS World Petroleum Assessment 2000—Supporting Data," U.S. Geological Survey Open-File Report 2007-1021.

Murrell, J.C., et al., "Molecular biology and regulation of methane monooxygenase," Arch Microbiol 173:325-332, Springer-Verlag GmbH, Germany (2000).

Patras, L.E. and Tang, A., "Bioconversion of methane to methanol by Methylobacterium organophilum," Unocal Science and Technology Division, Brea, California, pp. 462-468.

Phillips, R.B., et al., "Integration of pulp and paper technology with bioethanol production," Biotechnology for Biofuels 6: 13-25, BioMed Central Ltd., England (2013).

Rudolf, A. et al., "Ethanol Production from Traditional and Emerging Raw Materials," in Yeast Biotechnology: Diversity and Applications, Satyanarayana, T., ed., pp. 489-513, Springer-Verlag GmbH, Gennany (2009).

Saka, S., and Kusdiana, D., "Biodiesel fuel from rapeseed oil as prepared in supercritical methanol," Fuel 80:225-231, Elsevier Ltd., England (2001).

Schrader, J., et al., "Methanol-based industrial biotechnology: current status and future perspectives of methylotrophic bacteria," Trends in Biotechnology 27(2): 1 07-115, Elsevier Ltd., England (2009).

Semrau, J.D., et ai., "Facultative methanotrophy: false leads, true results, and suggestions for future research," FEMS Microbial. Lett. 323:1-12, Blackwell Publishing Ltd., England (2011).

Stanley, S.H. and Dalton, 1-1., "Role of Ribulose-1,5-biphosphate Carboxylase/Oxygenase in Methylococcus capsulatus (Bath)," Journal of General Microbiology 28:2927-2935, Society for General Microbiology, England (1982).

Tinberg, C.E. and Lippard, S.J., "Dioxygen Activation in Soluble Methane Monooxygenase," Ace Chem Res 44 (4):280-288, American Chemical Society, United States (2011).

Trotsenko, Y.A. and Murrell, IC., "Metabolic Aspects of Aerobic Obligate Methanotrophy," Advances in Applied Microbiology 63: 183-229, Elsevier Inc., United States (2008).

Veazey, M.V., "GTL Tech Converts Methane to Ethylene without Fischer Tropsch," Rigzone.com., accessed at https://www.rigzone.com/news/oil_gas/a/149438/gtl_tech_converts_methane_to_ethylene_without_fischer_tropsch/, made available on Apr. 10, 2012,2 pages.

Wright, C.K. and Wimberly, M.C., "Recent land use change in the Western Corn Belt threatens grasslands and wetlands," Proc Natl Acad Sci USA. J 10(10):4134-4139, National Academy of Sciences, United States (2012).

(56) References Cited

OTHER PUBLICATIONS

Yu, X. et al., "In vitro reconstitution and steady-state analysis of the fatty acid synthase from *Escherichia coli*," Proc Natl Acad Sci U.S.A. 108(46): 18643-18648, National Academy of Sciences, United States (2011).

Alayon, E.M.C., "Catalytic Conversion of Methane to Methanol Using Cu-Zeolites," Chimia 66(9):668-674, Schweizerische Chemische Gesellschaft, Switzerland (2012).

Arakawa, et al., "Catalysis Research of Relevance to Carbon Management: Progress, Challenges, and Opportunities," Chem. Rev. 101(4): 953-966, American Chemical Society, United States (2001).

Yurimoto, R, et al., "Assimilation, Dissimilation, and Detoxification of Formaldehyde, a Central Metabolic Intermediate of Methylotrophic Metabolism," The Chemical Record 5:367-375, The Japan Chemical Journal Forum and Wiley Periodicals, Inc., Japan (2005).

Yurimoto, R, et al., "Genomic organization and biochemistry of the ribulose monophosphate pathway and its application in biotechnology," App/ Microbial Biotechnol 84:407-416, Springer-Verlag, Germany (2009).

Nguyen, et al., "Systematic metabolic engineering of Methylomicrobium alcaliphilum 20Z for 2,3-butanediol production from methane", Metabolic Engineering 47, pp. 323-333, (2018).

Vecherskaya, et al., "Microaerobic and anaerobic metabolism of a Methylocystis parvus strain isolated from a denitrifying bioreactor", Environmental Microbiology Reports, vol. 1, Issue 5, pp. 442-449, (Oct. 8, 2009).

\* cited by examiner

1. Fermentative pathway:

2. Fermentative pathway with NADPH:

3. Thiobutanoate pathway:

4. Ketoacid pathway:

5. Methylmalate pathway:

6. Isobutanol pathway:

SEQUENCE LISTING

```
<160> NUMBER OF SEQ ID NOS: 175

<210> SEQ ID NO 1
<211> LENGTH: 1662
<212> TYPE: DNA
<213> ORGANISM: Methylococcus capsulatus

<400> SEQUENCE: 1
atgcgtgaaa cgatacctcc ccgcaccggc gccgacctgc tggtcgactc cctccaggcg     60
ctgggcgtcg aatacgtctt cggcgtgccc ggcggcgcga tactcccgat cctgaacgtg    120
ctggccgacc gcggcccgcg cttcatcgtt tgccgggacg aaaccggcgc cgccttcatg    180
gcccagtcct ggggccggat caccggccgg cccggcgtgg tgctcaccac ctccggcccc    240
ggcctcatca acgccgtctg tggcgtcgct accgccacag aggaccgcga cccgctggtc    300
gtcatcaccg gccaggtgcc gcgggccgtg caattcaagc agagccacat gaacctggat    360
tcggtcggcc tgttcgcgcc gatcaccaaa tggagcgtcg aggtcgagga accgaatact    420
gtatcggaaa tcctggtcaa cgccttccgc accgcgcaga cgccgtgcgc cggagccgtc    480
cacgtctcgg taccgaacga catgctcacc gcgccggtca ccgcgcaggc cctggcgccg    540
gccgaacccg ccgtctgggg aacggcccg gccgccgtcg tcgaacgcgc ggcgtccctg    600
ctgaacgatg ccaaagcccc ggccatcctg ctcggattgc gggccagcac acctggagcg    660
gcggcggcgg tccggcgttt cctggagcgg catccgctgc cggtggcgat gaccttcgaa    720
gccgccggca ccctgtcccg cgatctggtc gatcagttcg tcggccgggt cggctacgtg    780
ctcaaccagc cgggcgacga ggtgctgcgc caagccgatc tggtactcac gatcggctac    840
gacccgatcg aatacgaacc ttccgcctgg atctcaccgc agtcgcaggc gatccacctg    900
gatgccctgc ccgccgccgt cgaccgggcc taccaccctg ccgccgaact ggtcggcgac    960
atcgccgcca acctggccgc gctcggcagc ctgctccgaa tcgaggatcg agccggacgc   1020
```

-continued

```
cccgccgtcg ccgcggcgcg gcggcgtctg ctggaggagc aagcccgcgg cgcagcactg    1080
accggtatgc cgatccaccc cttgcgcttc attcacgacc ttcgggccac gctggacgac    1140
gaggcgacgg tgacctgcga cgtcggcgcc cacgagatct ggatggcccg ctacttcttc    1200
tgctacgccc gcgtcacct gctgttcagc atgggccacc agaccatggg cgtcgccctg     1260
ccctgggcca tcggcgcggc cctggcccgg cccggcaaga agtggtttc ggtatccggc      1320 gacggctcct tcctcatgac ctgcatggaa ctggaaaccg cggtgcgcct caaactgccg    1380
atcgtgcaca tcgtctggaa agacggcggc tacaacctga tccacagcct gcagatgcgc    1440
gactatgggc gcagcttcgg cgccgagttc ggccccaccg acttcgtcaa actggcggag    1500
gccttcggcg cgatcgggta ccggatcgag tccgcggacg ggatcgtccc tgtgctgaac    1560
cgggcgctcg cggccgacgc gccggtgctg atcgaagtgc ccatcgacta cagcgacaac    1620
gtccacctgg tcgaggcgat cgacgcctcg gcgcagcact ga                       1662
```

<210> SEQ ID NO 2
<211> LENGTH: 553
<212> TYPE: PRT
<213> ORGANISM: Methylococcus capsulatus

<400> SEQUENCE: 2

```
Met Arg Glu Thr Ile Pro Pro Arg Thr Gly Ala Asp Leu Leu Val Asp
1               5                   10                  15

Ser Leu Gln Ala Leu Gly Val Glu Tyr Val Phe Gly Val Pro Gly Gly
                20                  25                  30

Ala Ile Leu Pro Ile Leu Asn Val Leu Ala Asp Arg Gly Pro Arg Phe
            35                  40                  45

Ile Val Cys Arg Asp Glu Thr Gly Ala Ala Phe Met Ala Gln Ser Trp
        50                  55                  60

Gly Arg Ile Thr Gly Arg Pro Gly Val Val Leu Thr Thr Ser Gly Pro
65                  70                  75                  80

Gly Leu Ile Asn Ala Val Cys Gly Val Ala Thr Ala Thr Glu Asp Arg
                85                  90                  95

Asp Pro Leu Val Val Ile Thr Gly Gln Val Pro Arg Ala Val Gln Phe
            100                 105                 110

Lys Gln Ser His Met Asn Leu Asp Ser Val Gly Leu Phe Ala Pro Ile
        115                 120                 125

Thr Lys Trp Ser Val Glu Val Glu Pro Asn Thr Val Ser Glu Ile
    130                 135                 140

Leu Val Asn Ala Phe Arg Thr Ala Gln Thr Pro Cys Ala Gly Ala Val
145                 150                 155                 160

His Val Ser Val Pro Asn Asp Met Leu Thr Ala Pro Val Thr Ala Gln
                165                 170                 175

Ala Leu Ala Pro Ala Glu Pro Ala Val Trp Gly Thr Ala Pro Ala Ala
            180                 185                 190

Val Val Glu Arg Ala Ala Ser Leu Leu Asn Asp Ala Lys Ala Pro Ala
        195                 200                 205

Ile Leu Leu Gly Leu Arg Ala Ser Thr Pro Gly Ala Ala Ala Val
    210                 215                 220

Arg Arg Phe Leu Glu Arg His Pro Leu Pro Val Ala Met Thr Phe Glu
225                 230                 235                 240

Ala Ala Gly Thr Leu Ser Arg Asp Leu Val Asp Gln Phe Val Gly Arg
                245                 250                 255
```

Val Gly Tyr Val Leu Asn Gln Pro Gly Asp Glu Val Leu Arg Gln Ala
            260                 265                 270

Asp Leu Val Leu Thr Ile Gly Tyr Asp Pro Ile Glu Tyr Glu Pro Ser
        275                 280                 285

Ala Trp Ile Ser Pro Gln Ser Gln Ala Ile His Leu Asp Ala Leu Pro
    290                 295                 300

Ala Ala Val Asp Arg Ala Tyr His Pro Ala Ala Glu Leu Val Gly Asp
305                 310                 315                 320

Ile Ala Ala Asn Leu Ala Ala Leu Gly Ser Leu Leu Arg Ile Glu Asp
                325                 330                 335

Arg Ala Gly Arg Pro Ala Val Ala Ala Arg Arg Arg Leu Leu Glu
            340                 345                 350

Glu Gln Ala Arg Gly Ala Ala Leu Thr Gly Met Pro Ile His Pro Leu
        355                 360                 365

Arg Phe Ile His Asp Leu Arg Ala Thr Leu Asp Asp Glu Ala Thr Val
    370                 375                 380

Thr Cys Asp Val Gly Ala His Glu Ile Trp Met Ala Arg Tyr Phe Phe
385                 390                 395                 400

Cys Tyr Ala Pro Arg His Leu Leu Phe Ser Met Gly His Gln Thr Met
                405                 410                 415

Gly Val Ala Leu Pro Trp Ala Ile Gly Ala Ala Leu Ala Arg Pro Gly
        420                 425                 430

Lys Lys Val Val Ser Val Ser Gly Asp Gly Ser Phe Leu Met Thr Cys
    435                 440                 445

Met Glu Leu Glu Thr Ala Val Arg Leu Lys Leu Pro Ile Val His Ile
450                 455                 460

Val Trp Lys Asp Gly Gly Tyr Asn Leu Ile His Ser Leu Gln Met Arg
465                 470                 475                 480

Asp Tyr Gly Arg Ser Phe Gly Ala Glu Phe Gly Pro Thr Asp Phe Val
                485                 490                 495

Lys Leu Ala Glu Ala Phe Gly Ala Ile Gly Tyr Arg Ile Glu Ser Ala
        500                 505                 510

Asp Gly Ile Val Pro Val Leu Asn Arg Ala Leu Ala Ala Asp Ala Pro
    515                 520                 525

Val Leu Ile Glu Val Pro Ile Asp Tyr Ser Asp Asn Val His Leu Val
530                 535                 540

Glu Ala Ile Asp Ala Ser Ala Gln His
545                 550

<210> SEQ ID NO 3
<211> LENGTH: 1017
<212> TYPE: DNA
<213> ORGANISM: Methylococcus capsulatus

<400> SEQUENCE: 3
atgcagattt actacgacaa agacgccgac ctttccatca tccagggaaa gaaggttgcc      60
atcatcggct acggctcgca gggccacgcc acgccaaca acctcaagga ttccggagtg      120
caggtcgtgg tggggctgcg tccgggttcg gcttccgcca agaaggccga gaacgccggc      180
ctcgcggtcg cctcggtcga ggatgcggtc aaacaggcgg acgtcatcat gatcctggcg      240
ccggacgagc atcaggcccg cctctacaat gaacagatcg cgccgaacat caagcagggc      300
gccgccctcg ccttcgccca cggcttcaac atccacttcg agcagatcac cccgcgcgcc      360
gacctcgacg tgatcatgat cgcgcccaag ggtcccggcc atctggtacg ttccacctac      420

```
acccagggcg gcggcgtgcc ctcgctgatc gccgtgtacc agaatgccag cgggcgcgcc      480
aaggaactcg cgctgtccta tgcttcggcc aatggcggcg gtcgggctgg tatcatcgag      540
accaccttcc gcgaagagac cgaaaccgat ctgttcggcg aacaggccgt cctgtgtggc      600
ggcgccaccg cactggtgca ggcgggtttc gagacgctgg tcgaagccgg ttatgcgccc      660
gagatggcct atttcgagtg tctgcacgaa ctcaagctga tcgtcgacct gatgtacgaa      720
ggcggcatcg ccaacatgcg ttattcgatc tccaataccg cagagtacgg cgacctgacc      780
cgtggtccgc gcatcgtcac cgagcagacc aagcaggaaa tgaagaaaat cctgcgcgag      840
atccagaccg gcgaattcgc ccgtgagttc attttggaaa accaggccgg agccgccacc      900
ctgaaagcga aacgccgtct cggccgagag catctcatcg agagcgtggg cgccaggctg      960
cgcgacatga tgccgtggat caaggccaac cgcattgtgg acacgagcaa gaactga       1017
```

```
<210> SEQ ID NO 4
<211> LENGTH: 338
<212> TYPE: PRT
<213> ORGANISM: Methylococcus capsulatus

<400> SEQUENCE: 4

Met Gln Ile Tyr Tyr Asp Lys Asp Ala Asp Leu Ser Ile Ile Gln Gly
1               5                   10                  15

Lys Lys Val Ala Ile Gly Tyr Gly Ser Gln Gly His Ala His Ala
            20                  25                  30

Asn Asn Leu Lys Asp Ser Gly Val Gln Val Val Gly Leu Arg Pro
        35                  40                  45

Gly Ser Ala Ser Ala Lys Lys Ala Glu Asn Ala Gly Leu Ala Val Ala
50                  55                  60

Ser Val Glu Asp Ala Val Lys Gln Ala Asp Val Ile Met Ile Leu Ala
65                  70                  75                  80

Pro Asp Glu His Gln Ala Arg Leu Tyr Asn Glu Gln Ile Ala Pro Asn
                85                  90                  95

Ile Lys Gln Gly Ala Ala Leu Ala Phe Ala His Gly Phe Asn Ile His
            100                 105                 110

Phe Glu Gln Ile Thr Pro Arg Ala Asp Leu Asp Val Ile Met Ile Ala
        115                 120                 125

Pro Lys Gly Pro Gly His Leu Val Arg Ser Thr Tyr Thr Gln Gly Gly
    130                 135                 140

Gly Val Pro Ser Leu Ile Ala Val Tyr Gln Asn Ala Ser Gly Arg Ala
145                 150                 155                 160

Lys Glu Leu Ala Leu Ser Tyr Ala Ser Ala Asn Gly Gly Gly Arg Ala
                165                 170                 175

Gly Ile Ile Glu Thr Thr Phe Arg Glu Glu Thr Glu Thr Asp Leu Phe
            180                 185                 190

Gly Glu Gln Ala Val Leu Cys Gly Gly Ala Thr Ala Leu Val Gln Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Arg Tyr Ser Ile Ser Asn Thr Ala Glu Tyr
                245                 250                 255

Gly Asp Leu Thr Arg Gly Pro Arg Ile Val Thr Glu Gln Thr Lys Gln
            260                 265                 270
```

```
Glu Met Lys Lys Ile Leu Arg Glu Ile Gln Thr Gly Glu Phe Ala Arg
            275                 280                 285

Glu Phe Ile Leu Glu Asn Gln Ala Gly Ala Ala Thr Leu Lys Ala Lys
            290                 295                 300

Arg Arg Leu Gly Arg Glu His Leu Ile Glu Ser Val Gly Ala Arg Leu
305                 310                 315                 320

Arg Asp Met Met Pro Trp Ile Lys Ala Asn Arg Ile Val Asp Thr Ser
                    325                 330                 335

Lys Asn

<210> SEQ ID NO 5
<211> LENGTH: 1689
<212> TYPE: DNA
<213> ORGANISM: Methylococcus capsulatus

<400> SEQUENCE: 5
```

| | | | | | |
|---|---|---|---|---|---|
| atgaccgaca | agcaccccg | tccccattcg | tcccaggtcg | tcgacggcat | ggagcgcgcc | 60 |
| ccgagccgcg | cgatgctgca | cgccgtcggc | ttcgccgatg | ccgacttcgc | caaaccgcag | 120 |
| atcggcatcg | cttccacctg | ggcgatggtg | acgccgtgca | acatgcacat | caacaagctc | 180 |
| gccgaggacg | cagcacgcgg | cgtcgacggc | ggcggcggca | aggcagtgat | cttcaacacc | 240 |
| atcaccattt | ccgacggcat | ctcgatgggc | accgaaggaa | tgaaatactc | cctcgtgtcg | 300 |
| cggaagtca | tcgccgactc | gatcgaaacc | gtggtggcct | gtcagggtta | tgacggcgtg | 360 |
| gtcgccatcg | gcggctgcga | caagaacatg | cccggctgcc | tgatcgccct | cgcccgcctc | 420 |
| aaccgtccgg | cggtgttcgt | ctatggcggc | accatcctgc | cgggctgcca | cgacggcaag | 480 |
| aagctggacg | tggtgtcggt | gttcgaagcg | gtcggcgccc | gcgccaacca | ccgcatcgac | 540 |
| gatgccgaac | tgcacgccat | cgaatccaat | gccatccccg | gtccgggctc | ctgcggtggc | 600 |
| atgtataccg | ccaacaccat | ggcctccgcc | atcgaggcat | tagggatgag | cctgccgggc | 660 |
| agttcggccc | aggtggccat | ttcccgcgcc | aaggaactgg | attgcgagcg | ggccggcgcg | 720 |
| caggtcctca | agctcctgga | cctggggctc | aaaccccgcg | acatcatgac | caagaaggcg | 780 |
| ttcgagaacg | ccatcacggt | ggtgatcgcc | ctgggcggct | ccaccaacgc | cgtgctgcac | 840 |
| ctcctggcca | tggccaacgc | ctgcggcgtc | gacctgaagc | tcgacgattt | cacccgcatc | 900 |
| gggcgcaaag | tgccgatgct | ggcggatctg | aaacccagcg | gcagatactc | catgccgaa | 960 |
| ctggtggaaa | tcggcggcat | ccagccgctg | atgaagacct | tgctggacgc | gggactcctg | 1020 |
| cacggcgact | gcatgaccgt | aaccggcaag | accctggaag | aaaacctggc | cgacgcgccc | 1080 |
| gactacccgg | ccggacaaga | catgatccgg | tcgctggaca | ccccatcaa | aaaggacagc | 1140 |
| catctggtga | tcctcaaggg | caacctggcg | ccggaaggcg | cggtcgccaa | gatcaccggc | 1200 |
| aaggaaggac | tgagcttcac | cggcaccgcc | cgcgtattcg | actgcgagga | agcggcgctc | 1260 |
| acggccatcc | tcgacggcac | gatcgtgaaa | ggcgacgtca | tcgtcatccg | ctatgaaggc | 1320 |
| cccaagggcg | ccccggcat | gcgcgagatg | ctctcgccga | cctcggcggt | catgggcaag | 1380 |
| ggattgggca | aggaggtcgc | cctcatcacc | gacggccgct | tttccggcgg | cacccacggc | 1440 |
| ttcgtggtcg | gccacatcac | gccggaagcc | tacaccggcg | gccccctggc | gatcgtccgg | 1500 |
| gacggcgata | ccatcaccat | cgacgccgag | acccgcgaat | tgagcctgca | cgtcaccgac | 1560 |
| gatgaaatcg | gccggcgcct | ggcgcagtgg | actcaaccgg | cgccgcgcta | caccaagggc | 1620 |
| gtgctggcca | aatacgccag | gttggtgagc | ccggcctcgg | aaggcgccgt | caccgacgac | 1680 |
| ggcctctga | | | | | | 1689 |

<210> SEQ ID NO 6
<211> LENGTH: 562
<212> TYPE: PRT
<213> ORGANISM: Methylococcus capsulatus

<400> SEQUENCE: 6

Met Thr Asp Lys His Pro Arg Pro His Ser Ser Gln Val Val Asp Gly
1               5                   10                  15

Met Glu Arg Ala Pro Ser Arg Ala Met Leu His Ala Val Gly Phe Ala
            20                  25                  30

Asp Ala Asp Phe Ala Lys Pro Gln Ile Gly Ile Ala Ser Thr Trp Ala
        35                  40                  45

Met Val Thr Pro Cys Asn Met His Ile Asn Lys Leu Ala Glu Asp Ala
    50                  55                  60

Ala Arg Gly Val Asp Gly Gly Gly Lys Ala Val Ile Phe Asn Thr
65                  70                  75                  80

Ile Thr Ile Ser Asp Gly Ile Ser Met Gly Thr Glu Gly Met Lys Tyr
                85                  90                  95

Ser Leu Val Ser Arg Glu Val Ile Ala Asp Ser Ile Glu Thr Val Val
            100                 105                 110

Ala Cys Gln Gly Tyr Asp Gly Val Ala Ile Gly Gly Cys Asp Lys
        115                 120                 125

Asn Met Pro Gly Cys Leu Ile Ala Leu Ala Arg Leu Asn Arg Pro Ala
130                 135                 140

Val Phe Val Tyr Gly Gly Thr Ile Leu Pro Gly Cys His Asp Gly Lys
145                 150                 155                 160

Lys Leu Asp Val Val Ser Val Phe Glu Ala Val Gly Ala Arg Ala Asn
                165                 170                 175

His Arg Ile Asp Asp Ala Glu Leu His Ala Ile Glu Ser Asn Ala Ile
            180                 185                 190

Pro Gly Pro Gly Ser Cys Gly Gly Met Tyr Thr Ala Asn Thr Met Ala
        195                 200                 205

Ser Ala Ile Glu Ala Leu Gly Met Ser Leu Pro Gly Ser Ser Ala Gln
    210                 215                 220

Val Ala Ile Ser Arg Ala Lys Glu Leu Asp Cys Glu Arg Ala Gly Ala
225                 230                 235                 240

Gln Val Leu Lys Leu Leu Asp Leu Gly Leu Lys Pro Arg Asp Ile Met
                245                 250                 255

Thr Lys Lys Ala Phe Glu Asn Ala Ile Thr Val Val Ile Ala Leu Gly
            260                 265                 270

Gly Ser Thr Asn Ala Val Leu His Leu Leu Ala Met Ala Asn Ala Cys
        275                 280                 285

Gly Val Asp Leu Lys Leu Asp Asp Phe Thr Arg Ile Gly Arg Lys Val
    290                 295                 300

Pro Met Leu Ala Asp Leu Lys Pro Ser Gly Arg Tyr Ser Met Ala Glu
305                 310                 315                 320

Leu Val Glu Ile Gly Gly Ile Gln Pro Leu Met Lys Thr Leu Leu Asp
                325                 330                 335

Ala Gly Leu Leu His Gly Asp Cys Met Thr Val Thr Gly Lys Thr Leu
            340                 345                 350

Glu Glu Asn Leu Ala Asp Ala Pro Asp Tyr Pro Ala Gly Gln Asp Met
        355                 360                 365

Ile Arg Ser Leu Asp Asn Pro Ile Lys Lys Asp Ser His Leu Val Ile

```
                    370                 375                 380
Leu Lys Gly Asn Leu Ala Pro Glu Gly Ala Val Ala Lys Ile Thr Gly
385                 390                 395                 400

Lys Glu Gly Leu Ser Phe Thr Gly Thr Ala Arg Val Phe Asp Cys Glu
                405                 410                 415

Glu Ala Ala Leu Thr Ala Ile Leu Asp Gly Thr Ile Val Lys Gly Asp
                420                 425                 430

Val Ile Val Ile Arg Tyr Glu Gly Pro Lys Gly Gly Pro Gly Met Arg
                435                 440                 445

Glu Met Leu Ser Pro Thr Ser Ala Val Met Gly Lys Gly Leu Gly Lys
                450                 455                 460

Glu Val Ala Leu Ile Thr Asp Gly Arg Phe Ser Gly Gly Thr His Gly
465                 470                 475                 480

Phe Val Val Gly His Ile Thr Pro Glu Ala Tyr Thr Gly Gly Pro Leu
                485                 490                 495

Ala Ile Val Arg Asp Gly Asp Thr Ile Thr Ile Asp Ala Glu Thr Arg
                500                 505                 510

Glu Leu Ser Leu His Val Thr Asp Asp Glu Ile Gly Arg Arg Leu Ala
                515                 520                 525

Gln Trp Thr Gln Pro Ala Pro Arg Tyr Thr Lys Gly Val Leu Ala Lys
                530                 535                 540

Tyr Ala Arg Leu Val Ser Pro Ala Ser Glu Gly Ala Val Thr Asp Asp
545                 550                 555                 560

Gly Leu

<210> SEQ ID NO 7
<211> LENGTH: 1650
<212> TYPE: DNA
<213> ORGANISM: Methylococcus capsulatus

<400> SEQUENCE: 7
atgggcacgg ttgagcctgg cgctatcgga caacatctgc tcgcctgcct ttaccaggcg      60
ggcgtcgggc acatcttcgg cgttccggc gattacgtgc tgggcttcta tgatctgatg     120
gccaaaggtc ccgtccggca tatcgggacc acgcgggagg acaccgccgc cttcgccgcc     180
gacggctatg cccgctgccg gggcatgggc gcgctggcgg tgacttacgg ggtcggtgcg     240
ctcaacaccg tcaacgccgt cgccggcgcc tatgcggaat cctcgccggt ggtggtcatc     300
agcggtgcgc gggggtgcg cgagcaaagg gaagacccgt tgatccacca ccgcttcggg     360
ccgttccggt tccagcgcga gatattcgaa cggatcacct gcgccgccgt ggtgctggac     420
gatccggtga tcgccttccg gcaggtggag cgtgcgctcg cggccgcccg tcagcactgc     480
aagccggtgt acatcgagat tcccgccgac cgggtgatgg cgccgggata tccgattcca     540
caggaaaccc cggaaacgcc ttccagcgac gattcggccc tggcggaggc ggtcgccgag     600
gccgcggagc tcctgggccg tgcggtgtcg ccggtgatcc ttgcaggcgt cgagttgcac     660
cggcgagggc tccaggacgc cctcgtcggc ctcgtcgagc aggcgcgcct gccggtggcg     720
gcgaccttga ccggcaagtc ggtgttcgcc gagcgccatc ccgcctatct gggggtgtac     780
gagggtgcga tgagcacgga aaacgcgcgc tacatggtcg agcagtccga cctcctgctg     840
atgctcgggg tcacgctgaa cgatgtcgac acgggcatct acacggcgcg tctcgatccg     900
cagcgcatcg tccgcgcagc ccagaacgag gtcgtgattc gccatcaccg ctatccccgc     960
gtcctgctcg cggacttcgt cacggccctg gcgcggtccg tcaaggcccg gggcgaggcg    1020
```

```
tttccgatgc cggcggggcc ggaaccgtgg gactttcccg cgccggaccg gccgatgacg    1080
atcgcccggc tggtggagcg gctcgaccgc gcgctgacct ccgacatgat cgtagtgtgc    1140
gacgtcggcg actgcctgtt cgcagccacc gacctgcgcg tgcacgagcg cagcgaattc    1200
ctggcgtccg ccttctatac ctcgatgggg ttcgcggtgc ccgccgccct cggggcccag    1260
atcgcccgtc cggaccaccg ggcgctgatc ctggtcggcg acggtgcctt ccagatgacc    1320
ggaacggagc tgtcgaccca tgcccgtctc ggcctggcgc ccatcgtggt ggtgctcgac    1380
aatcgcggtt acagcaccga gcgcttcatc ctcgacggag ccttcaacga catcgccgac    1440
tggcgcttcc accggctggg cgaggtgttc ggccccctac agggctacga cgcgcccgac    1500
gaagcggcgt tcgaaaacgc gctcagcgaa gcgctggtca accgaaacat gccgagcctc    1560
atcaacgtcc gtctttcccc cggcgatgcc tcgatagcca tgaagcgtct cgccgggcat    1620
ctgcagtgcc gggtcaaggg cgagggctga                                    1650
```

<210> SEQ ID NO 8
<211> LENGTH: 549
<212> TYPE: PRT
<213> ORGANISM: Methylococcus capsulatus

<400> SEQUENCE: 8

```
Met Gly Thr Val Glu Pro Gly Ala Ile Gly Gln His Leu Leu Ala Cys
1               5                   10                  15

Leu Tyr Gln Ala Gly Val Gly His Ile Phe Gly Val Pro Gly Asp Tyr
            20                  25                  30

Val Leu Gly Phe Tyr Asp Leu Met Ala Lys Gly Pro Val Arg His Ile
        35                  40                  45

Gly Thr Thr Arg Glu Asp Thr Ala Ala Phe Ala Ala Asp Gly Tyr Ala
    50                  55                  60

Arg Cys Arg Gly Met Gly Ala Leu Ala Val Thr Tyr Gly Val Gly Ala
65                  70                  75                  80

Leu Asn Thr Val Asn Ala Val Ala Gly Ala Tyr Ala Glu Ser Ser Pro
                85                  90                  95

Val Val Val Ile Ser Gly Ala Pro Gly Val Arg Glu Gln Arg Glu Asp
            100                 105                 110

Pro Leu Ile His His Arg Phe Gly Pro Phe Arg Phe Gln Arg Glu Ile
        115                 120                 125

Phe Glu Arg Ile Thr Cys Ala Ala Val Val Leu Asp Asp Pro Val Ile
    130                 135                 140

Ala Phe Arg Gln Val Glu Arg Ala Leu Ala Ala Arg Gln His Cys
145                 150                 155                 160

Lys Pro Val Tyr Ile Glu Ile Pro Ala Asp Arg Val Met Ala Pro Gly
                165                 170                 175

Tyr Pro Ile Pro Gln Glu Thr Pro Glu Thr Pro Ser Ser Asp Asp Ser
            180                 185                 190

Ala Leu Ala Glu Ala Val Ala Glu Ala Ala Glu Leu Leu Gly Arg Ala
        195                 200                 205

Val Ser Pro Val Ile Leu Ala Gly Val Glu Leu His Arg Arg Gly Leu
    210                 215                 220

Gln Asp Ala Leu Val Gly Leu Val Glu Gln Arg Leu Pro Val Ala
225                 230                 235                 240

Ala Thr Leu Thr Gly Lys Ser Val Phe Ala Glu Arg His Pro Ala Tyr
                245                 250                 255

Leu Gly Val Tyr Glu Gly Ala Met Ser Thr Glu Asn Ala Arg Tyr Met
```

```
                260                 265                 270
Val Glu Gln Ser Asp Leu Leu Leu Met Leu Gly Val Thr Leu Asn Asp
            275                 280                 285

Val Asp Thr Gly Ile Tyr Thr Ala Arg Leu Asp Pro Gln Arg Ile Val
        290                 295                 300

Arg Ala Ala Gln Asn Glu Val Val Ile Arg His His Arg Tyr Pro Arg
305                 310                 315                 320

Val Leu Leu Ala Asp Phe Val Thr Ala Leu Ala Arg Ser Val Lys Ala
                325                 330                 335

Arg Gly Glu Ala Phe Pro Met Pro Ala Gly Pro Glu Pro Trp Asp Phe
            340                 345                 350

Pro Ala Pro Asp Arg Pro Met Thr Ile Ala Arg Leu Val Glu Arg Leu
        355                 360                 365

Asp Arg Ala Leu Thr Ser Asp Met Ile Val Val Cys Asp Val Gly Asp
        370                 375                 380

Cys Leu Phe Ala Ala Thr Asp Leu Arg Val His Glu Arg Ser Glu Phe
385                 390                 395                 400

Leu Ala Ser Ala Phe Tyr Thr Ser Met Gly Phe Ala Val Pro Ala Ala
                405                 410                 415

Leu Gly Ala Gln Ile Ala Arg Pro Asp His Arg Ala Leu Ile Leu Val
            420                 425                 430

Gly Asp Gly Ala Phe Gln Met Thr Gly Thr Glu Leu Ser Thr His Ala
        435                 440                 445

Arg Leu Gly Leu Ala Pro Ile Val Val Leu Asp Asn Arg Gly Tyr
        450                 455                 460

Ser Thr Glu Arg Phe Ile Leu Asp Gly Ala Phe Asn Asp Ile Ala Asp
465                 470                 475                 480

Trp Arg Phe His Arg Leu Gly Glu Val Phe Gly Pro Leu Gln Gly Tyr
                485                 490                 495

Asp Ala Pro Asp Glu Ala Ala Phe Glu Asn Ala Leu Ser Glu Ala Leu
            500                 505                 510

Val Asn Arg Asn Met Pro Ser Leu Ile Asn Val Arg Leu Ser Pro Gly
        515                 520                 525

Asp Ala Ser Ile Ala Met Lys Arg Leu Ala Gly His Leu Gln Cys Arg
        530                 535                 540

Val Lys Gly Glu Gly
545

<210> SEQ ID NO 9
<211> LENGTH: 1083
<212> TYPE: DNA
<213> ORGANISM: Saccharomyces cerevisiae

<400> SEQUENCE: 9
atgtcttatc ctgagaaatt tgaaggtatc gctattcaat cacacgaaga ttggaaaaac      60
ccaaagaaga caaagtatga cccaaaacca ttttacgatc atgacattga cattaagatc     120
gaagcatgtg gtgtctgcgg tagtgatatt cattgtgcag ctggtcattg gggcaatatg     180
aagatgccgc tagtcgttgg tcatgaaatc gttggtaaag ttgtcaagct agggcccaag     240
tcaaacagtg ggttgaaagt cggtcaacgt gttggtgtag gtgctcaagt cttttcatgc     300
ttggaatgtg accgttgtaa gaatgataat gaaccatact gcaccaagtt tgttaccaca     360
tacagtcagc cttatgaaga cggctatgtg tcgcagggtg gctatgcaaa ctacgtcaga     420
gttcatgaac attttgtggt gcctatccca gagaatattc catcacattt ggctgctcca     480
```

-continued

```
ctattatgtg gtggtttgac tgtgtactct ccattggttc gtaacggttg cggtccaggt      540
aaaaaagttg gtatagttgg tcttggtggt atcggcagta tgggtacatt gatttccaaa      600
gccatggggg cagagacgta tgttatttct cgttcttcga gaaaagaga agatgcaatg       660 aagatgggcg ccgatcacta cattgctaca ttagaagaag gtgattgggg tgaaaagtac      720
tttgacacct tcgacctgat tgtagtctgt gcttcctccc ttaccgacat tgacttcaac     780
attatgccaa aggctatgaa ggttggtggt agaattgtct caatctctat accagaacaa     840
cacgaaatgt tatcgctaaa gccatatggc ttaaaggctg tctccatttc ttacagtgct     900
ttaggttcca tcaaagaatt gaaccaactc ttgaaattag tctctgaaaa agatatcaaa     960
atttgggtgg aaacattacc tgttggtgaa gccggcgtcc atgaagcctt cgaaaggatg    1020
gaaaagggtg acgttagata tagatttacc ttagtcggct acgacaaaga attttcagac    1080
tag                                                                  1083
```

<210> SEQ ID NO 10
<211> LENGTH: 360
<212> TYPE: PRT
<213> ORGANISM: Saccharomyces cerevisiae

<400> SEQUENCE: 10

```
Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255
```

```
Ile Asp Phe Asn Ile Met Pro Lys Ala Met Lys Val Gly Gly Arg Ile
                260                 265                 270

Val Ser Ile Ser Ile Pro Glu Gln His Glu Met Leu Ser Leu Lys Pro
            275                 280                 285

Tyr Gly Leu Lys Ala Val Ser Ile Ser Tyr Ser Ala Leu Gly Ser Ile
        290                 295                 300

Lys Glu Leu Asn Gln Leu Leu Lys Leu Val Ser Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360

<210> SEQ ID NO 11
<211> LENGTH: 783
<212> TYPE: DNA
<213> ORGANISM: Methylococcus capsulatus

<400> SEQUENCE: 11
atggcagcaa caaccattgg tggtgcagct gcggcggaag cgccgctgct ggacaagaag    60
tggctcacgt tcgcactggc gatttacacc gtgttctacc tgtgggtgcg gtggtacgaa   120
ggtgtctatg gctggtccgc cggactggac tcgttcgcgc cggagttcga gacctactgg   180
atgaatttcc tgtacaccga gatcgtcctg gagatcgtga cggcttcgat cctgtggggc   240
tatctctgga gacccgcga ccgcaacctg gccgcgctga ccccgcgtga agagctgcgc   300
cgcaacttca cccacctggt gtggctggtg gcctacgcct gggccatcta ctggggcgca   360
tcctacttca ccgagcagga cggcacctgg catcagacga tcgtgcgcga caccgacttc   420
acgccgtcgc acatcatcga gttctatctg agctacccga tctacatcat caccggtttt   480
gcggcgttca tctacgccaa gacgcgtctg ccgttcttcg aagggcat ctcgctgccg   540 tacctggtgc tggtggtggg tccgttcatg attctgccga acgtgggtct gaacgaatgg   600
ggccacacct tctggttcat ggaagagctg ttcgtggcgc cgctgcacta cggcttcgtg   660
atcttcggct ggctggcact ggccgtcatg ggcaccctga cccagacctt ctacagcttc   720
gctcagggcg gctggggca gtcgctctgt gaagccgtgg acgaaggctt gatcgcgaaa   780
taa                                                                 783

<210> SEQ ID NO 12
<211> LENGTH: 260
<212> TYPE: PRT
<213> ORGANISM: Methylococcus capsulatus

<400> SEQUENCE: 12

Met Ala Ala Thr Thr Ile Gly Gly Ala Ala Ala Glu Ala Pro Leu
1               5                   10                  15

Leu Asp Lys Lys Trp Leu Thr Phe Ala Leu Ala Ile Tyr Thr Val Phe
                20                  25                  30

Tyr Leu Trp Val Arg Trp Tyr Glu Gly Val Tyr Gly Trp Ser Ala Gly
            35                  40                  45

Leu Asp Ser Phe Ala Pro Glu Phe Glu Thr Tyr Trp Met Asn Phe Leu
        50                  55                  60

Tyr Thr Glu Ile Val Leu Glu Ile Val Thr Ala Ser Ile Leu Trp Gly
65                  70                  75                  80
```

```
Tyr Leu Trp Lys Thr Arg Asp Arg Asn Leu Ala Ala Leu Thr Pro Arg
                 85                  90                  95

Glu Glu Leu Arg Arg Asn Phe Thr His Leu Val Trp Leu Val Ala Tyr
            100                 105                 110

Ala Trp Ala Ile Tyr Trp Gly Ala Ser Tyr Phe Thr Glu Gln Asp Gly
        115                 120                 125

Thr Trp His Gln Thr Ile Val Arg Asp Thr Asp Phe Thr Pro Ser His
    130                 135                 140

Ile Ile Glu Phe Tyr Leu Ser Tyr Pro Ile Tyr Ile Thr Gly Phe
145                 150                 155                 160

Ala Ala Phe Ile Tyr Ala Lys Thr Arg Leu Pro Phe Phe Ala Lys Gly
                165                 170                 175

Ile Ser Leu Pro Tyr Leu Val Leu Val Val Gly Pro Phe Met Ile Leu
            180                 185                 190

Pro Asn Val Gly Leu Asn Glu Trp Gly His Thr Phe Trp Phe Met Glu
        195                 200                 205

Glu Leu Phe Val Ala Pro Leu His Tyr Gly Phe Val Ile Phe Gly Trp
    210                 215                 220

Leu Ala Leu Ala Val Met Gly Thr Leu Thr Gln Thr Phe Tyr Ser Phe
225                 230                 235                 240

Ala Gln Gly Gly Leu Gly Gln Ser Leu Cys Glu Ala Val Asp Glu Gly
                245                 250                 255

Leu Ile Ala Lys
            260

<210> SEQ ID NO 13
<211> LENGTH: 744
<212> TYPE: DNA
<213> ORGANISM: Methylococcus capsulatus

<400> SEQUENCE: 13
atgagtgctg cgcaatctgc ggttcgttcg cacgccgaag cggtccaggt atcccggacc      60
atcgactgga tggcgttgtt cgtggtgttt ttcgtgatcg tgggctcgta ccacattcat     120
gccatgctca ccatgggtga ctgggacttc tggtcggact ggaaagaccg tcgactgtgg     180
gtcacggtga ccccgatcgt actggtcacc ttcccggcgg ccgtacaatc ctacctgtgg     240
gagcggtatc gtctgccctg gggagccacc gtgtgcgtcc tgggtctgct gctgggcgag     300
tggatcaacc gttatttcaa cttctggggc tggacctact cccgatcaa cttcgtgttc      360 cctgcctcgc tggtgccggg cgccatcatc ctggacaccg tgctgatgct gtcgggcagc     420
tacctgttca ccgcgatcgt cggtgcgatg ggctggggtc tgatcttcta cccgggcaac     480
tggccgatca tcgcgccgct gcacgtgccg gtggaataca acggcatgct gatgtcgatc     540
gccgacatcc agggttacaa ctatgtgcgt acgggtacgc tgagtacat ccgcatggta      600 gagaagggca ccctgcgtac cttcggtaag gacgtgcgc cggtatcggc attcttctcc      660
gcgttcatgt cgatcctgat ctacttcatg tggcacttca tcggtcgctg gttctccaac     720
gaacggttcc tgcagagcac ctga                                            744

<210> SEQ ID NO 14
<211> LENGTH: 247
<212> TYPE: PRT
<213> ORGANISM: Methylococcus capsulatus

<400> SEQUENCE: 14
```

```
Met Ser Ala Ala Gln Ser Ala Val Arg Ser His Ala Glu Ala Val Gln
1               5                   10                  15

Val Ser Arg Thr Ile Asp Trp Met Ala Leu Phe Val Val Phe Phe Val
            20                  25                  30

Ile Val Gly Ser Tyr His Ile His Ala Met Leu Thr Met Gly Asp Trp
        35                  40                  45

Asp Phe Trp Ser Asp Trp Lys Asp Arg Arg Leu Trp Val Thr Val Thr
    50                  55                  60

Pro Ile Val Leu Val Thr Phe Pro Ala Ala Val Gln Ser Tyr Leu Trp
65                  70                  75                  80

Glu Arg Tyr Arg Leu Pro Trp Gly Ala Thr Val Cys Val Leu Gly Leu
                85                  90                  95

Leu Leu Gly Glu Trp Ile Asn Arg Tyr Phe Asn Phe Trp Gly Trp Thr
            100                 105                 110

Tyr Phe Pro Ile Asn Phe Val Phe Pro Ala Ser Leu Val Pro Gly Ala
        115                 120                 125

Ile Ile Leu Asp Thr Val Leu Met Leu Ser Gly Ser Tyr Leu Phe Thr
    130                 135                 140

Ala Ile Val Gly Ala Met Gly Trp Gly Leu Ile Phe Tyr Pro Gly Asn
145                 150                 155                 160

Trp Pro Ile Ile Ala Pro Leu His Val Pro Val Glu Tyr Asn Gly Met
                165                 170                 175

Leu Met Ser Ile Ala Asp Ile Gln Gly Tyr Asn Tyr Val Arg Thr Gly
            180                 185                 190

Thr Pro Glu Tyr Ile Arg Met Val Glu Lys Gly Thr Leu Arg Thr Phe
        195                 200                 205

Gly Lys Asp Val Ala Pro Val Ser Ala Phe Phe Ser Ala Phe Met Ser
    210                 215                 220

Ile Leu Ile Tyr Phe Met Trp His Phe Ile Gly Arg Trp Phe Ser Asn
225                 230                 235                 240

Glu Arg Phe Leu Gln Ser Thr
                245

<210> SEQ ID NO 15
<211> LENGTH: 1245
<212> TYPE: DNA
<213> ORGANISM: Methylococcus capsulatus

<400> SEQUENCE: 15
atgaaaacaa taaggaccg gattgcaaaa tggtctgcaa tcggactgct gtccgccgtg      60
gcagcgaccg ccttctatgc gccgagcgcc agcgcccacg gtgagaaatc gcaggccgcg     120
ttcatgcgta tgcgtaccat ccactggtac gacctgagct ggtcgaaaga gaaagtcaag     180
atcaacgaga ccgtggaaat caaaggcaag ttccacgtgt tcgaaggctg gccggaaacg     240
gtcgacgaac cggatgtggc gttcctgaac gtcggcatgc cggtccggt gttcatccgc      300 aaggaatcgt acatcggcgg tcagctggtg ccgcgttccg tacgtctgga atcggcaag     360 acctatgact tccgggttgt cctcaaagcc cgtcgtccgg tgactggca cgttcacacc      420 atgatgaacg tccagggcgg tggaccgatc atcggtcccg gcaaatggat caccgtggaa     480
ggctccatga gtgaattccg caaccccgtc accaccctga ccggtcagac ggtggacctg     540
gagaactaca acgaaggcaa cacctatttc tggcacgcct tctggttcgc catcggagtt     600
gcctggatcg gctactggtc gcgtcgaccg atcttcatcc ccgtctgct gatggtggat      660 gccggtcgtg cggatgaact ggtgtccgcc accgaccgca aggtggcgat gggcttcctg     720
```

```
gccgccacca tcctgatcgt ggtcatggcc atgtccagcg ccaacagcaa gtacccgatc      780
accatcccgc tgcaggccgg caccatgcgt ggcatgaagc cgctggaact gccggcgccg      840
acggtatcgg tgaaagtgga agacgccacc taccgggtac cgggccgcgc catgcggatg      900
aagctgacca tcaccaacca cggcaacagc ccgatccggc tgggtgagtt ctacaccgcc      960
tcggtgcgtt tcctggattc cgacgtgtac aaggacacca ccggctatcc ggaagacctg     1020
ctggccgaag acggcctgag cgtcagcgac aacagcccgc tggctccggg tgagacgcgc     1080
acggtcgacg tgacggcgtc cgacgcggcg tgggaagtgt accgtctgtc cgacatcatc     1140
tacgatccgg acagccgttt cgccggtctg ctgttcttct tcgacgccac tggcaaccgc     1200
caggtcgtcc agatcgacgc accgctgatc ccgtcgttca tgtaa                    1245
```

<210> SEQ ID NO 16
<211> LENGTH: 414
<212> TYPE: PRT
<213> ORGANISM: Methylococcus capsulatus

<400> SEQUENCE: 16

```
Met Lys Thr Ile Lys Asp Arg Ile Ala Lys Trp Ser Ala Ile Gly Leu
1               5                   10                  15

Leu Ser Ala Val Ala Ala Thr Ala Phe Tyr Ala Pro Ser Ala Ser Ala
                20                  25                  30

His Gly Glu Lys Ser Gln Ala Ala Phe Met Arg Met Thr Ile His
        35                  40                  45

Trp Tyr Asp Leu Ser Trp Ser Lys Glu Lys Val Lys Ile Asn Glu Thr
    50                  55                  60

Val Glu Ile Lys Gly Lys Phe His Val Phe Glu Gly Trp Pro Glu Thr
65                  70                  75                  80

Val Asp Glu Pro Asp Val Ala Phe Leu Asn Val Gly Met Pro Gly Pro
                85                  90                  95

Val Phe Ile Arg Lys Glu Ser Tyr Ile Gly Gly Gln Leu Val Pro Arg
                100                 105                 110

Ser Val Arg Leu Glu Ile Gly Lys Thr Tyr Asp Phe Arg Val Val Leu
                115                 120                 125

Lys Ala Arg Arg Pro Gly Asp Trp His Val His Thr Met Met Asn Val
    130                 135                 140

Gln Gly Gly Gly Pro Ile Ile Gly Pro Gly Lys Trp Ile Thr Val Glu
145                 150                 155                 160

Gly Ser Met Ser Glu Phe Arg Asn Pro Val Thr Thr Leu Thr Gly Gln
                165                 170                 175

Thr Val Asp Leu Glu Asn Tyr Asn Glu Gly Asn Thr Tyr Phe Trp His
                180                 185                 190

Ala Phe Trp Phe Ala Ile Gly Val Ala Trp Ile Gly Tyr Trp Ser Arg
        195                 200                 205

Arg Pro Ile Phe Ile Pro Arg Leu Leu Met Val Asp Ala Gly Arg Ala
    210                 215                 220

Asp Glu Leu Val Ser Ala Thr Asp Arg Lys Val Ala Met Gly Phe Leu
225                 230                 235                 240

Ala Ala Thr Ile Leu Ile Val Val Met Ala Met Ser Ser Ala Asn Ser
                245                 250                 255

Lys Tyr Pro Ile Thr Ile Pro Leu Gln Ala Gly Thr Met Arg Gly Met
                260                 265                 270

Lys Pro Leu Glu Leu Pro Ala Pro Thr Val Ser Val Lys Val Glu Asp
```

```
              275                 280                 285
Ala Thr Tyr Arg Val Pro Gly Arg Ala Met Arg Met Lys Leu Thr Ile
         290                 295                 300

Thr Asn His Gly Asn Ser Pro Ile Arg Leu Gly Glu Phe Tyr Thr Ala
305                 310                 315                 320

Ser Val Arg Phe Leu Asp Ser Asp Val Tyr Lys Asp Thr Thr Gly Tyr
                 325                 330                 335

Pro Glu Asp Leu Leu Ala Glu Asp Gly Leu Ser Val Ser Asp Asn Ser
             340                 345                 350

Pro Leu Ala Pro Gly Glu Thr Arg Thr Val Asp Val Thr Ala Ser Asp
         355                 360                 365

Ala Ala Trp Glu Val Tyr Arg Leu Ser Asp Ile Ile Tyr Asp Pro Asp
     370                 375                 380

Ser Arg Phe Ala Gly Leu Leu Phe Phe Phe Asp Ala Thr Gly Asn Arg
385                 390                 395                 400

Gln Val Val Gln Ile Asp Ala Pro Leu Ile Pro Ser Phe Met
                 405                 410
```

<210> SEQ ID NO 17
<211> LENGTH: 783
<212> TYPE: DNA
<213> ORGANISM: Methylococcus capsulatus

<400> SEQUENCE: 17

```
atggcagcaa caaccattgg tggtgcagct gcggcggaag cgccgctgct ggacaagaag    60
tggctcacgt tcgcactggc gatttacacc gtgttctacc tgtgggtgcg gtggtacgaa   120
ggtgtctatg gctggtccgc cggactggac tcgttcgcgc ggagttcga gacctactgg    180
atgaatttcc tgtacaccga gatcgtcctg agatcgtga cggcttcgat cctgtggggc    240
tatctctgga gacccgcga ccgcaacctg gccgcgctga ccccgcgtga agagctgcgc    300
cgcaacttca cccacctggt gtggctggtg gcctacgcct gggccatcta ctggggcgca   360
tcctacttca ccgagcagga cggcacctgg catcagacga tcgtgcgcga caccgacttc    420
acgccgtcgc acatcatcga gttctatctg agctacccga tctacatcat caccggtttt    480
gcggcgttca tctacgccaa gacgcgtctg ccgttcttcg cgaagggcat ctcgctgccg    540
tacctggtgc tggtggtggg tccgttcatg attctgccga acgtgggtct gaacgaatgg    600
ggccacacct tctggttcat ggaagagctg ttcgtggcgc cgctgcacta cggcttcgtg    660
atcttcggct ggctggcact ggccgtcatg ggcaccctga cccagacctt ctacagcttc    720
gctcagggcg ggctggggca gtcgctctgt gaagccgtgg acgaaggctt gatcgcgaaa    780
taa                                                                 783
```

<210> SEQ ID NO 18
<211> LENGTH: 260
<212> TYPE: PRT
<213> ORGANISM: Methylococcus capsulatus

<400> SEQUENCE: 18

```
Met Ala Ala Thr Thr Ile Gly Gly Ala Ala Ala Glu Ala Pro Leu
1               5                  10                  15

Leu Asp Lys Lys Trp Leu Thr Phe Ala Leu Ala Ile Tyr Thr Val Phe
                 20                  25                  30

Tyr Leu Trp Val Arg Trp Tyr Glu Gly Val Tyr Gly Trp Ser Ala Gly
             35                  40                  45
```

```
Leu Asp Ser Phe Ala Pro Glu Phe Glu Thr Tyr Trp Met Asn Phe Leu
 50                  55                  60
Tyr Thr Glu Ile Val Leu Glu Ile Val Thr Ala Ser Ile Leu Trp Gly
 65                      70                  75                  80
Tyr Leu Trp Lys Thr Arg Asp Arg Asn Leu Ala Ala Leu Thr Pro Arg
                 85                  90                  95
Glu Glu Leu Arg Arg Asn Phe Thr His Leu Val Trp Leu Val Ala Tyr
            100                 105                 110
Ala Trp Ala Ile Tyr Trp Gly Ala Ser Tyr Phe Thr Glu Gln Asp Gly
        115                 120                 125
Thr Trp His Gln Thr Ile Val Arg Asp Thr Asp Phe Thr Pro Ser His
    130                 135                 140
Ile Ile Glu Phe Tyr Leu Ser Tyr Pro Ile Tyr Ile Thr Gly Phe
145                 150                 155                 160
Ala Ala Phe Ile Tyr Ala Lys Thr Arg Leu Pro Phe Phe Ala Lys Gly
                165                 170                 175
Ile Ser Leu Pro Tyr Leu Val Leu Val Gly Pro Phe Met Ile Leu
            180                 185                 190
Pro Asn Val Gly Leu Asn Glu Trp Gly His Thr Phe Trp Phe Met Glu
        195                 200                 205
Glu Leu Phe Val Ala Pro Leu His Tyr Gly Phe Val Ile Phe Gly Trp
    210                 215                 220
Leu Ala Leu Ala Val Met Gly Thr Leu Thr Gln Thr Phe Tyr Ser Phe
225                 230                 235                 240
Ala Gln Gly Gly Leu Gly Gln Ser Leu Cys Glu Ala Val Asp Glu Gly
                245                 250                 255
Leu Ile Ala Lys
        260

<210> SEQ ID NO 19
<211> LENGTH: 744
<212> TYPE: DNA
<213> ORGANISM: Methylococcus capsulatus

<400> SEQUENCE: 19
atgagtgctg cgcaatctgc ggttcgttcg cacgccgaag cggtccaggt atcccggacc      60
atcgactgga tggcgttgtt cgtggtgttt ttcgtgatcg tgggctcgta ccacattcac     120
gccatgctca ccatgggtga ctgggacttc tggtcggact ggaaagaccg tcgactgtgg     180
gtcacggtga ccccgatcgt actggtcacc ttcccggcgg ccgtacaatc ctacctgtgg     240
gagcggtatc gtctgccctg gggagccacc gtgtgcgtcc tgggtctgct gctgggcgag     300
tggatcaacc gttatttcaa cttctggggc tggacctact tcccgatcaa cttcgtgttc     360
cctgcctcgc tggtgccggg cgccatcatc ctggacaccg tgctgatgct gtcgggcagc     420
tacctgttca ccgcgatcgt cggtgcgatg ggctggggtc tgatcttcta cccgggcaac     480
tggccgatca tcgcgccgct gcacgtgccg gtggaataca acggcatgct gatgtcgatc     540
gccgacatcc agggttacaa ctatgtgcgt acgggtacgc ctgagtacat ccgcatggta     600
gagaagggca cctgcgctac cttcggtaag acgtgggcgc cggtatcggc attcttctcc     660
gcgttcatgt cgatcctgat ctacttcatg tggcacttca tcggtcgctg gttctccaac     720
gaacggttcc tgcagagcac ctga                                           744

<210> SEQ ID NO 20
<211> LENGTH: 247
```

-continued

```
<212> TYPE: PRT
<213> ORGANISM: Methylococcus capsulatus

<400> SEQUENCE: 20

Met Ser Ala Ala Gln Ser Ala Val Arg Ser His Ala Glu Ala Val Gln
1               5                   10                  15

Val Ser Arg Thr Ile Asp Trp Met Ala Leu Phe Val Val Phe Phe Val
            20                  25                  30

Ile Val Gly Ser Tyr His Ile His Ala Met Leu Thr Met Gly Asp Trp
        35                  40                  45

Asp Phe Trp Ser Asp Trp Lys Asp Arg Arg Leu Trp Val Thr Val Thr
    50                  55                  60

Pro Ile Val Leu Val Thr Phe Pro Ala Ala Val Gln Ser Tyr Leu Trp
65                  70                  75                  80

Glu Arg Tyr Arg Leu Pro Trp Gly Ala Thr Val Cys Val Leu Gly Leu
                85                  90                  95

Leu Leu Gly Glu Trp Ile Asn Arg Tyr Phe Asn Phe Trp Gly Trp Thr
            100                 105                 110

Tyr Phe Pro Ile Asn Phe Val Phe Pro Ala Ser Leu Val Pro Gly Ala
        115                 120                 125

Ile Ile Leu Asp Thr Val Leu Met Leu Ser Gly Ser Tyr Leu Phe Thr
    130                 135                 140

Ala Ile Val Gly Ala Met Gly Trp Gly Leu Ile Phe Tyr Pro Gly Asn
145                 150                 155                 160

Trp Pro Ile Ile Ala Pro Leu His Val Pro Val Glu Tyr Asn Gly Met
                165                 170                 175

Leu Met Ser Ile Ala Asp Ile Gln Gly Tyr Asn Tyr Val Arg Thr Gly
            180                 185                 190

Thr Pro Glu Tyr Ile Arg Met Val Glu Lys Gly Thr Leu Arg Thr Phe
        195                 200                 205

Gly Lys Asp Val Ala Pro Val Ser Ala Phe Ser Ala Phe Met Ser
    210                 215                 220

Ile Leu Ile Tyr Phe Met Trp His Phe Ile Gly Arg Trp Phe Ser Asn
225                 230                 235                 240

Glu Arg Phe Leu Gln Ser Thr
                245

<210> SEQ ID NO 21
<211> LENGTH: 1245
<212> TYPE: DNA
<213> ORGANISM: Methylococcus capsulatus

<400> SEQUENCE: 21
atgaaaacaa taaggaccg gattgcaaaa tggtctgcaa tcggactgct gtccgccgtg      60
gcagcgaccg ccttctatgc gccgagcgcc agcgcccacg gtgagaaatc gcaggccgcg     120
ttcatgcgta tgcgtaccat ccactggtac gacctgagct ggtcgaaaga gaaagtcaag     180
atcaacgaga ccgtggaaat caaaggcaag ttccacgtgt tcgaaggctg gccggaaacg     240
gtcgacgaac cggatgtggc gttcctgaac gtcggcatgc cgggtccggt gttcatccgc     300
aaggaatcgt acatcggcgg tcagctggtg ccgcgttccg tacgtctgga atcggcaag     360 acctatgact ccgggttgt cctcaaagcc cgtcgtccgg gtgactggca cgttcacacc     420
atgatgaacg tccagggcgg tggaccgatc atcggtcccg gcaaatggat caccgtggaa     480
ggctccatga gtgaattccg caaccccgtc accaccctga ccggtcagac ggtggacctg     540
```

```
gagaactaca acgaaggcaa cacctatttc tggcacgcct tctggttcgc catcggagtt    600
gcctggatcg gctactggtc gcgtcgaccg atcttcatcc cccgtctgct gatggtggat    660
gccggtcgtg cggacgaact ggtgtccgcc accgaccgca aggtggcgat gggcttcctg    720
gccgccacca tcctgatcgt ggtcatggcc atgtccagcg ccaacagcaa gtacccgatc    780
accatcccgc tgcaggccgg caccatgcgt ggcatgaagc cgctggaact gccggcgccg    840
acggtatcgg tgaaagtgga agacgccacc taccgggtac cgggccgcgc catgcggatg    900
aagctgacca tcaccaacca cggcaacagc ccgatccggc tgggtgagtt ctacaccgcc    960
tcggtgcgtt tcctggattc cgacgtgtac aaggacacca ccggctatcc ggaagacctg    1020
ctggccgaag acggcctgag cgtcagcgac aacagcccgc tggctccggg tgagacccgc    1080
acggtcgacg tgacggcgtc cgacgcggcg tgggaagtgt accgtctgtc cgacatcatc    1140
tacgatccgg acagccgttt cgccggtctg ctgttcttct tcgacgccac tggcaaccgc    1200
caggtcgtcc agatcgacgc accgctgatc ccgtcgttca tgtaa                    1245
```

<210> SEQ ID NO 22
<211> LENGTH: 414
<212> TYPE: PRT
<213> ORGANISM: Methylococcus capsulatus

<400> SEQUENCE: 22

```
Met Lys Thr Ile Lys Asp Arg Ile Ala Lys Trp Ser Ala Ile Gly Leu
1               5                   10                  15
Leu Ser Ala Val Ala Ala Thr Ala Phe Tyr Ala Pro Ser Ala Ser Ala
                20                  25                  30
His Gly Glu Lys Ser Gln Ala Ala Phe Met Arg Met Arg Thr Ile His
            35                  40                  45
Trp Tyr Asp Leu Ser Trp Ser Lys Glu Lys Val Lys Ile Asn Glu Thr
        50                  55                  60
Val Glu Ile Lys Gly Lys Phe His Val Phe Glu Gly Trp Pro Glu Thr
65                  70                  75                  80
Val Asp Glu Pro Asp Val Ala Phe Leu Asn Val Gly Met Pro Gly Pro
                85                  90                  95
Val Phe Ile Arg Lys Glu Ser Tyr Ile Gly Gly Gln Leu Val Pro Arg
            100                 105                 110
Ser Val Arg Leu Glu Ile Gly Lys Thr Tyr Asp Phe Arg Val Val Leu
        115                 120                 125
Lys Ala Arg Arg Pro Gly Asp Trp His Val His Thr Met Met Asn Val
    130                 135                 140
Gln Gly Gly Gly Pro Ile Ile Gly Pro Gly Lys Trp Ile Thr Val Glu
145                 150                 155                 160
Gly Ser Met Ser Glu Phe Arg Asn Pro Val Thr Thr Leu Thr Gly Gln
                165                 170                 175
Thr Val Asp Leu Glu Asn Tyr Asn Glu Gly Asn Thr Tyr Phe Trp His
            180                 185                 190
Ala Phe Trp Phe Ala Ile Gly Val Ala Trp Ile Gly Tyr Trp Ser Arg
        195                 200                 205
Arg Pro Ile Phe Ile Pro Arg Leu Leu Met Val Asp Ala Gly Arg Ala
    210                 215                 220
Asp Glu Leu Val Ser Ala Thr Asp Arg Lys Val Ala Met Gly Phe Leu
225                 230                 235                 240
Ala Ala Thr Ile Leu Ile Val Val Met Ala Met Ser Ser Ala Asn Ser
                245                 250                 255
```

Lys Tyr Pro Ile Thr Ile Pro Leu Gln Ala Gly Thr Met Arg Gly Met
            260                 265                 270

Lys Pro Leu Glu Leu Pro Ala Pro Thr Val Ser Val Lys Val Glu Asp
        275                 280                 285

Ala Thr Tyr Arg Val Pro Gly Arg Ala Met Arg Met Lys Leu Thr Ile
    290                 295                 300

Thr Asn His Gly Asn Ser Pro Ile Arg Leu Gly Glu Phe Tyr Thr Ala
305                 310                 315                 320

Ser Val Arg Phe Leu Asp Ser Asp Val Tyr Lys Asp Thr Thr Gly Tyr
                325                 330                 335

Pro Glu Asp Leu Leu Ala Glu Asp Gly Leu Ser Val Ser Asp Asn Ser
            340                 345                 350

Pro Leu Ala Pro Gly Glu Thr Arg Thr Val Asp Val Thr Ala Ser Asp
        355                 360                 365

Ala Ala Trp Glu Val Tyr Arg Leu Ser Asp Ile Ile Tyr Asp Pro Asp
    370                 375                 380

Ser Arg Phe Ala Gly Leu Leu Phe Phe Phe Asp Ala Thr Gly Asn Arg
385                 390                 395                 400

Gln Val Val Gln Ile Asp Ala Pro Leu Ile Pro Ser Phe Met
                405                 410

<210> SEQ ID NO 23
<211> LENGTH: 1584
<212> TYPE: DNA
<213> ORGANISM: Methylococcus capsulatus

<400> SEQUENCE: 23
atggcactta gcaccgcaac caaggccgcg acggacgcgc tggctgccaa tcgggcaccc      60
accagcgtga atgcacagga agtgcaccgt tggctccaga gcttcaactg ggatttcaag     120
aacaaccgga ccaagtacgc caccaagtac aagatggcga acgagaccaa ggaacagttc     180
aagctgatcg ccaaggaata tgcgcgcatg gaggcagtca aggacgaaag gcagttcggt     240
agcctgcagg atgcgctgac cgcctcaac gccggtgttc gcgttcatcc gaagtggaac     300
gagaccatga agtggtttc gaacttcctg gaagtgggcg aatacaacgc catcgccgct     360
accgggatgc tgtgggattc cgcccaggcg gcggaacaga gaacggcta tctggcccag     420 gtgttggatg aaatccgcca cacccaccag tgtgcctacg tcaactacta cttcgcgaag     480
aacggccagg accoggccgg tcacaacgat gctcgccgca cccgtaccat cggtccgctg     540
tggaagggca tgaagcgcgt gttttccgac ggcttcattt ccggcgacgc cgtggaatgc     600
tccctcaacc tgcagctggt gggtgaggcc tgcttcacca atccgctgat cgtcgcagtg     660
accgaatggg ctgccgccaa cggcgatgaa atcaccccga cggtgttcct gtcgatcgag     720
accgacgaac tgcgccacat ggccaacggt taccagaccg tcgtttccat cgccaacgat     780
ccggcttccg ccaagtatct caacacggac ctgaacaacg ccttctggac cagcagaag     840 tacttcacgc cggtgttggg catgctgttc gagtatggct ccaagttcaa ggtcgagccg     900
tgggtcaaga cgtggaaccg ctgggtgtac gaggactggg gcggcatctg gatcggccgt     960
ctgggcaagt acggggtgga gtcgccgcgc agcctcaagg acgccaagca ggacgcttac    1020
tgggctcacc acgacctgta tctgctggct tatgcgctgt ggccgaccgg cttcttccgt    1080
ctggcgctgc cggatcagga agaaatggag tggttcgagg ccaactaccc cggctggtac    1140
gaccactacg gcaagatcta cgaggaatgg cgcgcccgcg gttgcgagga tccgtcctcg    1200

-continued

```
ggcttcatcc cgctgatgtg gttcatcgaa acaaccatc ccatctacat cgatcgcgtg    1260
tcgcaagtgc cgttctgccc gagcttggcc aagggcgcca gcaccctgcg cgtgcacgag    1320
tacaacggcc agatgcacac cttcagcgac cagtggggcg agcgcatgtg gctggccgag    1380
ccggagcgct acgagtgcca gaacatcttc gaacagtacg aaggacgcga actgtcggaa    1440
gtgatcgccg aactgcacgg gctgcgcagt gatggcaaga ccctgatcgc ccagccgcat    1500
gtccgtggcg acaagctgtg gacgttggac gatatcaaac gcctgaactg cgtcttcaag    1560
aacccggtga aggcattcaa ttga                                           1584
```

<210> SEQ ID NO 24
<211> LENGTH: 527
<212> TYPE: PRT
<213> ORGANISM: Methylococcus capsulatus

<400> SEQUENCE: 24

```
Met Ala Leu Ser Thr Ala Thr Lys Ala Ala Thr Asp Ala Leu Ala Ala
1               5                   10                  15

Asn Arg Ala Pro Thr Ser Val Asn Ala Gln Glu Val His Arg Trp Leu
            20                  25                  30

Gln Ser Phe Asn Trp Asp Phe Lys Asn Arg Thr Lys Tyr Ala Thr
        35                  40                  45

Lys Tyr Lys Met Ala Asn Glu Thr Lys Glu Gln Phe Lys Leu Ile Ala
    50                  55                  60

Lys Glu Tyr Ala Arg Met Glu Ala Val Lys Asp Glu Arg Gln Phe Gly
65                  70                  75                  80

Ser Leu Gln Asp Ala Leu Thr Arg Leu Asn Ala Gly Val Arg Val His
                85                  90                  95

Pro Lys Trp Asn Glu Thr Met Lys Val Val Ser Asn Phe Leu Glu Val
            100                 105                 110

Gly Glu Tyr Asn Ala Ile Ala Ala Thr Gly Met Leu Trp Asp Ser Ala
        115                 120                 125

Gln Ala Ala Glu Gln Lys Asn Gly Tyr Leu Ala Gln Val Leu Asp Glu
    130                 135                 140

Ile Arg His Thr His Gln Cys Ala Tyr Val Asn Tyr Tyr Phe Ala Lys
145                 150                 155                 160

Asn Gly Gln Asp Pro Ala Gly His Asn Asp Ala Arg Arg Thr Arg Thr
                165                 170                 175

Ile Gly Pro Leu Trp Lys Gly Met Lys Arg Val Phe Ser Asp Gly Phe
            180                 185                 190

Ile Ser Gly Asp Ala Val Glu Cys Ser Leu Asn Leu Gln Leu Val Gly
        195                 200                 205

Glu Ala Cys Phe Thr Asn Pro Leu Ile Val Ala Val Thr Glu Trp Ala
    210                 215                 220

Ala Ala Asn Gly Asp Glu Ile Thr Pro Thr Val Phe Leu Ser Ile Glu
225                 230                 235                 240

Thr Asp Glu Leu Arg His Met Ala Asn Gly Tyr Gln Thr Val Val Ser
                245                 250                 255

Ile Ala Asn Asp Pro Ala Ser Ala Lys Tyr Leu Asn Thr Asp Leu Asn
            260                 265                 270

Asn Ala Phe Trp Thr Gln Gln Lys Tyr Phe Thr Pro Val Leu Gly Met
        275                 280                 285

Leu Phe Glu Tyr Gly Ser Lys Phe Lys Val Glu Pro Trp Val Lys Thr
    290                 295                 300
```

```
Trp Asn Arg Trp Val Tyr Glu Asp Trp Gly Ile Trp Ile Gly Arg
305                 310                 315                 320

Leu Gly Lys Tyr Gly Val Glu Ser Pro Arg Ser Leu Lys Asp Ala Lys
            325                 330                 335

Gln Asp Ala Tyr Trp Ala His His Asp Leu Tyr Leu Leu Ala Tyr Ala
                340                 345                 350

Leu Trp Pro Thr Gly Phe Phe Arg Leu Ala Leu Pro Asp Gln Glu Glu
        355                 360                 365

Met Glu Trp Phe Glu Ala Asn Tyr Pro Gly Trp Tyr Asp His Tyr Gly
370                 375                 380

Lys Ile Tyr Glu Glu Trp Arg Ala Arg Gly Cys Glu Asp Pro Ser Ser
385                 390                 395                 400

Gly Phe Ile Pro Leu Met Trp Phe Ile Glu Asn Asn His Pro Ile Tyr
                405                 410                 415

Ile Asp Arg Val Ser Gln Val Pro Phe Cys Pro Ser Leu Ala Lys Gly
                420                 425                 430

Ala Ser Thr Leu Arg Val His Glu Tyr Asn Gly Gln Met His Thr Phe
            435                 440                 445

Ser Asp Gln Trp Gly Glu Arg Met Trp Leu Ala Glu Pro Glu Arg Tyr
450                 455                 460

Glu Cys Gln Asn Ile Phe Glu Gln Tyr Glu Gly Arg Glu Leu Ser Glu
465                 470                 475                 480

Val Ile Ala Glu Leu His Gly Leu Arg Ser Asp Gly Lys Thr Leu Ile
                485                 490                 495

Ala Gln Pro His Val Arg Gly Asp Lys Leu Trp Thr Leu Asp Asp Ile
            500                 505                 510

Lys Arg Leu Asn Cys Val Phe Lys Asn Pro Val Lys Ala Phe Asn
        515                 520                 525

<210> SEQ ID NO 25
<211> LENGTH: 1170
<212> TYPE: DNA
<213> ORGANISM: Methylococcus capsulatus

<400> SEQUENCE: 25
atgagcatgt taggagaaag acgccgcggt ctgaccgatc cggaaatggc ggccgtcatt     60
ttgaaggcgc ttcctgaagc tccgctggac ggcaacaaca agatgggtta tttcgtcacc    120
ccccgctgga aacgcttgac ggaatatgaa gccctgaccg tttatgcgca gcccaacgcc    180
gactggatcg ccggcggcct ggactggggc gactggaccc agaaattcca cggcggccgc    240
ccttcctggg gcaacgagac cacggagctg cgcaccgtcg actggttcaa gcaccgtgac    300
ccgctccgcc gttggcatgc gccgtacgtc aaggacaagg ccgaggaatg cgctacacc     360 gaccgcttcc tgcagggtta ctccgccgac ggtcagatcg ggcgatgaa cccgacctgg     420 cgggacgagt tcatcaaccg gtattggggc gccttcctgt caacgaata cggattgttc     480 aacgctcatt cgcagggcgc ccgggaggcg ctgtcgacga taacccgcgt cagcctggct    540
ttctggggct cgacaagat cgacatcgcc cagatgatcc aactcgaacg gggtttcctc     600
gccaagatcg tacccggttt cgacgagtcc acagcggtgc cgaaggccga atggacgaac    660
ggggaggtct acaagagcgc ccgtctggcc gtggaagggc tgtggcagga ggtgttcgac    720
tggaacgaga cgctttctc ggtgcacgcc gtctatgacg cgctgttcgg tcagttcgtc     780
cgccgcgagt tctttcagcg gctggctccc cgcttcggcg acaatctgac gccattcttc    840
atcaaccagg cccagacata cttccagatc gccaagcagg gcgtacagga tctgtattac    900
```

```
aactgtctgg gtgacgatcc ggagttcagc gattacaacc gtaccgtgat gcgcaactgg    960
accggcaagt ggctggagcc cacgatcgcc gctctgcgcg acttcatggg gctgtttgcg   1020
aagctgccgg cgggcaccac tgacaaggaa gaaatcaccg cgtccctgta ccgggtggtc   1080
gacgactgga tcgaggacta cgccagcagg atcgacttca aggcggaccg cgatcagatc   1140
gttaaagcgg ttctggcagg attgaaataa                                    1170
```

<210> SEQ ID NO 26
<211> LENGTH: 389
<212> TYPE: PRT
<213> ORGANISM: Methylococcus capsulatus

<400> SEQUENCE: 26

```
Met Ser Met Leu Gly Glu Arg Arg Gly Leu Thr Asp Pro Glu Met
1               5                   10                  15

Ala Ala Val Ile Leu Lys Ala Leu Pro Glu Ala Pro Leu Asp Gly Asn
            20                  25                  30

Asn Lys Met Gly Tyr Phe Val Thr Pro Arg Trp Lys Arg Leu Thr Glu
        35                  40                  45

Tyr Glu Ala Leu Thr Val Tyr Ala Gln Pro Asn Ala Asp Trp Ile Ala
    50                  55                  60

Gly Gly Leu Asp Trp Gly Asp Trp Thr Gln Lys Phe His Gly Arg
65                  70                  75                  80

Pro Ser Trp Gly Asn Glu Thr Thr Glu Leu Arg Thr Val Asp Trp Phe
                85                  90                  95

Lys His Arg Asp Pro Leu Arg Arg Trp His Ala Pro Tyr Val Lys Asp
            100                 105                 110

Lys Ala Glu Glu Trp Arg Tyr Thr Asp Arg Phe Leu Gln Gly Tyr Ser
        115                 120                 125

Ala Asp Gly Gln Ile Arg Ala Met Asn Pro Thr Trp Arg Asp Glu Phe
    130                 135                 140

Ile Asn Arg Tyr Trp Gly Ala Phe Leu Phe Asn Glu Tyr Gly Leu Phe
145                 150                 155                 160

Asn Ala His Ser Gln Gly Ala Arg Glu Ala Leu Ser Asp Val Thr Arg
                165                 170                 175

Val Ser Leu Ala Phe Trp Gly Phe Asp Lys Ile Asp Ile Ala Gln Met
            180                 185                 190

Ile Gln Leu Glu Arg Gly Phe Leu Ala Lys Ile Val Pro Gly Phe Asp
        195                 200                 205

Glu Ser Thr Ala Val Pro Lys Ala Glu Trp Thr Asn Gly Glu Val Tyr
    210                 215                 220

Lys Ser Ala Arg Leu Ala Val Glu Gly Leu Trp Gln Glu Val Phe Asp
225                 230                 235                 240

Trp Asn Glu Ser Ala Phe Ser Val His Ala Val Tyr Asp Ala Leu Phe
                245                 250                 255

Gly Gln Phe Val Arg Arg Glu Phe Gln Arg Leu Ala Pro Arg Phe
            260                 265                 270

Gly Asp Asn Leu Thr Pro Phe Phe Ile Asn Gln Ala Gln Thr Tyr Phe
        275                 280                 285

Gln Ile Ala Lys Gln Gly Val Gln Asp Leu Tyr Tyr Asn Cys Leu Gly
    290                 295                 300

Asp Asp Pro Glu Phe Ser Asp Tyr Asn Arg Thr Val Met Arg Asn Trp
305                 310                 315                 320
```

```
Thr Gly Lys Trp Leu Glu Pro Thr Ile Ala Ala Leu Arg Asp Phe Met
            325                 330                 335

Gly Leu Phe Ala Lys Leu Pro Ala Gly Thr Thr Asp Lys Glu Glu Ile
        340                 345                 350

Thr Ala Ser Leu Tyr Arg Val Val Asp Asp Trp Ile Glu Asp Tyr Ala
            355                 360                 365

Ser Arg Ile Asp Phe Lys Ala Asp Arg Asp Gln Ile Val Lys Ala Val
    370                 375                 380

Leu Ala Gly Leu Lys
385

<210> SEQ ID NO 27
<211> LENGTH: 426
<212> TYPE: DNA
<213> ORGANISM: Methylococcus capsulatus

<400> SEQUENCE: 27
atgagcgtaa acagcaacgc atacgacgcc ggcatcatgg gcctgaaagg caaggacttc      60
gccgatcagt tctttgccga cgaaaaccaa gtggtccatg aaagcgacac ggtcgttctg     120
gtcctcaaga gtcggacga gatcaatacc tttatcgagg atccttct gacggactac        180 aagaagaacg tcaatccgac ggtaaacgtg aagaccgcg cgggttactg gtggatcaag      240
gccaacggca gatcgaggt cgattgcgac gagatttccg agctgttggg cggcagttc       300 aacgtctacg acttcctcgt cgacgtttcc tccaccatcg gccgggccta ccctgggc       360 aacaagttca ccattaccag tgagctgatg ggcctggacc gcaagctcga agactatcac     420
gcttaa                                                                426

<210> SEQ ID NO 28
<211> LENGTH: 138
<212> TYPE: PRT
<213> ORGANISM: Methylococcus capsulatus

<400> SEQUENCE: 28

Met Ser Val Asn Ser Asn Ala Tyr Asp Ala Gly Ile Met Gly Leu Lys
1               5                   10                  15

Gly Lys Asp Phe Ala Asp Gln Phe Phe Ala Asp Glu Asn Gln Val Val
            20                  25                  30

His Glu Ser Asp Thr Val Val Leu Val Leu Lys Lys Ser Asp Glu Ile
        35                  40                  45

Asn Thr Phe Ile Glu Glu Ile Leu Leu Thr Asp Tyr Lys Lys Asn Val
    50                  55                  60

Asn Pro Thr Val Asn Val Glu Asp Arg Ala Gly Tyr Trp Trp Ile Lys
65                  70                  75                  80

Ala Asn Gly Lys Ile Glu Val Asp Cys Asp Glu Ile Ser Glu Leu Leu
                85                  90                  95

Gly Arg Gln Phe Asn Val Tyr Asp Phe Leu Val Asp Val Ser Ser Thr
            100                 105                 110

Ile Gly Arg Ala Tyr Thr Leu Gly Asn Lys Phe Thr Ile Thr Ser Glu
        115                 120                 125

Leu Met Gly Leu Asp Arg Lys Leu Glu Asp
    130                 135

<210> SEQ ID NO 29
<211> LENGTH: 513
<212> TYPE: DNA
<213> ORGANISM: Methylococcus capsulatus
```

<400> SEQUENCE: 29

```
atggcgaaac tgggtataca cagcaacgac acccgcgacg cctgggtgaa caagatcgcg     60
cagctcaaca ccctggaaaa agcggccgag atgctgaagc agttccggat ggaccacacc    120
acgccgttcc gcaacagcta cgaactggac aacgactacc tctggatcga ggccaagctc    180
gaagagaagg tcgccgtcct caaggcacgc gccttcaacg aggtggactt ccgtcataag    240
accgctttcg gcgaggatgc caagtccgtt ctggacggca ccgtcgcgaa gatgaacgcg    300
gccaaggaca gtgggaggc ggagaagatc catatcggtt tccgccaggc ctacaagccg     360
ccgatcatgc cggtgaacta tttcctggac ggcgagcgtc agttggggac cggctgatg    420
gaactgcgca acctcaacta ctacgacacg ccgctggaag aactgcgcaa acagcgcggt    480
gtgcgggtgg tgcatctgca gtcgccgcac tga                                513
```

<210> SEQ ID NO 30
<211> LENGTH: 170
<212> TYPE: PRT
<213> ORGANISM: Methylococcus capsulatus

<400> SEQUENCE: 30

```
Met Ala Lys Leu Gly Ile His Ser Asn Asp Thr Arg Asp Ala Trp Val
1               5                   10                  15
Asn Lys Ile Ala Gln Leu Asn Thr Leu Glu Lys Ala Ala Glu Met Leu
            20                  25                  30
Lys Gln Phe Arg Met Asp His Thr Thr Pro Phe Arg Asn Ser Tyr Glu
        35                  40                  45
Leu Asp Asn Asp Tyr Leu Trp Ile Glu Ala Lys Leu Glu Glu Lys Val
    50                  55                  60
Ala Val Leu Lys Ala Arg Ala Phe Asn Glu Val Asp Phe Arg His Lys
65                  70                  75                  80
Thr Ala Phe Gly Glu Asp Ala Lys Ser Val Leu Asp Gly Thr Val Ala
                85                  90                  95
Lys Met Asn Ala Ala Lys Asp Lys Trp Glu Ala Glu Lys Ile His Ile
            100                 105                 110
Gly Phe Arg Gln Ala Tyr Lys Pro Pro Ile Met Pro Val Asn Tyr Phe
        115                 120                 125
Leu Asp Gly Glu Arg Gln Leu Gly Thr Arg Leu Met Glu Leu Arg Asn
    130                 135                 140
Leu Asn Tyr Tyr Asp Thr Pro Leu Glu Glu Leu Arg Lys Gln Arg Gly
145                 150                 155                 160
Val Arg Val Val His Leu Gln Ser Pro His
                165                 170
```

<210> SEQ ID NO 31
<211> LENGTH: 312
<212> TYPE: DNA
<213> ORGANISM: Methylococcus capsulatus

<400> SEQUENCE: 31

```
atggtcgaat cggcatttca gccattttcg ggcgacgcag acgaatggtt cgaggaacca    60
cggccccagg ccggtttctt cccttccgcg gactggcatc tgctcaaacg ggacgagacc   120
tacgcagcct atgccaagga tctcgatttc atgtggcggt gggtcatcgt ccgggaagaa   180
aggatcgtcc aggagggttg ctcgatcagc ctggagtcgt cgatccgcgc cgtgacgcac   240
gtactgaatt attttggtat gaccgaacaa cgcgccccgg cagaggaccg gaccggcgga   300
```
gttcaacatt ga 312

<210> SEQ ID NO 32
<211> LENGTH: 103
<212> TYPE: PRT
<213> ORGANISM: Methylococcus capsulatus

<400> SEQUENCE: 32

Met Val Glu Ser Ala Phe Gln Pro Phe Ser Gly Asp Ala Asp Glu Trp
1               5                   10                  15

Phe Glu Glu Pro Arg Pro Gln Ala Gly Phe Phe Pro Ser Ala Asp Trp
            20                  25                  30

His Leu Leu Lys Arg Asp Glu Thr Tyr Ala Ala Tyr Ala Lys Asp Leu
        35                  40                  45

Asp Phe Met Trp Arg Trp Val Ile Val Arg Glu Arg Ile Val Gln
    50                  55                  60

Glu Gly Cys Ser Ile Ser Leu Glu Ser Ser Ile Arg Ala Val Thr His
65                  70                  75                  80

Val Leu Asn Tyr Phe Gly Met Thr Glu Gln Arg Ala Pro Ala Glu Asp
                85                  90                  95

Arg Thr Gly Gly Val Gln His
            100

<210> SEQ ID NO 33
<211> LENGTH: 1047
<212> TYPE: DNA
<213> ORGANISM: Methylococcus capsulatus

<400> SEQUENCE: 33
atgcagcgag ttcacactat cacggcggtg acggaggatg gcgaatcgct ccgcttcgaa      60
tgccgttcgg acgaggacgt catcaccgcc gccctgcgcc agaacatctt tctgatgtcg     120
tcctgccgga agggcggctg tgcgacctgc aaggccttgt gcagcgaagg ggactacgac     180
ctcaagggct gcagcgttca ggcgctgccg ccggaagagg aggaggaagg gttggtgttg     240
ttgtgccgga cctaccccga gaccgacctg gaaatcgaac tgccctatac ccattgccgc     300
atcagttttg gtgaggtcgg cagtttcgag gcggaggtcg tcggcctcaa ctgggtttcg     360
agcaacaccg tccagtttct tttgcagaag cggcccgacg agtgcggcaa ccgtggcgtg     420
aaattcgaac cggtcagtt catggacctg accatccccg gcaccgatgt ctcccgctcc     480
tactcgccgg cgaaccttcc taatcccgaa ggccgcctgg agttcctgat ccgcgtgtta     540
ccggagggac ggttttcgga ctacctgcgc aatgacgcgc gtgtcggaca ggtcctctcg     600
gtcaaagggc cactgggcgt gttcggtctc aaggagcggg gcatggcgcc cgcctatttc     660
gtggccggcg gcaccgggtt ggcgccggtg gtctcgatgg tgcggcagat gcaggagtgg     720
accgcgccga cgagacccg catctatttc ggtgtgaaca ccgagccgga attgttctac     780
atcgacgagc tcaaatccct ggaacgatcg atgcgcaatc tcaccgtgaa ggcctgtgtc     840
tggcacccga gcggggactg ggaaggcgag cagggctcgc ccatcgatgc gttgcgggaa     900
gacctggagt cctccgacgc caaccccgac atttatttgt gcggtccgcc gggcatgatc     960
gatgccgcct gcgagctggt acgcagccgc ggtatccccg cgaacaggt cttcttcgaa     1020
aaattcctgc cgtccggggc ggcctga                                         1047

<210> SEQ ID NO 34
<211> LENGTH: 348

<212> TYPE: PRT
<213> ORGANISM: Methylococcus capsulatus

<400> SEQUENCE: 34

```
Met Gln Arg Val His Thr Ile Thr Ala Val Thr Glu Asp Gly Glu Ser
1               5                   10                  15

Leu Arg Phe Glu Cys Arg Ser Asp Glu Asp Val Ile Thr Ala Ala Leu
            20                  25                  30

Arg Gln Asn Ile Phe Leu Met Ser Ser Cys Arg Glu Gly Gly Cys Ala
        35                  40                  45

Thr Cys Lys Ala Leu Cys Ser Glu Gly Asp Tyr Asp Leu Lys Gly Cys
    50                  55                  60

Ser Val Gln Ala Leu Pro Pro Glu Glu Glu Gly Leu Val Leu
65                  70                  75                  80

Leu Cys Arg Thr Tyr Pro Lys Thr Asp Leu Glu Ile Glu Leu Pro Tyr
                85                  90                  95

Thr His Cys Arg Ile Ser Phe Gly Val Gly Ser Phe Glu Ala Glu
            100                 105                 110

Val Val Gly Leu Asn Trp Val Ser Ser Asn Thr Val Gln Phe Leu Leu
        115                 120                 125

Gln Lys Arg Pro Asp Glu Cys Gly Asn Arg Gly Val Lys Phe Glu Pro
    130                 135                 140

Gly Gln Phe Met Asp Leu Thr Ile Pro Gly Thr Asp Val Ser Arg Ser
145                 150                 155                 160

Tyr Ser Pro Ala Asn Leu Pro Asn Pro Glu Gly Arg Leu Glu Phe Leu
                165                 170                 175

Ile Arg Val Leu Pro Glu Gly Arg Phe Ser Asp Tyr Leu Arg Asn Asp
            180                 185                 190

Ala Arg Val Gly Gln Val Leu Ser Val Lys Gly Pro Leu Gly Val Phe
        195                 200                 205

Gly Leu Lys Glu Arg Gly Met Ala Pro Arg Tyr Phe Val Ala Gly Gly
    210                 215                 220

Thr Gly Leu Ala Pro Val Val Ser Met Val Arg Gln Met Gln Glu Trp
225                 230                 235                 240

Thr Ala Pro Asn Glu Thr Arg Ile Tyr Phe Gly Val Asn Thr Glu Pro
                245                 250                 255

Glu Leu Phe Tyr Ile Asp Glu Leu Lys Ser Leu Glu Arg Ser Met Arg
            260                 265                 270

Asn Leu Thr Val Lys Ala Cys Val Trp His Pro Ser Gly Asp Trp Glu
        275                 280                 285

Gly Glu Gln Gly Ser Pro Ile Asp Ala Leu Arg Glu Asp Leu Glu Ser
    290                 295                 300

Ser Asp Ala Asn Pro Asp Ile Tyr Leu Cys Gly Pro Pro Gly Met Ile
305                 310                 315                 320

Asp Ala Ala Cys Glu Leu Val Arg Ser Arg Gly Ile Pro Gly Glu Gln
                325                 330                 335

Val Phe Phe Glu Lys Phe Leu Pro Ser Gly Ala Ala
            340                 345
```

<210> SEQ ID NO 35
<211> LENGTH: 1806
<212> TYPE: DNA
<213> ORGANISM: Methylococcus capsulatus

<400> SEQUENCE: 35

| | |
|---|---|
| atgcaaattt gcaaactggc aagtggctgc ggcgggtcga tgctggcgat ggccgccgtg | 60 |
| ctagccgcgc aatccacgca cgccaattcg gagctggacc ggctgtcgaa ggacgaccgg | 120 |
| aactgggtca tgcagaccaa ggactacagc gccacccact tcagccggct gacggaaatc | 180 |
| aatagccaca cgtcaagaa cctgaaggtg gcctggaccc tgtccaccgg cacgttgcat | 240 |
| ggccacgaag gtgcgccgtt ggtggtggac ggcatcatgt acatccacac gccgttcccc | 300 |
| aacaacgtct atgcagtcga cctgaacgac acccgcaaga tgctgtggca gtacaagccc | 360 |
| aagcagaatc cggcggcccg cgcggtggct tgctgcgacg tggtcaaccg cggtctggcc | 420 |
| tacgtgccgg ccggcgagca cggtccggcg aagatcttcc tcaaccagct tgacggccac | 480 |
| atcgtcgcac tcaacgccaa gaccggcgaa gagatatgga agatggaaaa ttccgacatc | 540 |
| gccatgggct ccacccctca cggcgcgcct ttcgtggtga aggacaaggt actggtaggt | 600 |
| tcggccgggg ccgagctggg cgtgcgtggc tacgtcacgg cctataacat caaggacggg | 660 |
| aagcaggagt ggcgggccta tgccaccggt cccgacgaag acttgttgct ggacaaggac | 720 |
| ttcaacaagg acaacccgca ttacggtcag ttcggcctgg ggctctcaac ctgggagggt | 780 |
| gatgcctgga agatcggcgg cggcaccaat tggggctggt atgcctatga tcccaagttg | 840 |
| gacatgatct actacggttc cggcaatccg gcacccggga acgagaccat gcggcccggc | 900 |
| gacaacaaat ggaccatgac catctggggc gcgacgccg acaccggccg gccaagttc | 960 |
| ggctaccaga gacgccgca cgacgagtgg gattacgccg tgtcaacta catgggtctg | 1020 |
| tccgaacagg aagtggacgg caagctgacg ccgctgctga cccatcccga ccgcaacggt | 1080 |
| ctggtgtata cgctgaaccg ggaaaccggc gccctggtca atgccttcaa gatcgatgac | 1140 |
| accgtcaact gggtgaaaaa ggtcgatctg aagaccggcc tgccgatccg cgatccggag | 1200 |
| tacagcaccc gcatggacca caatgccaaa ggcatctgtc cctcggccat gggctatcac | 1260 |
| aaccagggca tcgagtccta cgatccggac aagaagctgt tcttcatggg cgtgaaccac | 1320 |
| atctgcatgg actgggagcc gttcatgctg ccctaccgcg ccggccagtt ctttgtgggg | 1380 |
| gcgaccctca acatgtatcc gggacccaag gggatgctgg gtcaggtcaa ggcgatgaac | 1440 |
| gcggtcaccg gcaagatgga atgggaagtg ccggagaagt tgcggtctg ggtggcacc | 1500 |
| ttggcgaccg ccggcgacct cgtgttctac ggtaccctcg acggcttcat caaggcccgc | 1560 |
| gacacccgta ccggcgagct gaagtggcag ttccagttgc cctccggcgt gatcggccat | 1620 |
| cccatcacct atcagcacaa cggcaagcaa tacattgcca tctactccgg cgtcggcggc | 1680 |
| tggccaggag tagggctggt attcgacctg aaggacccga ccgcaggtct gggagctgtg | 1740 |
| ggtgcgttca gggaactggc gcattacacc cagatgggtg gatcggtgtt cgtgttctcg | 1800 |
| ctttga | 1806 |

<210> SEQ ID NO 36
<211> LENGTH: 601
<212> TYPE: PRT
<213> ORGANISM: Methylococcus capsulatus

<400> SEQUENCE: 36

Met Gln Ile Cys Lys Leu Ala Ser Gly Cys Gly Gly Ser Met Leu Ala
1               5                   10                  15

Met Ala Ala Val Leu Ala Ala Gln Ser Thr His Ala Asn Ser Glu Leu
            20                  25                  30

Asp Arg Leu Ser Lys Asp Asp Arg Asn Trp Val Met Gln Thr Lys Asp
        35                  40                  45

```
Tyr Ser Ala Thr His Phe Ser Arg Leu Thr Glu Ile Asn Ser His Asn
 50                  55                  60

Val Lys Asn Leu Lys Val Ala Trp Thr Leu Ser Thr Gly Thr Leu His
 65                  70                  75                  80

Gly His Glu Gly Ala Pro Leu Val Val Asp Gly Ile Met Tyr Ile His
                     85                  90                  95

Thr Pro Phe Pro Asn Asn Val Tyr Ala Val Asp Leu Asn Asp Thr Arg
                100                 105                 110

Lys Met Leu Trp Gln Tyr Lys Pro Lys Gln Asn Pro Ala Ala Arg Ala
                115                 120                 125

Val Ala Cys Cys Asp Val Val Asn Arg Gly Leu Ala Tyr Val Pro Ala
        130                 135                 140

Gly Glu His Gly Pro Ala Lys Ile Phe Leu Asn Gln Leu Asp Gly His
145                 150                 155                 160

Ile Val Ala Leu Asn Ala Lys Thr Gly Glu Glu Ile Trp Lys Met Glu
                165                 170                 175

Asn Ser Asp Ile Ala Met Gly Ser Thr Leu Thr Gly Ala Pro Phe Val
                180                 185                 190

Val Lys Asp Lys Val Leu Val Gly Ser Ala Gly Ala Glu Leu Gly Val
                195                 200                 205

Arg Gly Tyr Val Thr Ala Tyr Asn Ile Lys Asp Gly Lys Gln Glu Trp
                210                 215                 220

Arg Ala Tyr Ala Thr Gly Pro Asp Glu Asp Leu Leu Leu Asp Lys Asp
225                 230                 235                 240

Phe Asn Lys Asp Asn Pro His Tyr Gly Gln Phe Gly Leu Gly Leu Ser
                245                 250                 255

Thr Trp Glu Gly Asp Ala Trp Lys Ile Gly Gly Gly Thr Asn Trp Gly
                260                 265                 270

Trp Tyr Ala Tyr Asp Pro Lys Leu Asp Met Ile Tyr Tyr Gly Ser Gly
                275                 280                 285

Asn Pro Ala Pro Trp Asn Glu Thr Met Arg Pro Gly Asp Asn Lys Trp
                290                 295                 300

Thr Met Thr Ile Trp Gly Arg Asp Ala Asp Thr Gly Arg Ala Lys Phe
305                 310                 315                 320

Gly Tyr Gln Lys Thr Pro His Asp Glu Trp Asp Tyr Ala Gly Val Asn
                325                 330                 335

Tyr Met Gly Leu Ser Glu Gln Glu Val Asp Gly Lys Leu Thr Pro Leu
                340                 345                 350

Leu Thr His Pro Asp Arg Asn Gly Leu Val Tyr Thr Leu Asn Arg Glu
                355                 360                 365

Thr Gly Ala Leu Val Asn Ala Phe Lys Ile Asp Asp Thr Val Asn Trp
                370                 375                 380

Val Lys Lys Val Asp Leu Lys Thr Gly Leu Pro Ile Arg Asp Pro Glu
385                 390                 395                 400

Tyr Ser Thr Arg Met Asp His Asn Ala Lys Gly Ile Cys Pro Ser Ala
                405                 410                 415

Met Gly Tyr His Asn Gln Gly Ile Glu Ser Tyr Asp Pro Asp Lys Lys
                420                 425                 430

Leu Phe Phe Met Gly Val Asn His Ile Cys Met Asp Trp Glu Pro Phe
                435                 440                 445

Met Leu Pro Tyr Arg Ala Gly Gln Phe Phe Val Gly Ala Thr Leu Asn
                450                 455                 460

Met Tyr Pro Gly Pro Lys Gly Met Leu Gly Gln Val Lys Ala Met Asn
```

```
                465                 470                 475                 480
            Ala Val Thr Gly Lys Met Glu Trp Glu Val Pro Glu Lys Phe Ala Val
                            485                 490                 495

Trp Gly Gly Thr Leu Ala Thr Ala Gly Asp Leu Val Phe Tyr Gly Thr
                        500                 505                 510

Leu Asp Gly Phe Ile Lys Ala Arg Asp Thr Arg Thr Gly Glu Leu Lys
                        515                 520                 525

Trp Gln Phe Gln Leu Pro Ser Gly Val Ile Gly His Pro Ile Thr Tyr
                    530                 535                 540

Gln His Asn Gly Lys Gln Tyr Ile Ala Ile Tyr Ser Gly Val Gly Gly
            545                 550                 555                 560

Trp Pro Gly Val Gly Leu Val Phe Asp Leu Lys Asp Pro Thr Ala Gly
                                565                 570                 575

Leu Gly Ala Val Gly Ala Phe Arg Glu Leu Ala His Tyr Thr Gln Met
                            580                 585                 590

Gly Gly Ser Val Phe Val Phe Ser Leu
                        595                 600
```

```
<210> SEQ ID NO 37
<211> LENGTH: 573
<212> TYPE: DNA
<213> ORGANISM: Methylococcus capsulatus

<400> SEQUENCE: 37
atgctcacca gcagtcctta ttaccggtcc ggctacgtat tcgtctaccg caaggacacg      60
ggactgagca tccaagattg aacagcgcg gcactgaaga ccgtgaagcg gatcgcattc     120
atgccggata ccccggctga cgatgatc cgcaccatcg ccgctacaa cgacatgttc       180
aactacatgc actctctggt cggtttcaag tcgcggcgta accagtacgt gcgctacgac    240
ccggccaagc tggtggcgga agtcgccgac ggcaacgcgg aagtcgcggt gttgtggggg    300
ccggcggcgg cgcgctatgt cagaggggcg gggctggcca tgaccgtcat ccccgacgac    360
aaccggcggt ccgacggcga gaaagtgccc caccactatt cgacttccgt cggcgtgcgc    420
aagggcgagg aggccctgct caagcagatc gaccaggttc tggcccgctt cggcaaggaa    480
gtgaatgcgg tgctggaggc ggaaggcatt ccgctgttgc ccatggatga aaaaccggcc    540
aggacggctt cccatgatcg aaggaaaggc tag                                 573
```

```
<210> SEQ ID NO 38
<211> LENGTH: 190
<212> TYPE: PRT
<213> ORGANISM: Methylococcus capsulatus

<400> SEQUENCE: 38

Met Leu Thr Ser Ser Pro Tyr Tyr Arg Ser Gly Tyr Val Phe Val Tyr
1               5                   10                  15

Arg Lys Asp Thr Gly Leu Ser Ile Gln Asp Trp Asn Ser Ala Ala Leu
            20                  25                  30

Lys Thr Val Lys Arg Ile Ala Phe Met Pro Asp Thr Pro Ala Glu Thr
        35                  40                  45

Met Ile Arg Thr Ile Gly Arg Tyr Asn Asp Met Phe Asn Tyr Met His
    50                  55                  60

Ser Leu Val Gly Phe Lys Ser Arg Arg Asn Gln Tyr Val Arg Tyr Asp
65                  70                  75                  80

Pro Ala Lys Leu Val Ala Glu Val Ala Asp Gly Asn Ala Glu Val Ala
                85                  90                  95
```

Val Leu Trp Gly Pro Ala Ala Ala Arg Tyr Val Arg Gly Ala Gly Leu
                100                 105                 110

Ala Met Thr Val Ile Pro Asp Asn Arg Arg Ser Asp Gly Glu Lys
        115                 120                 125

Val Pro His His Tyr Ser Thr Ser Val Gly Val Arg Lys Gly Glu Glu
    130                 135                 140

Ala Leu Leu Lys Gln Ile Asp Gln Val Leu Ala Arg Phe Gly Lys Glu
145                 150                 155                 160

Val Asn Ala Val Leu Glu Ala Glu Gly Ile Pro Leu Leu Pro Met Asp
                165                 170                 175

Glu Lys Pro Ala Arg Thr Ala Ser His Asp Arg Lys Gly
        180                 185                 190

<210> SEQ ID NO 39
<211> LENGTH: 480
<212> TYPE: DNA
<213> ORGANISM: Methylococcus capsulatus

<400> SEQUENCE: 39
atgaagctga agaatgcgag gttcgacgtg gctggcatgt gtgtcgccgg gttgttggcg      60
ctgcccgcgc aggccgacat taccctgcgg catgccgtca ccggcgagac gctggagttg     120
tcctacgcca aggcgggcgg cgacacgcaa gccgtcaagc agttcctgca gaccggcaag     180 aaccettaca acggcaacaa ggaggtagtg aacagggac atagtctgta tctgtcagcc      240
tgttccggct gccacggcca tgaggccgaa ggcaagctcg gtccgggatt ggcggacgac     300
tattggacct atccccgcgc ggccaccgac gtcggtttgt tcgaaatcct gttcggcggc     360
gcgcagggca tgatggggcc gcagtacgtc aacctcaaca tgacgaaat gctcaagatc     420 atggcctgga tccgcagcct ttaccggggc gatccagcca aggccgaatg gctgaaatga     480

<210> SEQ ID NO 40
<211> LENGTH: 159
<212> TYPE: PRT
<213> ORGANISM: Methylococcus capsulatus

<400> SEQUENCE: 40

Met Lys Leu Lys Asn Ala Arg Phe Asp Val Ala Gly Met Cys Val Ala
1               5                   10                  15

Gly Leu Leu Ala Leu Pro Ala Gln Ala Asp Ile Thr Leu Arg His Ala
                20                  25                  30

Val Thr Gly Glu Thr Leu Glu Leu Ser Tyr Ala Lys Ala Gly Gly Asp
        35                  40                  45

Thr Gln Ala Val Lys Gln Phe Leu Gln Thr Gly Lys Asn Pro Tyr Asn
    50                  55                  60

Gly Asn Lys Glu Val Val Glu Gln Gly His Ser Leu Tyr Leu Ser Ala
65                  70                  75                  80

Cys Ser Gly Cys His Gly His Glu Ala Glu Gly Lys Leu Gly Pro Gly
                85                  90                  95

Leu Ala Asp Asp Tyr Trp Thr Tyr Pro Arg Ala Ala Thr Asp Val Gly
                100                 105                 110

Leu Phe Glu Ile Leu Phe Gly Gly Ala Gln Gly Met Met Gly Pro Gln
        115                 120                 125

Tyr Val Asn Leu Asn Asn Asp Glu Met Leu Lys Ile Met Ala Trp Ile
    130                 135                 140

Arg Ser Leu Tyr Arg Gly Asp Pro Ala Lys Ala Glu Trp Leu Lys

<210> SEQ ID NO 41
<211> LENGTH: 285
<212> TYPE: DNA
<213> ORGANISM: Methylococcus capsulatus

<400> SEQUENCE: 41

```
atgatgcaga aaacgagttt cgtcgcggcc gccatggccg tttcgttcgc ggcgggtgtc    60
caggcctatg acggtaccca ctgcaaggcg cccggaaact gctgggagcc caagcccggt   120
tatccggaca aggtcgccgg cagcaagtac gaccccaagc atgacccgaa cgagctcaac   180
aagcaggcgg agtcgatcaa ggcgatggaa gcccgcaacc agaagcgcgt ggagaactac   240
gccaagaccg gcaagttcgt ctacaaggtc gaagacatca aatga                   285
```

<210> SEQ ID NO 42
<211> LENGTH: 94
<212> TYPE: PRT
<213> ORGANISM: Methylococcus capsulatus

<400> SEQUENCE: 42

```
Met Met Gln Lys Thr Ser Phe Val Ala Ala Met Ala Val Ser Phe
1               5                  10                  15

Ala Ala Gly Val Gln Ala Tyr Asp Gly Thr His Cys Lys Ala Pro Gly
            20                  25                  30

Asn Cys Trp Glu Pro Lys Pro Gly Tyr Pro Asp Lys Val Ala Gly Ser
        35                  40                  45

Lys Tyr Asp Pro Lys His Asp Pro Asn Glu Leu Asn Lys Gln Ala Glu
    50                  55                  60

Ser Ile Lys Ala Met Glu Ala Arg Asn Gln Lys Arg Val Glu Asn Tyr
65                  70                  75                  80

Ala Lys Thr Gly Lys Phe Val Tyr Lys Val Glu Asp Ile Lys
                85                  90
```

<210> SEQ ID NO 43
<211> LENGTH: 1020
<212> TYPE: DNA
<213> ORGANISM: Methylococcus capsulatus

<400> SEQUENCE: 43

```
atgaatctag acccccccct tgccgacggc ctggaacgcg ccaaacgctt cgaacagggg    60
ctgcagcaag tcgtgctcgg gcaggagcgc ccgatccgcc tgctgaccct ggccgtgttc   120
gcccgcggtc atgcgctgct cgaaggcggc gtcggcgtcg ggaagaccac cttgctccgt   180
gcggtggcgc gcggcatcgg cggcgattac gagcggatcg agggcaccat cgacctgatg   240
ccgaacgatc tggtctatta cacctacctg gacgagcaag gtaggccggg cgtcgcgccg   300
gggcctttgc tcaagcacgg ggagcagctt tccattttt tcttcaacga gatcaaccgc   360
gcccggcccc aggtgcattc cctcctgcta cgggtcatgg ccgagcgcag cgtgtcggct   420
ttcaaccgcg agtaccggtt tccgtacctg caggtgttcg ccgaccgcaa ccgggtggaa   480
aaggaggaga ctttcgaatt gcccgcgcg gcgcgcgacc gcttcatgct cgaaatcgcc   540
atcgagccgc cggccgatcc tgcgcatatc gaccaaatcc tgttcgaccc gcgtttctac   600
gatcccgacc ggctggtcgc gtccgcgccg ccgatacgc tctcgttccg tgaactcaac   660
ggcattgccg aagccctgca aggcggcatc cacgtcagcg cccgtctcag atcctatgtc   720
caggatctgt ggcgcgcgac ccggcggccg gaggatttcg gcatcgctct ccacgaggcg   780
```

-continued

```
gattccggcg acatgatcga ggccggttcc agtccccgcg gcatgagcta cttggtccgg     840
ctggcgcggg tgcaggcgtg gctcagtggc cgggaccggg tcgagccgga ggacgttcaa     900
tacgtgttcg ctccggcggt cggccaccgc atcttcctca agccggtcta cgaataccgc     960
cgcgccgagc tgatcccgga gctggtcggc aagctgatcc gccggatcgc ggcgccatga    1020
```

<210> SEQ ID NO 44
<211> LENGTH: 339
<212> TYPE: PRT
<213> ORGANISM: Methylococcus capsulatus

<400> SEQUENCE: 44

```
Met Asn Leu Asp Thr Pro Leu Ala Asp Gly Leu Glu Arg Ala Lys Arg
1               5                   10                  15

Phe Glu Gln Gly Leu Gln Gln Val Val Leu Gly Gln Glu Arg Pro Ile
                20                  25                  30

Arg Leu Leu Thr Leu Ala Val Phe Ala Arg Gly His Ala Leu Leu Glu
            35                  40                  45

Gly Gly Val Gly Val Gly Lys Thr Thr Leu Leu Arg Ala Val Ala Arg
        50                  55                  60

Gly Ile Gly Gly Asp Tyr Glu Arg Ile Glu Gly Thr Ile Asp Leu Met
65                  70                  75                  80

Pro Asn Asp Leu Val Tyr Tyr Thr Tyr Leu Asp Glu Gln Gly Arg Pro
                85                  90                  95

Gly Val Ala Pro Gly Pro Leu Leu Lys His Gly Glu Gln Leu Ser Ile
                100                 105                 110

Phe Phe Phe Asn Glu Ile Asn Arg Ala Arg Pro Gln Val His Ser Leu
            115                 120                 125

Leu Leu Arg Val Met Ala Glu Arg Ser Val Ser Ala Phe Asn Arg Glu
        130                 135                 140

Tyr Arg Phe Pro Tyr Leu Gln Val Phe Ala Asp Arg Asn Arg Val Glu
145                 150                 155                 160

Lys Glu Glu Thr Phe Glu Leu Pro Ala Ala Arg Asp Arg Phe Met
                165                 170                 175

Leu Glu Ile Ala Ile Glu Pro Pro Ala Asp Pro Ala His Ile Asp Gln
            180                 185                 190

Ile Leu Phe Asp Pro Arg Phe Tyr Asp Pro Arg Leu Val Ala Ser
        195                 200                 205

Ala Pro Ala Asp Thr Leu Ser Phe Arg Glu Leu Asn Gly Ile Ala Glu
210                 215                 220

Ala Leu Gln Gly Gly Ile His Val Ser Ala Arg Leu Arg Ser Tyr Val
225                 230                 235                 240

Gln Asp Leu Trp Arg Ala Thr Arg Arg Pro Glu Asp Phe Gly Ile Ala
                245                 250                 255

Leu His Glu Ala Asp Ser Gly Asp Met Ile Glu Ala Gly Ser Ser Pro
            260                 265                 270

Arg Gly Met Ser Tyr Leu Val Arg Leu Ala Arg Val Gln Ala Trp Leu
        275                 280                 285

Ser Gly Arg Asp Arg Val Glu Pro Glu Asp Val Gln Tyr Val Phe Ala
    290                 295                 300

Pro Ala Val Gly His Arg Ile Phe Leu Lys Pro Val Tyr Glu Tyr Arg
305                 310                 315                 320

Arg Ala Glu Leu Ile Pro Glu Leu Val Gly Lys Leu Ile Arg Arg Ile
                325                 330                 335
```

Ala Ala Pro

<210> SEQ ID NO 45
<211> LENGTH: 873
<212> TYPE: DNA
<213> ORGANISM: Methylococcus capsulatus

<400> SEQUENCE: 45

```
gtggtttggt ctctcctgcc ggtcgcggcc ttggtatcgg ttccacttca tggcgccact      60
tcgctctcgt tcgacacgcc ccgcgccttc ggctacgtca tcggtgatct catccgccac     120
gaggttcggg tcgaaaccga tgcggggcag ggaatagagg ctgcgtccct gcccaaggaa     180
ggctggatca accgctggct gctgctgcgg cgggtcgaag tccgccgcga gggcaggcac     240
cggatactga cgctggaata ccagactttc tacgccccgt tggaagtgaa gaacctcacg     300
attcccggct cgagctgca actggccggt tcgggcgaac ggttggcggt cccggactgg     360
actttcacca ccgcgccgat ccgggagctg tcggtgctgc gcgccgaagg cccgtcgatg     420
cgtccggacg ccgcaccggc gccgctgccg actctcggcc ccgccgccgc gagcgtcggt     480
tccggcctcg cagccacggg cgcgctggcc tggtgggcct atctgagcgc ctggctgccg     540
ttcgtgtcgc gcggccgtca tttcgccgag gcccgccggg tgctgcggga tctgcgcggc     600
ctggagaca gccgggaggc attgcgcaga ggttttcct gtctgcacca ggctttcaat     660
cggacttcgg gtgagccgct gttcatcgaa gggctggacg agttcttccg gagccatccg     720
gcctacgatc tcttgcggga cgagatccag gacttcttcc tggcctcgta tgaagtcttt     780
ttcggagagg gcgcaccggc gccgtcgttc gacctggcgc gcatggaggc gttggcccgt     840
tcgtgccagc ttgccgaaag gaggcggcca tga                                   873
```

<210> SEQ ID NO 46
<211> LENGTH: 290
<212> TYPE: PRT
<213> ORGANISM: Methylococcus capsulatus

<400> SEQUENCE: 46

```
Val Val Trp Ser Leu Leu Pro Val Ala Ala Leu Val Ser Val Pro Leu
1               5                   10                  15

His Gly Ala Thr Ser Leu Ser Phe Asp Thr Pro Arg Ala Phe Gly Tyr
            20                  25                  30

Val Ile Gly Asp Leu Ile Arg His Glu Val Arg Val Glu Thr Asp Ala
        35                  40                  45

Gly Gln Gly Ile Glu Ala Ala Ser Leu Pro Lys Glu Gly Trp Ile Asn
    50                  55                  60

Arg Trp Leu Leu Leu Arg Arg Val Glu Val Arg Glu Gly Arg His
65                  70                  75                  80

Arg Ile Leu Thr Leu Glu Tyr Gln Thr Phe Tyr Ala Pro Leu Glu Val
                85                  90                  95

Lys Asn Leu Thr Ile Pro Gly Phe Glu Leu Gln Leu Ala Gly Ser Gly
            100                 105                 110

Glu Arg Leu Ala Val Pro Asp Trp Thr Phe Thr Thr Ala Pro Ile Arg
        115                 120                 125

Glu Leu Ser Val Leu Arg Ala Glu Gly Pro Ser Met Arg Pro Asp Ala
    130                 135                 140

Ala Pro Ala Pro Leu Pro Thr Leu Gly Pro Ala Ala Ala Ser Val Gly
145                 150                 155                 160
```

```
Ser Gly Leu Ala Ala Thr Gly Ala Leu Ala Trp Trp Ala Tyr Leu Ser
            165                 170                 175
Ala Trp Leu Pro Phe Val Ser Arg Gly Arg His Phe Ala Glu Ala Arg
        180                 185                 190
Arg Val Leu Arg Asp Leu Arg Gly Leu Gly Asp Ser Arg Glu Ala Leu
    195                 200                 205
Arg Arg Gly Phe Ser Cys Leu His Gln Ala Phe Asn Arg Thr Ser Gly
210                 215                 220
Glu Pro Leu Phe Ile Glu Gly Leu Asp Glu Phe Arg Ser His Pro
225                 230                 235                 240
Ala Tyr Asp Leu Leu Arg Asp Glu Ile Gln Asp Phe Leu Ala Ser
            245                 250                 255
Tyr Glu Val Phe Phe Gly Glu Gly Ala Pro Ala Pro Ser Phe Asp Leu
        260                 265                 270
Ala Arg Met Glu Ala Leu Ala Arg Ser Cys Gln Leu Ala Glu Arg Arg
    275                 280                 285
Arg Pro
    290
```

<210> SEQ ID NO 47
<211> LENGTH: 984
<212> TYPE: DNA
<213> ORGANISM: Methylococcus capsulatus

<400> SEQUENCE: 47

```
atgaccgatt gggcgctgga cacgccgtac ttgctgtggg gcctgccgct ggcgctgctt      60
ccgttgtggc ggttgccgct gcgccctgcc ccgtgttcct ggcatgcatt gttgcccgcc     120
gatactgcgt cgcgggccgt cgacctgagt ctgcgcctcg ccgtgccgg cgccatcctg     180
gcgctgctgc tgggcagtgc cggtctgcat cggcgcgagt acaccgtcga acgcaccggc     240
tacggcgccc acatggtgct gctgctggac cgcagccgca gcatggatga cagcttcgca     300
gggcgtactc ccacgggcgg cgaggaatcc aagtccgccg cggcggagcg cctcctgagc     360
ggtttcgtct cgagcggacg caacgatctg gtcggggtcg ccgccttcag cacctccccg     420
ttgttcgtgc tgccgctgac cgacaacaag gctgcggtgc tggcggcggt ccacgccatg     480
aagctgccgg tctggcgcca gacgcatgtg agcaaggggc tggcgatggc gctttcgtat     540
ttcggcgacg attcgaccgc gggttcgcgt atcgtcctgc tggtgtccga cggtgccgcc     600
gaggtggacc cggacagcga gctgaagctg cgccgctggt tcaaggagaa gggcgtacgg     660
ctgtactgga tattcctgcg caccgcgggc agccacggta tcttcgaaac tccggacaac     720
ccggaggaag acaacgccca ggcgcggccc gagcgctatc tgcatctgtt tttcaacagt     780
ctgggcatcc cctaccgcgc ctacgaggcg aagacgccg acgccctcaa gcgcgccatc     840
gccgacgtcg accgcgagga gcagcggccg ctgcgctatg ccgagcgggt gccgcggcgg     900
gatctgcaag ccttttgtta tctggcggcg gcgctggctc tggcctggct ggtcgccgcg     960
aagggcatgg aggtggcgcg atga                                             984
```

<210> SEQ ID NO 48
<211> LENGTH: 327
<212> TYPE: PRT
<213> ORGANISM: Methylococcus capsulatus

<400> SEQUENCE: 48

```
Met Thr Asp Trp Ala Leu Asp Thr Pro Tyr Leu Leu Trp Gly Leu Pro
1               5                   10                  15
```

Leu Ala Leu Leu Pro Leu Trp Arg Leu Pro Leu Arg Pro Ala Pro Cys
            20                  25                  30

Ser Trp His Ala Leu Leu Pro Ala Asp Thr Ala Ser Arg Ala Val Asp
        35                  40                  45

Leu Ser Leu Arg Leu Ala Gly Ala Gly Ala Ile Leu Ala Leu Leu Leu
 50                  55                  60

Gly Ser Ala Gly Leu His Arg Arg Glu Tyr Thr Val Glu Arg Thr Gly
 65                  70                  75                  80

Tyr Gly Ala His Met Val Leu Leu Asp Arg Ser Arg Ser Met Asp
                85                  90                  95

Asp Ser Phe Ala Gly Arg Thr Pro Thr Gly Gly Glu Glu Ser Lys Ser
            100                 105                 110

Ala Ala Ala Glu Arg Leu Leu Ser Gly Phe Val Ser Ser Gly Arg Asn
        115                 120                 125

Asp Leu Val Gly Val Ala Ala Phe Ser Thr Ser Pro Leu Phe Val Leu
130                 135                 140

Pro Leu Thr Asp Asn Lys Ala Ala Val Leu Ala Ala Val His Ala Met
145                 150                 155                 160

Lys Leu Pro Gly Leu Ala Gln Thr His Val Ser Lys Gly Leu Ala Met
                165                 170                 175

Ala Leu Ser Tyr Phe Gly Asp Asp Ser Thr Ala Gly Ser Arg Ile Val
            180                 185                 190

Leu Leu Val Ser Asp Gly Ala Ala Glu Val Asp Pro Asp Ser Glu Leu
        195                 200                 205

Lys Leu Arg Arg Trp Phe Lys Glu Lys Gly Val Arg Leu Tyr Trp Ile
    210                 215                 220

Phe Leu Arg Thr Ala Gly Ser His Gly Ile Phe Glu Thr Pro Asp Asn
225                 230                 235                 240

Pro Glu Glu Asp Asn Ala Gln Ala Arg Pro Glu Arg Tyr Leu His Leu
                245                 250                 255

Phe Phe Asn Ser Leu Gly Ile Pro Tyr Arg Ala Tyr Glu Ala Glu Asp
            260                 265                 270

Ala Asp Ala Leu Lys Arg Ala Ile Ala Asp Val Asp Arg Glu Glu Gln
        275                 280                 285

Arg Pro Leu Arg Tyr Ala Glu Arg Val Pro Arg Arg Asp Leu Gln Ala
290                 295                 300

Phe Cys Tyr Leu Ala Ala Ala Leu Ala Leu Ala Trp Leu Val Ala Ala
305                 310                 315                 320

Lys Gly Met Glu Val Ala Arg
                325

<210> SEQ ID NO 49
<211> LENGTH: 519
<212> TYPE: DNA
<213> ORGANISM: Methylococcus capsulatus

<400> SEQUENCE: 49
atgctggcct tgtcggcgtt gctggagctc aggcaatggc ggaaggccgc ggcggccaat      60
gccgatatcg ccgagctgct ggggggggcac gacatcgccc cggaacggct ggcggcggca     120
tcgccccaag tcctgttggc gcgggccgtg tatttcgtgc ggcacgagcg ctacggcgac     180
gcgctggagc tgctgaacct gctggagacc cggggcgatg cgccttccg cgccgacgtg      240 tattacaacc agggcaatct gcagcttgcc caggctctgg accgcgtcga aaaatcggaa     300

```
atggaccagg cccgggtctt cgccgaactg gccaaggaag cctaccggcg tgccttgtcg      360
ctggcacccg gccactggga cgccaaatac aacctggaag tggccatgcg cctcatgccc      420
gaaatggacc gggtcagccc tgccgatgac gaggcgcccg cggctgaatc caaacggctg      480
tggacaggtt tgcccggact cccgcgaggc ctgccttga                             519
```

<210> SEQ ID NO 50
<211> LENGTH: 172
<212> TYPE: PRT
<213> ORGANISM: Methylococcus capsulatus

<400> SEQUENCE: 50

```
Met Leu Ala Leu Ser Ala Leu Leu Glu Leu Arg Gln Trp Arg Lys Ala
1               5                   10                  15

Ala Ala Ala Asn Ala Asp Ile Ala Glu Leu Leu Gly Gly His Asp Ile
            20                  25                  30

Ala Pro Glu Arg Leu Ala Ala Ala Ser Pro Gln Val Leu Leu Ala Arg
        35                  40                  45

Ala Val Tyr Phe Val Arg His Glu Arg Tyr Gly Asp Ala Leu Glu Leu
    50                  55                  60

Leu Asn Leu Leu Glu Thr Arg Gly Asp Gly Ala Phe Arg Ala Asp Val
65                  70                  75                  80

Tyr Tyr Asn Gln Gly Asn Leu Gln Leu Ala Gln Ala Leu Asp Arg Val
                85                  90                  95

Glu Lys Ser Glu Met Asp Gln Ala Arg Val Phe Ala Glu Leu Ala Lys
            100                 105                 110

Glu Ala Tyr Arg Arg Ala Leu Ser Leu Ala Pro Gly His Trp Asp Ala
        115                 120                 125

Lys Tyr Asn Leu Glu Val Ala Met Arg Leu Met Pro Glu Met Asp Arg
    130                 135                 140

Val Ser Pro Ala Asp Asp Glu Ala Pro Ala Ala Glu Ser Lys Arg Leu
145                 150                 155                 160

Trp Thr Gly Leu Pro Gly Leu Pro Arg Gly Leu Pro
                165                 170
```

<210> SEQ ID NO 51
<211> LENGTH: 972
<212> TYPE: DNA
<213> ORGANISM: Methylococcus capsulatus

<400> SEQUENCE: 51

```
ttgagcatct ggcggcagcg cgttgccgat ccggttttg ccggcctgat tgtagccctc       60
cttctggcgg tagccgcctg tttcccgctc cggctggtgc tggagcggct ggtgttcagc      120
cacatcgtcg tcgtcgacat cacccgcagc atgaacgtcg aggactaccg gcgaggcgcg      180
cgcgccgtgt cgcggctgga attcgtcagg cagagcctga tcgcgccgt ggccgacctg       240 ccctgcggct ccgctgtggg ggtgggcgtt tcaccgaac gcgagccggc gctactgttc       300
gagccgatcg aaacctgcgc cggcttttcc gccatcagcg ccgccatcga acagctcgac      360
tggcgcatgg cctgggctgc cgacagtctg atcgccgcag gtctgcacaa caccctggat      420 tgctggggc gcggcgatgc ggacgtgatt ttcgtcaccg acggccatga ggcgccgcca       480
ctcaatcccc gctactgccc ggacttcagc gacctcagag gcaaggtccg ggggctgatc      540
gtcggagtgg aggactgag cctctcgccc atccccaagt acgacgagtc ggggcggcgt      600
tcgggcgttt atggcgagga cgaagtcccg cagcgctcga gcttcggcct gtcggagctg      660
```

```
ccgcccgagc agatcgaggg ctaccacgcc cgcaacgctc ccttcggcag cgagagagcc    720
gggggcacgg aacatctgtc ccagctcaag gaaggatatt tgcgccagct cgccgaagcc    780
gccggcctgg gctaccaccg cctggaatcg cccgaaggac tgggccgcgc tctcacggca    840
ccggccttgg cgcggcgcca gcggatcgcc acagacgtcc gctggattcc cgccgccctg    900
gcgctcgccg tactgatggc ggtgtatctg cgggtgctgc tgccgcgtcc tggatttca    960 acctcaaact ga                                                         972

<210> SEQ ID NO 52
<211> LENGTH: 323
<212> TYPE: PRT
<213> ORGANISM: Methylococcus capsulatus

<400> SEQUENCE: 52
```

Leu Ser Ile Trp Arg Gln Arg Val Ala Asp Pro Val Phe Ala Gly Leu
1               5                   10                  15

Ile Val Ala Leu Leu Ala Val Ala Ala Cys Phe Pro Leu Arg Leu
            20                  25                  30

Val Leu Glu Arg Leu Val Phe Ser His Ile Val Val Asp Ile Thr
        35                  40                  45

Arg Ser Met Asn Val Glu Asp Tyr Arg Arg Gly Ala Arg Ala Val Ser
    50                  55                  60

Arg Leu Glu Phe Val Arg Gln Ser Leu Ile Gly Ala Val Ala Asp Leu
65                  70                  75                  80

Pro Cys Gly Ser Ala Val Gly Val Gly Val Phe Thr Glu Arg Glu Pro
                85                  90                  95

Ala Leu Leu Phe Glu Pro Ile Glu Thr Cys Ala Gly Phe Ser Ala Ile
            100                 105                 110

Ser Ala Ala Ile Glu Gln Leu Asp Trp Arg Met Ala Trp Ala Ala Asp
        115                 120                 125

Ser Leu Ile Ala Ala Gly Leu His Asn Thr Leu Asp Leu Leu Gly Arg
    130                 135                 140

Gly Asp Ala Asp Val Ile Phe Val Thr Asp Gly His Glu Ala Pro Pro
145                 150                 155                 160

Leu Asn Pro Arg Tyr Cys Pro Asp Phe Ser Asp Leu Arg Gly Lys Val
                165                 170                 175

Arg Gly Leu Ile Val Gly Val Gly Gly Leu Ser Leu Ser Pro Ile Pro
            180                 185                 190

Lys Tyr Asp Glu Ser Gly Arg Arg Ser Gly Val Tyr Gly Glu Asp Glu
        195                 200                 205

Val Pro Gln Arg Ser Ser Phe Gly Leu Ser Glu Leu Pro Pro Glu Gln
    210                 215                 220

Ile Glu Gly Tyr His Ala Arg Asn Ala Pro Phe Gly Ser Glu Arg Ala
225                 230                 235                 240

Gly Gly Thr Glu His Leu Ser Gln Leu Lys Glu Gly Tyr Leu Arg Gln
                245                 250                 255

Leu Ala Glu Ala Ala Gly Leu Gly Tyr His Arg Leu Glu Ser Pro Glu
            260                 265                 270

Gly Leu Gly Arg Ala Leu Thr Ala Pro Ala Leu Ala Arg Arg Gln Arg
        275                 280                 285

Ile Ala Thr Asp Val Arg Trp Ile Pro Ala Ala Leu Ala Leu Ala Val
    290                 295                 300

Leu Met Ala Val Tyr Leu Arg Val Leu Leu Pro Arg Pro Gly Phe Ser
305                 310                 315                 320

Thr Ser Asn

<210> SEQ ID NO 53
<211> LENGTH: 525
<212> TYPE: DNA
<213> ORGANISM: Methylococcus capsulatus

<400> SEQUENCE: 53

```
atgaaaccga tgctcatcct gaccgcgttg ctgttcgcct ccgtttcgtt ggcgcacgga      60
cccacccccc aaaaggtcgt cgagaccgtg gagatcgcgg ctcccgtgga ccgggtctgg     120
aacgccgtga aggatttcgg tgccatcgcg cagtggaatc ccgctctggc caagagcgaa     180
agcaccggcg gcaacaccac cggcgagaag cgcatcctcc attttcccaa cggcgagcag     240
ctcaccgagg aactcgatgc ctacgacccg gcagcccacg aatacaccta ccggctgggc     300
aaggacaacg tcaaggcgct gccggccagt cctactccg ccgtgctcaa ggtcaaggcc      360
accgagacgg gcagccagat cgaatggaag agtcggctct atcgcggcga taccggaaac     420
ttcccgccgg acgagctgaa cgacgaggcc gccgttgcgg cgatgcagag gttttttccgc    480
gccgggctgg acaatctcaa gaaaagtctt gggcccctcg aatga                     525
```

<210> SEQ ID NO 54
<211> LENGTH: 174
<212> TYPE: PRT
<213> ORGANISM: Methylococcus capsulatus

<400> SEQUENCE: 54

```
Met Lys Pro Met Leu Ile Leu Thr Ala Leu Leu Phe Ala Ser Val Ser
1               5                   10                  15

Leu Ala His Gly Pro Thr Pro Gln Lys Val Val Glu Thr Val Glu Ile
            20                  25                  30

Ala Ala Pro Val Asp Arg Val Trp Asn Ala Val Lys Asp Phe Gly Ala
        35                  40                  45

Ile Ala Gln Trp Asn Pro Ala Leu Ala Lys Ser Glu Ser Thr Gly Gly
    50                  55                  60

Asn Thr Thr Gly Glu Lys Arg Ile Leu His Phe Pro Asn Gly Glu Gln
65                  70                  75                  80

Leu Thr Glu Glu Leu Asp Ala Tyr Asp Pro Ala Ala His Glu Tyr Thr
                85                  90                  95

Tyr Arg Leu Gly Lys Asp Asn Val Lys Ala Leu Pro Ala Ser Ser Tyr
            100                 105                 110

Ser Ala Val Leu Lys Val Lys Ala Thr Glu Thr Gly Ser Gln Ile Glu
        115                 120                 125

Trp Lys Ser Arg Leu Tyr Arg Gly Asp Thr Gly Asn Phe Pro Pro Asp
    130                 135                 140

Glu Leu Asn Asp Glu Ala Ala Val Ala Ala Met Gln Arg Phe Phe Arg
145                 150                 155                 160

Ala Gly Leu Asp Asn Leu Lys Lys Ser Leu Gly Pro Leu Glu
                165                 170
```

<210> SEQ ID NO 55
<211> LENGTH: 1530
<212> TYPE: DNA
<213> ORGANISM: Methylococcus capsulatus

<400> SEQUENCE: 55

```
atgctgcaaa aatacataga gaagattctg cgcgcccgtg tctacgacgt tgcccaggag      60
```

```
acccegctgg acccggcgcc cggcctgtcg cggcggctgg acaacacggt gctgatcaag    120
cgcgaggacc tgcagccggt gttctcgttc aagctgcgcg cgcctacaa caagatcgcc    180 tcgctcacac ccgaggcgcg cgcggccggc gtgatcgcgg cctccgccgg caaccacgcc    240
cagggcgtgg cactggcggc gcagcggctg ggcatccgcg ccgtgatcgt gatgccttgc    300
accaccccgc atatcaaggt cgatgcggtg cgcaaccgag cggtgaggt cgtactgcat    360 ggcgacgcct atgacgaagc ctacgaacat gcgctggaac tggcccgcga ccagtgcctg    420
accttcgtcc accectacga cgatccggaa gtcatcgccg gcaaggcac atcggcatg     480 gaaatcctgc ccagcacca ggacgccatc acgccatct tcgtgcctgt gggcggcggc    540
ggattgatcg ccggcatcgc cgcctacgtc aagttcgtgc cccggacat ccgcgtcatc    600 ggcgtggaac cagtggactc cgactgcctg caccgggcgc tgaaagccaa gcggcgggtg    660
atcctgaagc aggtgggcct gttcgccgac ggcgtcgcgg tgaagcaggt cggcaaggaa    720
ccgttccatc tcgcccacca gtgggtggac gaggtcgtga ccgtcgacac cgacgaaatc    780
tgcgccgcca tcaaggacat cttcgacgac acccgctcca tcgccgagcc ggcgggcgcg    840
ctgggcatcg ccgggctcaa gaaatacgtg gccgaaacag gaatcaagaa cgcgtgcctg    900
gtggcgatcg aaagcggcgc caacatcaac ttcgaccggc tgcgccacgt cgctgagcgc    960
gccgagatcg cgaaaagcg cgaactgctg ctggcagtga cgatcccccga gcggccccgc    1020 agcttcctcg aattctgccg ggtgctgggc cgccgcaaca tcaccgaatt caactaccgc    1080
ttcttcgacg aaaaggccgc ccaggtgttc gtcggcctcc cggtggcgag cggcgcgatc    1140
gaccgcgaaa gcctggtccg cgaattcgaa cgccagggtt tcggcgtgct cgacctgacc    1200
ggcaacgaac tcgccatcga acacatccgc tacatggtcg gcggccacgc gccgaaactg    1260
ctggacgaac aggtctacag cttcgaattc cccgagcgac ccggcgcgct gctgcgcttc    1320
ctgtccatca tgggcgggcg ctggaacatc agcctgttcc attaccgcaa ccacggcgcc    1380
gccttcggcc gggtactgat gggcatccag gtgccgaaac cggaacgcaa ggccttccgg    1440
gaattcctcg aagccatcgg ctacgccttc aaggaggaaa cccaaaatcc cgcctaccgg    1500
ctgttcgcgg gggcagcga gcggggtga                                       1530
```

<210> SEQ ID NO 56
<211> LENGTH: 509
<212> TYPE: PRT
<213> ORGANISM: Methylococcus capsulatus

<400> SEQUENCE: 56

```
Met Leu Gln Lys Tyr Ile Glu Lys Ile Leu Arg Ala Arg Val Tyr Asp
1               5                   10                  15

Val Ala Gln Glu Thr Pro Leu Asp Pro Ala Pro Gly Leu Ser Arg Arg
            20                  25                  30

Leu Asp Asn Thr Val Leu Ile Lys Arg Glu Asp Leu Gln Pro Val Phe
        35                  40                  45

Ser Phe Lys Leu Arg Gly Ala Tyr Asn Lys Ile Ala Ser Leu Thr Pro
    50                  55                  60

Glu Ala Arg Ala Ala Gly Val Ile Ala Ala Ser Ala Gly Asn His Ala
65                  70                  75                  80

Gln Gly Val Ala Leu Ala Ala Gln Arg Leu Gly Ile Arg Ala Val Ile
                85                  90                  95

Val Met Pro Cys Thr Thr Pro His Ile Lys Val Asp Ala Val Arg Asn
            100                 105                 110
```

```
Arg Gly Gly Glu Val Val Leu His Gly Asp Ala Tyr Asp Glu Ala Tyr
            115                 120                 125

Glu His Ala Leu Glu Leu Ala Arg Asp Gln Cys Leu Thr Phe Val His
            130                 135                 140

Pro Tyr Asp Asp Pro Glu Val Ile Ala Gly Gln Gly Thr Ile Gly Met
145                 150                 155                 160

Glu Ile Leu Arg Gln His Gln Asp Ala Ile His Ala Ile Phe Val Pro
            165                 170                 175

Val Gly Gly Gly Gly Leu Ile Ala Gly Ile Ala Ala Tyr Val Lys Phe
            180                 185                 190

Val Arg Pro Asp Ile Arg Val Ile Gly Val Glu Pro Val Asp Ser Asp
            195                 200                 205

Cys Leu His Arg Ala Leu Lys Ala Lys Arg Arg Val Ile Leu Lys Gln
            210                 215                 220

Val Gly Leu Phe Ala Asp Gly Val Ala Val Lys Gln Val Gly Lys Glu
225                 230                 235                 240

Pro Phe His Leu Ala His Gln Trp Val Asp Glu Val Val Thr Val Asp
            245                 250                 255

Thr Asp Glu Ile Cys Ala Ala Ile Lys Asp Ile Phe Asp Asp Thr Arg
            260                 265                 270

Ser Ile Ala Glu Pro Ala Gly Ala Leu Gly Ile Ala Gly Leu Lys Lys
            275                 280                 285

Tyr Val Ala Glu Thr Gly Ile Lys Asn Ala Cys Leu Val Ala Ile Glu
            290                 295                 300

Ser Gly Ala Asn Ile Asn Phe Asp Arg Leu Arg His Val Ala Glu Arg
305                 310                 315                 320

Ala Glu Ile Gly Glu Lys Arg Glu Leu Leu Leu Ala Val Thr Ile Pro
            325                 330                 335

Glu Arg Pro Gly Ser Phe Leu Glu Phe Cys Arg Val Leu Gly Arg Arg
            340                 345                 350

Asn Ile Thr Glu Phe Asn Tyr Arg Phe Phe Asp Glu Lys Ala Ala Gln
            355                 360                 365

Val Phe Val Gly Leu Pro Val Ala Ser Gly Ala Ile Asp Arg Glu Ser
            370                 375                 380

Leu Val Arg Glu Phe Glu Arg Gln Gly Phe Gly Val Leu Asp Leu Thr
385                 390                 395                 400

Gly Asn Glu Leu Ala Ile Glu His Ile Arg Tyr Met Val Gly Gly His
            405                 410                 415

Ala Pro Lys Leu Leu Asp Glu Gln Val Tyr Ser Phe Glu Phe Pro Glu
            420                 425                 430

Arg Pro Gly Ala Leu Leu Arg Phe Leu Ser Ile Met Gly Gly Arg Trp
            435                 440                 445

Asn Ile Ser Leu Phe His Tyr Arg Asn His Gly Ala Ala Phe Gly Arg
            450                 455                 460

Val Leu Met Gly Ile Gln Val Pro Lys Pro Glu Arg Lys Ala Phe Arg
465                 470                 475                 480

Glu Phe Leu Glu Ala Ile Gly Tyr Ala Phe Lys Glu Glu Thr Gln Asn
            485                 490                 495

Pro Ala Tyr Arg Leu Phe Ala Gly Gly Ser Glu Arg Gly
            500                 505

<210> SEQ ID NO 57
<211> LENGTH: 1545
```

<212> TYPE: DNA
<213> ORGANISM: Methylococcus capsulatus

<400> SEQUENCE: 57

```
atgcacgaca gactgatcat tttcgacacg accttgcgcg acggagagca gagccccggc    60
gcgtccatga cccgcgatga aaaggtccgc atcgcccggg cgctggagcg tctgaaggtc   120
gacgtcatcg aggcgggctt cccgccgcc agccccggcg atttcgaggc cgtccaggcc   180
gtggcccgga ccatcaagga cagcagggtc tgcggcctgg cccgcgccct cgaccgcgac   240
atcgaccgcg ccggcgaagc cctcaaggac gcccagcgcg cccgcatcca caccttcatc   300
gccacctcgc ccatccacat gcggcacaag ctgcagatgt cgcccgacca ggtggtggaa   360
tacgcggtca aggccgtcaa gcgggcccgc cagtacaccg acgacgtgga attctcgccc   420
gaggacgccg acgctccga ggaggatttc ctctgccgca tcctggaagc cgtgatcgat   480
gcggggcga ccacgctgaa catccccgac accgtcggct acgccttccc ggaacagttc   540
gggcacatga tcgccggct gatcgagcgg attccgaact ccgacaaggc cgtgttctcg   600
gttcactgcc acaacgacct gggactggcg gtcgccaatt cgctggccgc cgtgctgcac   660
ggcgcgcgcc aggtggaatg caccatcaac gggctgggcg agcgggccgg caacgccgcg   720
ctggaagaga tcgtcatggc ggtgcgcacc cgtaaagaca tcttcccctg ccacaccgac   780
atcgagacac gggaaatcgt ggcctgctcc aaactggtct ccagcatcac cggtttcccg   840
atccagccca caaggccat cgtcggcgcc aacgccttcg cccacgagtc gggcatccac   900
caggacggtg tgctcaagag ccgggaaacc tacgagatca tgagcgccga ggacgtgggg   960
tggagcacca accgcatggt gctgggcaaa cattccggcc gcaacgcgtt ccgtacccgg  1020
atgcaggaac tcggcatcga gttcgcctcg aagaggaac tgaactcggt gttccagcgc  1080
ttcaaggtgc tggccgacaa gaagcacgag atcttcgacg aggacctcca ggccctcatc  1140
accgaagccg cgcagaagc cgaagacgaa cgggtcaagc tggtcgcgct gcgggtctgc  1200
tcggaaacgg gcgagattcc ccacgcccag gtcaccatca aggtggacaa cgaggaacgc  1260
accggcacat cgagcggcgg cggcgccgtg gacgccagcc tcaaggccat cgaatcgctg  1320
ctgcacacgg acaccgcgct gacgctgtac tcggtcaaca acatcaccag cggcaccgac  1380
gcccagggcg aggtcaccgt gcggctcgag aaaggcgggc gcatcgtcaa cggccagggc  1440
gccgataccg acatcgtgat cgcctcggcc aaggcctacg tcaacgccgt gaacaagctg  1500
ctggcgccca tccagcgcac ccacccgcaa gtcggggatg tgtga                  1545
```

<210> SEQ ID NO 58
<211> LENGTH: 514
<212> TYPE: PRT
<213> ORGANISM: Methylococcus capsulatus

<400> SEQUENCE: 58

```
Met His Asp Arg Leu Ile Ile Phe Asp Thr Thr Leu Arg Asp Gly Glu
 1               5                  10                  15

Gln Ser Pro Gly Ala Ser Met Thr Arg Asp Glu Lys Val Arg Ile Ala
            20                  25                  30

Arg Ala Leu Glu Arg Leu Lys Val Asp Val Ile Glu Ala Gly Phe Pro
        35                  40                  45

Ala Ala Ser Pro Gly Asp Phe Glu Ala Val Gln Ala Val Ala Arg Thr
    50                  55                  60

Ile Lys Asp Ser Arg Val Cys Gly Leu Ala Arg Ala Leu Asp Arg Asp
65                  70                  75                  80
```

-continued

```
Ile Asp Arg Ala Gly Glu Ala Leu Lys Asp Ala Gln Arg Ala Arg Ile
                85                  90                  95
His Thr Phe Ile Ala Thr Ser Pro Ile His Met Arg His Lys Leu Gln
            100                 105                 110
Met Ser Pro Asp Gln Val Val Glu Tyr Ala Val Lys Ala Val Lys Arg
        115                 120                 125
Ala Arg Gln Tyr Thr Asp Asp Val Glu Phe Ser Pro Glu Asp Ala Gly
    130                 135                 140
Arg Ser Glu Glu Asp Phe Leu Cys Arg Ile Leu Glu Ala Val Ile Asp
145                 150                 155                 160
Ala Gly Ala Thr Thr Leu Asn Ile Pro Asp Thr Val Gly Tyr Ala Phe
                165                 170                 175
Pro Glu Gln Phe Gly His Met Ile Gly Arg Leu Ile Glu Arg Ile Pro
            180                 185                 190
Asn Ser Asp Lys Ala Val Phe Ser Val His Cys His Asn Asp Leu Gly
        195                 200                 205
Leu Ala Val Ala Asn Ser Leu Ala Ala Val Leu His Gly Ala Arg Gln
    210                 215                 220
Val Glu Cys Thr Ile Asn Gly Leu Gly Glu Arg Ala Gly Asn Ala Ala
225                 230                 235                 240
Leu Glu Glu Ile Val Met Ala Val Arg Thr Arg Lys Asp Ile Phe Pro
                245                 250                 255
Cys His Thr Asp Ile Glu Thr Arg Glu Ile Val Ala Cys Ser Lys Leu
            260                 265                 270
Val Ser Ser Ile Thr Gly Phe Pro Ile Gln Pro Asn Lys Ala Ile Val
        275                 280                 285
Gly Ala Asn Ala Phe Ala His Glu Ser Gly Ile His Gln Asp Gly Val
    290                 295                 300
Leu Lys Ser Arg Glu Thr Tyr Glu Ile Met Ser Ala Glu Asp Val Gly
305                 310                 315                 320
Trp Ser Thr Asn Arg Met Val Leu Gly Lys His Ser Gly Arg Asn Ala
                325                 330                 335
Phe Arg Thr Arg Met Gln Glu Leu Gly Ile Glu Phe Ala Ser Glu Glu
            340                 345                 350
Glu Leu Asn Ser Val Phe Gln Arg Phe Lys Val Leu Ala Asp Lys Lys
        355                 360                 365
His Glu Ile Phe Asp Glu Asp Leu Gln Ala Leu Ile Thr Glu Ala Gly
    370                 375                 380
Ala Glu Ala Glu Asp Glu Arg Val Lys Leu Val Ala Leu Arg Val Cys
385                 390                 395                 400
Ser Glu Thr Gly Glu Ile Pro His Ala Gln Val Thr Ile Lys Val Asp
                405                 410                 415
Asn Glu Glu Arg Thr Gly Thr Ser Ser Gly Gly Gly Ala Val Asp Ala
            420                 425                 430
Ser Leu Lys Ala Ile Glu Ser Leu Leu His Thr Asp Thr Ala Leu Thr
        435                 440                 445
Leu Tyr Ser Val Asn Asn Ile Thr Ser Gly Thr Asp Ala Gln Gly Glu
    450                 455                 460
Val Thr Val Arg Leu Glu Lys Gly Gly Arg Ile Val Asn Gly Gln Gly
465                 470                 475                 480
Ala Asp Thr Asp Ile Val Ile Ala Ser Ala Lys Ala Tyr Val Asn Ala
                485                 490                 495
```

Val Asn Lys Leu Leu Ala Pro Ile Gln Arg Thr His Pro Gln Val Gly
            500                 505                 510

Asp Val

<210> SEQ ID NO 59
<211> LENGTH: 1413
<212> TYPE: DNA
<213> ORGANISM: Methylococcus capsulatus

<400> SEQUENCE: 59

```
atgagcggaa aaccccttta cgacaagctg tgggacgacc acgtcgtgca tgtcgatgcg     60
gacggatcgt gcctgatcta catcgatcgt catctaatcc acgaggtgac ctcgcctcag    120
gcattcgaag gctgcggat ggcggggcgt gtaccctggc gggtggatgc caatcttgcg    180
gtggccgacc acaacgtccc caccgccgac cgcgacaggg gtatcgccga tccggtgtcg    240
cgcctgcagg tggaaaccct ggacaagaac tgcgccgatt cggcatcac cgaattcgcg    300
atggacgacg tgcgccaggg tatcgtgcat gtgatcgggc cgagcagggg cgcgaccctg    360
ccgggcatga ccatcgtttg cggcgattcg catacttcga ctcacggtgc tttcggggcg    420
ctcgccttcg ggatcggcac ttccgaggtc gagcacgtac tggccacgca atgcctggtg    480
cagcgcaagg cgaagaacat gctggtccgc gtccagggca agctggcgcc gggcgtgacg    540
gcgaaagatc tggtactggc ggtcatcggc cgtatcggaa ccgccggcgg caccggctac    600
accatcgaat cgctggcga agccattcgc ggcctgtcga tggaaggccg gatgacggtc    660
tgcaacatgg cgatcgaggc gggcgcacgt gccggcctgg tggcggtgga cgaagtcacg    720
ctcgactatc tcgagggccg cccgttcgct ccggcgggcg cgttgtggga gcgggcggtc    780
gaggcatgga agaccctgca cagcgatccg gatgcggtat cgacaaggt cgtcgagatc    840
gatgccgcca gcatcaagcc gcaggtgacc tggggaactt cgccggaaca ggtcgtgccg    900
gtggatgccg aggtgcccga cccggccacg gaagccgatc ccgtgcgcg ggaaagcatg    960
gagcgggcgc tgcagtacat ggatctcctg ccgggcacgc caatcggcgc gatccgggtc   1020
gatcgggtgt tcatcggctc ctgcaccaat gccaggatcg aggatctgcg cgccgcggcg   1080
gaagtcgtcc gggggcacaa gcgcgctgcc agcgtgaagc aggcactggt ggtgcccggc   1140
tcgggttttgg tcaagcggca ggcggagcag gaggggctgg acaaggtgtt cctcgaggcc   1200
ggtttcgaat ggcgcgaccc gggttgttcc atgtgtctgg cgatgaacgc cgaccgcctg   1260
gaacccggcg agcgttgcgc ctcgacctcc aaccggaatt ttgaggggcg ccagggctat   1320
ggcgggcgta cccatctggt gagtccgccc atggcggctg cggcggccat tcacgggcat   1380
ttcgtcgaca tcaccgaagg agggcgcgca tga                                 1413
```

<210> SEQ ID NO 60
<211> LENGTH: 470
<212> TYPE: PRT
<213> ORGANISM: Methylococcus capsulatus

<400> SEQUENCE: 60

Met Ser Gly Lys Thr Leu Tyr Asp Lys Leu Trp Asp Asp His Val Val
1               5                   10                  15

His Val Asp Ala Asp Gly Ser Cys Leu Ile Tyr Ile Asp Arg His Leu
            20                  25                  30

Ile His Glu Val Thr Ser Pro Gln Ala Phe Glu Gly Leu Arg Met Ala
        35                  40                  45

Gly Arg Val Pro Trp Arg Val Asp Ala Asn Leu Ala Val Ala Asp His

```
              50                  55                  60
Asn Val Pro Thr Ala Asp Arg Asp Arg Gly Ile Ala Asp Pro Val Ser
 65                  70                  75                  80
Arg Leu Gln Val Glu Thr Leu Asp Lys Asn Cys Ala Asp Phe Gly Ile
                     85                  90                  95
Thr Glu Phe Ala Met Asp Val Arg Gln Gly Ile Val His Val Ile
                    100                 105                 110
Gly Pro Glu Gln Gly Ala Thr Leu Pro Gly Met Thr Ile Val Cys Gly
                    115                 120                 125
Asp Ser His Thr Ser Thr His Gly Ala Phe Gly Ala Leu Ala Phe Gly
                    130                 135                 140
Ile Gly Thr Ser Glu Val Glu His Val Leu Ala Thr Gln Cys Leu Val
145                 150                 155                 160
Gln Arg Lys Ala Lys Asn Met Leu Val Arg Val Gln Gly Lys Leu Ala
                    165                 170                 175
Pro Gly Val Thr Ala Lys Asp Leu Val Leu Ala Val Ile Gly Arg Ile
                    180                 185                 190
Gly Thr Ala Gly Gly Thr Gly Tyr Thr Ile Glu Phe Ala Gly Glu Ala
                    195                 200                 205
Ile Arg Gly Leu Ser Met Glu Gly Arg Met Thr Val Cys Asn Met Ala
210                 215                 220
Ile Glu Ala Gly Ala Arg Ala Gly Leu Val Ala Val Asp Glu Val Thr
225                 230                 235                 240
Leu Asp Tyr Leu Glu Gly Arg Pro Phe Ala Pro Ala Gly Ala Leu Trp
                    245                 250                 255
Glu Arg Ala Val Glu Ala Trp Lys Asp Leu His Ser Asp Pro Asp Ala
                    260                 265                 270
Val Phe Asp Lys Val Val Glu Ile Asp Ala Ala Ser Ile Lys Pro Gln
                    275                 280                 285
Val Thr Trp Gly Thr Ser Pro Glu Gln Val Val Pro Val Asp Ala Glu
                    290                 295                 300
Val Pro Asp Pro Ala Thr Glu Ala Asp Pro Val Arg Arg Glu Ser Met
305                 310                 315                 320
Glu Arg Ala Leu Gln Tyr Met Asp Leu Leu Pro Gly Thr Pro Ile Gly
                    325                 330                 335
Ala Ile Arg Val Asp Arg Val Phe Ile Gly Ser Cys Thr Asn Ala Arg
                    340                 345                 350
Ile Glu Asp Leu Arg Ala Ala Glu Val Val Arg Gly His Lys Arg
                    355                 360                 365
Ala Ala Ser Val Lys Gln Ala Leu Val Val Pro Gly Ser Gly Leu Val
                    370                 375                 380
Lys Arg Gln Ala Glu Gln Gly Leu Asp Lys Val Phe Leu Glu Ala
385                 390                 395                 400
Gly Phe Glu Trp Arg Asp Pro Gly Cys Ser Met Cys Leu Ala Met Asn
                    405                 410                 415
Ala Asp Arg Leu Glu Pro Gly Glu Arg Cys Ala Ser Thr Ser Asn Arg
                    420                 425                 430
Asn Phe Glu Gly Arg Gln Gly Tyr Gly Gly Arg Thr His Leu Val Ser
                    435                 440                 445
Pro Ala Met Ala Ala Ala Ala Ile His Gly His Phe Val Asp Ile
                    450                 455                 460
Thr Glu Gly Gly Arg Ala
465                 470
```

<210> SEQ ID NO 61
<211> LENGTH: 639
<212> TYPE: DNA
<213> ORGANISM: Methylococcus capsulatus

<400> SEQUENCE: 61

```
atgaagcctt tcaagaaatt cacttcgcga gtcgtgccgt tggaccgcgc caatgtcgac      60
accgacgcca tcattcccaa gcagttcctg aagtccatcc gccgcagcgg gttcggtccc     120
tatctgttcg acgagtggcg ttacctggac cgtggcgagc ccgacatgga ttgcagccac     180
cgtccgctca acccggagtt cgtgctcaac ctgcccctgt acgccggcgc caggatattg     240
ctggcccgca agaacttcgg ctgtggctcc tcgcgcgagc atgcgccctg ggcgctggag     300
gattacggct ccgcgccat catcgcgccg agtttcgccg atatcttcta caacaactgc     360
ttcaagaacg gcatcctgcc catcgtgctc gacgaggcca cggtcgaccg gctgtttagc     420
gaggccgggc ccggcttcga gctcaccgtc gacctggagt cgcagaccgt ggcgacgccg     480
ttcggcgaga ccttccattt cgacgtggat gcctcccgca agcatcgtct gctgaacggc     540
ctggacgaca tcggtctgac ccttcagcat gccgatgcca tccgcgccta cgaagccgcc     600
cgcaggaagt ccgcaccctg gctgtttgcc gtcccttga                           639
```

<210> SEQ ID NO 62
<211> LENGTH: 212
<212> TYPE: PRT
<213> ORGANISM: Methylococcus capsulatus

<400> SEQUENCE: 62

Met Lys Pro Phe Lys Lys Phe Thr Ser Arg Val Val Pro Leu Asp Arg
1               5                   10                  15

Ala Asn Val Asp Thr Asp Ala Ile Ile Pro Lys Gln Phe Leu Lys Ser
            20                  25                  30

Ile Arg Arg Ser Gly Phe Gly Pro Tyr Leu Phe Asp Glu Trp Arg Tyr
        35                  40                  45

Leu Asp Arg Gly Glu Pro Asp Met Asp Cys Ser His Arg Pro Leu Asn
    50                  55                  60

Pro Glu Phe Val Leu Asn Leu Pro Cys Tyr Ala Gly Ala Arg Ile Leu
65                  70                  75                  80

Leu Ala Arg Lys Asn Phe Gly Cys Gly Ser Ser Arg Glu His Ala Pro
                85                  90                  95

Trp Ala Leu Glu Asp Tyr Gly Arg Ala Ile Ile Ala Pro Ser Phe
            100                 105                 110

Ala Asp Ile Phe Tyr Asn Asn Cys Phe Lys Asn Gly Ile Leu Pro Ile
        115                 120                 125

Val Leu Asp Glu Ala Thr Val Asp Arg Leu Phe Ser Glu Ala Gly Pro
    130                 135                 140

Gly Phe Glu Leu Thr Val Asp Leu Glu Ser Gln Thr Val Ala Thr Pro
145                 150                 155                 160

Phe Gly Glu Thr Phe His Phe Asp Val Asp Ala Ser Arg Lys His Arg
                165                 170                 175

Leu Leu Asn Gly Leu Asp Asp Ile Gly Leu Thr Leu Gln His Ala Asp
            180                 185                 190

Ala Ile Arg Ala Tyr Glu Ala Ala Arg Arg Lys Ser Ala Pro Trp Leu
        195                 200                 205

Phe Ala Val Pro

<210> SEQ ID NO 63
<211> LENGTH: 1083
<212> TYPE: DNA
<213> ORGANISM: Methylococcus capsulatus

<400> SEQUENCE: 63

| | | | | | |
|---|---|---|---|---|---|
| atgactatca | aaatcgctgt | cttgcccggt | gacggcatcg | gtcccgaaat | cgtcgccgag | 60 |
| gccctgaagg | ttctggactg | cctgcggtcc | gacttcggcc | tcgcggtcga | aaccgaacac | 120 |
| gccctgatcg | gcggcgcagc | ctatgatgcg | cacggcacgc | cgttccccaa | ggaaaccctg | 180 |
| gagctgtgcc | gggctgccga | ttcgatcctg | cttggagcgg | tcggcggtcc | caaatgggag | 240 |
| ccgttggatt | attcgctgcg | gcccgagcgg | gggctcctgg | gcttgcgttc | ggagctggaa | 300 |
| ctgttttcca | acctgcgccc | ggcggtgctc | taccctcagc | tggtgtcggc | ttcgaccctc | 360 |
| aagcccgagg | tggtcgccgg | cctcgacatc | atgatcgtgc | gggagctgac | cggcggcata | 420 |
| tatttcggca | agccgcgcgg | tcgtcgcatc | aacgaggacg | gagagcggga | gggctacaac | 480 |
| accctggtat | acagcgaatc | ggaaatccgc | cgcatagccc | atagcgcgtt | ccagatcgcc | 540 |
| cggaagcgta | acaggcgcct | gtgcagcatc | gacaaggcca | atgtgctgga | atgcacggaa | 600 |
| ctgtggcgcg | aggtggtgat | cgaggtcggc | aaggactatc | ccgacgtggc | gctgagccac | 660 |
| atgtacgtgg | acaacgccgc | gatgcagctg | gtccgtaacc | gaagcagtt | cgacgtgatg | 720 |
| ctgaccgaca | acatgttcgg | cgacatcctg | tccgactgtg | ccgccatgct | gaccggctcg | 780 |
| atcggcatgc | tgccttcggc | ttccctcgcc | gagagcggca | aggggatgta | cgagcccatc | 840 |
| cacggttcgg | ccccggatat | cgccggccgc | ggcatcgcca | acccgatcgc | caccatcctg | 900 |
| tcgctggcca | tgatgttgcg | ctacagcttc | gatgacgcgg | tctcggcaga | gcggatcggg | 960 |
| aaggcggtgc | agacggcgct | ggatcagggt | ttccgcacgg | cggacatcgc | ctcggaaggc | 1020 |
| accgtcgagg | tcggtaccgc | tgcgatgggc | gatgccatcg | tcgccgcctt | gcgcgccgtc | 1080 |
| tga | | | | | | 1083 |

<210> SEQ ID NO 64
<211> LENGTH: 360
<212> TYPE: PRT
<213> ORGANISM: Methylococcus capsulatus

<400> SEQUENCE: 64

Met Thr Ile Lys Ile Ala Val Leu Pro Gly Asp Gly Ile Gly Pro Glu
1               5                   10                  15

Ile Val Ala Glu Ala Leu Lys Val Leu Asp Cys Leu Arg Ser Asp Phe
            20                  25                  30

Gly Leu Ala Val Glu Thr Glu His Ala Leu Ile Gly Gly Ala Ala Tyr
        35                  40                  45

Asp Ala His Gly Thr Pro Phe Pro Lys Glu Thr Leu Glu Leu Cys Arg
    50                  55                  60

Ala Ala Asp Ser Ile Leu Leu Gly Ala Val Gly Gly Pro Lys Trp Glu
65                  70                  75                  80

Pro Leu Asp Tyr Ser Leu Arg Pro Glu Arg Gly Leu Leu Gly Leu Arg
                85                  90                  95

Ser Glu Leu Glu Leu Phe Ser Asn Leu Arg Pro Ala Val Leu Tyr Pro
            100                 105                 110

Gln Leu Val Ser Ala Ser Thr Leu Lys Pro Glu Val Val Ala Gly Leu
        115                 120                 125

```
Asp Ile Met Ile Val Arg Glu Leu Thr Gly Gly Ile Tyr Phe Gly Lys
        130                 135                 140

Pro Arg Gly Arg Ile Asn Glu Asp Gly Glu Arg Glu Gly Tyr Asn
145                 150                 155                 160

Thr Leu Val Tyr Ser Glu Ser Glu Ile Arg Arg Ile Ala His Ser Ala
                165                 170                 175

Phe Gln Ile Ala Arg Lys Arg Asn Arg Arg Leu Cys Ser Ile Asp Lys
            180                 185                 190

Ala Asn Val Leu Glu Cys Thr Glu Leu Trp Arg Glu Val Val Ile Glu
        195                 200                 205

Val Gly Lys Asp Tyr Pro Asp Val Ala Leu Ser His Met Tyr Val Asp
    210                 215                 220

Asn Ala Ala Met Gln Leu Val Arg Asn Pro Lys Gln Phe Asp Val Met
225                 230                 235                 240

Leu Thr Asp Asn Met Phe Gly Asp Ile Leu Ser Asp Cys Ala Ala Met
                245                 250                 255

Leu Thr Gly Ser Ile Gly Met Leu Pro Ser Ala Ser Leu Ala Glu Ser
            260                 265                 270

Gly Lys Gly Met Tyr Glu Pro Ile His Gly Ser Ala Pro Asp Ile Ala
        275                 280                 285

Gly Arg Gly Ile Ala Asn Pro Ile Ala Thr Ile Leu Ser Leu Ala Met
    290                 295                 300

Met Leu Arg Tyr Ser Phe Asp Asp Ala Val Ser Ala Glu Arg Ile Gly
305                 310                 315                 320

Lys Ala Val Gln Thr Ala Leu Asp Gln Gly Phe Arg Thr Ala Asp Ile
                325                 330                 335

Ala Ser Glu Gly Thr Val Glu Val Gly Thr Ala Met Gly Asp Ala
            340                 345                 350

Ile Val Ala Ala Leu Arg Ala Val
        355                 360

<210> SEQ ID NO 65
<211> LENGTH: 1477
<212> TYPE: DNA
<213> ORGANISM: Marinobacter algicola

<400> SEQUENCE: 65
atggcgaccc agcagcagca gaacggcgcc tcggcgagcg gcgtcctgga acagttgcgc      60
gggaagcatg tcctgataac cggtaccacc ggtttccttg caaggtagt cctggaaaag     120 ctgatccgca cagtcccgga catcggcggc atccacctcc tgatccgggg caacaagagg     180
catccggccg cccgtgaacg gttcttgaac gagatcgcca gcagttcggt cttcgagcgt     240
ctgcgccacg acgacaacga ggccttcgaa accttcctgg aagaaagggt gcactgtata     300
accggagagg tcaccgagag tcgtttcggc cttaccccgg agcgcttccg cgcgctggcg     360
ggtcaggtgg acgccttcat caattcggcc gcctccgtca acttccgcga ggaactggac     420
aaggcgctga agatcaatac gctgtgcctg agaatgtcg cggcccttgc tgaactcaac     480
agtgcgatgg cggtcatcca ggtttcgacc tgctacgtta acggcaagaa tagcgggcag     540
atcaccgaat cggtcatcaa gcccgcgggg gagtccatcc gcgtagcac cgatgggtac     600 tatgaaatcg aagaattggt gcacctgctg caggacaaaa tcagcgatgt gaaggcccga     660
tactccggga aggttctgga aaaaaaattg gtggacctag catccgggga agccaataac     720
tacgggtgga gcgatacata taccttcacc aagtggctgg gcgaacagct cctcatgaag     780
```

```
gccctgagcg gcagatcgct gaccatcgtg cggccgtcga tcatcgagtc ggcattggaa      840
gagcccagcc cggggtggat tgaaggcgtc aaggtcgccg atgccatcat actggcctac      900
gcgagggaga aggtatcgct ctttcctggc aagcggagcg gcatcatcga cgtcatccca      960
gtggatctgg tggccaattc gatcattctg tccctggcgg aggcgctctc cggttcgggc     1020
cagcggcgta tctatcagtg ctgcagcggc ggctcgaacc ccatctccct cgggaagttc     1080
atcgactatc tgatggcgga ggcgaagacc aactacgcgg cctacgatca gctgttctac     1140
cgccgcccca ccaagccgtt cgtggccgtc aaccgcaaac tcttcgacgt cgtcgtgggc     1200
ggcatgcggg tcccgctctc gatcgcgggc aaagccatgc gcctggcggg acaaaaccgc     1260
gaactgaagg tcctgaagaa tctggatacg acccggtccc tggccaccat tttcggggttc     1320 tacaccgctc cggactacat ctttcgcaat gacagcctga tggccctggc ctcgcgcatg     1380
ggcgagctgg accgcgtgtt gttccccgtt gacgcccgtc agatcgactg cagctgtat     1440 ctgtgcaaaa tccacctcgg cgggctgaat cggtacg                               1477

<210> SEQ ID NO 66
<211> LENGTH: 511
<212> TYPE: PRT
<213> ORGANISM: Marinobacter algicola

<400> SEQUENCE: 66

Met Ala Thr Gln Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
            20                  25                  30

Leu Gly Lys Val Val Leu Glu Lys Leu Ile Arg Thr Val Pro Asp Ile
        35                  40                  45

Gly Gly Ile His Leu Leu Ile Arg Gly Asn Lys Arg His Pro Ala Ala
    50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
            100                 105                 110

Pro Glu Arg Phe Arg Ala Leu Ala Gly Gln Val Asp Ala Phe Ile Asn
        115                 120                 125

Ser Ala Ala Ser Val Asn Phe Arg Glu Glu Leu Asp Lys Ala Leu Lys
    130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
    210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
```

```
                245                 250                 255
Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
    290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335

Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
        435                 440                 445

Arg Asn Asp Ser Leu Met Ala Leu Ala Ser Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala
            500                 505                 510

<210> SEQ ID NO 67
<211> LENGTH: 1377
<212> TYPE: DNA
<213> ORGANISM: Acinetobacter baylyi

<400> SEQUENCE: 67
atgcgccccc tgcacccat cgacttcatc ttcctgagcc tggaaaagcg gcagcagccc      60
atgcacgtcg gcggcctgtt cctgttccag atcccggaca cgccccgca caccttcatc     120 caggacctgg tcaacgacat ccgcatctcc aagagcatcc cggtgccgcc cttcaacaac    180
aagctgaacg gcctgttctg gacgaagac gaggagttcg acctggacca ccatttccgg     240
cacatcgccc tgccgcatcc cggccgcatc cgggaactgc tgatctacat ctcccaggag    300
cacagcaccc tgctggaccg cgcgaagccg ctgtggacct gcaacatcat cgaaggcatc    360
gagggcaacc ggttcgccat gtatttcaag atccaccatg cgatggtcga cggcgtggcc    420
ggcatgcgcc tgatcgaaaa gtcgctgtcc catgacgtca ccgagaagag catcgtcccg    480
ccctggtgcg tggaaggcaa gcgggcgaag cgcctgcggg agccgaagac cggcaagatc    540
aagaagatca tgtcgggcat caagtcccag ctgcaggcca cccccaccgt catccaggaa    600
ctgtcgcaga ccgtgttcaa ggacatcggc cgcaacccgg accacgtcag ctcgttccag    660
```

-continued

```
gcccccctgct ccatcctgaa ccagcgggtg tccagctcgc gccggttcgc cgcgcagtcg      720
ttcgacctgg accgcttccg gaacatcgcg aagtccctga acgtcaccat caacgacgtc      780
gtgctggccg tgtgcagcgg cgccctgcgc gcgtacctga tgagccacaa ctcgctgccg      840
tccaagcccc tgatcgcgat ggtcccggcg tcgatccgca cgacgacag cgacgtgtcg       900 aaccggatca ccatgatcct ggccaacctg gcgacccata aggacgaccc gctgcagcgc      960
ctggagatca tccgccggag cgtccagaac tcgaagcagc gcttcaagcg gatgacctcc     1020
gaccagatcc tgaactacag cgcggtcgtg tatggcccgg ccggcctgaa catcatcagc     1080
ggcatgatgc ccagcgcca ggccttcaac ctggtcatct cgaacgtgcc gggcccgcgc      1140
gagccgctgt actggaacgg cgccaagctg gacgcgctgt atcccgcctc catcgtcctg     1200
gacggccagg ccctgaacat caccatgacc agctacctgg acaagctgga ggtcggcctg     1260
atcgcgtgcc gcaacgccct gccgcggatg cagaacctgc tgacccatct ggaggaagag     1320
atccagctgt tcgaaggcgt gatcgcgaag caggaggaca tcaagaccgc caactga       1377
```

<210> SEQ ID NO 68
<211> LENGTH: 458
<212> TYPE: PRT
<213> ORGANISM: Acinetobacter baylyi

<400> SEQUENCE: 68

```
Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Arg Arg Phe Ala Ala Gln Ser
225                 230                 235                 240

Phe Asp Leu Asp Arg Phe Arg Asn Ile Ala Lys Ser Leu Asn Val Thr
```

Ile Asn Asp Val Val Leu Ala Val Cys Ser Gly Ala Leu Arg Ala Tyr
            245                 250                 255
        260                 265                 270

Leu Met Ser His Asn Ser Leu Pro Ser Lys Pro Leu Ile Ala Met Val
        275                 280                 285

Pro Ala Ser Ile Arg Asn Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
    370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
    450                 455

<210> SEQ ID NO 69
<211> LENGTH: 1428
<212> TYPE: DNA
<213> ORGANISM: Psychrobacter articus

<400> SEQUENCE: 69
atgcgcctgc tgaccgccgt cgaccagctg ttcctgctgc tggagtcccg caagcacccg      60
atgcacgtgg cggcctgtt cctgttcgaa ctgccggaga cgccgacat ctcgttcgtc     120 caccagctgt gaagcagat gcaggactcc gacgtcccgc ccaccttccc cttcaaccag    180
gtgctggaac acatgatgtt ctggaaggag acaagaact tcgacgtcga caccatctg     240 caccatgtgc cctgccgaa gcccgcgcgc gtccgggagc tgctgatgta cgtgtcccgc    300
gaacacggcc ggctgctgga ccgcgcgatg ccgctgtggg aatgccatgt catcgagggc   360
atccagccgg aaaccgaggg cagccccgag cggttcgccc tgtatttcaa gatccaccat  420
tcgctggtcg acggcatcgc cgcgatgcgc ctggtgaaga gagcctgtc gcagtcgccg   480 aacgaaccg tgaccctgcc gatctggagc ctgatggccc accatcggaa ccagatcgac    540
gcgatcttcc ccaaggagcg gagcgccctg cgcatcctga aggaacaggt ctcgaccatc  600
aagccggtgt tcaccgagct gctgaacaac ttcaagaact acaacgacga ctcgtatgtc  660
tccaccttcg acgcgccccg cagcatcctg aaccgccgga tcagcgcctc gcgccggatc  720
gccgcgcagt cgtacgacat caagcggttc aacgacatcg ccgaacgcat caacatctcc  780
aagaacgacg tgtgctggc cgtgtgcagc ggcgcgatcc gccgctacct gatcagcatg  840
gacgcgctgc cgagcaagcc cctgatcgcc ttcgtcccga tgtcgctgcg caccgacgac  900

-continued

```
tccatcgcgg gcaaccagct gtcgttcgtg ctggccaacc tgggcaccca cctggacgac      960
cccctgtccc ggatcaagct gatccatcgc tccatgaaca acagcaagcg ccggttccgc     1020
cggatgaacc aggcccaggt catcaactac agcatcgtgt cgtatgcctg ggagggcatc     1080
aacctggcga ccgacctgtt cccgaagaag caggccttca acctgatcat ctcgaacgtg     1140
ccgggcagcg agaagcccct gtactggaac ggcgcgcgcc tggaaagcct gtatccggcc     1200
tcgatcgtgt tcaacggcca ggccatgaac atcaccctgg cgtcctacct ggacaagatg     1260
gagttcggca tcaccgcctg cagcaaggcg ctgccgcacg tccaggacat gctgatgctg     1320
atcgaggaag agctgcagct gctggagtcc gtcagcaagg aactggagtt caacggcatc     1380
accgtgaagg acaagtcgga aaagaagctg aagaagctgg ccccgtga                 1428
```

<210> SEQ ID NO 70
<211> LENGTH: 475
<212> TYPE: PRT
<213> ORGANISM: Psychrobacter articus

<400> SEQUENCE: 70

```
Met Arg Leu Leu Thr Ala Val Asp Gln Leu Phe Leu Leu Leu Glu Ser
1               5                   10                  15

Arg Lys His Pro Met His Val Gly Gly Leu Phe Leu Phe Glu Leu Pro
                20                  25                  30

Glu Asn Ala Asp Ile Ser Phe Val His Gln Leu Val Lys Gln Met Gln
            35                  40                  45

Asp Ser Asp Val Pro Pro Thr Phe Pro Phe Asn Gln Val Leu Glu His
        50                  55                  60

Met Met Phe Trp Lys Glu Asp Lys Asn Phe Asp Val Glu His His Leu
65                  70                  75                  80

His His Val Ala Leu Pro Lys Pro Ala Arg Val Arg Glu Leu Leu Met
                85                  90                  95

Tyr Val Ser Arg Glu His Gly Arg Leu Leu Asp Arg Ala Met Pro Leu
                100                 105                 110

Trp Glu Cys His Val Ile Glu Gly Ile Gln Pro Glu Thr Glu Gly Ser
            115                 120                 125

Pro Glu Arg Phe Ala Leu Tyr Phe Lys Ile His His Ser Leu Val Asp
        130                 135                 140

Gly Ile Ala Ala Met Arg Leu Val Lys Lys Ser Leu Ser Gln Ser Pro
145                 150                 155                 160

Asn Glu Pro Val Thr Leu Pro Ile Trp Ser Leu Met Ala His Arg
                165                 170                 175

Asn Gln Ile Asp Ala Ile Phe Pro Lys Glu Arg Ser Ala Leu Arg Ile
            180                 185                 190

Leu Lys Glu Gln Val Ser Thr Ile Lys Pro Val Phe Thr Glu Leu Leu
        195                 200                 205

Asn Asn Phe Lys Asn Tyr Asn Asp Asp Ser Tyr Val Ser Thr Phe Asp
        210                 215                 220

Ala Pro Arg Ser Ile Leu Asn Arg Arg Ile Ser Ala Ser Arg Arg Ile
225                 230                 235                 240

Ala Ala Gln Ser Tyr Asp Ile Lys Arg Phe Asn Asp Ile Ala Glu Arg
                245                 250                 255

Ile Asn Ile Ser Lys Asn Asp Val Val Leu Ala Val Cys Ser Gly Ala
                260                 265                 270

Ile Arg Arg Tyr Leu Ile Ser Met Asp Ala Leu Pro Ser Lys Pro Leu
            275                 280                 285
```

```
Ile Ala Phe Val Pro Met Ser Leu Arg Thr Asp Asp Ser Ile Ala Gly
    290                 295                 300

Asn Gln Leu Ser Phe Val Leu Ala Asn Leu Gly Thr His Leu Asp Asp
305                 310                 315                 320

Pro Leu Ser Arg Ile Lys Leu Ile His Arg Ser Met Asn Asn Ser Lys
                325                 330                 335

Arg Arg Phe Arg Arg Met Asn Gln Ala Gln Val Ile Asn Tyr Ser Ile
                340                 345                 350

Val Ser Tyr Ala Trp Glu Gly Ile Asn Leu Ala Thr Asp Leu Phe Pro
            355                 360                 365

Lys Lys Gln Ala Phe Asn Leu Ile Ile Ser Asn Val Pro Gly Ser Glu
        370                 375                 380

Lys Pro Leu Tyr Trp Asn Gly Ala Arg Leu Glu Ser Leu Tyr Pro Ala
385                 390                 395                 400

Ser Ile Val Phe Asn Gly Gln Ala Met Asn Ile Thr Leu Ala Ser Tyr
                405                 410                 415

Leu Asp Lys Met Glu Phe Gly Ile Thr Ala Cys Ser Lys Ala Leu Pro
                420                 425                 430

His Val Gln Asp Met Leu Met Leu Ile Glu Glu Leu Gln Leu Leu
            435                 440                 445

Glu Ser Val Ser Lys Glu Leu Glu Phe Asn Gly Ile Thr Val Lys Asp
    450                 455                 460

Lys Ser Glu Lys Lys Leu Lys Lys Leu Ala Pro
465                 470                 475

<210> SEQ ID NO 71
<211> LENGTH: 1386
<212> TYPE: DNA
<213> ORGANISM: Rhodococcus opacus

<400> SEQUENCE: 71
atgtccgtga tgtccccgac cgaggcgatg ttcgtcctgt tcgagacccc gagccacccg      60
atgcacatgg gcgcgctgga gctgttcgag ccgccgcgcg agtcgggccc ggaccacgcc     120
cgcctgatgt tcgaggcgct gatctcccag gaaggcgcca cgacaccttc cgccggcgc     180 gccgtccggc cgctgcgcgg cgcgtcgtac ccctggtggt ccgtcgacga ccgggtggac     240
ctgggctatc acgtccgcca taccgccgtg ccgggccggg ccgcatgga ggacctgctg     300 tcgctggtgt cccagatgca cggcatgccc ctggacccgc agcacccat gtgggagatc     360 catgtcatcg aaggcctggc cgacggccgc accgcggtgt tcagcaagat ccatctgtcg     420
ctgatggacg gcccggccgg cctgcggctg ctgcaccatg cgctgagcac cgacccggac     480
gcccgcgact gccccgcgcc gtggaccccc ggcgtcagcg gcacctcgcg gcgcgaatcg     540
gccctgccgg tcgccgcggt gcgggcgggc gtgcgcgccg cgacctccat cgtcggcgtg     600
ctgcccgccc tggcgaaggt cgcctacgac ggcgtgcggg accagcacct gaccctgccg     660
ctgcagagcc cgcccaccat gctgaacgtc ccgtgggcc gggcccgcaa gctggccgcg     720
cggagctggc cgatccggcg cctggtctcg gtggccgcgg ccgcgcgcac caccatcaac     780
gccgtcgtgc tggcgatgtg ctcgggcgcc ctgcgccact acctggtcga gcagtatgcc     840
ctgccggaag cgcccctgac cgccatgctg cccgtgccgc tggacctggg cggcaccatg     900
atcggcccgc gtgccgcgcga ccacggcgtc ggcgcgatgg tcgtgggcct ggcgaccgac     960
gaggccgacc ccgccgcgcg gctggcccgc atcagcgagt cggtcgaaca caccaaccgc    1020
```

```
gtgttcggcg cgctgtccca tacccagttc caggtcatgt ccgccctggc gatcagcccg    1080
atcctgctgg aacccgtccg gcgcttcgtg gacgacaccc cgcccccgtt caacgtgatg    1140
atctcgtaca tgccgggtcc gtcccggccg cgctattgga acggcgcgcg gctggacgcc    1200
gtctaccccg cgccgaccgt gctgggcggc caggccctga gcatcaccct gacctcccgc    1260
agcggccagc tggacgtcgg cgtcgtgggc gaccggcagg ccgtgccgca cctgcagcgc    1320
atcatcaccc atctggagac ctccctgacc gacctggaaa acgccgtggc cgcgagcggc    1380
acctga                                                               1386
```

<210> SEQ ID NO 72
<211> LENGTH: 461
<212> TYPE: PRT
<213> ORGANISM: Rhodococcus opacus

<400> SEQUENCE: 72

```
Met Ser Val Met Ser Pro Thr Glu Ala Met Phe Val Leu Phe Glu Thr
1               5                   10                  15

Pro Ser His Pro Met His Met Gly Ala Leu Glu Leu Phe Glu Pro Pro
                20                  25                  30

Arg Glu Ser Gly Pro Asp His Ala Arg Leu Met Phe Glu Ala Leu Ile
            35                  40                  45

Ser Gln Glu Gly Ala Ser Asp Thr Phe Arg Arg Arg Ala Val Arg Pro
        50                  55                  60

Leu Arg Gly Ala Ser Tyr Pro Trp Trp Ser Val Asp Asp Arg Val Asp
65                  70                  75                  80

Leu Gly Tyr His Val Arg His Thr Ala Val Pro Gly Arg Gly Arg Met
                85                  90                  95

Glu Asp Leu Leu Ser Leu Val Ser Gln Met His Gly Met Pro Leu Asp
            100                 105                 110

Pro Gln His Pro Met Trp Glu Ile His Val Ile Glu Gly Leu Ala Asp
        115                 120                 125

Gly Arg Thr Ala Val Phe Ser Lys Ile His Leu Ser Leu Met Asp Gly
130                 135                 140

Pro Ala Gly Leu Arg Leu Leu His His Ala Leu Ser Thr Asp Pro Asp
145                 150                 155                 160

Ala Arg Asp Cys Pro Ala Pro Trp Thr Pro Gly Val Ser Gly Thr Ser
                165                 170                 175

Arg Arg Glu Ser Ala Leu Pro Val Ala Val Arg Ala Gly Val Arg
            180                 185                 190

Ala Ala Thr Ser Ile Val Gly Val Leu Pro Ala Leu Ala Lys Val Ala
        195                 200                 205

Tyr Asp Gly Val Arg Asp Gln His Leu Thr Leu Pro Leu Gln Ser Pro
210                 215                 220

Pro Thr Met Leu Asn Val Pro Val Gly Arg Ala Arg Lys Leu Ala Ala
225                 230                 235                 240

Arg Ser Trp Pro Ile Arg Arg Leu Val Ser Val Ala Ala Ala Arg
                245                 250                 255

Thr Thr Ile Asn Ala Val Val Leu Ala Met Cys Ser Gly Ala Leu Arg
            260                 265                 270

His Tyr Leu Val Glu Gln Tyr Ala Leu Pro Glu Ala Pro Leu Thr Ala
        275                 280                 285

Met Leu Pro Val Pro Leu Asp Leu Gly Gly Thr Met Ile Gly Pro Arg
290                 295                 300
```

```
Gly Arg Asp His Gly Val Gly Ala Met Val Val Gly Leu Ala Thr Asp
305                 310                 315                 320
Glu Ala Asp Pro Ala Ala Arg Leu Ala Arg Ile Ser Glu Ser Val Glu
            325                 330                 335
His Thr Asn Arg Val Phe Gly Ala Leu Ser His Thr Gln Phe Gln Val
        340                 345                 350
Met Ser Ala Leu Ala Ile Ser Pro Ile Leu Leu Glu Pro Val Arg Arg
    355                 360                 365
Phe Val Asp Asp Thr Pro Pro Phe Asn Val Met Ile Ser Tyr Met
370                 375                 380
Pro Gly Pro Ser Arg Pro Arg Tyr Trp Asn Gly Ala Arg Leu Asp Ala
385                 390                 395                 400
Val Tyr Pro Ala Pro Thr Val Leu Gly Gly Gln Ala Leu Ser Ile Thr
                405                 410                 415
Leu Thr Ser Arg Ser Gly Gln Leu Asp Val Gly Val Gly Asp Arg
            420                 425                 430
Gln Ala Val Pro His Leu Gln Arg Ile Ile Thr His Leu Glu Thr Ser
        435                 440                 445
Leu Thr Asp Leu Glu Asn Ala Val Ala Ala Ser Gly Thr
    450                 455                 460

<210> SEQ ID NO 73
<211> LENGTH: 1356
<212> TYPE: DNA
<213> ORGANISM: Rhodococcus opacus

<400> SEQUENCE: 73
atgccggtca ccgactccat cttcctgctg ggcgaaagcc gcgagcaccc gatgcacgtg      60
ggctccctgg aactgttcac cccccggac gacgccggcc cggactacgt caagtcgatg     120
cacgagaccc tgctgaagca taccgacgtg accccacct tccgcaagaa gccggcgggc     180
cccgtcggct cgctgggcaa cgtgtggtgg ccgacgagt ccgacgtcga cctggaatac     240
cacgtgcgcc atagcgcgct gccggcccc tatcgcgtcc gggaactgct gaccctgacc     300
tcgcggctgc acggcaccct gctggaccgc atcggccgc tgtgggagat gtacctgatc     360
gaaggcctga gcgacggccg cttcgccatc tataccaagc tgcaccatag cctgatggac     420
ggcgtctcgg gcctgcgcct gctgatgcgg accctgtcga ccgacccgga cgtgcgcgac     480
gccccgcccc gtggaacct gccgcggccc gccgcggcca acggcgcggc cccggacctg     540
tggtcggtcg tgaacggcgt ccgcggacc gtcggcgacg tggccggcct ggcgcccgcc     600
tccctgcgca tcgcgcggac cgcgatgggc cagcacgaca tgcgcttccc gtacgaggcg     660
ccccggacca tgctgaacgt gccgatcggc ggcgcccgcc ggttcgcggc ccagtcctgg     720 ccctggaac gcgtccatgc cgtgcggaag gcggccggcg tcagcgtgaa cgacgtcgtg     780
atggccatgt gcgcgggcgc cctgcgcggc tatctggagg aacagaacgc gctgccggac     840
gagcccctga tcgcgatggt cccggtgtcc ctgcgggacg aacagcaggc ggacgccggc     900
ggcaacgccg tcggcgtgac cctgtgcaac ctggcgaccg acgtcgacga ccccgccgag     960
cgcctgaccg cgatcagcgc ctcgatgtcc cagggcaagg aactgttcgg cagcctgacc    1020
tcgatgcagg cgctggcctg gtcggcggtg aacatgtccc cgatcgccct gaccccggtc    1080
cccggcttcg tgcggttcac cccccgccc ttcaacgtca tcatcagcaa cgtgccgggc    1140 cccccgcaaga ccatgtactg gaacggctcc cggctggacg gcatctatcc gaccagcgtc    1200
gtgctggacg gccaggccct gaacatcacc ctgaccacca acggcggcaa cctggacttc    1260
```
ggcgtcatcg gctgccgccg gtccgtgccg agcctgcagc gcatcctgtt ctacctggaa    1320
gcggccctgg gcgagctgga agcggccctg ctgtga    1356

<210> SEQ ID NO 74
<211> LENGTH: 451
<212> TYPE: PRT
<213> ORGANISM: Rhodococcus opacus

<400> SEQUENCE: 74

Met Pro Val Thr Asp Ser Ile Phe Leu Leu Gly Glu Ser Arg Glu His
1               5                   10                  15

Pro Met His Val Gly Ser Leu Glu Leu Phe Thr Pro Pro Asp Asp Ala
                20                  25                  30

Gly Pro Asp Tyr Val Lys Ser Met His Glu Thr Leu Leu Lys His Thr
            35                  40                  45

Asp Val Asp Pro Thr Phe Arg Lys Lys Pro Ala Gly Pro Val Gly Ser
        50                  55                  60

Leu Gly Asn Val Trp Trp Ala Asp Glu Ser Asp Val Asp Leu Glu Tyr
65                  70                  75                  80

His Val Arg His Ser Ala Leu Pro Ala Pro Tyr Arg Val Arg Glu Leu
                85                  90                  95

Leu Thr Leu Thr Ser Arg Leu His Gly Thr Leu Leu Asp Arg His Arg
            100                 105                 110

Pro Leu Trp Glu Met Tyr Leu Ile Glu Gly Leu Ser Asp Gly Arg Phe
        115                 120                 125

Ala Ile Tyr Thr Lys Leu His His Ser Leu Met Asp Gly Val Ser Gly
130                 135                 140

Leu Arg Leu Leu Met Arg Thr Leu Ser Thr Asp Pro Asp Val Arg Asp
145                 150                 155                 160

Ala Pro Pro Pro Trp Asn Leu Pro Arg Pro Ala Ala Ala Asn Gly Ala
                165                 170                 175

Ala Pro Asp Leu Trp Ser Val Val Asn Gly Val Arg Arg Thr Val Gly
            180                 185                 190

Asp Val Ala Gly Leu Ala Pro Ala Ser Leu Arg Ile Ala Arg Thr Ala
        195                 200                 205

Met Gly Gln His Asp Met Arg Phe Pro Tyr Glu Ala Pro Arg Thr Met
210                 215                 220

Leu Asn Val Pro Ile Gly Gly Ala Arg Arg Phe Ala Ala Gln Ser Trp
225                 230                 235                 240

Pro Leu Glu Arg Val His Ala Val Arg Lys Ala Ala Gly Val Ser Val
                245                 250                 255

Asn Asp Val Val Met Ala Met Cys Ala Gly Ala Leu Arg Gly Tyr Leu
            260                 265                 270

Glu Glu Gln Asn Ala Leu Pro Asp Glu Pro Leu Ile Ala Met Val Pro
        275                 280                 285

Val Ser Leu Arg Asp Glu Gln Gln Ala Asp Ala Gly Gly Asn Ala Val
290                 295                 300

Gly Val Thr Leu Cys Asn Leu Ala Thr Asp Val Asp Asp Pro Ala Glu
305                 310                 315                 320

Arg Leu Thr Ala Ile Ser Ala Ser Met Ser Gln Gly Lys Glu Leu Phe
                325                 330                 335

Gly Ser Leu Thr Ser Met Gln Ala Leu Ala Trp Ser Ala Val Asn Met
            340                 345                 350

```
Ser Pro Ile Ala Leu Thr Pro Val Pro Gly Phe Val Arg Phe Thr Pro
        355                 360                 365

Pro Pro Phe Asn Val Ile Ile Ser Asn Val Pro Gly Pro Arg Lys Thr
370                 375                 380

Met Tyr Trp Asn Gly Ser Arg Leu Asp Gly Ile Tyr Pro Thr Ser Val
385                 390                 395                 400

Val Leu Asp Gly Gln Ala Leu Asn Ile Thr Leu Thr Thr Asn Gly Gly
                405                 410                 415

Asn Leu Asp Phe Gly Val Ile Gly Cys Arg Arg Ser Val Pro Ser Leu
            420                 425                 430

Gln Arg Ile Leu Phe Tyr Leu Glu Ala Ala Leu Gly Glu Leu Glu Ala
        435                 440                 445

Ala Leu Leu
    450

<210> SEQ ID NO 75
<211> LENGTH: 1395
<212> TYPE: DNA
<213> ORGANISM: Rhodococcus opacus

<400> SEQUENCE: 75
```

| | | | | |
|---|---|---|---|---|
| atgccccctgc cgatgtcccc cctggactcc atgttcctgc tgggcgaaag ccgcgagcac | | | | 60 |
| ccgatgcacg tgggcggcgt cgaaatcttc cagctgcccg agggcgccga cacctacgac | | | | 120 |
| atgcgggcga tgctggaccg cgccctggcg gacggcgacg gcatcgtcac cccgcggctg | | | | 180 |
| gccaagcgcg cgcgccggtc gttcagctcg ctgggccagt ggtcctggga accgtggac | | | | 240 |
| gacatcgacc tgggccacca tatccggcac gacgccctgc cggcccctgg cggcgaggcc | | | | 300 |
| gaactgatgg cgctgtgctc gcgcctgcac ggctccctgc tggaccgcag ccggccgctg | | | | 360 |
| tgggagatgc atctgatcga aggcctgagc gacgccgct tcgccgtcta ccaagatc | | | | 420 |
| caccatgccg tcgcggacgg cgtgaccgcc atgaagatgc tgcggaacgc gctgagcgag | | | | 480 |
| aactcggacg accgcgacgt gccggccccc tggcagccgc gtggcccgcg gccccagcgc | | | | 540 |
| acccccctcca gcaagggctt ctccctgagc ggcctggccg gctcgaccct gcggaccgcg | | | | 600 |
| cgcgagaccg tcggcgaagt ggccggcctg gtccggccc tggcgggcac cgtgagccgg | | | | 660 |
| gccttccgcg accagggcgg cccgctggcc ctgtcggcgc cgaagaccc cttcaacgtc | | | | 720 |
| cccatcaccg gcgcccgcca gttcgccgcg cagtcgtggc cgctggaacg cctgcggctg | | | | 780 |
| gtggccaagc tgtcggactc caccatcaac gacgtcgtgc tggccatgtc gtccggcgcg | | | | 840 |
| ctgcggtcct acctggagga ccagaacgcc ctgccggcgg accccctgat cgcgatggtc | | | | 900 |
| ccggtgtccc tgaagagcca gcgcgaagcc gcgaccggca acaacatcgg cgtcctgatg | | | | 960 |
| tgcaacctgg caccccacct gcgggagccg gcgaccgcc tggaaaccat ccggaccagc | | | | 1020 |
| atgcgcgagg gcaaggaagc ctatggctcg atgaccgcga cccagatcct ggccatgtcc | | | | 1080 |
| gcgctgggcg ccgcgccgat cggcgccagc atgctgttcg ccataactc gcgcgtccgg | | | | 1140 |
| ccgcccttca acctgatcat ctccaacgtg ccggcccca gctcgccgct gtactggaac | | | | 1200 |
| ggcgcccgcc tggacgcgat ctatccgctg agcgtcccg tggacggcca gggcctgaac | | | | 1260 |
| atcacctgca cctcgaacga cgacatcatc tccttcggcg tcaccggctg ccggtccgcc | | | | 1320 |
| gtgccggacc tgaagagcat ccccgcgcgc ctgggccatg agctgcgggc cctggaacgc | | | | 1380 |
| gcggtgggca tctga | | | | 1395 |

<210> SEQ ID NO 76

```
<211> LENGTH: 464
<212> TYPE: PRT
<213> ORGANISM: Rhodococcus opacus

<400> SEQUENCE: 76
```

| | | | | | | | | | | | | | | |
|---|---|---|---|---|---|---|---|---|---|---|---|---|---|---|
| Met | Pro | Leu | Pro | Met | Ser | Pro | Leu | Asp | Ser | Met | Phe | Leu | Leu | Gly | Glu |
| 1 | | | | 5 | | | | | 10 | | | | | 15 | |

| Ser | Arg | Glu | His | Pro | Met | His | Val | Gly | Gly | Val | Glu | Ile | Phe | Gln | Leu |
|---|---|---|---|---|---|---|---|---|---|---|---|---|---|---|---|
| | | | 20 | | | | 25 | | | | | 30 | | | |

| Pro | Glu | Gly | Ala | Asp | Thr | Tyr | Asp | Met | Arg | Ala | Met | Leu | Asp | Arg | Ala |
|---|---|---|---|---|---|---|---|---|---|---|---|---|---|---|---|
| | | | 35 | | | | | 40 | | | | | 45 | | |

| Leu | Ala | Asp | Gly | Asp | Gly | Ile | Val | Thr | Pro | Arg | Leu | Ala | Lys | Arg | Ala |
|---|---|---|---|---|---|---|---|---|---|---|---|---|---|---|---|
| | 50 | | | | | 55 | | | | | 60 | | | | |

| Arg | Arg | Ser | Phe | Ser | Ser | Leu | Gly | Gln | Trp | Ser | Trp | Glu | Thr | Val | Asp |
|---|---|---|---|---|---|---|---|---|---|---|---|---|---|---|---|
| 65 | | | | | 70 | | | | | 75 | | | | | 80 |

| Asp | Ile | Asp | Leu | Gly | His | His | Ile | Arg | His | Asp | Ala | Leu | Pro | Ala | Pro |
|---|---|---|---|---|---|---|---|---|---|---|---|---|---|---|---|
| | | | | 85 | | | | | 90 | | | | | 95 | |

| Gly | Gly | Glu | Ala | Glu | Leu | Met | Ala | Leu | Cys | Ser | Arg | Leu | His | Gly | Ser |
|---|---|---|---|---|---|---|---|---|---|---|---|---|---|---|---|
| | | | | 100 | | | | | 105 | | | | | 110 | |

| Leu | Leu | Asp | Arg | Ser | Arg | Pro | Leu | Trp | Glu | Met | His | Leu | Ile | Glu | Gly |
|---|---|---|---|---|---|---|---|---|---|---|---|---|---|---|---|
| | | | 115 | | | | | 120 | | | | | 125 | | |

| Leu | Ser | Asp | Gly | Arg | Phe | Ala | Val | Tyr | Thr | Lys | Ile | His | His | Ala | Val |
|---|---|---|---|---|---|---|---|---|---|---|---|---|---|---|---|
| | 130 | | | | | 135 | | | | | 140 | | | | |

| Ala | Asp | Gly | Val | Thr | Ala | Met | Lys | Met | Leu | Arg | Asn | Ala | Leu | Ser | Glu |
|---|---|---|---|---|---|---|---|---|---|---|---|---|---|---|---|
| 145 | | | | | 150 | | | | | 155 | | | | | 160 |

| Asn | Ser | Asp | Asp | Arg | Asp | Val | Pro | Ala | Pro | Trp | Gln | Pro | Arg | Gly | Pro |
|---|---|---|---|---|---|---|---|---|---|---|---|---|---|---|---|
| | | | | 165 | | | | | 170 | | | | | 175 | |

| Arg | Pro | Gln | Arg | Thr | Pro | Ser | Ser | Lys | Gly | Phe | Ser | Leu | Ser | Gly | Leu |
|---|---|---|---|---|---|---|---|---|---|---|---|---|---|---|---|
| | | | 180 | | | | | 185 | | | | | 190 | | |

| Ala | Gly | Ser | Thr | Leu | Arg | Thr | Ala | Arg | Glu | Thr | Val | Gly | Glu | Val | Ala |
|---|---|---|---|---|---|---|---|---|---|---|---|---|---|---|---|
| | 195 | | | | | 200 | | | | | 205 | | | | |

| Gly | Leu | Val | Pro | Ala | Leu | Ala | Gly | Thr | Val | Ser | Arg | Ala | Phe | Arg | Asp |
|---|---|---|---|---|---|---|---|---|---|---|---|---|---|---|---|
| | 210 | | | | | 215 | | | | | 220 | | | | |

| Gln | Gly | Gly | Pro | Leu | Ala | Leu | Ser | Ala | Pro | Lys | Thr | Pro | Phe | Asn | Val |
|---|---|---|---|---|---|---|---|---|---|---|---|---|---|---|---|
| 225 | | | | | 230 | | | | | 235 | | | | | 240 |

| Pro | Ile | Thr | Gly | Ala | Arg | Gln | Phe | Ala | Ala | Gln | Ser | Trp | Pro | Leu | Glu |
|---|---|---|---|---|---|---|---|---|---|---|---|---|---|---|---|
| | | | 245 | | | | | 250 | | | | | 255 | | |

| Arg | Leu | Arg | Leu | Val | Ala | Lys | Leu | Ser | Asp | Ser | Thr | Ile | Asn | Asp | Val |
|---|---|---|---|---|---|---|---|---|---|---|---|---|---|---|---|
| | | | 260 | | | | | 265 | | | | | 270 | | |

| Val | Leu | Ala | Met | Ser | Ser | Gly | Ala | Leu | Arg | Ser | Tyr | Leu | Glu | Asp | Gln |
|---|---|---|---|---|---|---|---|---|---|---|---|---|---|---|---|
| | 275 | | | | | 280 | | | | | 285 | | | | |

| Asn | Ala | Leu | Pro | Ala | Asp | Pro | Leu | Ile | Ala | Met | Val | Pro | Val | Ser | Leu |
|---|---|---|---|---|---|---|---|---|---|---|---|---|---|---|---|
| | 290 | | | | | 295 | | | | | 300 | | | | |

| Lys | Ser | Gln | Arg | Glu | Ala | Ala | Thr | Gly | Asn | Asn | Ile | Gly | Val | Leu | Met |
|---|---|---|---|---|---|---|---|---|---|---|---|---|---|---|---|
| 305 | | | | | 310 | | | | | 315 | | | | | 320 |

| Cys | Asn | Leu | Gly | Thr | His | Leu | Arg | Glu | Pro | Ala | Asp | Arg | Leu | Glu | Thr |
|---|---|---|---|---|---|---|---|---|---|---|---|---|---|---|---|
| | | | | 325 | | | | | 330 | | | | | 335 | |

| Ile | Arg | Thr | Ser | Met | Arg | Glu | Gly | Lys | Glu | Ala | Tyr | Gly | Ser | Met | Thr |
|---|---|---|---|---|---|---|---|---|---|---|---|---|---|---|---|
| | | | 340 | | | | | 345 | | | | | 350 | | |

| Ala | Thr | Gln | Ile | Leu | Ala | Met | Ser | Ala | Leu | Gly | Ala | Ala | Pro | Ile | Gly |
|---|---|---|---|---|---|---|---|---|---|---|---|---|---|---|---|
| | | 355 | | | | | 360 | | | | | 365 | | | |

| Ala | Ser | Met | Leu | Phe | Gly | His | Asn | Ser | Arg | Val | Arg | Pro | Pro | Phe | Asn |
|---|---|---|---|---|---|---|---|---|---|---|---|---|---|---|---|
| | 370 | | | | | 375 | | | | | 380 | | | | |

| Leu | Ile | Ile | Ser | Asn | Val | Pro | Gly | Pro | Ser | Ser | Pro | Leu | Tyr | Trp | Asn |
|---|---|---|---|---|---|---|---|---|---|---|---|---|---|---|---|

```
                385                 390                 395                 400
Gly Ala Arg Leu Asp Ala Ile Tyr Pro Leu Ser Val Pro Val Asp Gly
                    405                 410                 415

Gln Gly Leu Asn Ile Thr Cys Thr Ser Asn Asp Ile Ile Ser Phe
                420                 425                 430

Gly Val Thr Gly Cys Arg Ser Ala Val Pro Asp Leu Lys Ser Ile Pro
                435                 440                 445

Ala Arg Leu Gly His Glu Leu Arg Ala Leu Glu Arg Ala Val Gly Ile
            450                 455                 460
```

<210> SEQ ID NO 77
<211> LENGTH: 1407
<212> TYPE: DNA
<213> ORGANISM: Rhodococcus opacus

<400> SEQUENCE: 77

```
atggccccga ccgactccct gttcctgctg ggcgaatccc gcgagcaccc gatgcacgtg      60
ggcggcctgg cggtcttcac cccggcgag ggcagctcgg ccgcgacgt ccgcgccatg       120
ttcgacgccg cgctggtcgg cgaccgggtg ccgcgccgt ccgcaagcg ggcccgccgg       180
agcgtgacct cgctgggcca gtgggctgg acaccctgc cgacgacga ggtcgacctg       240
gaacaccatg tgcgccggga cgccctgccg cagccgggtg gcatggcgga actgatgacc     300
ctggtctccc gcctgcatgg caccctgctg accgcagcc ggccgctgtg ggagatgcac       360
ctgatcgaag gcctggccga cggccggtac gcggtgtata ccaagatcca ccatgccctg     420
gcggacggcg ccagcgcgat cgcctgctg cgggactcga tgtccgagga cccgcatcgc       480
cggaacatgc cgacccctg gcagccgcgc aacccctgt cggccgtccc ggacgccggc       540
gtcgcggtga cccccggccc cggcagcgcc ctgcccgcga tggcctggga cgccgcgcg       600
tccgccgcgg gcgaagtcgc cggcctgctg ccggccgcgc tgggcaccgt ggaccgggcc     660
ctgcacggca aggcggcgc cctgtccctg accgcgccgc ataccctgtt caacgtcccc       720
atcagcggcg cccgccacgt ggccgcgcgg tcgttcccga tcgagcgcat ccggctgctg     780
gccaagcatg ccgacgcgac catcaacgac atcgtgctga ccatgtgcgc cggcaccctg     840
cgcgcgtacc tgcacacccg cgacgccctg ccggacaacc cctgatcgc gatggtcccg       900
gtgagcctgc cgcccccga accggcacc ggcgaccgcg cccctggcgg caaccgggtc        960
ggcgtgctga tgtgcaacct ggccacccac ctgccggacc ccgcgcatcg cctggagacc    1020
gtccggaact gcatgaacga aggcaaggcc gcgctgcagg ccatgtcgcc ggcgcaggtc    1080
ctggccatgt ccgcgctggg cgccgcgccg ctgggcgtgg agatgttcct gggccgccgg    1140
ggccccctgc gccgcccctt caacgtcgtg atctcgaacg tggcgggccc cgcgcacccc    1200
ctgtactgga acggcgcccg gctggaatcc ctgtatccgc tgagcatccc caccaccggc    1260
caggccctga catcacctg cacctccagc gacgaccaga tcgtcttcgg cctgaccggc     1320
tgccgccgga ccgtgccgga cctgcacccc atgctggacc agctggacgc ggagctggac    1380
ctgctggaaa ccgcggtcgg cctgtga                                         1407
```

<210> SEQ ID NO 78
<211> LENGTH: 468
<212> TYPE: PRT
<213> ORGANISM: Rhodococcus opacus

<400> SEQUENCE: 78

Met Ala Pro Thr Asp Ser Leu Phe Leu Leu Gly Glu Ser Arg Glu His

-continued

```
1               5                   10                  15
Pro Met His Val Gly Leu Ala Val Phe Thr Pro Ala Glu Gly Ser
            20                  25                  30

Ser Ala Ala Asp Val Arg Ala Met Phe Asp Ala Ala Leu Val Gly Asp
            35                  40                  45

Arg Val Ala Ala Pro Phe Arg Lys Arg Ala Arg Ser Val Thr Ser
    50                  55                  60

Leu Gly Gln Trp Gly Trp Asp Thr Leu Arg Asp Asp Glu Val Asp Leu
65                  70                  75                  80

Glu His His Val Arg Arg Asp Ala Leu Pro Gln Pro Gly Gly Met Ala
                85                  90                  95

Glu Leu Met Thr Leu Val Ser Arg Leu His Gly Thr Leu Leu Asp Arg
                100                 105                 110

Ser Arg Pro Leu Trp Glu Met His Leu Ile Glu Gly Leu Ala Asp Gly
            115                 120                 125

Arg Tyr Ala Val Tyr Thr Lys Ile His His Ala Leu Ala Asp Gly Ala
    130                 135                 140

Ser Ala Met Arg Leu Leu Arg Asp Ser Met Ser Glu Asp Pro His Arg
145                 150                 155                 160

Arg Asn Met Pro Thr Pro Trp Gln Pro Arg Asn Pro Leu Ser Ala Val
                165                 170                 175

Pro Asp Ala Gly Val Ala Val Thr Pro Gly Pro Gly Ser Ala Leu Pro
                180                 185                 190

Ala Met Ala Trp Asp Ala Ala Arg Ser Ala Ala Gly Glu Val Ala Gly
            195                 200                 205

Leu Leu Pro Ala Ala Leu Gly Thr Val Asp Arg Ala Leu His Gly Lys
210                 215                 220

Gly Gly Ala Leu Ser Leu Thr Ala Pro His Thr Leu Phe Asn Val Pro
225                 230                 235                 240

Ile Ser Gly Ala Arg His Val Ala Ala Arg Ser Phe Pro Ile Glu Arg
                245                 250                 255

Ile Arg Leu Leu Ala Lys His Ala Asp Ala Thr Ile Asn Asp Ile Val
            260                 265                 270

Leu Thr Met Cys Ala Gly Thr Leu Arg Ala Tyr Leu His Thr Arg Asp
            275                 280                 285

Ala Leu Pro Asp Asn Pro Leu Ile Ala Met Val Pro Val Ser Leu Arg
    290                 295                 300

Ala Pro Glu Thr Gly Thr Gly Asp Arg Ala Pro Gly Gly Asn Arg Val
305                 310                 315                 320

Gly Val Leu Met Cys Asn Leu Ala Thr His Leu Pro Asp Pro Ala His
                325                 330                 335

Arg Leu Glu Thr Val Arg Asn Cys Met Asn Glu Gly Lys Ala Ala Leu
                340                 345                 350

Gln Ala Met Ser Pro Ala Gln Val Leu Ala Met Ser Ala Leu Gly Ala
            355                 360                 365

Ala Pro Leu Gly Val Glu Met Phe Leu Gly Arg Arg Gly Pro Leu Arg
    370                 375                 380

Pro Pro Phe Asn Val Val Ile Ser Asn Val Ala Gly Pro Arg Thr Pro
385                 390                 395                 400

Leu Tyr Trp Asn Gly Ala Arg Leu Glu Ser Leu Tyr Pro Leu Ser Ile
                405                 410                 415

Pro Thr Thr Gly Gln Ala Leu Asn Ile Thr Cys Thr Ser Ser Asp Asp
            420                 425                 430
```

```
Gln Ile Val Phe Gly Leu Thr Gly Cys Arg Arg Thr Val Pro Asp Leu
        435                 440                 445

His Pro Met Leu Asp Gln Leu Asp Ala Glu Leu Asp Leu Leu Glu Thr
    450                 455                 460

Ala Val Gly Leu
465

<210> SEQ ID NO 79
<211> LENGTH: 11299
<212> TYPE: DNA
<213> ORGANISM: Artificial Sequence
<220> FEATURE:
<223> OTHER INFORMATION: pCM132

<400> SEQUENCE: 79 gacccttttcc gacgctcacc gggctggttg ccctcgccgc tgggctggcg gccgtctatg      60
gccctgcaaa cgcgccagaa cgccgtcga  agccgtgtgc gagacaccgc ggccgccggc     120
gttgtggata cctcgcggaa aacttggccc tcactgacag atgaggggcg gacgttgaca     180
cttgaggggc cgactcaccc ggcgcggcgt tgacagatga ggggcaggct cgatttcggc     240
cggcgacgtg gagctggcca gcctcgcaaa tcggcgaaaa cgcctgattt tacgcgagtt     300
tcccacagat gatgtggaca agcctgggga taagtgccct gcggtattga cacttgaggg     360
gcgcgactac tgacagatga ggggcgcgat ccttgacact tgaggggcag agtgctgaca     420
gatgaggggc gcacctattg acatttgagg ggctgtccac aggcagaaaa tccagcattt     480
gcaagggttt ccgcccgttt ttcggccacc gctaacctgt cttttaacct gcttttaaac     540
caatatttat aaaccttgtt tttaaccagg gctgcgccct gtgcgcgtga ccgcgcacgc     600 cgaaggggg tgccccccct tctcgaaccc tcccggcccg ctaacgcggg cctcccatcc     660 ccccagggc tgcgcccctc ggccgcgaac ggcctcaccc caaaaatggc agccaagctg      720
accacttctg cgctcggccc ttccggctgg ctggtttatt gctgataaat ctggagccgg     780
tgagcgtggg tctcgcggta tcattgcagc actggggcca gatggtaagc cctcccgtat     840
cgtagttatc tacacgacgg ggagtcaggc aactatggat gaacgaaata gacagatcgc     900
tgagataggt gcctcactga ttaagcattg gtaactgtca gaccaagttt actcatatat     960
actttagatt gatttaaaac ttcatttttta atttaaaagg atctaggtga agatcctttt    1020
tgataatctc atgaccaaaa tcccttaacg tgagttttcg ttccactgag cgtcagaccc    1080
cgtagaaaag atcaaggat cttcttgaga tcctttttttt ctgcgcgtaa tctgctgctt     1140
gcaaacaaaa aaaccaccgc taccagcggt ggtttgtttg ccggatcaag agctaccaac    1200 tcttttttccg aaggtaactg gcttcagcag agcgcagata ccaaatactg tccttctagt    1260
gtagccgtag ttaggccacc acttcaagaa ctctgtagca ccgcctacat acctcgctct    1320
gctaatcctg ttaccagtgg ctgctgccag tggcgataag tcgtgtctta ccgggttgga    1380
ctcaagacga tagttaccgg ataaggcgca gcggtcgggc tgaacggggg gttcgtgcac    1440
acagcccagc ttggagcgaa cgacctacac cgaactgaga tacctacagc gtgagctatg    1500
agaaagcgcc acgcttcccg aagggagaaa ggcggacagg tatccggtaa gcggcagggt    1560
cggaacagga gagcgcacga gggagcttcc agggggaaac gcctggtatc tttatagtcc    1620
tgtcgggttt cgccacctct gacttgagcg tcgatttttg tgatgctcgt caggggggcg    1680
gagcctatgg aaaaacgcca gcaacgcggc ctttttacgg ttcctggcct tttgctggcc    1740
ttttgctcac atgttctttc ctgcgttatc ccctgattct gtggataacc gtattaccgc    1800
```

```
ctttgagtga gctgataccg ctcgccgcag ccgaacgacc gagcgcagcg agtcagtgag    1860
cgaggaagcg gaagagcgcc caatacgcaa accgcctctc cccgcgcgtt ggccgattca    1920
ttaatgcagc tggcacgaca ggtttcccga ctggaaagcg ggcagtgagc gcaacgcaat    1980
taatgtgagt tagctcactc attaggcacc ccaggcttta cactttatgc ttccggctcg    2040
tatgttgtgt ggaattgtga gcggataaca atttcacaca ggaaacagct atgaccatga    2100
ttacgccaag cttgcatgcc tgcaggtcga ctctagagga tcaattcggc ttccaccgga    2160
attagcttga aatagtacat aatggatttc cttacgcgaa atacgggcag acatggcctg    2220
cccggttatt attattttg acaccagacc aactggtaat ggtagcgacc ggcgctcagc    2280
tgtaattccg ccgatactga cgggctccag gagtcgtcgc caccaatccc catatggaaa    2340
ccgtcgatat tcagccatgt gccttcttcc gcgtgcagca gatggcgatg ctggtttcc    2400
atcagttgct gttgactgta gcggctgatg ttgaactgga agtcgccgcg ccactggtgt    2460
gggccataat tcaattcgcg cgtcccgcag cgcagaccgt tttcgctcgg gaagacgtac    2520
ggggtataca tgtctgacaa tggcagatcc cagcggtcaa acaggcggc agtaaggcgg    2580
tcggatagt tttcttgcgg ccctaatccg agccagttta cccgctctgc tacctgcgcc    2640
agctggcagt tcaggccaat ccgcgccgga tgcggtgtat cgctcgccac ttcaacatca    2700
acggtaatcg ccatttgacc actaccatca atccggtagg ttttccggct gataaataag    2760
gttttcccct gatgctgcca cgcgtgagcg gtcgtaatca gcaccgcatc agcaagtgta    2820
tctgccgtgc actgcaacaa cgctgcttcg gcctggtaat ggcccgccgc cttccagcgt    2880
tcgacccagg cgttagggtc aatgcgggtc gcttcactta cgccaatgtc gttatccagc    2940
ggtgcacggg tgaactgatc gcgcagcggc gtcagcagtt gtttttatc gccaatccac    3000
atctgtgaaa gaaagcctga ctggcggtta aattgccaac gcttattacc cagctcgatg    3060
caaaaatcca tttcgctggt ggtcagatgc gggatggcgt gggacgcggc ggggagcgtc    3120
acactgaggt tttccgccag acgccactgc tgccaggcgc tgatgtgccc ggcttctgac    3180
catgcggtcg cgttcggttg cactacgcgt actgtgagcc agagttgccc ggcgctctcc    3240
ggctgcggta gttcaggcag ttcaatcaac tgtttacctt gtggagcgac atccagaggc    3300
acttcaccgc ttgccagcgg cttaccatcc agcgccacca tccagtgcag gagctcgtta    3360
tcgctatgac ggaacaggta ttcgctggtc acttcgatgg tttgcccgga taaacggaac    3420
tggaaaaact gctgctggtg ttttgcttcc gtcagcgctg gatgcggcgt gcggtcggca    3480
aagaccagac cgttcataca gaactggcga tcgttcggcg tatcgccaaa atcaccgccg    3540
taagccgacc acgggttgcc gttttcatca tatttaatca gcgactgatc cacccagtcc    3600
cagacgaagc cgcccgtaa acggggatac tgacgaaacg cctgccagta tttagcgaaa    3660
ccgccaagac tgttacccat cgcgtgggcg tattcgcaaa ggatcagcgg gcgcgtctct    3720
ccaggtagcg aaagccattt tttgatggac catttcggca cagccgggaa gggctggtct    3780
tcatccacgc gcgcgtacat cgggcaaata atatcggtgg ccgtggtgtc ggctccgccg    3840
ccttcatact gcaccgggcg ggaaggatcc acagatttga tccagcgata cagcgcgtcg    3900
tgattagcgc cgtggcctga ttcattcccc agcgaccaga tgatcacact cgggtgatta    3960
cgatcgcgct gcaccattcg cgttacgcgt tcgctcatcg ccggtagcca gcgcggatca    4020
tcggtcagac gattcattgg caccatgccg tgggtttcaa tattggcttc atccaccaca    4080
tacaggccgt agcggtcgca cagcgtgtac cacagcggat ggttcggata atgcgaacag    4140
```

```
cgcacggcgt taaagttgtt ctgcttcatc agcaggatat cctgcaccat cgtctgctca   4200
tccatgacct gaccatgcag aggatgatgc tcgtgacggt taacgcctcg aatcagcaac   4260
ggcttgccgt tcagcagcag cagaccattt tcaatccgca cctcgcggaa accgacatcg   4320
caggcttctg cttcaatcag cgtgccgtcg cggtgtgca gttcaaccac cgcacgatag    4380
agattcggga tttcggcgct ccacagtttc gggttttcga cgttcagacg tagtgtgacg   4440
cgatcggcat aaccaccacg ctcatcgata atttcaccgc cgaaaggcgc ggtgccgctg   4500
gcgacctgcg tttcacccctg ccataaagaa actgttaccc gtaggtagtc acgcaactcg  4560
ccgcacatct gaacttcagc ctccagtaca gcgcggctga aatcatcatt aaagcgagtg   4620
gcaacatgga aatcgctgat ttgtgtagtc ggtttatgca gcaacgagac gtcacggaaa   4680
atgccgctca tccgccacat atcctgatct tccagataac tgccgtcact ccaacgcagc   4740
accatcaccg cgaggcggtt ttctccggcg cgtaaaaatg cgctcaggtc aaattcagac   4800
ggcaaacgac tgtcctggcc gtaaccgacc cagcgcccgt tgcaccacag atgaaacgcc   4860
gagttaacgc catcaaaaat aattcgcgtc tggccttcct gtagccagct ttcatcaaca   4920
ttaaatgtga gcgagtaaca acccgtcgga ttctccgtgg gaacaaacgg cggattgacc   4980
gtaatgggat aggttacgtt ggtgtagatg gcgcatcgt aaccgtgcat ctgccagttt    5040
gaggggacga cgacagtatc ggcctcagga agatcgcact ccagccagct ttccggcacc   5100
gcttctggtg ccggaaacca ggcaaagcgc cattcgccat tcaggctgcg caactgttgg   5160
gaagggcgat cggtgcgggc ctcttcgcta ttacgccagc tggcgaaagg gggatgtgct   5220
gcaaggcgat taagttgggt aacgccaggg ttttcccggt cgacccgtaa tcttacgtca   5280
gtaacttcca cagtagttca ccaccttttc cctatagatc ttccgtgcag tttaagccga   5340
attgatcccc gggtaccgag ctcgaatcta gaattccctg cttttcctgat gcaaaaacga   5400 ggctagttta ccgtatctgt gggggatgg cttgtagata tgacgacagg aagagtttgt   5460
agaaacgcaa aaaggccatc cgtcaggatg gccttctgct taatttgatg cctggcagtt   5520
tatggcgggc gtcctgcccg ccacccctccg ggccgttgct tcgcaacgtt caaatccgct   5580
cccggcggat ttgtcctact caggagagcg ttcaccgaca aacaacagat aaaacgaaag   5640
gcccagtctt tcgactgagc cttcgttttt atttgatgcc tggcagttcc ctactctcgc   5700
atggggagac cccacactac catcggcgct acggcgtttc acttctgagt tcggcatggg   5760
gtcaggtggg accaccgcgc tactgccgcc aggcaaattc tgttttatca gaccgcttct   5820
gcgttctgat ttaatctgta tcaggctgaa aaattcactg gcgtcgtttt acaacgtcg    5880 tgactgggaa aaccctggcg ttacccaact taatcgcctt gcagcacatc ccccctttcgc  5940 cagctggcgt aatagcgaag aggcccgcac cgatcgccct tcccaacagt tgcgcagcct   6000
gaatggcgaa tggcgcctga tgcggtattt tctccttacg catctgtgcg gtatttcaca   6060
ccgcatatgg tgcactctca gtacaatctg ctctgatgcc gcatagttaa gccagccccg   6120
acacccgcca cacccgctg acgcgccctg acgggcttgt ctgctcccgg catccgctta    6180
cagacaagct gtgaccgtct ccgggagctg catgtgtcag aggttttcac cgtcatcacc   6240
gaaacgcgcg agacgaaagg gcctcgtgat acgcctattt ttataggtta atgtcatgat   6300
aataatggtt tcttagcacc ctttctcggt ccttcaacgt tcctgacaac gagcctcctt   6360
ttcgccaatc catcgacaat caccgcgagt ccctgctcga acgctgcgtc cggaccggct   6420
tcgtcgaagg cgtctatcgc ggcccgcaac agcggcgaga gcggagcctg ttcaacggtg   6480
ccgccgcgct cgccggcatc gctgtcgccg gcctgctcct caagcacggc cccaacagtg   6540
```

```
aagtagctga ttgtcatcag cgcattgacg gcgtccccgg ccgaaaaacc cgcctcgcag    6600
aggaagcgaa gctgcgcgtc ggccgtttcc atctgcggtg cgcccggtcg cgtgccggca    6660
tggatgcgcg cgccatcgcg gtaggcgagc agcgcctgcc tgaagctgcg ggcattcccg    6720
atcagaaatg agcgccagtc gtcgtcggct ctcggcaccg aatgcgtatg attctccgcc    6780
agcatggctt cggccagtgc gtcgagcagc gcccgcttgt tcctgaagtg ccagtaaagc    6840
gccggctgct gaaccccaa ccgttccgcc agtttgcgtg tcgtcagacc gtctacgccg    6900
acctcgttca acaggtccag ggcggcacgg atcactgtat tcggctgcaa ctttgtcatg    6960
attgacactt tatcactgat aaacataata tgtccaccaa cttatcagtg ataaagaatc    7020
cgcgcgttca atcggaccag cggaggctgg tccggaggcc agacgtgaaa cccaacatac    7080
ccctgatcgt aattctgagc actgtcgcgc tcgacgctgt cggcatcggc ctgattatgc    7140
cggtgctgcc gggcctcctg cgcgatctgg ttcactcgaa cgacgtcacc gcccactatg    7200
gcattctgct ggcgctgtat gcgttggtgc aatttgcctg cgcacctgtg ctgggcgcgc    7260
tgtcggatcg tttcgggcgg cggccaatct tgctcgtctc gctggccggc gccactgtcg    7320
actacgccat catggcgaca gcgccttttcc tttgggttct ctatatcggg cggatcgtgg    7380
ccggcatcac cggggcgact ggggcggtag ccggcgctta tattgccgat gacctgcagg    7440
gggggggggg cgctgaggtc tgcctcgtga agaaggtgtt gctgactcat accaggcctg    7500
aatcgcccca tcatccagcc agaaagtgag ggagccacgg ttgatgagag ctttgttgta    7560
ggtggaccag ttggtgattt tgaacttttg ctttgccacg gaacggtctg cgttgtcggg    7620
aagatgcgtg atctgatcct tcaactcagc aaaagttcga tttattcaac aaagccgccg    7680
tcccgtcaag tcagcgtaat gctctgccag tgttacaacc aattaaccaa ttctgattag    7740
aaaaactcat cgagcatcaa atgaaactgc aatttattca tatcaggatt atcaatacca    7800 tattttttgaa aaagccgttt ctgtaatgaa ggagaaaact caccgaggca gttccatagg    7860
atggcaagat cctggtatcg gtctgcgatt ccgactcgtc caacatcaat acaacctatt    7920
aatttcccct cgtcaaaaat aaggttatca agtgagaaat caccatgagt gacgactgaa    7980
tccggtgaga atggcaaaag cttatgcatt tctttccaga cttgttcaac aggccagcca    8040
ttacgctcgt catcaaaatc actcgcatca accaaaccgt tattcattcg tgattgcgcc    8100
tgagcgagac gaaatacgcg atcgctgtta aaaggacaat tacaaacagg aatcgaatgc    8160
aaccggcgca ggaacactgc cagcgcatca acaatatttt cacctgaatc aggatattct    8220
tctaatacct ggaatgctgt ttccccgggg atcgcagtgg tgagtaacca tgcatcatca    8280
ggagtacgga taaaatgctt gatggtcgga agaggcataa attccgtcag ccagtttagt    8340
ctgaccatct catctgtaac atcattggca acgctacctt tgccatgttt cagaaacaac    8400
tctggcgcat cgggcttccc atacaatcga tagattgtcg cacctgattg cccgacatta    8460
tcgcgagccc atttataccc atataaatca gcatccatgt tggaatttaa tcgcggcctc    8520
gagcaagacg tttcccgttg aatatggctc ataacacccc ttgtattact gtttatgtaa    8580
gcagacagtt ttattgttca tgatgatata ttttttatctt gtgcaatgta acatcagaga    8640
ttttgagaca caacgtggct ttccccccccc ccctgcagg tccgacacgg ggatggatgg    8700
cgttcccgat catggtcctg cttgcttcgg gtggcatcgg aatgccggcg ctgcaagcaa    8760
tgttgtccag gcaggtggat gaggaacgtc aggggcagct gcaaggctca ctggcggcgc    8820
tcaccagcct gacctcgatc gtcggacccc tcctcttcac ggcgatctat gcggcttcta    8880
```

```
taacaacgtg gaacgggtgg gcatggattg caggcgctgc cctctacttg ctctgcctgc    8940
cggcgctgcg tcgcgggctt tggagcggcg cagggcaacg agccgatcgc tgatcgtgga    9000
aacgataggc ctatgccatg cgggtcaagg cgacttccgg caagctatac gcgccctaga    9060
attgtcaatt ttaatcctct gtttatcggc agttcgtaga gcgcgccgtg cgtcccgagc    9120
gatactgagc gaagcaagtg cgtcgagcag tgcccgcttg ttcctgaaat gccagtaaag    9180
cgctggctgc tgaaccccca gccggaactg accccacaag gccctagcgt ttgcaatgca    9240
ccaggtcatc attgacccag gcgtgttcca ccaggccgct gcctcgcaac tcttcgcagg    9300
cttcgccgac ctgctcgcgc cacttcttca cgcgggtgga atccgatccg cacatgaggc    9360
ggaaggtttc cagcttgagc gggtacggct cccggtgcga gctgaaatag tcgaacatcc    9420
gtcgggccgt cggcgacagc ttgcggtact tctcccatat gaatttcgtg tagtggtcgc    9480
cagcaaacag cacgacgatt tcctcgtcga tcaggacctg caacgggac gttttcttgc    9540
cacggtccag gacgcggaag cggtgcagca gcgacaccga ttccaggtgc ccaacgcggt    9600
cggacgtgaa gcccatcgcc gtcgcctgta ggcgcgacag gcattcctcg gccttcgtgt    9660
aataccggcc attgatcgac cagcccaggt cctggcaaag ctcgtagaac gtgaaggtga    9720
tcggctcgcc gataggggtg cgcttcgcgt actccaacac ctgctgccac accagttcgt    9780
catcgtcggc ccgcagctcg acgccggtgt aggtgatctt cacgtccttg ttgacgtgga    9840
aaatgacctt gttttgcagc gcctcgcgcg ggattttctt gttgcgcgtg gtgaacaggg    9900
cagagcgggc cgtgtcgttt ggcatcgctc gcatcgtgtc cggccacggc gcaatatcga    9960
acaaggaaag ctgcatttcc ttgatctgct gcttcgtgtg tttcagcaac gcggcctgct   10020
tggcctcgct gacctgtttt gccaggtcct cgccggcggt ttttcgcttc ttggtcgtca   10080
tagttcctcg cgtgtcgatg gtcatcgact tcgccaaacc tgccgcctcc tgttcgagac   10140
gacgcgaacg ctccacggcg gccgatggcg cgggcagggc aggggagcc agttgcacgc   10200
tgtcgcgctc gatcttggcc gtagcttgct ggaccatcga gccgacggac tggaaggttt   10260
cgcggggcgc acgcatgacg gtgcggcttg cgatggtttc ggcatcctcg gcggaaaacc   10320
ccgcgtcgat cagttcttgc ctgtatgcct tccggtcaaa cgtccgattc attcaccctc   10380
cttgcgggat tgccccgact cacgccgggg caatgtgccc ttattcctga tttgacccgc   10440
ctggtgcctt ggtgtccaga taatccacct tatcggcaat gaagtcggtc ccgtagaccg   10500
tctggccgtc cttctcgtac ttggtattcc gaatcttgcc ctgcacgaat accagctccg   10560
cgaagtcgct cttcttgatg gagcgcatgg ggacgtgctt ggcaatcacg cgcacccccc   10620
ggccgtttta gcggctaaaa aagtcatggc tctgccctcg ggcggaccac gcccatcatg   10680
accttgccaa gctcgtcctg cttctcttcg atcttcgcca gcagggcgag gatcgtggca   10740
tcaccgaacc gcgccgtgcg cgggtcgtcg gtgagccaga gtttcagcag gccgcccagg   10800
cggcccaggt cgccattgat gcgggccagc tcgcggacgt gctcatagtc cacgacgccc   10860
gtgattttgt agccctggcc gacggccagc aggtaggcct acaggctcat gccggccgcc   10920
gccgcctttt cctcaatcgc tcttcgttcg tctggaaggc agtacacctt gataggtggg   10980
ctgcccttcc tggttggctt ggtttcatca gccatccgct tgccctcatc tgttacgccg   11040
gcggtagccg gccagcctcg cagagcagga ttcccgttga gcaccgccag gtgcgaataa   11100
gggacagtga agaaggaaca cccgctcgcg ggtgggccta cttcacctat cctgcccggc   11160
tgacgccgtt ggatacacca aggaaagtct acacgaaccc tttggcaaaa tcctgtatat   11220
cgtgcgaaaa aggatggata taccgaaaaa atcgctataa tgaccccgaa gcagggttat   11280
```
gcagcggaaa agatccgtc                                                  11299

<210> SEQ ID NO 80
<211> LENGTH: 7341
<212> TYPE: DNA
<213> ORGANISM: Artificial Sequence
<220> FEATURE:
<223> OTHER INFORMATION: pJSvec

<400> SEQUENCE: 80

| | |
|---|---|
| gacccttttcc gacgctcacc gggctggttg ccctcgccgc tgggctggcg gccgtctatg | 60 |
| gccctgcaaa cgcgccagaa cgccgtcga agccgtgtgc gagacaccgc ggccgccggc | 120 |
| gttgtggata cctcgcggaa aacttggccc tcactgacag atgaggggcg gacgttgaca | 180 |
| cttgaggggc cgactcaccc ggcgcggcgt tgacagatga ggggcaggct cgatttcggc | 240 |
| cggcgacgtg gagctggcca gcctcgcaaa tcggcgaaaa cgcctgattt tacgcgagtt | 300 |
| tcccacagat gatgtggaca gcctgggga taagtgccct gcggtattga cacttgaggg | 360 |
| gcgcgactac tgacagatga ggggcgcgat ccttgacact tgaggggcag agtgctgaca | 420 |
| gatgaggggc gcacctattg acatttgagg ggctgtccac aggcagaaaa tccagcattt | 480 |
| gcaagggttt ccgcccgttt ttcggccacc gctaacctgt cttttaacct gcttttaaac | 540 |
| caatatttat aaaccttgtt tttaaccagg ctgcgccct gtgcgcgtga ccgcgcacgc | 600 |
| cgaagggggg tgccccccct tctcgaaccc tcccggcccg ctaacgcggg cctcccatcc | 660 |
| ccccaggggc tgcgccctc ggccgcgaac ggcctcaccc caaaaatggc agccaagctg | 720 |
| accacttctg cgctcggccc ttccggctgg ctggtttatt gctgataaat ctggagccgg | 780 |
| tgagcgtggg tctcgcggta tcattgcagc actggggcca gatggtaagc cctcccgtat | 840 |
| cgtagttatc tacacgacgg ggagtcaggc aactatggat gaacgaaata gacagatcgc | 900 |
| tgagataggt gcctcactga ttaagcattg gtaactgtca gaccaagttt actcatatat | 960 |
| actttagatt gatttaaaac ttcatttta atttaaaagg atctaggtga agatccttt | 1020 |
| tgataatctc atgaccaaaa tcccttaacg tgagttttcg ttccactgag cgtcagaccc | 1080 |
| cgtagaaaag atcaaaggat cttcttgaga tcctttttt ctgcgcgtaa tctgctgctt | 1140 |
| gcaaacaaaa aaaccaccgc taccagcggt ggtttgtttg ccggatcaag agctaccaac | 1200 |
| tctttttccg aaggtaactg gcttcagcag agcgcagata ccaaatactg tccttctagt | 1260 |
| gtagccgtag ttaggccacc acttcaagaa ctctgtagca ccgcctacat acctcgctct | 1320 |
| gctaatcctg ttaccagtgg ctgctgccag tggcgataag tcgtgtctta ccgggttgga | 1380 |
| ctcaagacga tagttaccgg ataaggcgca gcggtcgggc tgaacggggg gttcgtgcac | 1440 |
| acagcccagc ttggagcgaa cgacctacac cgaactgaga tacctacagc gtgagctatg | 1500 |
| agaaagcgcc acgcttcccg aagggagaaa ggcggacagg tatccggtaa gcggcagggt | 1560 |
| cggaacagga gagcgcacga gggagcttcc agggggaaac gcctggtatc tttatagtcc | 1620 |
| tgtcgggttt cgccacctct gacttgagcg tcgatttttg tgatgctcgt caggggggcg | 1680 |
| gagcctatgg aaaaacgcca gcaacgcggc cttttacgg ttcctggcct tttgctggcc | 1740 |
| ttttgctcac atgttctttc ctgcgttatc ccctgattct gtggataacc gtattaccgc | 1800 |
| ctttgagtga gctgataccg ctcgccgcag ccgaacgacc gagcgcagcg agtcagtgag | 1860 |
| cgaggaagcg gaagagcgcc caatacgcaa accgcctctc cccgcgcgtt ggccgattca | 1920 |
| ttaatgcagc tggcaggaag cggcgatggc ggagctgaat tacattccca accgcgtggc | 1980 |

-continued

```
acaacaactg gcgggcaaac agtcgttgct gattggcgtt gccacctcca gtctggccct    2040
gcacgcgccg tcgcaaattg tcgcggcgat taaatctcgc gccgatcaac tgggtgccag    2100
cgtggtggtg tcgatggtag aacgaagcgg cgtcgaagcc tgtaaagcgg cggtgcacaa    2160
tcttctcgcg caacgcgtca gtgggctgat cattaactat ccgctggatg accaggatgc    2220
cattgctgtg gaagctgcct gcactaatgt tccggcgtta tttcttgatg tctctgacca    2280
gacacccatc aacagtatta ttttctccca tgaagacggt acgcgactgg gcgtggagca    2340
tctggtcgca ttgggtcacc agcaaatcgc gctgttagcg ggcccattaa gttctgtctc    2400
ggcgcgtctg cgtctggctg gctggcataa atatctcact cgcaatcaaa ttcagccgat    2460
agcggaacgg gaaggcgact ggagtgccat gtccggtttt caacaaacca tgcaaatgct    2520
gaatgagggc atcgttccca ctgcgatgct ggttgccaac gatcagatgg cgctgggcgc    2580
aatgcgcgcc attaccgagt ccgggctgcg cgttggtgcg gatatctcgg tagtgggata    2640
cgacgatacc gaagacagct catgttatat cccgccgtca accaccatca aacaggattt    2700
tcgcctgctg gggcaaacca gcgtggaccg cttgctgcaa ctctctcagg gccaggcggt    2760
gaagggcaat cagctgttgc ccgtctcact ggtgaaaaga aaaccaccc tggcgcccaa    2820 tacgcaaacc gcctctcccc gcgcgttggc cgattcatta atgcagctgg cacgacaggt    2880
ttcccgactg gaaagcgggc agtgagcgca acgcaattaa tgtgagttag cgcgaattga    2940
tctggtttga cagcttatca tcgactcac ggtgcaccaa tgcttctggc gtcaggcagc    3000
catcggaagc tgtggtatgg ctgtgcaggt cgtaaatcac tgcataattc gtgtcgctca    3060
aggcgcactc ccgttctgga taatgttttt tgcgccgaca tcataacggt tctggcaaat    3120
attctgaaat gagctgttga caattaatca tccggctcgt ataatgtgtg gaattgtgag    3180
cggataacaa tttcacacag gaaacagcgc cgctgagaaa aagcgaagcg gcactgctct    3240
ttaacaattt atcagacaat ctgtgtgggc actcgaccgg aattatcgat taactttatt    3300
attaaaaatt aaagaggtat atattaatgt atcgattaaa taaggaggaa taaacccaga    3360
acgcagaagc ggtctgataa aacagaattt gcctggcggc agtagcgcgg tggtcccacc    3420
tgaccccatg ccgaactcag aagtgaaacg ccgtagcgcc gatggtagtg tggggtctcc    3480
ccatgcgaga gtagggaact gccaggcatc aaataaaacg aaaggctcag tcgaaagact    3540 gggccttcg ttatctgt tgtttgtcgg tgaacgctct cctgagtagg acaaatcttg    3600
taggtggacc agttggtgat tttgaacttt tgctttgcca cggaacggtc tgcgttgtcg    3660
ggaagatgcg tgatctgatc cttcaactca gcaaaagttc gatttattca acaaagccgc    3720
cgtcccgtca gtcagcgta atgctctgcc agtgttacaa ccaattaacc aattctgatt    3780
agaaaaactc atcgagcatc aaatgaaact gcaatttatt catatcagga ttatcaatac    3840 catattttg aaaaagccgt ttctgtaatg aaggagaaaa ctcaccgagg cagttccata    3900
ggatggcaag atcctggtat cggtctgcga ttccgactcg tccaacatca atacaaccta    3960 ttaattccc ctcgtcaaaa ataaggttat caagtgagaa atcaccatga gtgacgactg    4020
aatccggtga gaatggcaaa agcttatgca tttctttcca gacttgttca acaggccagc    4080
cattacgctc gtcatcaaaa tcactcgcat caaccaaacc gttattcatt cgtgattgcg    4140
cctgagcgag acgaaatacg cgatcgctgt taaaaggaca attacaaaca ggaatcgaat    4200
gcaaccggcg caggaacact gccagcgcat caacaatatt ttcacctgaa tcaggatatt    4260
cttctaatac ctggaatgct gttttcccgg ggatcgcagt ggtgagtaac catgcatcat    4320
caggagtacg gataaaatgc ttgatggtcg gaagaggcat aaattccgtc agccagttta    4380
```

```
gtctgaccat ctcatctgta acatcattgg caacgctacc tttgccatgt tcagaaaca    4440 actctggcgc atcgggcttc ccatacaatc gatagattgt cgcacctgat tgcccgacat    4500
tatcgcgagc ccatttatac ccatataaat cagcatccat gttggaattt aatcgcggcc    4560
tcgagcaaga cgtttcccgt tgaatatggc tcataacacc ccttgtatta ctgtttatgt    4620
aagcagacag ttttattgtt catgatgata tattttatc ttgtgcaatg taacatcaga    4680
gattttgaga cacaacgtgg ctttccccccc cccccctgca ggtccgacac ggggatggat    4740
ggcgttcccg atcatggtcc tgcttgcttc gggtggcatc ggaatgccgg cgctgcaagc    4800
aatgttgtcc aggcaggtgg atgaggaacg tcagggcag ctgcaaggct cactggcggc    4860
gctcaccagc ctgacctcga tcgtcggacc cctcctcttc acggcgatct atgcggcttc    4920
tataacaacg tggaacgggt gggcatggat tgcaggcgct gccctctact tgctctgcct    4980
gccggcgctg cgtcgcgggc tttggagcgg cgcagggcaa cgagccgatc gctgatcgtg    5040
gaaacgatag gcctatgcca tgcgggtcaa ggcgacttcc ggcaagctat acgcgcccta    5100
gaattgtcaa ttttaatcct ctgtttatcg gcagttcgta gagcgcgccg tgcgtcccga    5160
gcgatactga gcgaagcaag tgcgtcgagc agtgcccgct tgttcctgaa atgccagtaa    5220
agcgctggct gctgaacccc cagccggaac tgaccccaca aggccctagc gtttgcaatg    5280
caccaggtca tcattgaccc aggcgtgttc caccaggccg ctgcctcgca actcttcgca    5340
ggcttcgccg acctgctcgc gccacttctt cacgcgggtg gaatccgatc cgcacatgag    5400
gcggaaggtt tccagcttga gcgggtacgg ctcccggtgc gagctgaaat agtcgaacat    5460
ccgtcgggcc gtcggcgaca gcttgcggta cttctcccat atgaatttcg tgtagtggtc    5520
gccagcaaac agcacgacga tttcctcgtc gatcaggacc tggcaacggg acgttttctt    5580
gccacggtcc aggacgcgga agcggtgcag cagcgacacc gattccaggt gcccaacgcg    5640
gtcggacgtg aagcccatcg ccgtcgcctg taggcgcgac aggcattcct cggccttcgt    5700
gtaataccgg ccattgatcg accagcccag gtcctggcaa agctcgtaga acgtgaaggt    5760
gatcggctcg ccgataggg tgcgcttcgc gtactccaac acctgctgcc acaccagttc    5820
gtcatcgtcg gcccgcagct cgacgccggt gtaggtgatc ttcacgtcct tgttgacgtg    5880
gaaaatgacc ttgttttgca gcgcctcgcg cgggattttc ttgttgcgcg tggtgaacag    5940
ggcagagcgg gccgtgtcgt ttggcatcgc tcgcatcgtg tccggccacg cgcaatatc    6000 gaacaaggaa agctgcattt ccttgatctg ctgcttcgtg tgtttcagca acgcggcctg    6060
cttggcctcg ctgacctgtt ttgccaggtc ctcgccggcg ttttttcgct tcttggtcgt    6120
catagttcct cgcgtgtcga tggtcatcga cttcgccaaa cctgccgcct cctgttcgag    6180
acgacgcgaa cgctccacgg cggccgatgg cgcgggcagg gcaggggagg ccagttgcac    6240
gctgtcgcgc tcgatcttgg ccgtagcttg ctggaccatc gagccgacgg actggaaggt    6300
ttcgcggggc gcacgcatga cggtgcggct tgcgatggtt tcggcatcct cggcggaaaa    6360
ccccgcgtcg atcagttctt gcctgtatgc cttccggtca acgtccgat tcattcaccc    6420 tccttgcggg attgcccga ctcacgccgg ggcaatgtgc ccttattcct gatttgaccc    6480
gcctggtgcc ttggtgtcca gataatccac cttatcggca atgaagtcgg tcccgtagac    6540
cgtctggccg tccttctcgt acttggtatt ccgaatcttg ccctgcacga ataccagctc    6600
cgcgaagtcg ctcttcttga tggagcgcat ggggacgtgc ttggcaatca cgcgcacccc    6660
ccggccgttt tagcggctaa aaaagtcatg gctctgccct cgggcggacc acgcccatca    6720
```

| | |
|---|---:|
| tgaccttgcc aagctcgtcc tgcttctctt cgatcttcgc cagcagggcg aggatcgtgg | 6780 |
| catcaccgaa ccgcgccgtg cgcgggtcgt cggtgagcca gagtttcagc aggccgccca | 6840 |
| ggcggcccag gtcgccattg atgcgggcca gctcgcggac gtgctcatag tccacgacgc | 6900 |
| ccgtgatttt gtagccctgg ccgacggcca gcaggtaggc ctacaggctc atgccggccg | 6960 |
| ccgccgcctt ttcctcaatc gctcttcgtt cgtctggaag gcagtacacc ttgataggtg | 7020 |
| ggctgccctt cctggttggc ttggtttcat cagccatccg cttgccctca tctgttacgc | 7080 |
| cggcggtagc cggccagcct cgcagagcag gattcccgtt gagcaccgcc aggtgcgaat | 7140 |
| aagggacagt gaagaaggaa cacccgctcg cgggtgggcc tacttcacct atcctgcccg | 7200 |
| gctgacgccg ttggatacac caaggaaagt ctacacgaac cctttggcaa aatcctgtat | 7260 |
| atcgtgcgaa aaaggatgga tataccgaaa aaatcgctat aatgaccccg aagcagggtt | 7320 |
| atgcagcgga aaagatccgt c | 7341 |

<210> SEQ ID NO 81
<211> LENGTH: 10705
<212> TYPE: DNA
<213> ORGANISM: Artificial Sequence
<220> FEATURE:
<223> OTHER INFORMATION: pMZT3

<400> SEQUENCE: 81

| | |
|---|---:|
| tcaccctgtc gggcaatgcc gaggcattct ggcagcagcg cccccctgcc tgtagtggat | 60 |
| tacgtgccgg tctgttccat cctaccaccg gctattcact gccgctggcg gttgccgtgg | 120 |
| ccgaccgcct gagcgcactt gatgtcttta cgtcggcctc aattcaccag gctattaggc | 180 |
| attttgcccg cgagcgctgg cagcagcagc gcttttttccg catgctgaat cgcatgctgt | 240 |
| ttttagccgg acccgccgat tcacgctggc gggttatgca gcgttttttat ggtttacctg | 300 |
| aagatttaat tgcccgtttt tatgcgggaa aactcacgct gaccgatcgg ctacgtattc | 360 |
| tgagcggcaa gccgcctgtt ccggtattag cagcattgca agccattatg acgactcatc | 420 |
| gttaagagac agaacgaagt gtgaccagaa cgcagaagcg gtctgataaa acagaatttg | 480 |
| cctggcggca gtagcgcggt ggtcccacct gaccccatgc cgaactcaga agtgaaacgc | 540 |
| cgtagcgccg atggtagtgt ggggtctccc catgcgagag tagggaactg ccaggcatca | 600 |
| aataaaacga aaggctcagt cgaaagactg ggcctttcgt tttatctgtt gtttgtcggt | 660 |
| gaacgctctc ctgagtagga caaatcttgt aggtggacca gttggtgatt ttgaacttt | 720 |
| gctttgccac ggaacggtct gcgttgtcgg gaagatgcgt gatctgatcc ttcaactcag | 780 |
| caaaagttcg atttattcaa caaagccgcc gtcccgtcaa gtcagcgtaa tgctctgcca | 840 |
| gtgttacaac caattaacca attctgatta gaaaaactca tcgagcatca aatgaaactg | 900 |
| caatttattc atatcaggat tatcaatacc atatttttga aaaagccgtt tctgtaatga | 960 |
| aggagaaaac tcaccgaggc agttccatag gatggcaaga tcctggtatc ggtctgcgat | 1020 |
| tccgactcgt ccaacatcaa tacaacctat taatttcccc tcgtcaaaaa taaggttatc | 1080 |
| aagtgagaaa tcaccatgag tgacgactga atccggtgag aatggcaaaa gcttatgcat | 1140 |
| ttctttccag acttgttcaa caggccagcc attacgctcg tcatcaaaat cactcgcatc | 1200 |
| aaccaaaccg ttattcattc gtgattgcgc ctgagcgaga cgaaatacgc gatcgctgtt | 1260 |
| aaaaggacaa ttacaaacag gaatcgaatg caaccggcgc aggaacactg ccagcgcatc | 1320 |
| aacaatattt tcacctgaat caggatattc ttctaatacc tggaatgctg ttttcccggg | 1380 |
| gatcgcagtg gtgagtaacc atgcatcatc aggagtacgg ataaaatgct tgatggtcgg | 1440 |

```
aagaggcata aattccgtca gccagtttag tctgaccatc tcatctgtaa catcattggc    1500
aacgctacct ttgccatgtt tcagaaacaa ctctggcgca tcgggcttcc catacaatcg    1560
atagattgtc gcacctgatt gcccgacatt atcgcgagcc catttatacc catataaatc    1620
agcatccatg ttggaattta atcgcggcct cgagcaagac gtttcccgtt gaatatggct    1680
cataacaccc cttgtattac tgtttatgta agcagacagt tttattgttc atgatgatat    1740
atttttatct tgtgcaatgt aacatcagag attttgagac acaacgtggc tttcccccc     1800 ccccctgcag gtccgacacg gggatggatg gcgttcccga tcatggtcct gcttgcttcg    1860
ggtggcatcg gaatgccggc gctgcaagca atgttgtcca ggcaggtgga tgaggaacgt    1920
caggggcagc tgcaaggctc actggcggcg ctcaccagcc tgacctcgat cgtcggaccc    1980
ctcctcttca cggcgatcta tgcggcttct ataacaacgt ggaacgggtg gcatggatt     2040 gcaggcgctg ccctctactt gctctgcctg ccggcgctgc gtcgcgggct ttggagcggc    2100
gcagggcaac gagccgatcg ctgatcgtgg aaacgatagg cctatgccat gcgggtcaag    2160
gcgacttccg gcaagctata cgcgccctag aattgtcaat tttaatcctc tgtttatcgg    2220
cagttcgtag agcgcgccgt gcgtcccgag cgatactgag cgaagcaagt gcgtcgagca    2280
gtgcccgctt gttcctgaaa tgccagtaaa gcgctggctg ctgaaccccc agccggaact    2340
gaccccacaa ggccctagcg tttgcaatgc accaggtcat cattgaccca ggcgtgttcc    2400
accaggccgc tgcctcgcaa ctcttcgcag gcttcgccga cctgctcgcg ccacttcttc    2460
acgcgggtgg aatccgatcc gcacatgagg cggaaggttt ccagcttgag cgggtacggc    2520
tcccggtgcg agctgaaata gtcgaacatc cgtcgggccg tcggcgacag cttgcggtac    2580
ttctcccata tgaatttcgt gtagtggtcg ccagcaaaca gcacgacgat ttcctcgtcg    2640
atcaggacct ggcaacggga cgttttcttg ccacggtcca ggacgcggaa gcggtgcagc    2700
agcgacaccg attccaggtg cccaacgcgg tcggacgtga agcccatcgc cgtcgcctgt    2760
aggcgcgaca ggcattcctc ggccttcgtg taataccggc cattgatcga ccagcccagg    2820
tcctggcaaa gctcgtagaa cgtgaaggtg atcggctcgc cgatagggt gcgcttcgcg     2880 tactccaaca cctgctgcca caccagttcg tcatcgtcgg cccgcagctc gacgccggtg    2940
taggtgatct tcacgtcctt gttgacgtgg aaaatgacct tgttttgcag cgcctcgcgc    3000
gggattttct tgttgcgcgt ggtgaacagg gcagagcggg ccgtgtcgtt tggcatcgct    3060
cgcatcgtgt ccggccacgg cgcaatatcg aacaaggaaa gctgcatttc cttgatctgc    3120
tgcttcgtgt gtttcagcaa cgcggcctgc ttggcctcgc tgacctgttt gccaggtcc     3180 tcgccggcgg ttttcgctt cttggtcgtc atagttcctc gcgtgtcgat ggtcatcgac      3240
ttcgccaaac ctgccgcctc ctgttcgaga cgacgcgaac gctccacggc ggccgatggc    3300
gcgggcaggg caggggagc cagttgcacg ctgtcgcgct cgatcttggc cgtagcttgc     3360
tggaccatcg agccgacgga ctggaaggtt tcgcggggcg cacgcatgac ggtgcggctt    3420
gcgatggttt cggcatcctc ggcggaaaac cccgcgtcga tcagttcttg cctgtatgcc    3480
ttccggtcaa acgtccgatt cattcaccct ccttgcggga ttgccccgac tcacgccggg    3540
gcaatgtgcc cttattcctg atttgacccg cctggtgcct tggtgtccag ataatccacc    3600
ttatcggcaa tgaagtcggt cccgtagacc gtctggccgt ccttctcgta cttggtattc    3660
cgaatcttgc cctgcacgaa taccagctcc gcgaagtcgc tcttcttgat ggagcgcatg    3720
gggacgtgct tggcaatcac gcgcacccc cggccgtttt agcggctaaa aaagtcatgg      3780
```

```
ctctgccctc gggcggacca cgcccatcat gaccttgcca agctcgtcct gcttctcttc   3840
gatcttcgcc agcagggcga ggatcgtggc atcaccgaac cgcgccgtgc gcgggtcgtc   3900
ggtgagccag agtttcagca ggccgcccag gcggcccagg tcgccattga tgcgggccag   3960
ctcgcggacg tgctcatagt ccacgacgcc cgtgattttg tagccctggc cgacggccag   4020
caggtaggcc tacaggctca tgccggccgc cgccgccttt cctcaatcg ctcttcgttc   4080
gtctggaagg cagtacacct tgataggtgg gctgccttc ctggttggct tggtttcatc   4140
agccatccgc ttgccctcat ctgttacgcc ggcggtagcc ggccagcctc gcagagcagg   4200
attcccgttg agcaccgcca ggtgcgaata agggacagtg aagaaggaac acccgctcgc   4260
gggtgggcct acttcaccta tcctgcccgg ctgacgccgt tggatacacc aaggaaagtc   4320
tacacgaacc ctttggcaaa atcctgtata tcgtgcgaaa aaggatggat ataccgaaaa   4380
aatcgctata atgaccccga agcagggtta tgcagcggaa aagatccgtc gaccctttcc   4440
gacgctcacc gggctggttg ccctcgccgc tgggctggcg gccgtctatg gccctgcaaa   4500
cgcgccagaa acgccgtcga agccgtgtgc gagacaccgc ggccgccggc gttgtggata   4560
cctcgcggaa aacttggccc tcactgacag atgaggggcg gacgttgaca cttgaggggc   4620
cgactcaccc ggcgcggcgt tgacagatga ggggcaggct cgatttcggc cggcgacgtg   4680
gagctggcca gcctcgcaaa tcggcgaaaa cgcctgattt tacgcgagtt tcccacagat   4740
gatgtgacag agcctgggga taagtgccct gcggtattga cacttgaggg gcgcgactac   4800
tgacagatga ggggcgcgat ccttgacact tgaggggcag agtgctgaca gatgaggggc   4860
gcacctattg acatttgagg ggctgtccac aggcagaaaa tccagcattt gcaagggttt   4920
ccgcccgttt ttcggccacc gctaacctgt cttttaacct gcttttaaac caatatttat   4980
aaaccttgtt tttaaccagg gctgcgccct gtgcgcgtga ccgcgcacgc cgaaggggg   5040
tgccccccct tctcgaaccc tcccggcccg ctaacgcggg cctcccatcc ccccagggc   5100
tgcgcccctc ggccgcgaac ggcctcaccc caaaaatggc agccaagctg accacttctg   5160
cgctcggccc ttccggctgg ctggtttatt gctgataaat ctggagccgg tgagcgtggg   5220
tctcgcggta tcattgcagc actggggcca atggtaagc cctcccgtat cgtagttatc   5280
tacacgacgg ggagtcaggc aactatggat gaacgaaata gacagatcgc tgagataggt   5340
gcctcactga ttaagcattg gtaactgtca gaccaagttt actcatatat actttagatt   5400
gatttaaaac ttcatttta atttaaaagg atctaggtga agatccttt tgataatctc   5460
atgaccaaaa tcccttaacg tgagttttcg ttccactgag cgtcagaccc cgtagaaaag   5520
atcaaaggat cttcttgaga tcctttttt ctgcgcgtaa tctgctgctt gcaaacaaaa   5580
aaaccaccgc taccagcggt ggtttgtttg ccggatcaag agctaccaac tcttttccg   5640
aaggtaactg gcttcagcag agcgcagata ccaaatactg tccttctagt gtagccgtag   5700
ttaggccacc acttcaagaa ctctgtagca ccgcctacat acctcgctct gctaatcctg   5760
ttaccagtgg ctgctgccag tggcgataag tcgtgtctta ccgggttgga ctcaagacga   5820
tagttaccgg ataaggcgca gcggtcgggc tgaacggggg gttcgtgcac acagcccagc   5880
ttggagcgaa cgacctacac cgaactgaga tacctacagc gtgagctatg agaaagcgcc   5940
acgcttcccg aagggagaaa ggcggacagg tatccggtaa gcggcagggt cggaacagga   6000
gagcgcacga gggagcttcc agggggaaac gcctggtatc tttatagtcc tgtcgggttt   6060
cgccacctct gacttgagcg tcgatttttg tgatgctcgt cagggggcg gagcctatgg   6120
aaaaacgcca gcaacgcggc ctttttacgg ttcctggcct tttgctggcc ttttgctcac   6180
```

-continued

```
atgttctttc ctgcgttatc ccctgattct gtggataacc gtattaccgc ctttgagtga    6240
gctgataccg ctcgccgcag ccgaacgacc gagcgcagcg agtcagtgag cgaggaagcg    6300
gaagagcgcc caatacgcaa accgcctctc cccgcgcgtt ggccgattca ttaatgcagc    6360
tggcagccag cgcttcgtta atacagatgt aggtgttcca cagggtagcc agcagcatcc    6420
tgcgatgcag atccggaaca taatggtgca gggcgctgac tttatagcta gctcagccct    6480
tggtacaatg ctagcgagca accaacactt aaagaggaga aaatgtatcc gtttataagg    6540
acagcccgaa tgacggtctg cgcaaaaaaa cacgttcatc tcactcgcga tgctgcggag    6600
cagttactgg ctgatattga tcgacgcctt gatcagttat tgcccgtgga gggagaacgg    6660
gatgttgtgg gtgccgcgat gcgtgaaggt gcgctggcac cgggaaaacg tattcgcccc    6720
atgttgctgt tgctgaccgc ccgcgatctg ggttgcgctg tcagccatga cggattactg    6780
gatttggcct gtgcggtgga aatggtccac gcggcttcgc tgatccttga cgatatgccc    6840
tgcatggacg atgcgaagct gcggcgcgga cgccctacca ttcattctca ttacggagag    6900
catgtggcaa tactggcggc ggttgccttg ctgagtaaag cctttggcgt aattgccgat    6960
gcagatggcc tcacgccgct ggcaaaaaat cgggcggttt ctgaactgtc aaacgccatc    7020
ggcatgcaag gattggttca gggtcagttc aaggatctgt ctgaagggga taagccgcgc    7080
agcgctgaag ctattttgat gacgaatcac tttaaaacca gcacgctgtt ttgtgcctcc    7140
atgcagatgg cctcgattgt tgcgaatgcc tccagcgaag cgcgtgattg cctgcatcgt    7200
ttttcacttg atcttggtca ggcatttcaa ctgctggacg atttgaccga tggcatgacc    7260
gacaccggta aggatagcaa tcaggacgcc ggtaaatcga cgctggtcaa tctgttaggc    7320 cctaggcgg ttgaagaacg tctgagacaa catcttcatc ttgccagtga gcatctctct    7380
gcggcctgcc aacacgggca cgccactcaa cattttattc aggcctggtt tgacaaaaaa    7440
ctcgctgccg tcagttaaag gtctctagac aggatgtgtc acacaggaaa ccatgaaacc    7500
aactacggta attggtgcag gcttcggtgg cctggcactg gcaattcgtc tacaggctgc    7560
ggggatcccc gtcttactgc ttgaacaacg tgataaaccc ggcggtcggg cttatgtcta    7620
cgaggatcag gggtttacct ttgatgcagg cccgacggtt atcaccgatc ccagtgccat    7680
tgaagaactg tttgcactgg caggaaaaca gttaaaagag tatgtcgaac tgctgccggt    7740
tacgccgttt taccgcctgt gttgggagtc agggaaggtc tttaattacg ataacgatca    7800
aacccggctc gaagcgcaga ttcagcagtt taatccccgc gatgtcgaag ttatcgtca    7860 gtttctggac tattcacgcg cggtgtttaa agaaggctat ctgaagctcg gtactgtccc    7920
ttttttatcg ttcagagaca tgcttcgcgc cgcacctcaa ctggcgaaac tgcaggcatg    7980
gagaagcgtt tacagtaagg ttgccagtta atcgaagat gaacatctgc gccaggcgtt    8040
ttcttcccac tcgctgttgg tgggcggcaa tcccttcgcc acctcatcca tttatacgtt    8100
gatacacgcg ctggagcgtg agtggggcgt ctggtttccg cgtggcggca ccggcgcatt    8160
agttcagggg atgataaagc tgtttcagga tctgggtggt gaagtcgtgt taaacgccag    8220
agtcagccat atggaaacga caggaaacaa gattgaagcc gtgcatttag aggacggtcg    8280
caggttcctg acgcaagccg tcgcgtcaaa tgcagatgtg gttcatacct atcgcgacct    8340
gttaagccag caccctgccg cggttaagca gtccaacaaa ctgcagacta agcgtatgag    8400
taactctctg tttgtgctct attttggttt gaatcaccat catgatcagc tcgcgcatca    8460
cacggtttgt ttcggcccgc gttaccgcga actgattgac gagattttta atcatgatgg    8520
```

```
cctcgcagaa gacttctcac tttatctgca cgcgccctgt gtcacggatt cgtcactggc    8580
gcctgaaggt tgcggcagtt actatgtgtt ggcgccggtg ccgcatttag gcaccgcgaa    8640
cctcgactgg acggttgagg ggccaaaact acgcgaccgt attttgagt accttgagca    8700
gcattacatg cctggcttac ggagtcagct ggtcacgcac cagatgttta cgccgtttga    8760
ttttcgcgac cagcttaatg cctatcaggg ctcagccttt tctgtggagc ccgttcttac    8820
ccagagcgcc tggtttcggc cgcataaccg cgataaaacc attactaatc tctacctggt    8880
cggcgcaggc acgcatcccg cgcaggcat tcctggcgtc atcggctcgg caaaagcgac     8940
agcaggtttg atgctggagg atctgattta agtgatcgtt gagtggtgaa cttaaagagg    9000
agaaaatgaa taatccgtcg ttactcaatc atgcggtcga aacgatggca gttggctcga    9060
aaagttttgc gacagcctca aagttatttt atgcaaaaac ccggcgcagc gtactgatgc    9120
tctacgcctg gtgccgccat tgtgacgatg ttattgacga ccagacgctg ggcttccagg    9180
cccggcagcc tgccttacaa cgcccgaac aacgtctgat gcaacttgag atgaaaacgc      9240
gccaggccta tgcaggatcg cagatgcacg aaccggcgtt tgcggctttt caggaagtgg    9300
ctatggctca tgatatcgcc ccggcttacg cgtttgatca tctggaaggc ttcgccatgg    9360
atgtacgcga agcgcaatac agccaactgg acgatacgct gcgctattgc tatcacgttg    9420
caggcgttgt cggcttgatg atggcgcaaa tcatgggcgt acgggataac gccacgctgg    9480
accgcgcctg tgaccttggg ctggcattc agttgaccaa tattgctcgc gatattgtgg     9540
acgatgcgca tgcgggccgc tgttatctgc cggcaagctg gctggagcat gaaggtctga    9600
acaaagagaa ttatgcggca cctgaaaacc gtcaggcgct gagccgtatc gcccgtcgtt    9660
tggtgcagga agcagaacct tactatttgt ctgccacagc gggcctggct gggttgcccc    9720
tgcgttcggc ctgggcaatc gctacggcga agcaggttta ccggaaaata ggtgtcaaag    9780
ttgaacaggc cggtcagcaa gcctgggatc agcggcagtc aacgaccacg cccgaaaaat    9840
taacgctgct gctggccgcc tctggtcagg cccttacttc ccggatgcgg gctcatcctc    9900
cccgccctgc gcatctctgg cagcgcccgc tctaatcacg tagcaagctg acagtttaaa    9960
gaggagaaaa tgggagcggc tatgcaaccg cattatgatc tgattctcgt gggggctgga   10020
ctcgcgaatg gccttatcgc cctgcgtctt cagcagcagc aacctgatat gcgtattttg   10080
cttatcgacg ccgcacccca ggcgggcggg aatcatacgt ggtcatttca ccacgatgat   10140
ttgactgaga gccaacatcg ttggatagct tcgctggtgg ttcatcactg gcccgactat   10200
caggtacgct ttcccacacg ccgtcgtaag ctgaacagcg gctacttctg tattacttct   10260
cagcgtttcg ctgaggtttt acagcgacag tttggcccgc acttgtggat ggataccgcg   10320
gtcgcagagg ttaatgcgga atctgttcgg ttgaaaaagg gtcaggttat cggtgcccgc   10380
gcggtgattg acgggcgggg ttatgcggca aactcagcac tgagcgtggg cttccaggcg   10440
tttattggcc aggaatggcg attgagccac ccgcatggtt tatcgtctcc cattatcatg   10500
gatgccacgg tcgatcagca aaatggttat cgcttcgtgt acagcctgcc gctctcgccg   10560
accagattgt taattgaaga cacgcactat atcgataatg cgacattaga tcctgaacgc   10620
gcgcggcaaa atatttgcga ctatgccgcg caacagggt tggcagcttca gacattgctg    10680
cgtgaagaac agggcgcctt accca                                         10705
```

<210> SEQ ID NO 82
<211> LENGTH: 1773
<212> TYPE: DNA
<213> ORGANISM: Methylosinus trichosporum

<400> SEQUENCE: 82

```
atggccagaa aaatgaccgg agcggaaatg gtcgtcgaag ccctgaagga tcagggcgtc      60
gagattatct tcggctatcc cggcggcgcc gtgcttccga tctatgacgc gctcttccac     120
caggagaagg tgcagcacat tctcgtgcgc cacgagcagg gcgccgccca tgcggccgag     180
ggctatgcgc gctcctccgg caaggtcggc gtgctgctgg tcacctccgg acccggcgcc     240
accaacacca tcaccggcct caccgatgcg ctgatggact ccattcccgt ggtctgcatc     300
accggccagg tgccgacgca tctcatcggc tcggacgcct tcaagagtg cgatacggtc      360
ggcatcaccc gtcactgcac caagcataat tatctggtga agagcgtcga cgatctgccg     420
cgcattctgc acgaggcctt ctatgtcgcc tcgagcgggc ggccgggccc tgtggtcatc     480
gacatcccca aggatgtgca attgccagc ggaacctata ccggcccgcg caacgtccat      540
cacaagacct atcagcccaa gctcgagggc gacacggagt ctatccgccg cgccgtgaag     600
atgatggccg ccgccaagcg gccgatcttc tacaccggcg gcggcgtcat caattccggt     660
cccgcggcct cgacgctgct gcgcgagctg gtgtcgctga ccggctttcc gatcacctcg     720
accttgatgg cctcggcgc ctatccgggc tccggcccca ttggctcgg catgctcggc       780
atgcacggca ccttcgaggc caataatgcg atgcatgatt gcgatctgat gatcgccgtc     840
ggcgcgcgtt cgacgatcg catcaccgga cggctcgacg ccttctcgcc cggctcgaag      900
aagatccaca tcgatatcga tcgctcctcg atcaataaga atgtgaagat cgatctgccg     960
atcgtcggcg actgcggcca tgtgctggag agtctggtgc gcgtctggcg ctccgaggcg    1020
atgcacgccg agaagcagcc gctcgacggc tggtggaaga cgatcgacca ttggcgcgag    1080
cgcaagtcgc tcgccttccg caattcggac aaggtgatca agccgcaata cgccgtgcag    1140
cggctctatg cgctcaccaa ggatcgcgat ccctacatca cgacggaagt cggccagcat    1200
cagatgtggg ccgcgcagca ttatcatttc gacgagccca atcgctggat gacttccggc    1260
gggctcggca ccatgggcta tggtctgccg gcggcgatcg gcgcgcagct cgcgcatccg    1320
aaatcgctgg tcgtcgacat cgccggcgag gcctcgatcc tgatgaacat tcaggagatg    1380
tcgacggcga tccaatatcg gctgccggtg aaggtgttca tcctcaacaa tgaatatatg    1440
ggcatggtgc gccagtggca ggagctgctg cacggcgggc gctactcgca ctcctattcg    1500
gaggcgctgc ccgatttcgt gaagctcgcc gaagccttcg ggggcaaggg catccgctgc    1560
tcggacccgg cggagctcga tagcgcgatt ctcgagatga tcgactatga cgggccggtg    1620
atcttcgatt gtctcgtcga gaaaaacgag aattgcttcc cgatgatccc gtcgggcaag    1680
gcgcataacg acatgctgct cgccgatctc ggcgacgacg ccggcgtcga gctcggctcg    1740
atcatcgacg agaagggcaa gatgctggtg tga                                 1773
```

<210> SEQ ID NO 83
<211> LENGTH: 1056
<212> TYPE: DNA
<213> ORGANISM: Methylosinus trichosporium

<400> SEQUENCE: 83

```
atgtccacca aagcctatgc cgttgcgtcc gccgaggcgc tcttcggccc gctcgcgatc      60
gagcgccgcg cgctcgggcc cgaggatgta gagatcgaca tcctctattg cggcgtctgc     120
cattccgatc tgcacacggc gcgcagtgaa tggccgggca cgcgctaccc atgcgtcccg     180
ggccacgaga ttgtcggccg cgtcaccgct gtcggcgcga aggtgacgaa attttcggtc     240
```

```
ggcgatctcg ccgccgtcgg ctgcatggtc gacagctgcc ggcgatgctt gtcctgcgac    300
gacgggctcg aacaatattg cgagcacggt ttcaccgcca cctataacgg cccgatctac    360
ggctcgggcg agaacacctt tggcggctat tcggagaaaa tcgtcgtcga cgcgcatttc    420
gtgctggcga tccaccattc tgagacgcag cttgccggag tcgcgccgct gctctgcgcc    480
ggcatcacca cttggtcgcc gctcaagcat tggggtgtcg gcccgggaaa atcggtcggc    540
atcgtcggca tcgcgggct cggccatatg ggggtcaagc tcgcccatgc gctcggcgcc    600
catgtcgtcg ccttcaccac ctcgccgtca agcgcgacg cggccctcgc gctcggcgcc    660
gacgaggtcg tcgtctccac agatcctgcc gctatggcgg cgcgggcggg aagcctcgac    720
ttcattctcg atacggtcgc cgtcgcccat gacctcgacg cttatgtgaa tctgttgaag    780
cgcgatggcg ctctggtgct cgtcggccgt ccggcgacgc cgcatccctc gccatcggcg    840
ggcgggttga tcttcaagcg cgccaggtc gccggctcgc tgatcggcgg cgtaaaggag    900
acgcaggaga tgctcgactt ctgcgccgag cgcggcattg tcgcggacat agagacgatc    960
gccatgcagc agatcgagac cgcctatgcg cgcatgctga agaatgatgt gaaataccgc    1020
ttcgtcatcg acatggcgac gctgaaggcg gcgtga                              1056
```

<210> SEQ ID NO 84  
<211> LENGTH: 1029  
<212> TYPE: DNA  
<213> ORGANISM: Methylococcus capsulatus

<400> SEQUENCE: 84

```
atgaaagctt gggtgatcga ccgaatcggc ccgctggact cgtcgcgaac tctgctacgc     60
gccaccgacc tcccggtgcc ggagcccggc cctggcgaaa tcctgctgca ggtggcggtt    120
tgcggcgtct gccacaccga atcgacgag atcgagggcc gcaccgcgcc gccgcgcctg    180
ccggtcgtgc ccggacacca agcggtcggt cggatcgcgg ctctcggctc cggcgtggcg    240
gaattcgctt tgggcgaccg cgtcggcgtg gcctggatct tttctgcctg cggagaatgc    300
gaattctgcc ggtcgggacg ggagaacctc tgtttcgcat tctgtgccac cgggcgcgat    360
gtcgacggcg gctacgccca gtacatgacc gtcccggcgg cctttgcttt ccgcattccg    420
gagggattca ccgatgccga agcggcgccg cttctgtgcg ccggcgccat cggttaccgt    480
tcgctcaatc tcagcgggct gaaaaacggc cagccgctgg ggctcaccgg gttcggggct    540
tccgcccatc tggtgctgat gatggcccgg taccggtttc ccgattcgga agtctatgtc    600
tttgcgcgtc atcccgagga gcgcgcgttc gcgctgcagc tgggcgcggt ctgggccggc    660
gacaccgcgg acattgctcc cgccccgctg gccgccatca tcgacacgac gccggcgtgg    720
aagccggtgg tcgcagcgct cgccaacctc gctcccggtg gccggctggt cgttaatgcg    780
atccgcaagg cgccggacga tcgcgcctgt ctcgccgaac tcgactatgc ccggcacttg    840
tggatggaac gggaaatcaa gtcggtcgcc aacgtggcgc gcagtgacgt ggcccgggttc    900 ctggcgctgg cggcggaaat gggcatccgt cccgagacga aggagtaccc gttcgaggat    960
gccgaccggg cgctgctcga cctcaagcaa cgccggattc gcggggcgaa ggtgttgcgg   1020
gtgacttga                                                          1029
```

<210> SEQ ID NO 85  
<211> LENGTH: 1068  
<212> TYPE: DNA  
<213> ORGANISM: Methylococcus capsulatus

<400> SEQUENCE: 85

```
atgcctacag ccaaagccta tgccgctttt tccgcagact cggcgctggc gccgttcgtc    60
ctgcagcggc gcgacccact gccccaggac atccgcatcg aatcctgta ctgcggtgtc    120
tgccattccg acctgcacca ggcacgcaat gagtggaatg cgaccacata tccttgtgtg    180
ccaggccatg agatcgtcgg caaggtcctt gaagtcggcc gcagcgtgac gaagttcaag    240
cccggcgaca cggtcgcggt gggctgcatg gtggattcct gccggacctg cccgaactgc    300
gtggacgccc tggaacagca ctgcgagcac ggccccgtct tcacctacaa cagccccgat    360
ccgcacggcg gcggcatgac cttcggtggc tatgccgaga gcatcgtggt cgacgaggcc    420
ttcgtgctgc ggataccgga cggactggac ctcgcggccg ccgccccgct gttgtgcgcc    480
gggattacca cctattcgcc cctgcggcac tggaaagtgg gggcgggtca gcgggtcggg    540
gtcgtcggtc tgggtggact gggacacatg gcgctcaagt tcgcgcatac cttcggcgcc    600
gaaacggtgc tgttcacgac gacgccggac aaggcggagg atgcccgtcg gctgggagcg    660
gacgaggtcg tcgtgtcgag ggatcccgag gccatggcgc ggcaggccgg ccggttcgat    720
ttcatcctcg acaccgtctc ggcgccccat gacatcgatg cctatctgaa cctgctgagg    780
cgggacggca cgctgaccct ggtcggcgta cctccgcaag gggtacaggt catgcccttc    840
agcctgatcg gcgggcgccg cgactggct ggttcattga tcggcggcat ccgggaaacc    900
caggagatgc tggatttctg cggcgaacac ggcatcgtct gcgacatcga gctgattccg    960
atccaaggaa tcaacgacgc cttcgagcgc atgctcaaaa gcgacgtgaa ataccgtttc   1020
gtgatcgaca tggcgacgct gaacggggag tcgtccggag ggcgatga                1068
```

<210> SEQ ID NO 86
<211> LENGTH: 1647
<212> TYPE: DNA
<213> ORGANISM: Lactococcus lactis

<400> SEQUENCE: 86

```
atgtacaccg tgggcgacta tctgctggac cggctgcatg aactgggcat cgaggaaatc    60
ttcggcgtcc ccggcgacta taacctgcag ttcctggacc agatcatcag ccgcaaggac    120
atgaagtggg tgggcaacgc caacgagctg aacgcctcgt acatggcgga cggctatgcc    180
cggaccaaga aggccgcggc cttcctgacc accttcggcg tcggcgaact gagcgccgtg    240
aacggcctgg cgggctcgta cgccgagaac ctgccggtcg tggaaatcgt cggctccccc    300
accagcaagg tgcagaacga gggcaagttc gtccaccata ccctggccga cggcgacttc    360
aagcacttca tgaagatgca tgaaccggtg accgcggccc gcaccctgct gaccgccgag    420
aacgcgaccg tcgaaatcga ccgcgtgctg agcgcgctgc tgaaggagcg gaagccggtc    480
tatatcaacc tgcccgtcga cgtggcggcc gcgaaggccg agaagccgtc cctgcccctg    540
aagaaggaaa accccaccct gaacacctcc gaccaggaga tcctgaacaa gatccaggaa    600
agcctgaaga cgccaagaa gccgatcgtg atcaccggcc acgagatcat ctcgttcggc    660
ctggaaaaca ccgtcaccca gttcatctcc aagaccaagc tgccgatcac caccctgaac    720
ttcggcaaga gctcggtgga cgagacctg ccctcgttcc tggcatcta acggcaag     780
ctgtccgaac cgaacctgaa ggagttcgtg gaaagcgcgg acttcatcct gatgctgggc    840
gtcaagctga ccgactccag caccggcgcc ttcacccacc atctgaacga gaacaagatg    900
atctcgctga acatcgacga gggcaagatc ttcaacgaat ccatccagaa cttcgacttc    960
gaaagcctga tctcgtccct gctggacctg tccggcatcg agtacaaggg caagtatatc   1020
```

| | |
|---|---|
| gacaagaagc aggaagactt cgtcccgagc aacgcgctgc tgtcgcagga ccgcctgtgg | 1080 |
| caggccgtgg agaacctgac ccagagcaac gagaccatcg tcgcggaaca gggcacctcg | 1140 |
| ttcttcggcg ccagctcgat cttcctgaag ccgaagtcgc acttcatcgg ccagcccctg | 1200 |
| tggggctcca tcggctacac cttccccgcc gcgctgggct cgcagatcgc ggacaaggaa | 1260 |
| tcccggcatc tgctgttcat cggcgacggc agcctgcagc tgaccgtgca ggagctgggc | 1320 |
| ctggccatcc gcgaaaagat caacccgatc tgcttcatca tcaacaacga cggctatacc | 1380 |
| gtcgagcggg aaatccacgg cccgaaccag tcgtacaacg acatccccat gtggaactat | 1440 |
| tccaagctgc cggagagctt cggcgccacc gaggaacgcg tcgtgtccaa gatcgtccgg | 1500 |
| accgagaacg agttcgtcag cgtgatgaag gaagcccagg cggaccccaa ccggatgtac | 1560 |
| tggatcgagc tggtgctggc gaaggaagac gccccgaagg tcctgaagaa gatgggcaag | 1620 |
| ctgttcgccg aacagaacaa gagctga | 1647 |

<210> SEQ ID NO 87
<211> LENGTH: 1692
<212> TYPE: DNA
<213> ORGANISM: Saccharomyces cerevisiae

<400> SEQUENCE: 87

| | |
|---|---|
| atgtcggaaa tcaccctggg caagtacctg ttcgagcggc tgaagcaggt caacgtcaac | 60 |
| accatcttcg gcctgcccgg cgacttcaac ctgagcctgc tggacaagat ctacgaggtc | 120 |
| gacggcctgc gctgggccgg caacgcgaac gaactgaacg ccgcgtacgc cgcggacggc | 180 |
| tatgcccgga tcaagggcct gtcggtcctg gtgaccacct tcggcgtggg cgagctgtcg | 240 |
| gccctgaacg gcatcgccgg ctcctacgcg gaacacgtcg gcgtgctgca tgtcgtgggc | 300 |
| gtcccgagca tctcggccca ggcgaagcag ctgctgctgc accatcccct gggcaacggc | 360 |
| gacttcaccg tgttccaccg catgtcgccc aacatcagcg agaccacctc gatgatcacc | 420 |
| gacatcgcca ccgcgccgag cgaaatcgac cgcctgatcc ggaccacctt catcacccag | 480 |
| cggccgtcgt acctgggcct gccgccaaac ctggtcgacc tgaaggtgcc gggcagcctg | 540 |
| ctggagaagc ccatcgacct gtcgctgaag ccgaacgacc ccgaggccga aaaggaagtc | 600 |
| atcgacaccg tgctggaact gatccagaac agcaagaacc cggtcatcct gtccgacgcc | 660 |
| tgcgcgagcc gccacaacgt gaagaaggag acccagaagc tgatcgacct gacccagttc | 720 |
| ccggccttcg tcaccccct gggcaagggc tccatcgacg agcagcatcc gcggtacggc | 780 |
| ggcgtctatg tgggcaccct gagcaagcag gacgtcaagc aggccgtgga aagcgcggac | 840 |
| ctgatcctgt cggtgggcgc cctgctgtcc gacttcaaca ccggctcctt cagctactcg | 900 |
| tataagacca agaacgtcgt ggagttccat tcggactacg tcaaggtgaa gaacgcgacc | 960 |
| ttcctgggcg tccagatgaa gttcgccctg cagaacctgc tgaaggtgat cccggacgtc | 1020 |
| gtgaagggct ataagtccgt cccggtgccc accaagaccc ccgccaacaa gggcgtcccg | 1080 |
| gcgtcgaccc ccctgaagca ggaatggctg tggaacgagc tgtccaagtt cctgcaggaa | 1140 |
| ggcgacgtga tcatctcgga caccggcacc tccgcgttcg gcatcaacca gaccatcttc | 1200 |
| ccgaaggacg cctacggcat cagccaggtc ctgtggggct cgatcggctt caccaccggc | 1260 |
| gccaccctgg gcgccgcgtt cgccgcggag gaaatcgacc cgaacaagcg cgtcatcctg | 1320 |
| ttcatcggca cggctccct gcagctgacc gtgcaggaaa tcagcaccat gatccggtgg | 1380 |
| ggcctgaagc cctacctgtt cgtgctgaac aacgacggct ataccatcga aagctgatc | 1440 |
| cacggcccgc atgcggaata caacgagatc cagacctggg accacctggc cctgctgccc | 1500 |

```
gccttcggcg cgaagaagta tgaaaaccat aagatcgcca ccaccggcga gtgggacgcg   1560
ctgaccaccg actccgagtt ccagaagaac agcgtcatcc gcctgatcga gctgaagctg   1620
ccggtgttcg acgccccga aagcctgatc aagcaggcgc agctgaccgc cgcgaccaac   1680
gccaagcagt ga                                                       1692

<210> SEQ ID NO 88
<211> LENGTH: 1908
<212> TYPE: DNA
<213> ORGANISM: Saccharomyces cerevisiae

<400> SEQUENCE: 88
atggcccccg tcaccatcga gaagttcgtc aaccaggaag agcggcatct ggtgtccaac     60
cggagcgcga ccatcccgtt cggcgagtac atcttcaagc gcctgctgag catcgacacc    120
aagtcggtgt tcggcgtgcc gggcgacttc aacctgagcc tgctggagta cctgtatagc    180
ccctcggtcg aatcggccgg cctgcgctgg gtgggcacct gcaacgaact gaacgccgcg    240
tacgccgcgg acggctactc ccggtatagc aacaagatcg gctgcctgat caccacctat    300
ggcgtcggcg aactgtcggc gctgaacggc atcgcgggc ccttcgccga aacgtgaag    360 gtcctgcaca tcgtgggcgt cgccaagtcg atcgactccc gcagctcgaa cttctcggac    420
cggaacctgc accatctggt cccgcagctg catgactcca acttcaaggg ccccaaccac    480
aaggtgtacc atgacatggt gaaggaccgc gtcgcgtgct ccgtggccta tctggaggac    540
atcgaaaccg cctgcgacca ggtggacaac gtcatccggg acatctacaa gtatagcaag    600
ccgggttaca tcttcgtccc cgcggacttc gccgacatgt ccgtgacctg cgacaacctg    660
gtgaacgtcc cgcgcatcag ccagcaggac tgcatcgtgt acccctccga aaaccagctg    720
agcgacatca tcaacaagat cacctcgtgg atctactcca gcaagacccc ggccatcctg    780
ggcgacgtcc tgaccgaccg gtatggcgtg agcaacttcc tgaacaagct gatctgcaag    840
accggcatct ggaacttctc gaccgtcatg ggcaagtcgg tgatcgacga atccaacccg    900
acctacatgg ccagtataaa cggcaaggaa ggcctgaagc aggtctacga gcacttcgaa    960
ctgtgcgacc tggtcctgca tttcggcgtg gacatcaacg agatcaacaa cggccactac   1020
accttcacct ataagccgaa cgcgaagatc atccagttcc atcccaacta catccgcctg   1080
gtggacaccg gcagggcaa cgaacagatg ttcaagggca tcaacttcgc cccgatcctg   1140
aaggagctgt ataagcgcat cgacgtcagc aagctgtcgc tgcagtacga cagcaacgtg   1200
acccagtata ccaacgagac catgcggctg gaagaccca ccaacggcca gtcgtccatc   1260
atcacccagg tccacctgca gaagaccatg ccgaagttcc tgaaccccgg cgacgtcgtg   1320
gtctgcgaga ccggctcctt ccagttcagc gtgcgcgact cgcgttccc gagccagctg   1380 aagtacatct cgcagggctt cttcctgtcc atcggcatgg ccctgcccgc cgcgctgggc   1440
gtcggcatcg cgatgcagga ccactcgaac gcccatatca cggcggcaa cgtgaaggaa   1500 gactacaagc cgcggctgat cctgttcgaa ggcgacggcg ccgcgcagat gaccatccag   1560
gagctgtcca ccatcctgaa gtgcaacatc ccgctggaag tcatcatctg gaacaacaac   1620
ggctacacca tcgagcgcgc catcatgggc cccaccccga gctataacga cgtgatgtcg   1680
tggaagtgga ccaagctgtt cgaagcgttc ggcgacttcg acggcaagta caccaactcc   1740
accctgatcc agtgcccgag caagctggcc ctgaagctgg aggaactgaa gaactcgaac   1800
aagcgctccg gcatcgagct gctggaagtc aagctgggcg agctggactt ccccgaacag   1860
```

```
ctgaagtgca tggtggaggc cgcggccctg aagcggaaca agaagtga              1908
```

<210> SEQ ID NO 89
<211> LENGTH: 1047
<212> TYPE: DNA
<213> ORGANISM: Saccharomyces cerevisiae

<400> SEQUENCE: 89

```
atgagcatcc ccgagaccca gaaggccatc atcttctacg agagcaacgg caagctggaa    60
cataaggaca tcccggtgcc caagcccaag ccgaacgaac tgctgatcaa cgtgaagtac   120
agcggcgtct gccacaccga cctgcacgcg tggcatggcg actggccgct gcccaccaag   180
ctgcccctgg tgggcggcca tgaaggcgcc ggcgtcgtgg tcggcatggg cgagaacgtc   240
aagggctgga agatcggcga ctacgcgggc atcaagtggc tgaacggcag ctgcatggcc   300
tgcgagtatt gcgaactggg caacgaatcg aactgcccgc acgcggacct gtccggctac   360
acccatgacg gcagcttcca ggagtatgcc accgcggacg ccgtgcaggc cgcgcacatc   420
ccgcagggca ccgacctggc ggaggtggcc cccatcctgt gcgccggcat caccgtctac   480
aaggcgctga gagcgccaa ctgcgcgcg ggccattggg ccgcgatctc gggcgccgcc   540
ggtggcctgg gctccctggc cgtgcagtac gcgaaggcga tgggctaccg cgtcctgggc   600
atcgacggcg tcccgggcaa ggaagagctg ttcacctccc tgggcggcga agtgttcatc   660
gacttcacca aggagaagga catcgtcagc gccgtggtca aggcgaccaa cggcggcgcc   720
cacggcatca tcaacgtgtc ggtctccgaa gccgcgatcg aggcgtcgac ccgctactgc   780
cgggccaacg gcaccgtggt cctggtgggc ctgcccgcgg cgccaagtg cagctcggac   840
gtcttcaacc atgtggtcaa gagcatctcg atcgtgggct cgtatgtcgg caaccgcgcc   900
gacacccgcg aggccctgga cttcttcgcc cgtggcctgg tcaagtcccc gatcaaggtg   960
gtcggcctgt ccagcctgcc cgagatctac gaaaagatgg agaagggcca gatcgccggc  1020
cgctatgtgg tcgacacctc caagtga                                     1047
```

<210> SEQ ID NO 90
<211> LENGTH: 1692
<212> TYPE: DNA
<213> ORGANISM: Saccharomyces cerevisiae

<400> SEQUENCE: 90

```
atgagcgaga tcaccctggg caagtacctg ttcgagcggc tgaagcaggt caacgtcaac    60
accgtcttcg gcctgcccgg cgacttcaac ctgagcctgc tggacaagat ctacgaggtc   120
gaaggcatgc gctgggcggg caacgccaac gagctgaacg ccgcgtacgc cgcggacggc   180
tatgcccgga tcaagggcat gtcgtgcatc atcaccacct tcggcgtggg cgagctgtcc   240
gccctgaacg gcatcgcggg cagctacgcc gaacacgtcg gcgtgctgca tgtcgtgggc   300
gtcccgagca tctcggccca ggcgaagcag ctgctgctgc accataccct gggcaacggc   360
gacttcaccg tgttccaccg catgtccgcg aacatcagcg agaccaccgc catgatcacc   420
gacatcgcca ccgcgccggc cgaaatcgac cgctgcatcc ggaccaccta cgtcacccag   480
cggcccgtgt atctgggcct gccggccaac ctggtcgacc tgaacgtgcc cgcgaagctg   540
ctgcagaccc cgatcgacat gtcgctgaag cccaacgacg ccgagtccga aaaggaagtc   600
atcgaccaca tcctggcgct ggtcaaggac gccaagaacc cggtgatcct ggcggacgcc   660
tgctgctccc gccacgacgt caaggccgag accaagaagc tgatcgacct gacccagttc   720
cccgccttcg tgaccccgat gggcaagggc tccatcgacg aacagcatcc gcggtacggc   780
```

```
ggcgtctatg tgggcaccct gagcaagccc gaagtcaagg aagccgtgga aagcgccgac      840
ctgatcctgt cggtcggcgc cctgctgtcc gacttcaaca ccggctcctt cagctactcg      900
tataagacca agaacatcgt ggagttccac agcgaccaca tgaagatccg caacgccacc      960
ttccccggcg tccagatgaa gttcgtgctg cagaagctgc tgaccaccat cgccgacgcc     1020
gcgaagggct acaagccggt cgcggtgccc gcccggaccc cggcgaacgc cgcggtcccc     1080
gcctcgaccc cgctgaagca ggaatggatg tggaaccagc tgggcaactt cctgcaggaa     1140
ggcgacgtcg tgatcgcgga aaccggcacc tccgccttcg gcatcaacca gaccaccttc     1200
ccgaacaaca cctacggcat cagccaggtg ctgtggggct cgatcggctt caccaccggc     1260
gccaccctgg gcgccgcgtt cgccgcggag gaaatcgacc gaagaagcg cgtcatcctg      1320
```

(Note: line 1320 appears as "gccacccctgg gcgccgcgtt cgccgcggag gaaatcgacc gaagaagcg cgtcatcctg")

```
ttcatcggcg acggcagcct gcagctgacc gtgcaggaaa tctcgaccat gatccggtgg     1380
ggcctgaagc cctacctgtt cgtcctgaac aacgacggct ataccatcga aagctgatc      1440 cacggcccga aggcccagta caacgaaatc cagggctggg accatctgtc gctgctgccc     1500
accttcggcg ccaaggacta tgagacccat cgcgtggcga ccaccggcga atgggacaag     1560
ctgacccagg acaagtcgtt caacgacaac tccaagatcc ggatgatcga gatcatgctg     1620
cccgtcttcg acgcgccgca gaacctggtg aacaggcca agctgaccgc cgcgaccaac      1680
```

(Note: line 1680 "cccgtcttcg acgcgccgca gaacctggtg aacaggcca agctgaccgc cgcgaccaac")

```
gcgaagcagt ga                                                          1692

<210> SEQ ID NO 91
<211> LENGTH: 3147
<212> TYPE: DNA
<213> ORGANISM: Saccharomyces cerevisiae

<400> SEQUENCE: 91
atgaagtcgg aatacaccat cggccgctat ctgctggacc gcctgagcga gctgggcatc       60
cgccacatct tcggcgtccc cggcgactac aacctgtcgt tcctggacta catcatggag      120
tataggggca tcgactgggt cggcaactgc aacgaactga cgccggcta cgccgcggac       180
```

(Note: line 180 "tataggggca tcgactgggt cggcaactgc aacgaactga cgccggcta cgccgcggac")

```
ggctatgccc gcatcaacgg catcggcgcg atcctgacca ccttcggcgt cggcgagctg      240
tccgccatca acgccatcgc gggcgcctac gcggaacagg tgccggtcgt gaagatcacc      300
ggcatcccca ccgccaaggt ccgcgacaac ggcctgtatg tgcaccatac cctgggcgac      360
ggccgcttcg accacttctt cgagatgttc cggaagtca ccgtggccga ggcgctgctg       420
```

(Note: line 420 "ggccgcttcg accacttctt cgagatgttc cggaagtca ccgtggccga ggcgctgctg")

```
agcgaggaaa cgccgcgca ggaaatcgac cgcgtgctga tctcgtgctg gcgccagaag       480
```

(Note: line 480 "agcgaggaaa cgccgcgca ggaaatcgac cgcgtgctga tctcgtgctg gcgccagaag")

```
cggccggtcc tgatcaacct gcccatcgac gtgtacgaca agccgatcaa caagccgctg      540
aagcccctgc tggactatac catcagctcg aacaaggaag ccgcgtgcga gttcgtcacc      600
gagatcgtgc cgatcatcaa ccgcgccaag aagcccgtca tcctggcgga ctacggcgtg      660
taccggtatc aggtccagca cgtgctgaag aacctggcgg agaagaccgg cttcccggtc      720
gccaccctgt cgatgggcaa gggcgtgttc aacgaagccc atccgcagtt catcggcgtc      780
tacaacggcg acgtgtccag ccctatctg cgccagcggg tcgacgaggc cgactgcatc       840
```

(Note: line 840 "tacaacggcg acgtgtccag ccctatctg cgccagcggg tcgacgaggc cgactgcatc")

```
atctcggtcg gcgtgaagct gaccgactcc accaccggcg gcttctccca cggcttcagc      900
aagcgcaacg tgatccatat cgaccgttc tccatcaagg ccaagggcaa gaagtacgcg       960
```

(Note: line 960 "aagcgcaacg tgatccatat cgaccgttc tccatcaagg ccaagggcaa gaagtacgcg")

```
cccatcacca tgaaggacgc cctgaccgaa ctgacctcga agatcgagca ccggaacttc     1020
gaagacctgg acatcaagcc gtacaagtcc gacaaccaga gtatttcgc gaaggagaag      1080
```

(Note: line 1080 "gaagacctgg acatcaagcc gtacaagtcc gacaaccaga gtatttcgc gaaggagaag")

```
cccatcaccc agaagcgctt cttcgaacgg atcgcccatt tcatcaagga aaggacgtc      1140
```

(Note: line 1140 "cccatcaccc agaagcgctt cttcgaacgg atcgcccatt tcatcaagga aaggacgtc")
```

| | |
|---|---|
| ctgctggcgg aacagggcac ctgcttcttc ggcgccagca ccatccagct gccgaaggac | 1200 |
| gcgaccttca tcggccagcc cctgtggggc tccatcggct cacccctgcc ggccctgctg | 1260 |
| ggcagccagc tggcggacca gaagcgtcgc aacatcctgc tgatcggcga cggcgccttc | 1320 |
| cagatgaccg cgcaggagat ctcgaccatg ctgcgcctgc agatcaagcc gatcatcttc | 1380 |
| ctgatcaaca cgacggcta ccatcgag cgcgccatcc acggccggga acaggtgtac | 1440 |
| aacaacatcc agatgtggcg gtatcataac gtcccgaagg tgctgggccc caaggaatgc | 1500 |
| agcctgacct tcaaggtcca gtcggagacc gaactggaga aggccctgct ggtcgccgac | 1560 |
| aaggactgcg agcacctgat cttcatcgaa gtcgtgatgg accgctacga caagccggag | 1620 |
| cccctggaac gcctgtccaa gcggttcgcc aaccagaaca cggctatgc gcggatcaac | 1680 |
| ggcatcggcg ccattttaac caccttcggc gtgggcgagc tgagcgcgat caacgcgatc | 1740 |
| gccggcgcct acgcggagca ggtgccggtg gtcaaaatta ccggcatccc caccgcgaag | 1800 |
| gtgcgggaca acggcctgta cgtccatcac accctgggcg acggccggtt cgaccatttc | 1860 |
| ttcgaaatgt tccgggaggt gaccgtcgcc gaggcgctgc tgtcggaaga aacgcggcc | 1920 |
| caggagatcg accgcgtcct gatcagctgc tggcggcaga agcgcccgt gctgatcaac | 1980 |
| ctgccgatcg acgtctatga caagcccatc aacaagcccc tgaagccgct gctggactac | 2040 |
| accatctcgt ccaacaagga agccgcctgc gagttcgtca ccgaaatcgt ccccatcatc | 2100 |
| aaccgcgcga agaagccggt gatcctggcc gactatggcg tctatcggta tcaggtgcag | 2160 |
| catgtcctga gaacctggc cgaaaagacc ggcttccccg tggccaccct gagcatgggc | 2220 |
| aagggcgtct tcaacgaggc gcaccccag ttcatcggcg tgtataacgg cgacgtgagc | 2280 |
| tcgccgtacc tgcggcagcg cgtggacgaa gccgactgca tcatcagcgt cggcgtcaag | 2340 |
| ctgaccgact cgaccaccgg cggcttctcg cacggcttct cgaagcggaa cgtcatccac | 2400 |
| atcgacccgt tctcgatcaa ggcgaagggc aagaagtatg ccccgatcac catgaaggac | 2460 |
| gcgctgaccg aactgaccag caagatcgaa catcgcaact tcgaggacct ggacatcaag | 2520 |
| ccctacaagt cggacaacca gaagtacttc gccaaggaaa agccgattac tcagaagcgc | 2580 |
| ttcttcgagc gcatcgcgca cttcatcaag gaaaaggacg tcctgctggc cgagcaaggc | 2640 |
| acctgcttct tcggtgcgtc gaccatccag ctgcccaagg acgccacctt catcggccag | 2700 |
| ccgctgtggg gctcgatcgg ctataccctg cccgcgctgc tgggctccca gctggccgat | 2760 |
| caaaaacgtc gcaatatttt actgatcggc gacggcgcgt tccagatgac cgcccaggag | 2820 |
| atcagcacca tgctgcggct gcagatcaag cccattatct tcctgattaa caacgacggc | 2880 |
| tataccatcg aacgggcgat ccacggccgc gagcaggtct ataataatat tcaaatgtgg | 2940 |
| cggtatcata tgtgcccaa ggtcctgggc ccgaaggaat gctcgctgac cttcaaggtg | 3000 |
| cagagcgaaa ccgagctgga aaaggccctg ctggtcgccg ataaggactg cgaacatctg | 3060 |
| atcttcatcg aggtggtcat ggaccggtat gacaagcccg aaccccctgga acggctgagc | 3120 |
| aagcgcttcg cgaaccagaa caactga | 3147 |

<210> SEQ ID NO 92
<211> LENGTH: 35
<212> TYPE: DNA
<213> ORGANISM: Artificial Sequence
<220> FEATURE:
<223> OTHER INFORMATION: JPS00082

<400> SEQUENCE: 92
tgcaaggtac actgtcagaa cgcagaagcg gtctg                          35

<210> SEQ ID NO 93
<211> LENGTH: 28
<212> TYPE: DNA
<213> ORGANISM: Artificial Sequence
<220> FEATURE:
<223> OTHER INFORMATION: JPS00031

<400> SEQUENCE: 93
ggtttattcc tccttattta atcgatac                                    28

<210> SEQ ID NO 94
<211> LENGTH: 34
<212> TYPE: DNA
<213> ORGANISM: Artificial Sequence
<220> FEATURE:
<223> OTHER INFORMATION: JPS00032

<400> SEQUENCE: 94
aaggaggaat aaaccatggg cacggttgag cctg                             34

<210> SEQ ID NO 95
<211> LENGTH: 33
<212> TYPE: DNA
<213> ORGANISM: Artificial Sequence
<220> FEATURE:
<223> OTHER INFORMATION: GMV257

<400> SEQUENCE: 95
cacatcctgt ctagatcagc cctcgccctt gac                              33

<210> SEQ ID NO 96
<211> LENGTH: 58
<212> TYPE: DNA
<213> ORGANISM: Artificial Sequence
<220> FEATURE:
<223> OTHER INFORMATION: JPS00118)

<400> SEQUENCE: 96
tctagacagg atgtgtcaca caggaaacca tgtcttatcc tgagaaattt gaaggtat    58

<210> SEQ ID NO 97
<211> LENGTH: 41
<212> TYPE: DNA
<213> ORGANISM: Artificial Sequence
<220> FEATURE:
<223> OTHER INFORMATION: JPS00119

<400> SEQUENCE: 97
acagtgtacc ttgcactagt ctgaaaattc tttgtcgtag c                     41

<210> SEQ ID NO 98
<211> LENGTH: 70
<212> TYPE: DNA
<213> ORGANISM: Artificial Sequence
<220> FEATURE:
<223> OTHER INFORMATION: ESG00087

<400> SEQUENCE: 98
gtgttggttg ctcgctagca ttgtaccaag ggctgagcta gctataaagt cagcgccctg    60
caccattatg                                                          70

<210> SEQ ID NO 99
<211> LENGTH: 46
<212> TYPE: DNA

<213> ORGANISM: Artificial Sequence
<220> FEATURE:
<223> OTHER INFORMATION: GMV251

<400> SEQUENCE: 99
gagcaaccaa cacttaaaga ggagaaaatg ggcacggttg agcctg    46

<210> SEQ ID NO 100
<211> LENGTH: 149
<212> TYPE: DNA
<213> ORGANISM: Artificial Sequence
<220> FEATURE:
<223> OTHER INFORMATION: IDT gBlock synthesized rnpB

<400> SEQUENCE: 100
gctagcacta gtgatcacgt gcttaagccg gcttatcggt cagtttcacc tgatttacgt    60
aaaaacccgc ttcggcgggt ttttgctttt ggaggggcag aaagatgaat gactgtccac    120
gacgctatac ccaaaagaaa accggtacc    149

<210> SEQ ID NO 101
<211> LENGTH: 35
<212> TYPE: DNA
<213> ORGANISM: Artificial Sequence
<220> FEATURE:
<223> OTHER INFORMATION: JPS00161

<400> SEQUENCE: 101
gcctgataca gattattgta ggtggaccag ttggt    35

<210> SEQ ID NO 102
<211> LENGTH: 34
<212> TYPE: DNA
<213> ORGANISM: Artificial Sequence
<220> FEATURE:
<223> OTHER INFORMATION: JPS00162

<400> SEQUENCE: 102
ggtttattcc tccttgattt gtcctactca ggag    34

<210> SEQ ID NO 103
<211> LENGTH: 34
<212> TYPE: DNA
<213> ORGANISM: Artificial Sequence
<220> FEATURE:
<223> OTHER INFORMATION: JPS00163

<400> SEQUENCE: 103
aaggaggaat aaaccgctag cactagtgat cacg    34

<210> SEQ ID NO 104
<211> LENGTH: 34
<212> TYPE: DNA
<213> ORGANISM: Artificial Sequence
<220> FEATURE:
<223> OTHER INFORMATION: JPS00164

<400> SEQUENCE: 104
taatctgtat caggcggtac cggttttctt ttgg    34

<210> SEQ ID NO 105
<211> LENGTH: 34
<212> TYPE: DNA
<213> ORGANISM: Artificial Sequence
<220> FEATURE:
<223> OTHER INFORMATION: JPS00172

<210> SEQ ID NO 105

<400> SEQUENCE: 105
atcagactaa gccttgtgct taagccggct tatc                     34

<210> SEQ ID NO 106
<211> LENGTH: 51
<212> TYPE: DNA
<213> ORGANISM: Artificial Sequence
<220> FEATURE:
<223> OTHER INFORMATION: JPS00173

<400> SEQUENCE: 106
aaggaggaat aaaccgctag cactagtgat cacttgacgg ctagctcagt c    51

<210> SEQ ID NO 107
<211> LENGTH: 33
<212> TYPE: DNA
<213> ORGANISM: Artificial Sequence
<220> FEATURE:
<223> OTHER INFORMATION: JPS00174

<400> SEQUENCE: 107
tgaacaggtc tgacttcagt gctgcgccga ggc                      33

<210> SEQ ID NO 108
<211> LENGTH: 51
<212> TYPE: DNA
<213> ORGANISM: Artificial Sequence
<220> FEATURE:
<223> OTHER INFORMATION: JPS00176

<400> SEQUENCE: 108
agtcagacct gttcattaaa gaggagaaaa tgcagattta ctacgacaaa g    51

<210> SEQ ID NO 109
<211> LENGTH: 34
<212> TYPE: DNA
<213> ORGANISM: Artificial Sequence
<220> FEATURE:
<223> OTHER INFORMATION: JPS00177

<400> SEQUENCE: 109
aagtgttggt tgctctcagt tcttgctcgt gtcc                     34

<210> SEQ ID NO 110
<211> LENGTH: 45
<212> TYPE: DNA
<213> ORGANISM: Artificial Sequence
<220> FEATURE:
<223> OTHER INFORMATION: JPS00157

<400> SEQUENCE: 110
gagcaaccaa cacttaaaga ggagaaaatg accgacaagc acccc          45

<210> SEQ ID NO 111
<211> LENGTH: 33
<212> TYPE: DNA
<213> ORGANISM: Artificial Sequence
<220> FEATURE:
<223> OTHER INFORMATION: JPS00178

<400> SEQUENCE: 111
aaggcttagt ctgattcaga ggccgtcgtc ggt                      33

<210> SEQ ID NO 112

<211> LENGTH: 430
<212> TYPE: DNA
<213> ORGANISM: Artificial Sequence
<220> FEATURE:
<223> OTHER INFORMATION: IDT gBlock synthesized Me-AM1 PmxaF

<400> SEQUENCE: 112

```
atggtgcagg gcgcttcccg cttggtcggg ccgcttcgcg agggcccgtt gacgacaacg      60
gtgcgatggg tcccggcccc ggtcaagacg atgccaatac gttgcgacac tacgccttgg     120
cactttaga attgccttat cgtcctgata agaaatgtcc gaccagctaa agacatcgcg     180
tccaatcaaa gcctagaaaa tataggcgaa gggacgctaa taagtctttc ataagaccgc     240
gcaaatctaa aaatatcctt agattcacga tgcggcactt cggatgactt ccgagcgagc     300
ctggaacctc agaaaaacgt ctgagagata ccgcgaggcc gaaaggcgag gcggttcagc     360
gaggagacgc aggatgagca ggtttgtgac atcagtctcg gccttggcgg ctagcgagca     420
accaacactt                                                            430
```

<210> SEQ ID NO 113
<211> LENGTH: 34
<212> TYPE: DNA
<213> ORGANISM: Artificial Sequence
<220> FEATURE:
<223> OTHER INFORMATION: JPS00169

<400> SEQUENCE: 113

```
agcgccctgc accattatgt tccggatctg catc                                  34
```

<210> SEQ ID NO 114
<211> LENGTH: 46
<212> TYPE: DNA
<213> ORGANISM: Artificial Sequence
<220> FEATURE:
<223> OTHER INFORMATION: GMV00251

<400> SEQUENCE: 114

```
gagcaaccaa cacttaaaga ggagaaaatg ggcacggttg agcctg                     46
```

<210> SEQ ID NO 115
<211> LENGTH: 32
<212> TYPE: DNA
<213> ORGANISM: Artificial Sequence
<220> FEATURE:
<223> OTHER INFORMATION: (PS00170

<400> SEQUENCE: 115

```
atggtgcagg gcgcttcccg cttggtcggg cc                                    32
```

<210> SEQ ID NO 116
<211> LENGTH: 19
<212> TYPE: DNA
<213> ORGANISM: Artificial Sequence
<220> FEATURE:
<223> OTHER INFORMATION: JPS00171

<400> SEQUENCE: 116

```
aagtgttggt tgctcgcta                                                   19
```

<210> SEQ ID NO 117
<211> LENGTH: 68
<212> TYPE: DNA
<213> ORGANISM: Artificial Sequence
<220> FEATURE:
<223> OTHER INFORMATION: JPS00153
```

<400> SEQUENCE: 117
accactcaac gatcagctag cactgtacct aggactgagc tagccgtcaa gtcagcgccc    60
tgcaccat    68

<210> SEQ ID NO 118
<211> LENGTH: 48
<212> TYPE: DNA
<213> ORGANISM: Artificial Sequence
<220> FEATURE:
<223> OTHER INFORMATION: JPS00151

<400> SEQUENCE: 118
tgatcgttga gtggtttaaa gaggagaaaa tgcgtgaaac gatacctc    48

<210> SEQ ID NO 119
<211> LENGTH: 33
<212> TYPE: DNA
<213> ORGANISM: Artificial Sequence
<220> FEATURE:
<223> OTHER INFORMATION: JPS00154

<400> SEQUENCE: 119
aagtgttggt tgctctcagt gctgcgccga ggc    33

<210> SEQ ID NO 120
<211> LENGTH: 33
<212> TYPE: DNA
<213> ORGANISM: Artificial Sequence
<220> FEATURE:
<223> OTHER INFORMATION: JPS00183

<400> SEQUENCE: 120
tgagctagct ataaagtgat cactagtgct agc    33

<210> SEQ ID NO 121
<211> LENGTH: 55
<212> TYPE: DNA
<213> ORGANISM: Artificial Sequence
<220> FEATURE:
<223> OTHER INFORMATION: JPS00185

<400> SEQUENCE: 121
ttatagctag ctcagcccctt ggtacaatgc tagctgatcg ttgagtggtt taaag    55

<210> SEQ ID NO 122
<211> LENGTH: 35
<212> TYPE: DNA
<213> ORGANISM: Artificial Sequence
<220> FEATURE:
<223> OTHER INFORMATION: J23100

<400> SEQUENCE: 122
ttgacggcta gctcagtcct aggtacagtg ctagc    35

<210> SEQ ID NO 123
<211> LENGTH: 35
<212> TYPE: DNA
<213> ORGANISM: Artificial Sequence
<220> FEATURE:
<223> OTHER INFORMATION: J23100 hybrid

<400> SEQUENCE: 123
ttgacggcta gctcagccct tggtacaatg ctagc    35

<210> SEQ ID NO 124
<211> LENGTH: 35
<212> TYPE: DNA
<213> ORGANISM: Artificial Sequence
<220> FEATURE:
<223> OTHER INFORMATION: J23115

<400> SEQUENCE: 124
tttatagcta gctcagccct tggtacaatg ctagc          35

<210> SEQ ID NO 125
<211> LENGTH: 22
<212> TYPE: DNA
<213> ORGANISM: Artificial Sequence
<220> FEATURE:
<223> OTHER INFORMATION: GMV00233

<400> SEQUENCE: 125
tgccagctgc attaatgaat cg          22

<210> SEQ ID NO 126
<211> LENGTH: 45
<212> TYPE: DNA
<213> ORGANISM: Artificial Sequence
<220> FEATURE:
<223> OTHER INFORMATION: GMV00235

<400> SEQUENCE: 126
ttaatgcagc tggcagccag cgcttcgtta atacagatgt aggtg          45

<210> SEQ ID NO 127
<211> LENGTH: 52
<212> TYPE: DNA
<213> ORGANISM: Artificial Sequence
<220> FEATURE:
<223> OTHER INFORMATION: GMV00433

<400> SEQUENCE: 127
gatcgttgag tggtgaactt aaagaggaga aaatgggcac ggttgagcct gg          52

<210> SEQ ID NO 128
<211> LENGTH: 19
<212> TYPE: DNA
<213> ORGANISM: Artificial Sequence
<220> FEATURE:
<223> OTHER INFORMATION: GMV00434

<400> SEQUENCE: 128
tgcattcgat tcctgtttg          19

<210> SEQ ID NO 129
<211> LENGTH: 19
<212> TYPE: DNA
<213> ORGANISM: Artificial Sequence
<220> FEATURE:
<223> OTHER INFORMATION: GMV00435

<400> SEQUENCE: 129
caggaatcga atgcaaccg          19

<210> SEQ ID NO 130
<211> LENGTH: 49
<212> TYPE: DNA
<213> ORGANISM: Artificial Sequence
<220> FEATURE:
<223> OTHER INFORMATION: GMV00436

<400> SEQUENCE: 130
gagcaaccaa cactcacaca ggaaaccatg catattacat acgatctgc       49

<210> SEQ ID NO 131
<211> LENGTH: 39
<212> TYPE: DNA
<213> ORGANISM: Artificial Sequence
<220> FEATURE:
<223> OTHER INFORMATION: GMV00437

<400> SEQUENCE: 131
gttcaccact caacgatctt aagcgtcaac gaaaccggt                 39

<210> SEQ ID NO 132
<211> LENGTH: 69
<212> TYPE: DNA
<213> ORGANISM: Artificial Sequence
<220> FEATURE:
<223> OTHER INFORMATION: GMV00438

<400> SEQUENCE: 132
tgaacaggtc tgactgctag cattgtacca agggctgagc tagctataaa gatttgtcct    60
actcaggag                                                            69

<210> SEQ ID NO 133
<211> LENGTH: 53
<212> TYPE: DNA
<213> ORGANISM: Artificial Sequence
<220> FEATURE:
<223> OTHER INFORMATION: GMV00439

<400> SEQUENCE: 133
agtcagacct gttcattaaa gaggagaaaa tgagcggaaa acccttttac gac           53

<210> SEQ ID NO 134
<211> LENGTH: 42
<212> TYPE: DNA
<213> ORGANISM: Artificial Sequence
<220> FEATURE:
<223> OTHER INFORMATION: GMV00440

<400> SEQUENCE: 134
aaggcttagt ctgattcaga cggcgcgcaa ggcggcgacg at             42

<210> SEQ ID NO 135
<211> LENGTH: 49
<212> TYPE: DNA
<213> ORGANISM: Artificial Sequence
<220> FEATURE:
<223> OTHER INFORMATION: GMV00441

<400> SEQUENCE: 135
atcagactaa gcctttcaca caggaaacca tgcacgacag actgatcat      49

<210> SEQ ID NO 136
<211> LENGTH: 35
<212> TYPE: DNA
<213> ORGANISM: Artificial Sequence
<220> FEATURE:
<223> OTHER INFORMATION: GMV00442

<400> SEQUENCE: 136
ggtttattcc tcctttcaca catccccgac ttgcg                     35

<210> SEQ ID NO 137
<211> LENGTH: 49
<212> TYPE: DNA
<213> ORGANISM: Artificial Sequence
<220> FEATURE:
<223> OTHER INFORMATION: ESG00084

<400> SEQUENCE: 137
gagacagaac gaagtgtgac cagaacgcag aagcggtctg ataaaacag        49

<210> SEQ ID NO 138
<211> LENGTH: 70
<212> TYPE: DNA
<213> ORGANISM: Artificial Sequence
<220> FEATURE:
<223> OTHER INFORMATION: ESG00088

<400> SEQUENCE: 138
gtgttggttg ctcgctagca ctgtacctag gactgagcta gccgtcaagt cagcgccctg        60
caccattatg        70

<210> SEQ ID NO 139
<211> LENGTH: 10705
<212> TYPE: DNA
<213> ORGANISM: Artificial Sequence
<220> FEATURE:
<223> OTHER INFORMATION: pMZT37

<400> SEQUENCE: 139
tcaccctgtc gggcaatgcc gaggcattct ggcagcagcg ccccctggcc tgtagtggat        60
tacgtgccgg tctgttccat cctaccaccg gctattcact gccgctggcg gttgccgtgg       120
ccgaccgcct gagcgcactt gatgtcttta cgtcggcctc aattcaccag gctattaggc       180
attttgcccg cgagcgctgg cagcagcagc gcttttttcg catgctgaat cgcatgctgt       240
ttttagccgg acccgccgat tcacgctggc gggttatgca gcgttttat ggtttacctg       300 aagatttaat tgcccgtttt tatgcgggaa aactcacgct gaccgatcgg ctacgtattc       360
tgagcggcaa gccgcctgtt ccggtattag cagcattgca agccattatg acgactcatc       420
gttaagagac agaacgaagt gtgaccagaa cgcagaagcg gtctgataaa acagaatttg       480
cctggcggca gtagcgcggt ggtcccacct gaccccatgc cgaactcaga agtgaaacgc       540
cgtagcgccg atggtagtgt ggggtctccc catgcgagag tagggaactg ccaggcatca       600
aataaaacga aaggctcagt cgaaagactg ggcctttcgt tttatctgtt gtttgtcggt       660
gaacgctctc ctgagtagga caaatcttgt aggtggacca gttggtgatt ttgaactttt       720
gctttgccac ggaacggtct gcgttgtcgg gaagatgcgt gatctgatcc ttcaactcag       780
caaaagttcg atttattcaa caaagccgcc gtcccgtcaa gtcagcgtaa tgctctgcca       840
gtgttacaac caattaacca attctgatta gaaaaactca tcgagcatca atgaaactg        900 caatttattc atatcaggat tatcaatacc atattttga aaaagccgtt tctgtaatga       960
aggagaaaac tcaccgaggc agttccatag gatggcaaga tcctggtatc ggtctgcgat      1020
tccgactcgt ccaacatcaa tacaacctat taatttcccc tcgtcaaaaa taaggttatc      1080
aagtgagaaa tcaccatgag tgacgactga atccggtgag aatggcaaaa gcttatgcat      1140
ttctttccag acttgttcaa caggccagcc attacgctcg tcatcaaaat cactcgcatc      1200
aaccaaaccg ttattcattc gtgattgcgc ctgagcgaga cgaaatacgc gatcgctgtt      1260
aaaaggacaa ttacaaacag gaatcgaatg caaccggcgc aggaacactg ccagcgcatc      1320

```
aacaatattt tcacctgaat caggatattc ttctaatacc tggaatgctg ttttcccggg    1380
gatcgcagtg gtgagtaacc atgcatcatc aggagtacgg ataaaatgct tgatggtcgg    1440
aagaggcata aattccgtca gccagtttag tctgaccatc tcatctgtaa catcattggc    1500
aacgctacct ttgccatgtt tcagaaacaa ctctggcgca tcgggcttcc catacaatcg    1560
atagattgtc gcacctgatt gcccgacatt atcgcgagcc catttatacc catataaatc    1620
agcatccatg ttggaattta atcgcggcct cgagcaagac gtttcccgtt gaatatggct    1680
cataacaccc cttgtattac tgtttatgta agcagacagt tttattgttc atgatgatat    1740
attttatct tgtgcaatgt aacatcagag attttgagac acaacgtggc tttccccccc    1800
cccctgcag gtccgacacg gggatggatg gcgttcccga tcatggtcct gcttgcttcg    1860
ggtggcatcg gaatgccggc gctgcaagca atgttgtcca ggcaggtgga tgaggaacgt    1920
caggggcagc tgcaaggctc actggcggcg ctcaccagcc tgacctcgat cgtcggaccc    1980
ctcctcttca cggcgatcta tgcggcttct ataacaacgt ggaacgggtg gcatggatt    2040
gcaggcgctg ccctctactt gctctgcctg ccggcgctgc gtcgcgggct ttggagcggc    2100
gcagggcaac gagccgatcg ctgatcgtgg aaacgatagg cctatgccat gcgggtcaag    2160
gcgacttccg gcaagctata cgcgccctag aattgtcaat tttaatcctc tgtttatcgg    2220
cagttcgtag agcgcgccgt gcgtcccgag cgatactgag cgaagcaagt gcgtcgagca    2280
gtgcccgctt gttcctgaaa tgccagtaaa gcgctggctg ctgaaccccc agccggaact    2340
gaccccacaa ggccctagcg tttgcaatgc accaggtcat cattgaccca ggcgtgttcc    2400
accaggccgc tgcctcgcaa ctcttcgcag gcttcgccga cctgctcgcg ccacttcttc    2460
acgcgggtgg aatccgatcc gcacatgagg cggaaggttt ccagcttgag cgggtacggc    2520
tcccggtgcg agctgaaata gtcgaacatc cgtcgggccg tcggcgacag cttgcggtac    2580
ttctcccata tgaatttcgt gtagtggtcg ccagcaaaca gcacgacgat ttcctcgtcg    2640
atcaggacct ggcaacggga cgttttcttg ccacggtcca ggacgcggaa gcggtgcagc    2700
agcgacaccg attccaggtg cccaacgcgg tcggacgtga agcccatcgc cgtcgcctgt    2760
aggcgcgaca ggcattcctc ggccttcgtg taataccggc cattgatcga ccagcccagg    2820
tcctggcaaa gctcgtagaa cgtgaaggtg atcggctcgc cgatagggt gcgcttcgcg    2880
tactccaaca cctgctgcca caccagttcg tcatcgtcgg cccgcagctc gacgccggtg    2940
taggtgatct tcacgtcctt gttgacgtgg aaaatgacct tgttttgcag cgcctcgcgc    3000
gggattttct tgttgcgcgt ggtgaacagg gcagagcggg ccgtgtcgtt tggcatcgct    3060
cgcatcgtgt ccggccacgg cgcaatatcg aacaaggaaa gctgcatttc cttgatctgc    3120
tgcttcgtgt gtttcagcaa gcggcctgc ttggcctcgc tgacctgttt tgccaggtcc    3180
tcgccggcgg ttttcgctt cttggtcgtc atagttcctc gcgtgtcgat ggtcatcgac    3240
ttcgccaaac ctgccgcctc ctgttcgaga cgacgcgaac gctccacggc ggccgatggc    3300
gcgggcaggg caggggagc cagttgcacg ctgtcgcgct cgatcttggc cgtagcttgc    3360
tggaccatcg agccgacgga ctggaaggtt tcgcggggcg cacgcatgac ggtgcggctt    3420
gcgatggttt cggcatcctc ggcggaaaac cccgcgtcga tcagttcttg cctgtatgcc    3480
ttccggtcaa acgtccgatt cattcaccct ccttgcggga ttgccccgac tcacgccggg    3540
gcaatgtgcc cttattcctg atttgacccg cctggtgcct tggtgtccag ataatccacc    3600
ttatcggcaa tgaagtcggt cccgtagacc gtctggccgt ccttctcgta cttggtattc    3660
```

-continued

```
cgaatcttgc cctgcacgaa taccagctcc gcgaagtcgc tcttcttgat ggagcgcatg    3720
gggacgtgct tggcaatcac gcgcacccccc cggccgtttt agcggctaaa aaagtcatgg    3780
ctctgccctc gggcggacca cgcccatcat gaccttgcca agctcgtcct gcttctcttc    3840
gatcttcgcc agcagggcga ggatcgtggc atcaccgaac cgcgccgtgc gcgggtcgtc    3900
ggtgagccag agtttcagca ggccgcccag gcggcccagg tcgccattga tgcgggccag    3960
ctcgcggacg tgctcatagt ccacgacgcc cgtgattttg tagccctggc cgacggccag    4020
caggtaggcc tacaggctca tgccggccgc cgccgccttt cctcaatcg ctcttcgttc    4080 gtctggaagg cagtacacct tgataggtgg gctgcccttc ctggttggct tggtttcatc    4140
agccatccgc ttgccctcat ctgttacgcc ggcggtagcc ggccagcctc gcagagcagg    4200
attcccgttg agcaccgcca ggtgcgaata agggacagtg aagaaggaac acccgctcgc    4260
gggtgggcct acttcaccta tcctgcccgg ctgacgccgt tggatacacc aaggaaagtc    4320
tacacgaacc ctttggcaaa atcctgtata tcgtgcgaaa aaggatggat ataccgaaaa    4380
aatcgctata atgaccccga agcagggtta tgcagcggaa aagatccgtc gacccttcc    4440 gacgctcacc gggctggttg ccctcgccgc tgggctggcg ccgtctatg gccctgcaaa    4500 cgcgccagaa acgccgtcga agccgtgtgc gagacaccgc ggccgccggc gttgtggata    4560
cctcgcggaa aacttggccc tcactgacag atgaggggcg gacgttgaca cttgagggc    4620 cgactcaccc ggcgcggcgt tgacagatga ggggcaggct cgatttcggc cggcgacgtg    4680
gagctggcca gcctcgcaaa tcggcgaaaa cgcctgattt tacgcgagtt cccacagat    4740 gatgtgacaa gcctggggga taagtgccct gcggtattga cacttgaggg gcgcgactac    4800
tgacagatga ggggcgcgat ccttgacact tgaggggcag agtgctgaca gatgagggc    4860 gcacctattg acatttgagg ggctgtccac aggcagaaaa tccagcattt gcaagggttt    4920
ccgcccgttt ttcggccacc gctaacctgt cttttaacct gcttttaaac caatatttat    4980
aaaccttgtt tttaaccagg gctgcgccct gtgcgcgtga ccgcgcacgc cgaaggggg    5040 tgcccccct tctcgaaccc tcccggcccg ctaacgcggg cctccatcc ccccagggc    5100 tgcgcccctc ggccgcgaac ggcctcaccc caaaaatggc agccaagctg accacttctg    5160
cgctcggccc ttccggctgg ctggtttatt gctgataaat ctggagccgg tgagcgtggg    5220
tctcgcggta tcattgcagc actggggcca atggtaagc cctcccgtat cgtagttatc    5280
tacacgacgg ggagtcaggc aactatggat gaacgaaata gacagatcgc tgagataggt    5340
gcctcactga ttaagcattg gtaactgtca gaccaagttt actcatatat actttagatt    5400
gatttaaaac ttcattttta atttaaaagg atcaggtga agatccttt tgataatctc    5460 atgaccaaaa tcccttaacg tgagttttcg ttccactgag cgtcagaccc cgtagaaaag    5520
atcaaaggat cttcttgaga tcctttttt ctgcgcgtaa tctgctgctt gcaaacaaaa    5580
aaaccaccgc taccagcggt ggtttgtttg ccggatcaag agctaccaac tcttttccg    5640 aaggtaactg gcttcagcag agcgcagata ccaaatactg tccttctagt gtagccgtag    5700
ttaggccacc acttcaagaa ctctgtagca ccgcctacat acctcgctct gctaatcctg    5760
ttaccagtgg ctgctgccag tggcgataag tcgtgtctta ccgggttgga ctcaagacga    5820
tagttaccgg ataaggcgca gcggtcgggc tgaacggggg gttcgtgcac acagcccagc    5880
ttggagcgaa cgacctacac cgaactgaga tacctacagc gtgagctatg agaaagcgcc    5940
acgcttcccg aagggagaaa ggcggacagg tatccggtaa gcggcagggt cggaacagga    6000
gagcgcacga gggagcttcc agggggaaac gcctggtatc tttatagtcc tgtcgggttt    6060
```

-continued

```
cgccacctct gacttgagcg tcgattttg tgatgctcgt cagggggcg gagcctatgg    6120
aaaaacgcca gcaacgcggc cttttacgg ttcctggcct tttgctggcc ttttgctcac   6180
atgttctttc ctgcgttatc ccctgattct gtggataacc gtattaccgc ctttgagtga   6240
gctgataccg ctcgccgcag ccgaacgacc gagcgcagcg agtcagtgag cgaggaagcg   6300
gaagagcgcc caatacgcaa accgcctctc cccgcgcgtt ggccgattca ttaatgcagc   6360
tggcagccag cgcttcgtta atacagatgt aggtgttcca cagggtagcc agcagcatcc   6420
tgcgatgcag atccggaaca taatggtgca gggcgctgac ttgacggcta gctcagtcct   6480
aggtacagtg ctagcgagca accaacactt aaagaggaga aaatgtatcc gtttataagg   6540
acagcccgaa tgacggtctg cgcaaaaaaa cacgttcatc tcactcgcga tgctgcggag   6600
cagttactgg ctgatattga tcgacgcctt gatcagttat tgcccgtgga gggagaacgg   6660
gatgttgtgg gtgccgcgat gcgtgaaggt gcgctggcac cgggaaaacg tattcgcccc   6720
atgttgctgt tgctgaccgc ccgcgatctg ggttgcgctg tcagccatga cggattactg   6780
gatttggcct gtgcggtgga aatggtccac gcggcttcgc tgatccttga cgatatgccc   6840
tgcatggacg atgcgaagct gcggcgcgga cgccctacca ttcattctca ttacggagag   6900
catgtggcaa tactggcggc ggttgccttg ctgagtaaag cctttggcgt aattgccgat   6960
gcagatggcc tcacgccgct ggcaaaaaat cgggcggttt ctgaactgtc aaacgccatc   7020
ggcatgcaag gattggttca gggtcagttc aaggatctgt ctgaagggga taagccgcgc   7080
agcgctgaag ctattttgat gacgaatcac tttaaaacca gcacgctgtt ttgtgcctcc   7140
atgcagatgg cctcgattgt tgcgaatgcc tccagcgaag cgcgtgattg cctgcatcgt   7200
ttttcacttg atcttggtca ggcatttcaa ctgctggacg atttgaccga tggcatgacc   7260
gacaccggta aggatagcaa tcaggacgcc ggtaaatcga cgctggtcaa tctgttaggc   7320
cctaggcgg ttgaagaacg tctgagacaa catcttcatc ttgccagtga gcatctctct    7380
gcggcctgcc aacacgggca cgccactcaa cattttattc aggcctggtt tgacaaaaaa   7440
ctcgctgccg tcagttaaag gtctctagac aggatgtgtc acacaggaaa ccatgaaacc   7500
aactacggta attggtgcag gcttcggtgg cctggcactg gcaattcgtc tacaggctgc   7560
ggggatcccc gtcttactgc ttgaacaacg tgataaaccc ggcggtcggg cttatgtcta   7620
cgaggatcag gggtttacct ttgatgcagg cccgacggtt atcaccgatc ccagtgccat   7680
tgaagaactg tttgcactgg caggaaaaca gttaaaagag tatgtcgaac tgctgccggt   7740
tacgccgttt taccgcctgt gttgggagtc agggaaggtc tttaattacg ataacgatca   7800
aacccggctc gaagcgcaga ttcagcagtt taatccccgc gatgtcgaag ttatcgtca    7860
gtttctggac tattcacgcg cggtgtttaa agaaggctat ctgaagctcg gtactgtccc   7920
ttttttatcg ttcagagaca tgcttcgcgc cgcacctcaa ctggcgaaac tgcaggcatg   7980
gagaagcgtt tacagtaagg ttgccagtta atcgaagat gaacatctgc gccaggcgtt    8040
ttctttccac tcgctgttgg tgggcggcaa tcccttcgcc acctcatcca tttatacgtt   8100
gatacacgcg ctggagcgtg agtggggcgt ctggtttccg cgtggcggca ccggcgcatt   8160
agttcagggg atgataaagc tgtttcagga tctgggtggt gaagtcgtgt aaacgccag    8220
agtcagccat atggaaacga caggaaacaa gattgaagcc gtgcatttag aggacggtcg   8280
caggttcctg acgcaagccg tcgcgtcaaa tgcagatgtg gttcatacct atcgcgacct   8340
gttaagccag caccctgccg cggttaagca gtccaacaaa ctgcagacta gcgtatgag   8400
```

```
taactctctg tttgtgctct attttggttt gaatcaccat catgatcagc tcgcgcatca   8460
cacggtttgt ttcggcccgc gttaccgcga actgattgac gagattttta atcatgatgg   8520
cctcgcagaa gacttctcac tttatctgca cgcgccctgt gtcacggatt cgtcactggc   8580
gcctgaaggt tgcggcagtt actatgtgtt ggcgccggtg ccgcatttag gcaccgcgaa   8640
cctcgactgg acggttgagg ggccaaaact acgcgaccgt attttttgagt accttgagca   8700
gcattacatg cctggcttac ggagtcagct ggtcacgcac cagatgttta cgccgtttga   8760
ttttcgcgac cagcttaatg cctatcaggg ctcagccttt tctgtggagc ccgttcttac   8820
ccagagcgcc tggtttcggc cgcataaccg cgataaaacc attactaatc tctacctggt   8880
cggcgcaggc acgcatcccg gcgcaggcat tcctggcgtc atcggctcgg caaaagcgac   8940
agcaggtttg atgctggagg atctgattta agtgatcgtt gagtggtgaa cttaaagagg   9000
agaaaatgaa taatccgtcg ttactcaatc atgcggtcga aacgatggca gttggctcga   9060
aaagttttgc gacagcctca aagttatttg atgcaaaaac ccggcgcagc gtactgatgc   9120
tctacgcctg gtgccgccat tgtgacgatg ttattgacga ccagacgctg ggcttccagg   9180
cccggcagcc tgccttacaa acgcccgaac aacgtctgat gcaacttgag atgaaaacgc   9240
gccaggccta tgcaggatcg cagatgcacg aaccggcgtt tgcggctttt caggaagtgg   9300
ctatggctca tgatatcgcc ccggcttacg cgtttgatca tctggaaggc ttcgccatgg   9360
atgtacgcga agcgcaatac agccaactgg acgatacgct cgctattgc tatcacgttg    9420
caggcgttgt cggcttgatg atggcgcaaa tcatgggcgt acgggataac gccacgctgg   9480
accgcgcctg tgaccttggg ctggcatttc agttgaccaa tattgctcgc gatattgtgg   9540
acgatgcgca tgcgggccgc tgttatctgc cggcaagctg gctggagcat gaaggtctga   9600
acaaagagaa ttatgcggca cctgaaaacc gtcaggcgct gagccgtatc gcccgtcgtt   9660
tggtgcagga agcagaacct tactatttgt ctgccacagc gggcctggct gggttgcccc   9720
tgcgttcggc ctgggcaatc gctacggcga agcaggttta ccggaaaata ggtgtcaaag   9780
ttgaacaggc cggtcagcaa gcctgggatc agcggcagtc aacgaccacg cccgaaaaat   9840
taacgctgct gctggccgcc tctggtcagg cccttacttc ccggatgcgg gctcatcctc   9900
cccgccctgc gcatctctgg cagcgcccgc tctaatcacg tagcaagctg acagtttaaa   9960
gaggagaaaa tgggagcggc tatgcaaccg cattatgatc tgattctcgt gggggctgga  10020
ctcgcgaatg gccttatcgc cctgcgtctt cagcagcagc aacctgatat gcgtattttg  10080
cttatcgacg ccgcacccca ggcgggcggg aatcatacgt ggtcatttca ccacgatgat  10140
ttgactgaga gccaacatcg ttggatagct tcgctggtgg ttcatcactg gcccgactat  10200
caggtacgct ttcccacacg ccgtcgtaag ctgaacagcg gctacttctg tattacttct  10260
cagcgtttcg ctgaggtttt acagcgacag tttggcccgc acttgtggat ggataccgcg  10320
gtcgcagagt taatgcgga atctgttcgg ttgaaaaagg gtcaggttat cggtgcccgc   10380
gcggtgattg acgggcgggg ttatgcggca aactcagcac tgagcgtggg cttccaggcg  10440
tttattggcc aggaatggcg attgagccac ccgcatggtt tatcgtctcc cattatcatg  10500
gatgccacgg tcgatcagca aaatggttat cgcttcgtgt acagcctgcc gctctcgccg  10560
accagattgt taattgaaga cacgcactat atcgataatg cgacattaga tcctgaacgc  10620
gcgcggcaaa atatttgcga ctatgccgcg caacagggtt ggcagcttca gacattgctg  10680
cgtgaagaac agggcgcctt accca                                       10705
```

<210> SEQ ID NO 140
<211> LENGTH: 411
<212> TYPE: DNA
<213> ORGANISM: Artificial Sequence
<220> FEATURE:
<223> OTHER INFORMATION: MaFAR-g1

<400> SEQUENCE: 140

| | | | | | |
|---|---|---|---|---|---|
| gagcaaccaa | cacttaaaga | ggagaaaatg | gcgacccagc | agcagcagaa | cggcgcctcg | 60 |
| gcgagcggcg | tcctggaaca | gttgcgcggg | aagcatgtcc | tgataaccgg | taccaccggt | 120 |
| ttccttggca | aggtagtcct | ggaaaagctg | atccgcacag | tcccggacat | cggcggcatc | 180 |
| cacctcctga | tccggggcaa | caagaggcat | ccggccgccc | gtgaacggtt | cttgaacgag | 240 |
| atcgccagca | gttcggtctt | cgagcgtctg | cgccacgacg | acaacgaggc | cttcgaaacc | 300 |
| ttcctggaag | aaagggtgca | ctgtataacc | ggagaggtca | ccgagagtcg | tttcggcctt | 360 |
| accccggagc | gcttccgcgc | gctggcgggt | caggtggacg | ccttcatcaa | t | 411 |

<210> SEQ ID NO 141
<211> LENGTH: 465
<212> TYPE: DNA
<213> ORGANISM: Artificial Sequence
<220> FEATURE:
<223> OTHER INFORMATION: MaFAR-g2

<400> SEQUENCE: 141

| | | | | | |
|---|---|---|---|---|---|
| gacgccttca | tcaattcggc | cgcctccgtc | aacttccgcg | aggaactgga | caaggcgctg | 60 |
| aagatcaata | cgctgtgcct | ggagaatgtc | gcggcccttg | ctgaactcaa | cagtgcgatg | 120 |
| gcggtcatcc | aggtttcgac | ctgctacgtt | aacggcaaga | atagcgggca | gatcaccgaa | 180 |
| tcggtcatca | gcccgcgggg | ggagtccatc | ccgcgtagca | ccgatgggta | ctatgaaatc | 240 |
| gaagaattgg | tgcacctgct | gcaggacaaa | atcagcgatg | tgaaggcccg | atactccggg | 300 |
| aaggttctgg | aaaaaaaatt | ggtggaccta | ggcatccggg | aagccaataa | ctacgggtgg | 360 |
| agcgatacat | ataccttcac | caagtggctg | ggcgaacagc | tcctcatgaa | ggccctgagc | 420 |
| ggcagatcgc | tgaccatcgt | gcggccgtcg | atcatcgagt | cggca | | 465 |

<210> SEQ ID NO 142
<211> LENGTH: 374
<212> TYPE: DNA
<213> ORGANISM: Artificial Sequence
<220> FEATURE:
<223> OTHER INFORMATION: MaFAR-g3

<400> SEQUENCE: 142

| | | | | | |
|---|---|---|---|---|---|
| atcatcgagt | cggcattgga | agagcccagc | ccggggtgga | ttgaaggcgt | caaggtcgcc | 60 |
| gatgccatca | tactggccta | cgcgagggag | aaggtatcgc | tctttcctgg | caagcggagc | 120 |
| ggcatcatcg | acgtcatccc | agtggatctg | gtggccaatt | cgatcattct | gtccctggcg | 180 |
| gaggcgctct | ccggttcggg | ccagcggcgt | atctatcagt | gctgcagcgg | cggctcgaac | 240 |
| cccatctccc | tcgggaagtt | catcgactat | ctgatggcgg | aggcgaagac | caactacgcg | 300 |
| gcctacgatc | agctgttcta | ccgccgcccc | accaagccgt | tcgtggccgt | caaccgcaaa | 360 |
| ctcttcgacg | tcgt | | | | | 374 |

<210> SEQ ID NO 143
<211> LENGTH: 376
<212> TYPE: DNA
<213> ORGANISM: Artificial Sequence
<220> FEATURE:

<223> OTHER INFORMATION: MaFAR-g4

<400> SEQUENCE: 143

```
actcttcgac gtcgtcgtgg gcggcatgcg ggtcccgctc tcgatcgcgg gcaaagccat      60
gcgcctggcg ggacaaaacc gcgaactgaa ggtcctgaag aatctggata cgacccggtc     120
cctggccacc attttcgggt tctacaccgc tccggactac atctttcgca atgacagcct     180
gatggccctg gcctcgcgca tgggcgagct ggaccgcgtg ttgttccccg ttgacgcccg     240
tcagatcgac tggcagctgt atctgtgcaa aatccacctc ggcgggctga atcggtacgc     300
gctcaaggaa cgtaagctgt actcgctccg ggccgccgac actcgcaaga aggcagcctg     360
agagacagaa cgaagt                                                     376
```

<210> SEQ ID NO 144
<211> LENGTH: 47
<212> TYPE: DNA
<213> ORGANISM: Artificial Sequence
<220> FEATURE:
<223> OTHER INFORMATION: GMV410

<400> SEQUENCE: 144

```
gagcaaccaa cacttaaaga ggagaaaatg cgcccctgc accccat      47
```

<210> SEQ ID NO 145
<211> LENGTH: 47
<212> TYPE: DNA
<213> ORGANISM: Artificial Sequence
<220> FEATURE:
<223> OTHER INFORMATION: GMV411

<400> SEQUENCE: 145

```
gagcaaccaa cacttaaaga ggagaaaatg cgcctgctga ccgccgt      47
```

<210> SEQ ID NO 146
<211> LENGTH: 47
<212> TYPE: DNA
<213> ORGANISM: Artificial Sequence
<220> FEATURE:
<223> OTHER INFORMATION: GMV412

<400> SEQUENCE: 146

```
gagcaaccaa cacttaaaga ggagaaaatg tccgtgatgt ccccgac      47
```

<210> SEQ ID NO 147
<211> LENGTH: 47
<212> TYPE: DNA
<213> ORGANISM: Artificial Sequence
<220> FEATURE:
<223> OTHER INFORMATION: GMV413

<400> SEQUENCE: 147

```
gagcaaccaa cacttaaaga ggagaaaatg ccggtcaccg actccat      47
```

<210> SEQ ID NO 148
<211> LENGTH: 47
<212> TYPE: DNA
<213> ORGANISM: Artificial Sequence
<220> FEATURE:
<223> OTHER INFORMATION: GMV414

<400> SEQUENCE: 148

```
gagcaaccaa cacttaaaga ggagaaaatg gccccgaccg actccct      47
```

```
<210> SEQ ID NO 149
<211> LENGTH: 47
<212> TYPE: DNA
<213> ORGANISM: Artificial Sequence
<220> FEATURE:
<223> OTHER INFORMATION: GMV415

<400> SEQUENCE: 149
gagcaaccaa cacttaaaga ggagaaaatg cccctgccga tgtcccc            47

<210> SEQ ID NO 150
<211> LENGTH: 35
<212> TYPE: DNA
<213> ORGANISM: Artificial Sequence
<220> FEATURE:
<223> OTHER INFORMATION: GMV416

<400> SEQUENCE: 150
acttcgttct gtctctcagt tggcggtctt gatgt                          35

<210> SEQ ID NO 151
<211> LENGTH: 35
<212> TYPE: DNA
<213> ORGANISM: Artificial Sequence
<220> FEATURE:
<223> OTHER INFORMATION: ACTTCGTTCTGTCTCTCACGGGGCCAGCTTCTTCA

<400> SEQUENCE: 151
acttcgttct gtctctcacg gggccagctt cttca                          35

<210> SEQ ID NO 152
<211> LENGTH: 35
<212> TYPE: DNA
<213> ORGANISM: Artificial Sequence
<220> FEATURE:
<223> OTHER INFORMATION: GMV418

<400> SEQUENCE: 152
acttcgttct gtctctcagg tgccgctcgc ggcca                          35

<210> SEQ ID NO 153
<211> LENGTH: 35
<212> TYPE: DNA
<213> ORGANISM: Artificial Sequence
<220> FEATURE:
<223> OTHER INFORMATION: GMV419

<400> SEQUENCE: 153
acttcgttct gtctctcaca gcagggccgc ttcca                          35

<210> SEQ ID NO 154
<211> LENGTH: 35
<212> TYPE: DNA
<213> ORGANISM: Artificial Sequence
<220> FEATURE:
<223> OTHER INFORMATION: GMV420

<400> SEQUENCE: 154
acttcgttct gtctctcaca ggccgaccgc ggttt                          35

<210> SEQ ID NO 155
<211> LENGTH: 35
<212> TYPE: DNA
<213> ORGANISM: Artificial Sequence
<220> FEATURE:
<223> OTHER INFORMATION: GMV421
```

<400> SEQUENCE: 155
acttcgttct gtctctcaga tgcccaccgc gcgtt                                35

<210> SEQ ID NO 156
<211> LENGTH: 1149
<212> TYPE: DNA
<213> ORGANISM: Saccharomyces cerevisiae

<400> SEQUENCE: 156

```
atgcgggcgc tggcgtattt caagaagggc gacatccatt tcaccaacga catccccgg     60
ccggagatcc agaccgacga cgaagtgatc atcgacgtct cctggtgcgg catctgcggc   120
agcgacctgc acgagtacct ggacggcccc atcttcatgc cgaaggacgg cgaatgccac   180
aagctgagca cgccgcgct gcccctggcg atgggccatg agatgtcggg catcgtctcc   240
aaagtgggcc cgaaggtgac caaggtcaaa gtgggcgacc acgtcgtggt cgacgccgcg   300
agctcgtgcg ccgacctgca ctgctggccc cattccaagt tctataacag caagccgtgc   360
gacgcctgcc agcgcggctc ggagaacctg tgcacccatg cgggcttcgt cggcctgggc   420
gtgatcagcg gcggcttcgc cgaacaggtg gtcgtgtcgc agcaccatat catcccggtc   480
cccaaggaga tcccctgga cgtcgccgcc ctggtcgagc gctgtcggt cacctggcac   540
gccgtgaaga tctccggctt caagaagggc tccagcgccc tggtcctggg cgcgggcccc   600
atcggcctgt gcaccatcct ggtgctgaag ggcatgggcg cgtcgaagat cgtcgtgtcc   660
gagatcgccg aacgtcgcat cgagatggcg aagaagctgg gcgtcgaagt gttcaacccg   720
agcaagcacg ccataagtc gatcgagatc ctgcggggcc tgaccaagtc ccacgacggc   780
ttcgactaca gctatgactg ctcgggcatc caggtcacct tcgaaaccag cctgaaggcc   840
ctgaccttca gggcaccgc caccaacatc gcggtctggg cccgaagcc cgtgccgttc   900
cagccgatgg acgtcacccc tgcaggagaag gtgatgaccg gctcgatcgg ctacgtcgtg   960
gaagacttcg aggaagtcgt gcgcgccatc cataacggcg acatcgcgat ggaggactgc  1020
aagcagctga tcaccggcaa gcagcggatc gaggacggct gggaaaaggg cttccaggag  1080
ctgatggacc acaaggaatc caacgtgaag atcctgctga ccccgaacaa ccacggcgaa  1140
atgaagtga                                                          1149
```

<210> SEQ ID NO 157
<211> LENGTH: 382
<212> TYPE: PRT
<213> ORGANISM: Saccharomyces cerevisiae

<400> SEQUENCE: 157

```
Met Arg Ala Leu Ala Tyr Phe Lys Lys Gly Asp Ile His Phe Thr Asn
1               5                   10                  15

Asp Ile Pro Arg Pro Glu Ile Gln Thr Asp Asp Glu Val Ile Ile Asp
            20                  25                  30

Val Ser Trp Cys Gly Ile Cys Gly Ser Asp Leu His Glu Tyr Leu Asp
        35                  40                  45

Gly Pro Ile Phe Met Pro Lys Asp Gly Glu Cys His Lys Leu Ser Asn
    50                  55                  60

Ala Ala Leu Pro Leu Ala Met Gly His Glu Met Ser Gly Ile Val Ser
65                  70                  75                  80

Lys Val Gly Pro Lys Val Thr Lys Val Lys Val Gly Asp His Val Val
                85                  90                  95

Val Asp Ala Ala Ser Ser Cys Ala Asp Leu His Cys Trp Pro His Ser
```

```
            100                 105                 110
Lys Phe Tyr Asn Ser Lys Pro Cys Asp Ala Cys Gln Arg Gly Ser Glu
        115                 120                 125

Asn Leu Cys Thr His Ala Gly Phe Val Gly Leu Gly Val Ile Ser Gly
    130                 135                 140

Gly Phe Ala Glu Gln Val Val Ser Gln His Ile Ile Pro Val
145                 150                 155                 160

Pro Lys Glu Ile Pro Leu Asp Val Ala Ala Leu Val Glu Pro Leu Ser
                165                 170                 175

Val Thr Trp His Ala Val Lys Ile Ser Gly Phe Lys Lys Gly Ser Ser
            180                 185                 190

Ala Leu Val Leu Gly Ala Gly Pro Ile Gly Leu Cys Thr Ile Leu Val
        195                 200                 205

Leu Lys Gly Met Gly Ala Ser Lys Ile Val Ser Glu Ile Ala Glu
    210                 215                 220

Arg Arg Ile Glu Met Ala Lys Lys Leu Gly Val Glu Val Phe Asn Pro
225                 230                 235                 240

Ser Lys His Gly His Lys Ser Ile Glu Ile Leu Arg Gly Leu Thr Lys
                245                 250                 255

Ser His Asp Gly Phe Asp Tyr Ser Tyr Asp Cys Ser Gly Ile Gln Val
            260                 265                 270

Thr Phe Glu Thr Ser Leu Lys Ala Leu Thr Phe Lys Gly Thr Ala Thr
        275                 280                 285

Asn Ile Ala Val Trp Gly Pro Lys Pro Val Pro Phe Gln Pro Met Asp
    290                 295                 300

Val Thr Leu Gln Glu Lys Val Met Thr Gly Ser Ile Gly Tyr Val Val
305                 310                 315                 320

Glu Asp Phe Glu Glu Val Val Arg Ala Ile His Asn Gly Asp Ile Ala
                325                 330                 335

Met Glu Asp Cys Lys Gln Leu Ile Thr Gly Lys Gln Arg Ile Glu Asp
            340                 345                 350

Gly Trp Glu Lys Gly Phe Gln Glu Leu Met Asp His Lys Glu Ser Asn
        355                 360                 365

Val Lys Ile Leu Leu Thr Pro Asn Asn His Gly Glu Met Lys
    370                 375                 380

<210> SEQ ID NO 158
<211> LENGTH: 47
<212> TYPE: DNA
<213> ORGANISM: Artificial Sequence
<220> FEATURE:
<223> OTHER INFORMATION: GMV00268

<400> SEQUENCE: 158
gagcaaccaa cacttaaaga ggagaaaatg cgggcgctgg cgtattt             47

<210> SEQ ID NO 159
<211> LENGTH: 35
<212> TYPE: DNA
<213> ORGANISM: Artificial Sequence
<220> FEATURE:
<223> OTHER INFORMATION: GMV00271

<400> SEQUENCE: 159
acttcgttct gtctctcact tcatttcgcc gtggt                           35

<210> SEQ ID NO 160
```

-continued

```
<211> LENGTH: 990
<212> TYPE: DNA
<213> ORGANISM: Escherichia coli

<400> SEQUENCE: 160
atgcatatta catacgatct gccggttgct attgatgaca ttattgaagc gaaacaacga      60
ctggctgggc gaatttataa acaggcatg  cctcgctcca actatttag  tgaacgttgc     120
aaaggtgaaa tattcctgaa gtttgaaaat atgcagcgta cgggttcatt taaaattcgt     180
ggcgcattta ataaattaag ttcactgacc gatgcggaaa aacgcaaagg cgtggtggcc     240
tgttctgcgg gcaaccatgc gcaagggtt  tccctctcct gcgcgatgct gggtatcgac     300
ggtaaagtgg tgatgccaaa aggtgcgcca aaatccaaag tagcggcaac gtgcgactac     360
tccgcagaag tcgttctgca tggtgataac ttcaacgaca ctatcgctaa agtgagcgaa     420
attgtcgaaa tggaaggccg tattttatc  ccaccttacg atgatccgaa agtgattgct     480
ggccagggaa cgattggtct ggaaattatg gaagatctct atgatgtcga taacgtgatt     540
gtgccaattg gtggtggcgg tttaattgct ggtattgcgg tggcaattaa atctattaac     600
ccgaccattc gtgttattgg cgtacagtct gaaaacgttc acggcatggc ggcttctttc     660
cactccgag  aaataaccac gcaccgaact accggcaccc tggcggatgg ttgtgatgtc     720
tcccgcccgg gtaatttaac ttacgaaatc gttcgtgaat tagtcgatga catcgtgctg     780
gtcagcgaag acgaaatcag aaacagtatg attgccttaa ttcagcgcaa taaagtcgtc     840
accgaaggcg caggcgctct ggcatgtgct gcattattaa gcggtaaatt agaccaatat     900
attcaaaaca gaaaaaccgt cagtattatt tccggcggca atatcgatct ttctcgcgtc     960
tctcaaatca ccggtttcgt tgacgcttaa                                      990

<210> SEQ ID NO 161
<211> LENGTH: 329
<212> TYPE: PRT
<213> ORGANISM: Escherichia coli

<400> SEQUENCE: 161

Met His Ile Thr Tyr Asp Leu Pro Val Ala Ile Asp Asp Ile Ile Glu
1               5                   10                  15

Ala Lys Gln Arg Leu Ala Gly Arg Ile Tyr Lys Thr Gly Met Pro Arg
                20                  25                  30

Ser Asn Tyr Phe Ser Glu Arg Cys Lys Gly Glu Ile Phe Leu Lys Phe
            35                  40                  45

Glu Asn Met Gln Arg Thr Gly Ser Phe Lys Ile Arg Gly Ala Phe Asn
        50                  55                  60

Lys Leu Ser Ser Leu Thr Asp Ala Glu Lys Arg Lys Gly Val Val Ala
65                  70                  75                  80

Cys Ser Ala Gly Asn His Ala Gln Gly Val Ser Leu Ser Cys Ala Met
                85                  90                  95

Leu Gly Ile Asp Gly Lys Val Val Met Pro Lys Gly Ala Pro Lys Ser
            100                 105                 110

Lys Val Ala Ala Thr Cys Asp Tyr Ser Ala Glu Val Val Leu His Gly
        115                 120                 125

Asp Asn Phe Asn Asp Thr Ile Ala Lys Val Ser Glu Ile Val Glu Met
    130                 135                 140

Glu Gly Arg Ile Phe Ile Pro Pro Tyr Asp Asp Pro Lys Val Ile Ala
145                 150                 155                 160

Gly Gln Gly Thr Ile Gly Leu Glu Ile Met Glu Asp Leu Tyr Asp Val
```

```
                        165                 170                 175
Asp Asn Val Ile Val Pro Ile Gly Gly Gly Gly Leu Ile Ala Gly Ile
                180                 185                 190

Ala Val Ala Ile Lys Ser Ile Asn Pro Thr Ile Arg Val Ile Gly Val
            195                 200                 205

Gln Ser Glu Asn Val His Gly Met Ala Ala Ser Phe His Ser Gly Glu
        210                 215                 220

Ile Thr Thr His Arg Thr Thr Gly Thr Leu Ala Asp Gly Cys Asp Val
225                 230                 235                 240

Ser Arg Pro Gly Asn Leu Thr Tyr Glu Ile Val Arg Glu Leu Val Asp
                245                 250                 255

Asp Ile Val Leu Val Ser Glu Asp Glu Ile Arg Asn Ser Met Ile Ala
            260                 265                 270

Leu Ile Gln Arg Asn Lys Val Val Thr Glu Gly Ala Gly Ala Leu Ala
        275                 280                 285

Cys Ala Ala Leu Leu Ser Gly Lys Leu Asp Gln Tyr Ile Gln Asn Arg
    290                 295                 300

Lys Thr Val Ser Ile Ile Ser Gly Gly Asn Ile Asp Leu Ser Arg Val
305                 310                 315                 320

Ser Gln Ile Thr Gly Phe Val Asp Ala
                325

<210> SEQ ID NO 162
<211> LENGTH: 590
<212> TYPE: PRT
<213> ORGANISM: Methylosinus trichosporium

<400> SEQUENCE: 162

Met Ala Arg Lys Met Thr Gly Ala Glu Met Val Val Glu Ala Leu Lys
1               5                   10                  15

Asp Gln Gly Val Glu Ile Ile Phe Gly Tyr Pro Gly Gly Ala Val Leu
            20                  25                  30

Pro Ile Tyr Asp Ala Leu Phe His Gln Glu Lys Val Gln His Ile Leu
        35                  40                  45

Val Arg His Glu Gln Gly Ala Ala His Ala Ala Glu Gly Tyr Ala Arg
    50                  55                  60

Ser Ser Gly Lys Val Gly Val Leu Leu Val Thr Ser Gly Pro Gly Ala
65                  70                  75                  80

Thr Asn Thr Ile Thr Gly Leu Thr Asp Ala Leu Met Asp Ser Ile Pro
                85                  90                  95

Val Val Cys Ile Thr Gly Gln Val Pro Thr His Leu Ile Gly Ser Asp
            100                 105                 110

Ala Phe Gln Glu Cys Asp Thr Val Gly Ile Thr Arg His Cys Thr Lys
        115                 120                 125

His Asn Tyr Leu Val Lys Ser Val Asp Leu Pro Arg Ile Leu His
    130                 135                 140

Glu Ala Phe Tyr Val Ala Ser Ser Gly Arg Pro Gly Pro Val Val Ile
145                 150                 155                 160

Asp Ile Pro Lys Asp Val Gln Phe Ala Ser Gly Thr Tyr Thr Gly Pro
                165                 170                 175

Arg Asn Val His His Lys Thr Tyr Gln Pro Lys Leu Glu Gly Asp Thr
            180                 185                 190

Glu Ser Ile Arg Arg Ala Val Lys Met Met Ala Ala Lys Arg Pro
        195                 200                 205
```

```
Ile Phe Tyr Thr Gly Gly Gly Val Ile Asn Ser Gly Pro Ala Ala Ser
210                 215                 220

Thr Leu Arg Glu Leu Val Ser Leu Thr Gly Phe Pro Ile Thr Ser
225                 230                 235                 240

Thr Leu Met Gly Leu Gly Ala Tyr Pro Gly Ser Gly Pro Asn Trp Leu
            245                 250                 255

Gly Met Leu Gly Met His Gly Thr Phe Glu Ala Asn Asn Ala Met His
                260                 265                 270

Asp Cys Asp Leu Met Ile Ala Val Gly Ala Arg Phe Asp Arg Ile
            275                 280                 285

Thr Gly Arg Leu Asp Ala Phe Ser Pro Gly Ser Lys Lys Ile His Ile
290                 295                 300

Asp Ile Asp Arg Ser Ser Ile Asn Lys Asn Val Lys Ile Asp Leu Pro
305                 310                 315                 320

Ile Val Gly Asp Cys Gly His Val Leu Glu Ser Leu Val Arg Val Trp
                325                 330                 335

Arg Ser Glu Ala Met His Ala Glu Lys Gln Pro Leu Asp Gly Trp Trp
                340                 345                 350

Lys Thr Ile Asp His Trp Arg Glu Arg Lys Ser Leu Ala Phe Arg Asn
            355                 360                 365

Ser Asp Lys Val Ile Lys Pro Gln Tyr Ala Val Gln Arg Leu Tyr Ala
370                 375                 380

Leu Thr Lys Asp Arg Asp Pro Tyr Ile Thr Thr Glu Val Gly Gln His
385                 390                 395                 400

Gln Met Trp Ala Ala Gln His Tyr His Phe Asp Glu Pro Asn Arg Trp
                405                 410                 415

Met Thr Ser Gly Gly Leu Gly Thr Met Gly Tyr Gly Leu Pro Ala Ala
                420                 425                 430

Ile Gly Ala Gln Leu Ala His Pro Lys Ser Leu Val Val Asp Ile Ala
            435                 440                 445

Gly Glu Ala Ser Ile Leu Met Asn Ile Gln Glu Met Ser Thr Ala Ile
            450                 455                 460

Gln Tyr Arg Leu Pro Val Lys Val Phe Ile Leu Asn Asn Glu Tyr Met
465                 470                 475                 480

Gly Met Val Arg Gln Trp Gln Glu Leu Leu His Gly Arg Tyr Ser
                485                 490                 495

His Ser Tyr Ser Glu Ala Leu Pro Asp Phe Val Lys Leu Ala Glu Ala
                500                 505                 510

Phe Gly Gly Lys Gly Ile Arg Cys Ser Asp Pro Ala Glu Leu Asp Ser
            515                 520                 525

Ala Ile Leu Glu Met Ile Asp Tyr Asp Gly Pro Val Ile Phe Asp Cys
530                 535                 540

Leu Val Glu Lys Asn Glu Asn Cys Phe Pro Met Ile Pro Ser Gly Lys
545                 550                 555                 560

Ala His Asn Asp Met Leu Leu Ala Asp Leu Gly Asp Asp Ala Gly Val
                565                 570                 575

Glu Leu Gly Ser Ile Ile Asp Glu Lys Gly Lys Met Leu Val
                580                 585                 590

<210> SEQ ID NO 163
<211> LENGTH: 351
<212> TYPE: PRT
<213> ORGANISM: Methylosinus trichosporium

<400> SEQUENCE: 163
```

```
Met Ser Thr Lys Ala Tyr Ala Val Ala Ser Glu Ala Leu Phe Gly
1               5                   10                  15

Pro Leu Ala Ile Glu Arg Arg Ala Leu Gly Pro Glu Asp Val Glu Ile
            20                  25                  30

Asp Ile Leu Tyr Cys Gly Val Cys His Ser Asp Leu His Thr Ala Arg
        35                  40                  45

Ser Glu Trp Pro Gly Thr Arg Tyr Pro Cys Val Pro Gly His Glu Ile
    50                  55                  60

Val Gly Arg Val Thr Ala Val Gly Ala Lys Val Thr Lys Phe Ser Val
65                  70                  75                  80

Gly Asp Leu Ala Ala Val Gly Cys Met Val Asp Ser Cys Arg Arg Cys
                85                  90                  95

Leu Ser Cys Asp Asp Gly Leu Glu Gln Tyr Cys Glu His Gly Phe Thr
            100                 105                 110

Ala Thr Tyr Asn Gly Pro Ile Tyr Gly Ser Gly Glu Asn Thr Phe Gly
        115                 120                 125

Gly Tyr Ser Glu Lys Ile Val Val Asp Ala His Phe Val Leu Ala Ile
    130                 135                 140

His His Ser Glu Thr Gln Leu Ala Gly Val Ala Pro Leu Leu Cys Ala
145                 150                 155                 160

Gly Ile Thr Thr Trp Ser Pro Leu Lys His Trp Gly Val Gly Pro Gly
                165                 170                 175

Lys Ser Val Gly Ile Val Gly Ile Gly Gly Leu Gly His Met Gly Val
            180                 185                 190

Lys Leu Ala His Ala Leu Gly Ala His Val Val Ala Phe Thr Thr Ser
                195                 200                 205

Pro Ser Lys Arg Asp Ala Ala Leu Ala Leu Gly Ala Asp Glu Val Val
        210                 215                 220

Val Ser Thr Asp Pro Ala Ala Met Ala Ala Arg Ala Gly Ser Leu Asp
225                 230                 235                 240

Phe Ile Leu Asp Thr Val Ala Val His Asp Leu Asp Ala Tyr Val
                245                 250                 255

Asn Leu Leu Lys Arg Asp Gly Ala Leu Val Leu Val Gly Val Pro Ala
            260                 265                 270

Thr Pro His Pro Ser Pro Ser Ala Gly Gly Leu Ile Phe Lys Arg Arg
        275                 280                 285

Gln Val Ala Gly Ser Leu Ile Gly Gly Val Lys Glu Thr Gln Glu Met
        290                 295                 300

Leu Asp Phe Cys Ala Glu Arg Gly Ile Val Ala Asp Ile Glu Thr Ile
305                 310                 315                 320

Ala Met Gln Gln Ile Glu Thr Ala Tyr Ala Arg Met Leu Lys Asn Asp
                325                 330                 335

Val Lys Tyr Arg Phe Val Ile Asp Met Ala Thr Leu Lys Ala Ala
            340                 345                 350

<210> SEQ ID NO 164
<211> LENGTH: 342
<212> TYPE: PRT
<213> ORGANISM: Methylococcus capsulatus

<400> SEQUENCE: 164

Met Lys Ala Trp Val Ile Asp Arg Ile Gly Pro Leu Asp Ser Ser Arg
1               5                   10                  15

Thr Leu Leu Arg Ala Thr Asp Leu Pro Val Pro Glu Pro Gly Pro Gly
```

```
            20                  25                  30
Glu Ile Leu Leu Gln Val Ala Val Cys Gly Val Cys His Thr Glu Ile
                35                  40                  45
Asp Glu Ile Glu Gly Arg Thr Ala Pro Pro Arg Leu Pro Val Val Pro
            50                  55                  60
Gly His Gln Ala Val Gly Arg Ile Ala Ala Leu Gly Ser Gly Val Ala
65                  70                  75                  80
Glu Phe Ala Leu Gly Asp Arg Val Gly Val Ala Trp Ile Phe Ser Ala
                85                  90                  95
Cys Gly Glu Cys Glu Phe Cys Arg Ser Gly Arg Glu Asn Leu Cys Phe
            100                 105                 110
Ala Phe Cys Ala Thr Gly Arg Asp Val Asp Gly Gly Tyr Ala Gln Tyr
            115                 120                 125
Met Thr Val Pro Ala Ala Phe Ala Phe Arg Ile Pro Glu Gly Phe Thr
            130                 135                 140
Asp Ala Glu Ala Ala Pro Leu Leu Cys Ala Gly Ala Ile Gly Tyr Arg
145                 150                 155                 160
Ser Leu Asn Leu Ser Gly Leu Lys Asn Gly Gln Pro Leu Gly Leu Thr
                165                 170                 175
Gly Phe Gly Ala Ser Ala His Leu Val Leu Met Met Ala Arg Tyr Arg
            180                 185                 190
Phe Pro Asp Ser Glu Val Tyr Val Phe Ala Arg His Pro Glu Glu Arg
            195                 200                 205
Ala Phe Ala Leu Gln Leu Gly Ala Val Trp Ala Gly Asp Thr Ala Asp
            210                 215                 220
Ile Ala Pro Ala Pro Leu Ala Ala Ile Ile Asp Thr Thr Pro Ala Trp
225                 230                 235                 240
Lys Pro Val Val Ala Leu Ala Asn Leu Ala Pro Gly Gly Arg Leu
                245                 250                 255
Val Val Asn Ala Ile Arg Lys Ala Pro Asp Asp Arg Ala Cys Leu Ala
            260                 265                 270
Glu Leu Asp Tyr Ala Arg His Leu Trp Met Glu Arg Glu Ile Lys Ser
            275                 280                 285
Val Ala Asn Val Ala Arg Ser Asp Val Ala Gly Phe Leu Ala Leu Ala
            290                 295                 300
Ala Glu Met Gly Ile Arg Pro Glu Thr Glu Tyr Pro Phe Glu Asp
305                 310                 315                 320
Ala Asp Arg Ala Leu Leu Asp Leu Lys Gln Arg Ile Arg Gly Ala
                325                 330                 335
Lys Val Leu Arg Val Thr
            340

<210> SEQ ID NO 165
<211> LENGTH: 355
<212> TYPE: PRT
<213> ORGANISM: Methylococcus capsulatus

<400> SEQUENCE: 165

Met Pro Thr Ala Lys Ala Tyr Ala Ala Phe Ser Ala Asp Ser Ala Leu
1               5                   10                  15
Ala Pro Phe Val Leu Gln Arg Arg Asp Pro Leu Pro Gln Asp Ile Arg
                20                  25                  30
Ile Gly Ile Leu Tyr Cys Gly Val Cys His Ser Asp Leu His Gln Ala
            35                  40                  45
```

```
Arg Asn Glu Trp Asn Ala Thr Thr Tyr Pro Cys Val Pro Gly His Glu
 50                  55                  60

Ile Val Gly Lys Val Leu Glu Val Gly Arg Ser Val Thr Lys Phe Lys
 65                  70                  75                  80

Pro Gly Asp Thr Val Ala Val Gly Cys Met Val Asp Ser Cys Arg Thr
                 85                  90                  95

Cys Pro Asn Cys Val Asp Ala Leu Glu Gln His Cys Glu His Gly Pro
                100                 105                 110

Val Phe Thr Tyr Asn Ser Pro Asp Pro His Gly Gly Met Thr Phe
                115                 120                 125

Gly Gly Tyr Ala Glu Ser Ile Val Val Asp Glu Ala Phe Val Leu Arg
130                 135                 140

Ile Pro Asp Gly Leu Asp Leu Ala Ala Ala Pro Leu Leu Cys Ala
145                 150                 155                 160

Gly Ile Thr Thr Tyr Ser Pro Leu Arg His Trp Lys Val Gly Ala Gly
                165                 170                 175

Gln Arg Val Gly Val Val Gly Leu Gly Gly Leu Gly His Met Ala Leu
                180                 185                 190

Lys Phe Ala His Thr Phe Gly Ala Glu Thr Val Leu Phe Thr Thr Thr
                195                 200                 205

Pro Asp Lys Ala Glu Asp Ala Arg Arg Leu Gly Ala Asp Glu Val Val
210                 215                 220

Val Ser Arg Asp Pro Glu Ala Met Ala Arg Gln Ala Gly Arg Phe Asp
225                 230                 235                 240

Phe Ile Leu Asp Thr Val Ser Ala Pro His Asp Ile Asp Ala Tyr Leu
                245                 250                 255

Asn Leu Leu Arg Arg Asp Gly Thr Leu Thr Leu Val Gly Val Pro Pro
                260                 265                 270

Gln Gly Val Gln Val Met Pro Phe Ser Leu Ile Gly Gly Arg Arg Arg
                275                 280                 285

Leu Ala Gly Ser Leu Ile Gly Gly Ile Arg Glu Thr Gln Glu Met Leu
290                 295                 300

Asp Phe Cys Gly Glu His Gly Ile Val Cys Asp Ile Glu Leu Ile Pro
305                 310                 315                 320

Ile Gln Gly Ile Asn Asp Ala Phe Glu Arg Met Leu Lys Ser Asp Val
                325                 330                 335

Lys Tyr Arg Phe Val Ile Asp Met Ala Thr Leu Asn Gly Glu Ser Ser
                340                 345                 350

Gly Gly Arg
355

<210> SEQ ID NO 166
<211> LENGTH: 548
<212> TYPE: PRT
<213> ORGANISM: Lactococcus lactis

<400> SEQUENCE: 166

Met Tyr Thr Val Gly Asp Tyr Leu Leu Asp Arg Leu His Glu Leu Gly
 1               5                  10                  15

Ile Glu Glu Ile Phe Gly Val Pro Gly Asp Tyr Asn Leu Gln Phe Leu
                20                  25                  30

Asp Gln Ile Ile Ser Arg Lys Asp Met Lys Trp Val Gly Asn Ala Asn
            35                  40                  45

Glu Leu Asn Ala Ser Tyr Met Ala Asp Gly Tyr Ala Arg Thr Lys Lys
 50                  55                  60
```

```
Ala Ala Ala Phe Leu Thr Thr Phe Gly Val Gly Glu Leu Ser Ala Val
 65                  70                  75                  80

Asn Gly Leu Ala Gly Ser Tyr Ala Glu Asn Leu Pro Val Val Glu Ile
             85                  90                  95

Val Gly Ser Pro Thr Ser Lys Val Gln Asn Glu Gly Lys Phe Val His
             100                 105                 110

His Thr Leu Ala Asp Gly Asp Phe Lys His Phe Met Lys Met His Glu
             115                 120                 125

Pro Val Thr Ala Ala Arg Thr Leu Leu Thr Ala Glu Asn Ala Thr Val
130             135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                 165                 170                 175

Ser Leu Pro Leu Lys Lys Glu Asn Pro Thr Ser Asn Thr Ser Asp Gln
             180                 185                 190

Glu Ile Leu Asn Lys Ile Gln Glu Ser Leu Lys Asn Ala Lys Lys Pro
                 195                 200                 205

Ile Val Ile Thr Gly His Glu Ile Ile Ser Phe Gly Leu Glu Asn Thr
210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Thr Leu Pro Ser Phe Leu Gly Ile
                 245                 250                 255

Tyr Asn Gly Lys Leu Ser Glu Pro Asn Leu Lys Glu Phe Val Glu Ser
             260                 265                 270

Ala Asp Phe Ile Leu Met Leu Gly Val Lys Leu Thr Asp Ser Ser Thr
             275                 280                 285

Gly Ala Phe Thr His His Leu Asn Glu Asn Lys Met Ile Ser Leu Asn
290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Gly Ile Glu Tyr Lys
                 325                 330                 335

Gly Lys Tyr Ile Asp Lys Lys Gln Glu Asp Phe Val Pro Ser Asn Ala
             340                 345                 350

Leu Leu Ser Gln Asp Arg Leu Trp Gln Ala Val Glu Asn Leu Thr Gln
             355                 360                 365

Ser Asn Glu Thr Ile Val Ala Glu Gln Gly Thr Ser Phe Phe Gly Ala
             370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                 405                 410                 415

Ala Asp Lys Glu Ser Arg His Leu Leu Phe Ile Gly Asp Gly Ser Leu
             420                 425                 430

Gln Leu Thr Val Gln Glu Leu Gly Leu Ala Ile Arg Glu Lys Ile Asn
             435                 440                 445

Pro Ile Cys Phe Ile Ile Asn Asn Asp Gly Tyr Thr Val Glu Arg Glu
             450                 455                 460

Ile His Gly Pro Asn Gln Ser Tyr Asn Asp Ile Pro Met Trp Asn Tyr
465                 470                 475                 480
```

-continued

```
Ser Lys Leu Pro Glu Ser Phe Gly Ala Thr Glu Arg Val Val Ser
            485                 490                 495

Lys Ile Val Arg Thr Glu Asn Glu Phe Val Ser Val Met Lys Glu Ala
        500                 505                 510

Gln Ala Asp Pro Asn Arg Met Tyr Trp Ile Glu Leu Val Leu Ala Lys
            515                 520                 525

Glu Asp Ala Pro Lys Val Leu Lys Lys Met Gly Lys Leu Phe Ala Glu
        530                 535                 540

Gln Asn Lys Ser
545

<210> SEQ ID NO 167
<211> LENGTH: 563
<212> TYPE: PRT
<213> ORGANISM: Saccharomyces cerevisiae

<400> SEQUENCE: 167

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300
```

```
Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Gln Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
        450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
                500                 505                 510

Ala Thr Thr Gly Glu Trp Asp Ala Leu Thr Thr Asp Ser Glu Phe Gln
            515                 520                 525

Lys Asn Ser Val Ile Arg Leu Ile Glu Leu Lys Leu Pro Val Phe Asp
        530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 168
<211> LENGTH: 635
<212> TYPE: PRT
<213> ORGANISM: Saccharomyces cerevisiae

<400> SEQUENCE: 168

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110
```

```
Gly Ser Phe Ala Glu Asn Val Lys Val Leu His Ile Val Gly Val Ala
            115                 120                 125

Lys Ser Ile Asp Ser Arg Ser Ser Asn Phe Ser Asp Arg Asn Leu His
        130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
        195                 200                 205

Asp Phe Ala Asp Met Ser Val Thr Cys Asp Asn Leu Val Asn Val Pro
210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
        355                 360                 365

Gln Met Phe Lys Gly Ile Asn Phe Ala Pro Ile Leu Lys Glu Leu Tyr
370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
                405                 410                 415

Gln Ser Ser Ile Ile Thr Gln Val His Leu Gln Lys Thr Met Pro Lys
            420                 425                 430

Phe Leu Asn Pro Gly Asp Val Val Cys Glu Thr Gly Ser Phe Gln
        435                 440                 445

Phe Ser Val Arg Asp Phe Ala Phe Pro Ser Gln Leu Lys Tyr Ile Ser
450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
                485                 490                 495

Asn Val Lys Glu Asp Tyr Lys Pro Arg Leu Ile Leu Phe Glu Gly Asp
            500                 505                 510

Gly Ala Ala Gln Met Thr Ile Gln Glu Leu Ser Thr Ile Leu Lys Cys
        515                 520                 525
```

```
Asn Ile Pro Leu Glu Val Ile Ile Trp Asn Asn Gly Tyr Thr Ile
            530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
                595                 600                 605

Glu Val Lys Leu Gly Leu Asp Phe Pro Glu Gln Leu Lys Cys Met
610                 615                 620

Val Glu Ala Ala Leu Lys Arg Asn Lys Lys
625                 630                 635

<210> SEQ ID NO 169
<211> LENGTH: 348
<212> TYPE: PRT
<213> ORGANISM: Saccharomyces cerevisiae

<400> SEQUENCE: 169

Met Ser Ile Pro Glu Thr Gln Lys Ala Ile Ile Phe Tyr Glu Ser Asn
1               5                   10                  15

Gly Lys Leu Glu His Lys Asp Ile Pro Val Pro Lys Pro Lys Pro Asn
                20                  25                  30

Glu Leu Leu Ile Asn Val Lys Tyr Ser Gly Val Cys His Thr Asp Leu
            35                  40                  45

His Ala Trp His Gly Asp Trp Pro Leu Pro Thr Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Glu
        115                 120                 125

Tyr Ala Thr Ala Asp Ala Val Gln Ala Ala His Ile Pro Gln Gly Thr
    130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
    210                 215                 220

Glu Lys Asp Ile Val Ser Ala Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
            260                 265                 270
```

Ala Gly Ala Lys Cys Ser Ser Asp Val Phe Asn His Val Val Lys Ser
        275                 280                 285

Ile Ser Ile Val Gly Ser Tyr Val Gly Asn Arg Ala Asp Thr Arg Glu
290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Gly Lys Gly
                325                 330                 335

Gln Ile Ala Gly Arg Tyr Val Val Asp Thr Ser Lys
            340                 345

<210> SEQ ID NO 170
<211> LENGTH: 563
<212> TYPE: PRT
<213> ORGANISM: Saccharomyces cerevisiae

<400> SEQUENCE: 170

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys 290                 295                 300
Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln

<210> SEQ ID NO 171
<211> LENGTH: 1048
<212> TYPE: PRT
<213> ORGANISM: Clostridium acetobutylicum

<400> SEQUENCE: 171

Met Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
            20                  25                  30

Ser Phe Leu Asp Tyr Ile Met Glu Tyr Lys Gly Ile Asp Trp Val Gly
        35                  40                  45

Asn Cys Asn Glu Leu Asn Ala Gly Tyr Ala Ala Asp Gly Tyr Ala Arg
    50                  55                  60

Ile Asn Gly Ile Gly Ala Ile Leu Thr Thr Phe Gly Val Gly Glu Leu
65                  70                  75                  80

Ser Ala Ile Asn Ala Ile Ala Gly Ala Tyr Ala Glu Gln Val Pro Val
                85                  90                  95

Val Lys Ile Thr Gly Ile Pro Thr Ala Lys Val Arg Asp Asn Gly Leu

```
            100                 105                 110
Tyr Val His His Thr Leu Gly Asp Gly Arg Phe Asp His Phe Glu
            115                 120                 125
Met Phe Arg Glu Val Thr Val Ala Glu Ala Leu Leu Ser Glu Glu Asn
            130                 135             140
Ala Ala Gln Glu Ile Asp Arg Val Leu Ile Ser Cys Trp Arg Gln Lys
145                 150                 155                 160
Arg Pro Val Leu Ile Asn Leu Pro Ile Asp Val Tyr Asp Lys Pro Ile
                    165                 170                 175
Asn Lys Pro Leu Lys Pro Leu Leu Asp Tyr Thr Ile Ser Ser Asn Lys
            180                 185                 190
Glu Ala Ala Cys Glu Phe Val Thr Glu Ile Val Pro Ile Ile Asn Arg
            195                 200                 205
Ala Lys Lys Pro Val Ile Leu Ala Asp Tyr Gly Val Tyr Arg Tyr Gln
            210                 215                 220
Val Gln His Val Leu Lys Asn Leu Ala Glu Lys Thr Gly Phe Pro Val
225                 230                 235                 240
Ala Thr Leu Ser Met Gly Lys Gly Val Phe Asn Glu Ala His Pro Gln
                    245                 250                 255
Phe Ile Gly Val Tyr Asn Gly Asp Val Ser Ser Pro Tyr Leu Arg Gln
            260                 265                 270
Arg Val Asp Glu Ala Asp Cys Ile Ile Ser Val Gly Val Lys Leu Thr
            275                 280                 285
Asp Ser Thr Thr Gly Gly Phe Ser His Gly Phe Ser Lys Arg Asn Val
            290                 295                 300
Ile His Ile Asp Pro Phe Ser Ile Lys Ala Lys Gly Lys Lys Tyr Ala
305                 310                 315                 320
Pro Ile Thr Met Lys Asp Ala Leu Thr Glu Leu Thr Ser Lys Ile Glu
                    325                 330                 335
His Arg Asn Phe Glu Asp Leu Asp Ile Lys Pro Tyr Lys Ser Asp Asn
            340                 345                 350
Gln Lys Tyr Phe Ala Lys Glu Lys Pro Ile Thr Gln Lys Arg Phe Phe
            355                 360                 365
Glu Arg Ile Ala His Phe Ile Lys Glu Lys Asp Val Leu Leu Ala Glu
            370                 375                 380
Gln Gly Thr Cys Phe Phe Gly Ala Ser Thr Ile Gln Leu Pro Lys Asp
385                 390                 395                 400
Ala Thr Phe Ile Gly Gln Pro Leu Trp Gly Ser Ile Gly Tyr Thr Leu
                    405                 410                 415
Pro Ala Leu Leu Gly Ser Gln Leu Ala Asp Gln Lys Arg Arg Asn Ile
            420                 425                 430
Leu Leu Ile Gly Asp Gly Ala Phe Gln Met Thr Ala Gln Glu Ile Ser
            435                 440                 445
Thr Met Leu Arg Leu Gln Ile Lys Pro Ile Ile Phe Leu Ile Asn Asn
450                 455                 460
Asp Gly Tyr Thr Ile Glu Arg Ala Ile His Gly Arg Glu Gln Val Tyr
465                 470                 475                 480
Asn Asn Ile Gln Met Trp Arg Tyr His Asn Val Pro Lys Val Leu Gly
                    485                 490                 495
Pro Lys Glu Cys Ser Leu Thr Phe Lys Val Gln Ser Glu Thr Glu Leu
            500                 505                 510
Glu Lys Ala Leu Leu Val Ala Asp Lys Asp Cys Glu His Leu Ile Phe
            515                 520                 525
```

```
Ile Glu Val Val Met Asp Arg Tyr Asp Lys Pro Glu Pro Leu Glu Arg
    530                 535                 540

Leu Ser Lys Arg Phe Ala Asn Gln Asn Asn Gly Tyr Ala Arg Ile Asn
545                 550                 555                 560

Gly Ile Gly Ala Ile Leu Thr Thr Phe Gly Val Gly Glu Leu Ser Ala
                565                 570                 575

Ile Asn Ala Ile Ala Gly Ala Tyr Ala Glu Gln Val Pro Val Val Lys
                580                 585                 590

Ile Thr Gly Ile Pro Thr Ala Lys Val Arg Asp Asn Gly Leu Tyr Val
            595                 600                 605

His His Thr Leu Gly Asp Gly Arg Phe Asp His Phe Phe Glu Met Phe
    610                 615                 620

Arg Glu Val Thr Val Ala Glu Ala Leu Leu Ser Glu Glu Asn Ala Ala
625                 630                 635                 640

Gln Glu Ile Asp Arg Val Leu Ile Ser Cys Trp Arg Gln Lys Arg Pro
                645                 650                 655

Val Leu Ile Asn Leu Pro Ile Asp Val Tyr Asp Lys Pro Ile Asn Lys
                660                 665                 670

Pro Leu Lys Pro Leu Leu Asp Tyr Thr Ile Ser Ser Asn Lys Glu Ala
            675                 680                 685

Ala Cys Glu Phe Val Thr Glu Ile Val Pro Ile Ile Asn Arg Ala Lys
    690                 695                 700

Lys Pro Val Ile Leu Ala Asp Tyr Gly Val Tyr Arg Tyr Gln Val Gln
705                 710                 715                 720

His Val Leu Lys Asn Leu Ala Glu Lys Thr Gly Phe Pro Val Ala Thr
                725                 730                 735

Leu Ser Met Gly Lys Gly Val Phe Asn Glu Ala His Pro Gln Phe Ile
            740                 745                 750

Gly Val Tyr Asn Gly Asp Val Ser Ser Pro Tyr Leu Arg Gln Arg Val
        755                 760                 765

Asp Glu Ala Asp Cys Ile Ile Ser Val Gly Val Lys Leu Thr Asp Ser
770                 775                 780

Thr Thr Gly Gly Phe Ser His Gly Phe Ser Lys Arg Asn Val Ile His
785                 790                 795                 800

Ile Asp Pro Phe Ser Ile Lys Ala Lys Gly Lys Lys Tyr Ala Pro Ile
                805                 810                 815

Thr Met Lys Asp Ala Leu Thr Glu Leu Thr Ser Lys Ile Glu His Arg
            820                 825                 830

Asn Phe Glu Asp Leu Asp Ile Lys Pro Tyr Lys Ser Asp Asn Gln Lys
    835                 840                 845

Tyr Phe Ala Lys Glu Lys Pro Ile Thr Gln Lys Arg Phe Phe Glu Arg
850                 855                 860

Ile Ala His Phe Ile Lys Glu Lys Asp Val Leu Leu Ala Glu Gln Gly
865                 870                 875                 880

Thr Cys Phe Phe Gly Ala Ser Thr Ile Gln Leu Pro Lys Asp Ala Thr
                885                 890                 895

Phe Ile Gly Gln Pro Leu Trp Gly Ser Ile Gly Tyr Thr Leu Pro Ala
            900                 905                 910

Leu Leu Gly Ser Gln Leu Ala Asp Gln Lys Arg Arg Asn Ile Leu Leu
        915                 920                 925

Ile Gly Asp Gly Ala Phe Gln Met Thr Ala Gln Glu Ile Ser Thr Met
930                 935                 940
```

Leu Arg Leu Gln Ile Lys Pro Ile Ile Phe Leu Ile Asn Asn Asp Gly
945                 950                 955                 960

Tyr Thr Ile Glu Arg Ala Ile His Gly Arg Glu Gln Val Tyr Asn Asn
                965                 970                 975

Ile Gln Met Trp Arg Tyr His Asn Val Pro Lys Val Leu Gly Pro Lys
            980                 985                 990

Glu Cys Ser Leu Thr Phe Lys Val Gln Ser Glu Thr Glu Leu Glu Lys
        995                 1000                1005

Ala Leu  Leu Val Ala Asp Lys  Asp Cys Glu His  Leu  Ile Phe Ile
    1010             1015                 1020

Glu Val  Val Met Asp Arg Tyr  Asp Lys Pro Glu Pro  Leu Glu Arg
    1025             1030                 1035

Leu Ser  Lys Arg Phe Ala Asn  Gln Asn Asn
    1040             1045

<210> SEQ ID NO 172
<211> LENGTH: 645
<212> TYPE: DNA
<213> ORGANISM: Methylococcus capsulatus

<400> SEQUENCE: 172
atggcaagac cattgattca gctcgccctg gacacgctgg acatcccgca gaccctgaag      60
ctcgcaagcc tcaccgcgcc ctatgtcgat atcttcgaaa tcggcacccc cagcatcaag     120
cacaacggca tcgccctggt gaaggagttc aaaaaacgct tccccaacaa gctgctcctg     180
gtcgacctca aaaccatgga cgccggtgaa tacgaagcca ccccttcttc cgccgccggc     240
gccgacatca ccaccgtcct cggcgtcgca ggactggcca ccatcaaggg cgtcatcaac     300
gccgccaaca agcacaacgc cgaggtccag gtcgacctga tcaacgtccc cgacaaggcc     360
gcctgcgccc gtgagtccgc caaggccggc gcccagatcg tcggcatcca caccggcctc     420
gacgcccagg ccgccggcca gaccccttc gccgacctcc aggccatcgc caagctcggc     480
ctccccgtcc gcatctccgt cgccggcggc atcaaggcct ccaccgccca acaggtcgtc     540
aaaaccggtg ccaacatcat cgtcgtcgga gccgccatct acggcgccgc ctcccccgcc     600
gatgccgcgc gcgaaatcta cgaacaggtc gtcgccgctt ccgcc                     645

<210> SEQ ID NO 173
<211> LENGTH: 215
<212> TYPE: PRT
<213> ORGANISM: Methylococcus capsulatus

<400> SEQUENCE: 173

Met Ala Arg Pro Leu Ile Gln Leu Ala Leu Asp Thr Leu Asp Ile Pro
1               5                   10                  15

Gln Thr Leu Lys Leu Ala Ser Leu Thr Ala Pro Tyr Val Asp Ile Phe
            20                  25                  30

Glu Ile Gly Thr Pro Ser Ile Lys His Asn Gly Ile Ala Leu Val Lys
        35                  40                  45

Glu Phe Lys Lys Arg Phe Pro Asn Lys Leu Leu Leu Val Asp Leu Lys
    50                  55                  60

Thr Met Asp Ala Gly Glu Tyr Glu Ala Thr Pro Phe Phe Ala Ala Gly
65                  70                  75                  80

Ala Asp Ile Thr Thr Val Leu Gly Val Ala Gly Leu Ala Thr Ile Lys
                85                  90                  95

Gly Val Ile Asn Ala Ala Asn Lys His Asn Ala Glu Val Gln Val Asp
            100                 105                 110

```
Leu Ile Asn Val Pro Asp Lys Ala Ala Cys Ala Arg Glu Ser Ala Lys
        115                 120                 125

Ala Gly Ala Gln Ile Val Gly Ile His Thr Gly Leu Asp Ala Gln Ala
    130                 135                 140

Ala Gly Gln Thr Pro Phe Ala Asp Leu Gln Ala Ile Ala Lys Leu Gly
145                 150                 155                 160

Leu Pro Val Arg Ile Ser Val Ala Gly Gly Ile Lys Ala Ser Thr Ala
                165                 170                 175

Gln Gln Val Val Lys Thr Gly Ala Asn Ile Ile Val Val Gly Ala Ala
                180                 185                 190

Ile Tyr Gly Ala Ala Ser Pro Ala Asp Ala Ala Arg Glu Ile Tyr Glu
            195                 200                 205

Gln Val Val Ala Ala Ser Ala
    210                 215
```

```
<210> SEQ ID NO 174
<211> LENGTH: 531
<212> TYPE: DNA
<213> ORGANISM: Methylococcus capsulatus

<400> SEQUENCE: 174
atgcatcaga aactgatcat agacaaaatc tccggcatcc tcgccgccac cgatgccggc      60
tatgatgcaa aactgactgc catgctcgac caggcctccc gcatcttcgt cgcggggggcc    120
ggccggtcgg ggctggtcgc caagttcttc gccatgcgcc tcatgcacgg cggctatgac    180
gtcttcgtcg tcggcgaaat cgtcaccccc agcatccgca agggcgactt gctgatcgtg    240
atctccggct ccggtgaaac cgaaaccatg ctcgccttca ccaaaaaagc caaggagcag    300
ggcgcctcca tcgccctcat ctccaccgc gacagctcct ccctcggcga cctcgccgac    360
tccgtcttcc gcatcggctc cccagagctc ttcggaaaag tcgtcggcat gcccatgggc    420
accgtcttcg agctctccac cctcctcttc ctcgaggcca ccatctctca catcatccac    480
gagaaaggca tccccgaaga gaaatgaga actcgtcacg ccaacctgga a                531
```

```
<210> SEQ ID NO 175
<211> LENGTH: 177
<212> TYPE: PRT
<213> ORGANISM: Methylococcus capsulatus

<400> SEQUENCE: 175

Met His Gln Lys Leu Ile Ile Asp Lys Ile Ser Gly Ile Leu Ala Ala
1               5                   10                  15

Thr Asp Ala Gly Tyr Asp Ala Lys Leu Thr Ala Met Leu Asp Gln Ala
                20                  25                  30

Ser Arg Ile Phe Val Ala Gly Gly Arg Ser Gly Leu Val Ala Lys
            35                  40                  45

Phe Phe Ala Met Arg Leu Met His Gly Gly Tyr Asp Val Phe Val Val
    50                  55                  60

Gly Glu Ile Val Thr Pro Ser Ile Arg Lys Gly Asp Leu Leu Ile Val
65                  70                  75                  80

Ile Ser Gly Ser Gly Glu Thr Glu Thr Met Leu Ala Phe Thr Lys Lys
                85                  90                  95

Ala Lys Glu Gln Gly Ala Ser Ile Ala Leu Ile Ser Thr Arg Asp Ser
            100                 105                 110

Ser Ser Leu Gly Asp Leu Ala Asp Ser Val Phe Arg Ile Gly Ser Pro
        115                 120                 125
```

```
Glu Leu Phe Gly Lys Val Val Gly Met Pro Met Gly Thr Val Phe Glu
    130             135             140
Leu Ser Thr Leu Leu Phe Leu Glu Ala Thr Ile Ser His Ile Ile His
145             150             155             160
Glu Lys Gly Ile Pro Glu Glu Glu Met Arg Thr Arg His Ala Asn Leu
            165             170             175
Glu
```

BIOLOGICAL PRODUCTION OF MULTI-CARBON COMPOUNDS FROM METHANE

CROSS-REFERENCE TO RELATED APPLICATION

This application is continuation of U.S. patent application Ser. No. 15/648,920, filed Jul. 13, 2017, now U.S. Pat. No. 10,876,137, issued Dec. 29, 2020; which is a continuation of U.S. patent application Ser. No. 15/192,290, filed Jun. 24, 2016, now U.S. Pat. No. 9,745,603, issued Aug. 29, 2017; which is a divisional of U.S. patent application Ser. No. 14/989,859, filed Jan. 7, 2016, now U.S. Pat. No. 9,399,783, issued Jul. 26, 2016; which is a divisional of U.S. patent application Ser. No. 14/206,835, filed Mar. 12, 2014, now U.S. Pat. No. 9,267,158, issued Feb. 23, 2016; which claims priority from U.S. Provisional Application No. 61/782,830, filed Mar. 14, 2013, all of which are hereby incorporated by reference in their entireties.

REFERENCE TO SEQUENCE LISTING

This application includes a "Sequence Listing.ascii.txt," 331,569 bytes, created on Mar. 12, 2014, and submitted electronically via EFS-Web, which is hereby incorporated by reference in its entirety.

BACKGROUND OF THE INVENTION

Field of the Invention

The present invention is generally related to the fields of molecular biology and and methods of producing metabolically engineered microorganisms which utilize methane feedstocks for the biological production of bio-fuels and bio-chemicals such as 1-butanol, isobutanol, fatty alcohols, fatty acid esters, 2,3-butanediol and the like.

Background Art

Traditional fossil fuels (e.g., gasoline, diesel, kerosene and the like) and numerous chemicals (e.g., for use in pharmaceuticals, solvents, fertilizers, pesticides, plastics and the like) are derived (and refined from) non-renewable petroleum (oil) resources. Current estimates suggest that the world's supply of non-renewable petroleum will likely be exhausted somewhere between the years 2045 and 2065 (U.S. Department of the Interior, U.S. Geological Survey World Petroleum Assessment, 2000), with concomitant extensions or reductions of these estimates dependent on variables such as increased (or reduced) global demand, more efficient petroleum refining processes, more efficient use of energy and products derived from petroleum and the discovery of new petroleum sources/reserves.

Independent of any current or future methods contemplated to mitigate petroleum consumption, there is no debate that the world's supply of petroleum is a finite and a constantly diminishing (non-renewable) energy source. Thus, to meet the ever increasing global demands for energy consumption, renewable, biologically produced fuels (i.e., "bio-fuels" and "bio-diesel") have become an area of intense research, capital investment and government intervention.

For example, the U.S. "Energy Policy Act" of 2005 (42 USC, Title XV "Ethanol and Motor Fuels", § 1501-§ 1533; enacted into law Aug. 8, 2005), sets forth parameters and definitions of "renewable fuels", and established the "minimum ethanol" volume to gasoline volume blending requirements (presently E10: 10% ethanol:90% gasoline), with E15 (15% ethanol:85% gasoline) enacted as law and being "phased-in" across the U.S. The Energy Policy Act defines "renewable fuel" as a "motor vehicle fuel produced from grain, starch, oil-seeds, vegetable, animal, or fish materials including fats, greases, and oils, sugarcane, sugar beets, sugar components, tobacco, potatoes, or other biomass; or a natural gas produced from a biogas source, including a landfill, sewage waste treatment plant, feedlot, or other place where decaying organic material is found; and is used to replace or reduce the quantity of fossil fuel present in a fuel mixture used to operate a motor vehicle. The term "renewable fuel" includes (a) cellulosic biomass ethanol and waste derived ethanol; and (b) biodiesel, and any blending components derived from renewable fuel".

In addition to the current E10 ethanol/gasoline blends and ongoing adoption of E15 ethanol/gasoline blends, ethanol volumes of up to E85 (i.e., 85% ethanol:15% gasoline) are also presently being utilized in "flex-fuel" vehicles (i.e., vehicles with engines and fuel systems capable of combusting and delivering, respectively, 85% ethanol blended gasoline) and it is estimated that the production of E85 fuel will only continue to increase as the supply (i.e., production) of "flex-fuel" vehicles increase. However, an inherent limitation of "ethanol" blended fuels (due to the decreased or lower "energy content" of ethanol relative to gasoline) is that increasing the percentage of ethanol blended into gasoline reduces the overall fuel economy of the vehicle (e.g., fuel economy of vehicles operating on E85 is about 25-30% less than vehicles operating on E10 gasoline blends). This limitation of ethanol's total energy content has further facilitated research and development of alternative bio-fuel blending additives (e.g., terpenoid hydrocarbons, n-butanol, isobutanol and the like) to replace bio-ethanol. Also predicated on the assumption of a finite, diminishing supply of non-renewable petroleum resources, research in the areas of biologically derived (hereinafter, "bio-based") chemicals (e.g., for use in pharmaceuticals, solvents, fertilizers, pesticides, plastics and the like) are being pursued, wherein these "bio-based" chemicals are contemplated as a means for reducing or eliminating their equivalents traditionally derived from petroleum feed stocks.

A considerable topic of ongoing debate is whether the ethanol fuel provisions of the Energy Policy Act of 2005 (and similar policies of other countries) have reduced (or will reduce) dependence on foreign oil/petroleum sources and/or have mitigated (or will mitigate) greenhouse gas emissions (two perceived benefits of the Act). For example, bio-fuels such as ethanol were initially seen as a solution to energy and environmental problems (i.e., considered carbon neutral) because the carbon dioxide emitted when ethanol is combusted is equivalent to the carbon dioxide absorbed from the atmosphere when the ethanol feed stock crop is grown (e.g., corn ethanol, sugarcane ethanol, cellulosic ethanol from switchgrass, etc.).

A recent study by economists at Oregon State University (Jaeger & Egelkraut, 2011) suggests however, that once additional factors/consequences are considered, such as (a) the use of fossil fuels to produce bio-fuel feedstocks and transport bio-fuels, (b) the use of nitrogen fertilizers to grow bio-fuel feedstocks and (c) that growing bio-fuel feedstock crops often pushes food production onto previously unfarmed land (which typically requires clearing tress and heavy tilling of the land), the perceived environmental benefits of ethanol derived bio-fuels may be lost. Likewise, another recent study on the environmental impact of bio-fuel production concludes that high corn and soybean prices, prompted largely by the demand for bio-fuel feedstocks (and partly by government incentives to use them as fuels instead of food), are driving one of the most important land cover/land use change events in recent US history; the accelerated conversion of grassland to cropland in the US Corn Belt (Wright and Wimberly, 2013).

The shift from petroleum based diesel fuel as a (transportation) energy source (e.g., used in automobiles, trucks and other heavy equipment) to renewable bio-diesel fuels is another source of scientific and policy disagreement similar to the arguments set forth above with regard to ethanol bio-fuels. Bio-diesel is generally made from plant oils or animal fats (triacylglycerides) by transesterification with methanol or ethanol, resulting in fatty acid methyl esters and fatty acid ethyl esters. However, the limited supply of bioresources to obtain triacylglycerides has become a major bottleneck for bio-diesel production, the primary reason being that vegetable oil feedstocks are also food sources and their planting is geographically limited.

There is therefore a pressing need in the art for novel methods of producing bio-fuel, bio-diesel and bio-based chemical compositions which reduce the world's dependence/utilization of petroleum products, ameliorate ongoing depletion of arable food source "farmland" currently being diverted to grow bio-fuel feedstocks and generally improve the environmental footprint of future bio-fuel, bio-diesel and bio-based chemical compositions.

As mentioned previously above, ethanol is currently the most abundant bio-fuel produced, but due to certain limitations (e.g., low energy content, high water solubility, incompatibility/corrosive with many fuel systems), ethanol based bio-fuels may not be the best option to meet future energy demands. Butanol, in comparison, has several advantages over ethanol as a bio-fuel, such as its high blending compatibility with gasoline, its low solubility in water allow it to be stored and distributed using the existing petrochemical infrastructure, it has a much higher energy content than ethanol (thereby improving fuel economy) and has a lower vapor pressure than ethanol blends, which is important in reducing evaporative hydrocarbon emissions. Isobutanol has the same advantages as butanol, with the additional advantage of having a higher octane number due to its branched carbon chain, and it is also useful as a commodity chemical.

Various methods for producing renewable bio-fuel, bio-diesel and other bio-based chemicals are known and described in the art. For example, traditional fermentation and distillation methods for producing and extracting bio-ethanol from starch or sugar rich biomass (e.g., corn) and the hydrolysis, fermentation and distillation methods of producing bio-ethanol from ligno-cellulosic biomass are well known in the art (Rudolph et al., 2009; Kim et al, 2013; Philips et al., 2013). The production of bio-diesel via extraction and esterification of vegetable oils, used cooking oils and animal fats using alcohols is also well known in the art (Saka & Kusdiana, 2001).

In more recent efforts, researchers have started to look at alternative methods for producing bio-fuels, bio-diesel and bio-based chemicals. For example, methods for producing bio-fuels such as butanol and isobutanol in various microorganisms such as *Escherichia coli* (Atsumi et al., 2010), *Clostridium acetobutylicum* (Jang et al., 2012) and *Saccharomyces cerevisiae* (Avalos et al., 2013) have been described in the art. Furthermore, the complete biosynthetic pathway for isobutanol production has been engineered in yeast (see, U.S. Pat. Nos. 8,232,089; 7,993,889) and bacteria (see, U.S. Patent Publication No. 2011/0301388). Similarly, de novo biosynthesis of bio-diesel using genetically engineered *E. coli* has been described in the art (Xingye et al., 2011; Yangkai et al., 2011).

However, each of the methods set forth above (i.e., traditional biomass fermentation methods and engineered biological/microorganism methods) for producing bio-fuel, bio-diesel, bio-based chemicals and the like, are limited by the choice of feedstock (or substrate) used to produce the end product (e.g., bio-ethanol, bio-butanol, bio-diesel, etc.). For example, the growth substrates utilized by each of the microorganisms set forth above (i.e., *E. coli, C. acetobutylicum* and *S. cerevisiae*) are dependent, in one way or another, on substrate feedstocks derived from crop-based food sources (e.g., glucose (growth) substrates fed to microorganisms are derived from plant sources).

Thus, as set forth previously, there is an ongoing need in the art for novel methods of producing bio-fuel, bio-diesel and bio-based chemical compositions, which not only reduce dependence/utilization of petroleum products, but also ameliorate the ongoing depletion of arable food source "farmland" currently being diverted to grow bio-fuel feedstocks and generally improve the environmental footprint of future bio-fuel, bio-diesel and bio-based chemical compositions.

Methane ($CH_4$) has great value as a chemical feedstock for the production of chemicals and food additives, due to its widespread availability, abundant supply and low price (Kidnay et al., 2011). Methane, in the form of natural gas, can be obtained from shale gas, oil drilling, municipal solid waste, biomass gasification/conversion, and methanogenic archaea. Wellhead natural gas varies in composition from about 40% to 95% methane, wherein the other components include ethane, propane, butane, pentane, and heavier hydrocarbons, along with hydrogen sulfide, carbon dioxide, helium and nitrogen. The proportion of methane in the gas feedstock can be increased by gas conditioning, which can produce natural gas consisting of 85-95% (v/v) methane (U.S. Pat. No. 4,982,023).

Current industrial methods for utilizing methane from natural gas include the Fischer-Tropsch process for converting methane into ethylene, steam-methane reforming from methane synthesis gas, as well as direct conversion from methane to methanol using inorganic catalysts (Veazey, 2012; Alayon et al., 2012; U.S. Pat. No. 4,982,023). Although the economics of syngas-to-liquids and methanol-to-gasoline from natural gas have become more favorable, these thermochemical methods for methane conversion still suffer from serious drawbacks (Arakawa et al., 2001). For example: (1) industrial plant construction requires high capital expenditure, (2) operating costs are high, (3) thermochemical conversion plants require elevated temperatures (150° C. to 300° C.) and high pressures (tens of atmospheres), which add to capital and operational costs, (4) the gas-to-liquids process is not always selective in producing liquid fuel and chemical products, further requiring expensive distillation costs and (5) the inorganic catalysts required for producing methanol and other products are susceptible to poisoning by contaminants in the process stream, and therefore the gas streams must be cleaned and the catalysts periodically replaced.

Certain embodiments of the present invention, as set forth below (see, "Detailed Description"), are directed to methods for biosynthetic production of multi-carbon compounds such as fuels (bio-fuels) and chemicals (bio-based) from methane. It is contemplated herein that the methods according to the present invention, using biological catalysts or biocatalysts (e.g., a genetically modified host microorganism) provide a number of economic advantages over current "industrial" methods for utilizing methane from natural gas. These advantages include (1) lower processing temperatures and pressures; (2) high selectivity for the reactions and (3) renewability, all of which lead to substantially lower capital and operational expenses.

A number of microorganisms, including bacteria and yeast, use single-carbon (C1) substrates as their sole source of carbon. These methylotrophs or C1-metabolizers can convert carbon compounds that do not contain carbon-carbon bonds, such as methane ($CH_4$) or methanol ($CH_3OH$) into biomass (Gellissen et al., 2005; Trotsenko & Murrell, 2008; Chistoserdova et al., 2009; Schrader et al., 2009; Chistoserdova, 2011). With regard to methane utilization, one particularly important group of bacteria known as the methanotrophs, the "obligate" members of which convert methane into methanol ($CH_3OH$), formaldehyde ($H_2C=O$), formic acid (HCOOH) and ultimately $CO_2$ by sequential enzymatic oxidation (Hanson & Hanson, 1996; Trotsenko & Murrell, 2008; Rosenzweig & Ragsdale, 2011(a); Rosenzweig & Ragsdale 2011(b)). Certain "facultative" methanotrophs (e.g., from the genus *Methylocella*) can also be cultivated using methane, methanol or methylamines as growth substrates (Dunfield et al., 2003; Rosenzweig & Ragsdale, 2011(a); Rosenzweig & Ragsdale 2011(b); Semrau et al., 2011).

The initial step of methane oxidation to methanol in methanotrophs is carried out by the enzyme methane monooxygenase (MMO) (Hakemian & Rosenzweig, 2007; Rosenzweig & Ragsdale, 2011(b)). Methane monooxygenase (MMO) activity is expressed in two different forms: a particulate form (pMMO), which contains copper and is membrane-bound (Culpepper & Rosenzweig, 2012), and a soluble form (sMMO), which contains iron and is expressed when copper becomes limiting (Murrel et al., 2000; Hakemian & Rosenzweig, 2007; Tinberg & Lippard, 2007). The second step of converting methanol to formaldehyde is catalyzed by the enzyme methanol dehydrogenase (MDH), another membrane-bound enzyme (Anthony & Williams, 2003). From this point, the formaldehyde can be dissimilated into formate (by formaldehyde dehydrogenase) and carbon dioxide (by formate dehydrogenase). The dissimilation reactions generate reducing equivalents for the cell, but do not directly contribute to the production of biomass or other multi-carbon products, since the carbon is released as $CO_2$. In some methanotrophs, however, carbon dioxide can be fixed through the serine pathway and/or the Calvin-Benson-Bassham cycle (see below), both of which depend on methane consumption to support growth (Stanley & Dalton, 1982; Chistoserdova et al., 2005). Among the oxidized C1 products that can be generated in the above described reactions, formaldehyde is the most important product (or imtermediate), as it serves as a metabolite that can be "fixed" into multi-carbon compounds via its introduction (or assimilation) into a central metabolism pathway of the host microorganism.

For example, the assimilation of the carbon in the formaldehyde formed can occur via various metabolic routes (Hanson & Hanson, 1996; Yurimoto et al., 2005; Yurimoto et al., 2009; Trotsenko & Murrell, 2008; Rosenzweig & Ragsdale, 2011(a); Rosenzweig & Ragsdale, 2011(b)). For example, the Type I methanotrophs, which are members of the Gammaproteobacteria, use the ribulose monophosphate (RuMP) pathway (see, Hanson & Hanson, 1996). The Type II methanotrophs, which are members of the Alphaproteobacteria, utilize the serine pathway (Hanson & Hanson, 1996). The bacterium *Methylococcus capsulatus*, strain Bath, however, uses elements of both these pathways, and is sometimes referred to as a "Type X" methanotroph (Hanson & Hanson, 1996; Chistoserdova et al., 2005). *Methylococcus capsulatus* (Bath), also expresses the enzymes needed to fix carbon dioxide via the Calvin-Benson-Bassham cycle (Chistoserdova et al., 2005).

Turnover of these pathways (i.e., Type I, Type II or Type X) ultimately supplies multi-carbon intermediates for other pathways of central metabolism. For example, the 3-phospho-glyceraldehyde generated by the RuMP cycle can be converted into pyruvate, and the 2-phospho-glycerate generated by the serine cycle can eventually be converted into phosphoenolpyruvate, oxaloacetate and acetyl-CoA, among other intermediates.

Substantial efforts have been expended over the past 40 years to exploit methanotrophs for chemical production and transformations on an industrial scale. However, to date there are still significant deficiencies and unmet needs in the art for improved host microorganisms which can utilize "non-traditional" carbon sources such as oxidized single-carbon compounds (e.g., methane, methanol or formaldehyde) and produce industrial, commercially relevant, multi-carbon compounds such as ethanol, n-butanol, sec-butanol, isobutanol, tert-butanol, fatty alcohols, fatty acid methyl esters, 2,3-butanediol and the like.

The present invention fulfills a need in the art for improved host microorganisms (which can utilize methane as a sole-carbon source in the production of multi-carbon compounds) for use in the biological production of bio-fuels and bio-based chemical compositions. The metabolically engineered host microorganisms and methods of producing the same, as set forth in the present invention, further address a long felt need in the art to reduce dependence/consumption of petroleum products and mitigate the depletion of farmland currently being diverted to grow bio-fuel and bio-based chemical feedstocks.

SUMMARY OF THE INVENTION

The present invention provides metabolically engineered host microorganisms which metabolize methane ($CH_4$) as their sole carbon source to produce multi-carbon compounds for use in fuels (e.g., bio-fuel, bio-diesel) and bio-based chemicals. Furthermore, use of the metabolically engineered host microorganisms of the invention (which utilize methane as the sole carbon source) mitigate current industry practices and methods of producing multi-carbon compounds from petroleum or petroleum-derived feedstocks, and ameliorate much of the ongoing depletion of arable food source "farmland" currently being diverted to grow bio-fuel feedstocks, and as such, improve the environmental footprint of future bio-fuel, bio-diesel and bio-based chemical compositions.

Thus, in certain embodiments, the invention is directed to a method for producing isobutanol from a methane substrate comprising the steps of (a) providing a methanotrophic host microorganism that metabolizes methane ($CH_4$) to methanol ($CH_3OH$) and methanol to formaldehyde ($H_2C=O$); (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobutanol pathway; and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce isobutanol. In certain embodiments, the one or more polynucleotide ORFs introduced in step (b) encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol. In another embodiment, the ALS polypeptide comprises an amino acid sequence having at least 90% sequence homology to SEQ ID NO:2, the KARI polypeptide comprises an amino acid sequence having at least 90% sequence homology to SEQ ID NO:4, the DHAD polypeptide comprises an amino acid sequence having at least 90% sequence homology to SEQ ID NO:6, the KDC polypeptide comprises an amino acid sequence having at least 90% sequence homology to SEQ ID NO:8 and the ADH polypeptide comprises an amino acid sequence having at least 90% sequence homology to SEQ ID NO:10. In other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In other embodiments a method for producing isobutanol from a methane substrate further comprises the step of recovering the isobutanol produced.

In another embodiment, the invention is directed to a method for producing isobutanol from a methane substrate comprising the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce isobutanol. In certain embodiments, the one or more polynucleotide ORFs introduced in step (b) encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol. In certain other embodiments, the ALS polypeptide comprises an amino acid sequence having at least 90% sequence homology to SEQ ID NO:2, the KARI polypeptide comprises an amino acid sequence having at least 90% sequence homology to SEQ ID NO:4, the DHAD polypeptide comprises an amino acid sequence having at least 90% sequence homology to SEQ ID NO:6, the KDC polypeptide comprises an amino acid sequence having at least 90% sequence homology to SEQ ID NO:8 and the ADH polypeptide comprises an amino acid sequence having at least 90% sequence homology to SEQ ID NO:10. In another embodiment, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In other embodiments, the methane monooxygenase (MMO) is a soluble MMO of Enzyme Class EC 1.14.13.25 or a particulate MMO of Enzyme Class 1.14.18.3. In certain embodiments, the MMO comprises an amino acid sequence comprising at least 90% sequence homology to a particulate methane monooxygenase (pMMO) selected from the group consisting of SEQ ID NO:12, SEQ ID NO:14, SEQ ID NO: 16, SEQ ID NO:18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing isobutanol from a methane substrate further comprises the step of recovering the isobutanol produced.

In another embodiment, the invention is directed to a method for producing 1-butanol from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol. In certain embodiments, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 4.1.1.72, and EC 1.1.1.1. In yet other embodiments, the one or more polynucleotide ORFs introduced in step (b) encode a 1-butanol pathway polypeptide selected from the group consisting of L-threonine ammonia lyase, 2-ethylmalate synthase, isopropylmalate isomerase, 3-isopropylmalate dehydratase, 3-isopropylmalate dehydrogenase, 2-ketoacid decarboxylase (KDC) and alcohol dehydrogenase (ADH). In another embodiment, the L-threonine ammonia lyase catalyzes the substrate to product conversion of L-threonine to 2-oxybutanoate and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butyraldehyde and the ADH catalyzes the substrate to product conversion of butyraldehyde to 1-butanol. In another embodiment, the L-threonine ammonia lyase comprises an amino acid sequence having at least 90% sequence homology to SEQ ID NO:56, the 2-ethylmalate synthase comprises an amino acid sequence having at least 90% sequence homology to SEQ ID NO:58, the isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In certain other embodiments, the one or more polynucleotide ORFs introduced in step (b) encode the complete 1-butanol pathway comprising L-threonine ammonia lyase, 2-ethylmalate synthase, isopropylmalate isomerase, 3-isopropylmalate dehydrogenase, 2-ketoacid decarboxylase (KDC) and alcohol dehydrogenase (ADH). In other embodiments a method for producing 1-butanol from a methane substrate further comprises the step of recovering the 1-butanol produced.

In another embodiment, the invention is directed to a method for producing 1-butanol from a methane substrate comprising the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce 1-butanol. In certain embodiments, the one or more polynucleotide ORFs introduced in step (b) encode an 1-butanol pathway polypeptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-butanol pathway polypeptide selected from the group consisting of L-threonine ammonia lyase, 2-ethylmalate synthase, isopropylmalate isomerase, 3-isopropylmalate dehydrogenase, 2-ketoacid decarboxylase (KDC) and alcohol dehydrogenase (ADH). In yet other embodiments, the L-threonine ammonia lyase catalyzes the substrate to product conversion of L-threonine to 2-oxybutanoate and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butryaldehyde and the ADH catalyzes the substrate to product conversion of butyraldehyde to 1-butanol. In other embodiments, the L-threonine ammonia lyase comprises an amino acid sequence having at least 90% sequence homology to SEQ ID NO:56, the 2-ethylmalate synthase comprises an amino acid sequence having at least 90% sequence homology to SEQ ID NO:58, the isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In another embodiment, the methane monooxygenase (MMO) is a soluble MMO of Enzyme Class EC 1.14.13.25 or a particulate MMO of Enzyme Class 1.14.18.3. In certain other embodiments, the MMO comprises an amino acid sequence comprising at least 90% sequence homology to a particulate methane monooxygenase (pMMO) selected from the group consisting of SEQ ID NO:12, SEQ ID NO:14, SEQ ID NO:16, SEQ ID NO:18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing 1-butanol from a methane substrate further comprises the step of recovering the 1-butanol produced.

In certain other embodiments, the invention is directed to a method for producing fatty alcohols from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a fatty-acyl-CoA reductase (FAR), and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol. In one embodiment, the FAR polypeptide is further defined as a polypeptide from Enzyme Class EC 1.2.1.50. In another embodiment, the FAR polypeptide catalyzes the substrate to product conversion of fatty acetyl-CoA to a fatty alcohol. In yet other embodiments, the FAR polypeptide comprises an amino acid sequence having at least 90% sequence homology to SEQ ID NO:66. In other embodiments a method for producing fatty alcohols from a methane substrate further comprises the step of recovering the fatty alcohol produced.

In certain other embodiments, the invention is directed to a method for producing a fatty alcohol from a methane substrate comprising the steps of (a) providing a non-methanotroph host microorganism which has been genetically engineered to express a methane monooxygenase (MMO), (b) introducing into the host microorganism and expressing a polynucleotide open reading frame (ORF), under the control of suitable regulatory sequences, wherein the polynucleotide ORF encodes a fatty-acyl-CoA reductase (FAR), and (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous RuMP or serine pathway and the host metabolizes acetyl-CoA to produce a fatty alcohol. In certain embodiments, the FAR polypeptide catalyzes the substrate to product conversion of fatty acetyl-CoA to a fatty alcohol. In certain other embodiments, the FAR polypeptide comprises an amino acid sequence comprising at least 90% sequence homology to SEQ ID NO:66. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) selected from the group consisting of SEQ ID NO:12, SEQ ID NO:14, SEQ ID NO: 16, SEQ ID NO:18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing fatty alcohols from a methane substrate further comprises the step of recovering the fatty alcohol produced.

In another embodiment, the invention is directed to a method for producing a fatty acid ester from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a wax ester synthase (WES) and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty acyl-CoA and alcohols to produce a fatty acid ester. In certain embodiments, the WES polypeptide is further defined as a polypeptide from Enzyme Class EC 2.3.1.75. In another embodiment, the WES polypeptide catalyzes the substrate to product conversion of fatty acyl-CoA and alcohols to fatty acid esters. In other embodiments, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78. In other embodiments a method for producing fatty acid esters from a methane substrate further comprises the step of recovering the fatty acid esters produced.

In another embodiment, the invention is directed to a method for producing a fatty acid ester from a methane substrate comprising the steps of (a) providing a non-methanotroph host microorganism which has been genetically engineered to express a methane monooxygenase (MMO), (b) introducing into the host microorganism and expressing at least one polynucleotide open reading frame (ORF), under the control of suitable regulatory sequences, wherein the at least one polynucleotide ORF encodes a wax ester synthase (WES) and (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to acetyl-CoA through an endogenous RuMP or serine pathway and the host metabolizes fatty acyl-CoA and alcohols to produce a fatty acid ester. In certain embodiments, the WES polypeptide catalyzes the substrate to product conversion of fatty acyl-CoA and alcohols to fatty acid esters. In certain other embodiments, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) selected from the group consisting of SEQ ID NO:12, SEQ ID NO:14, SEQ ID NO: 16, SEQ ID NO:18, SEQ ID NO:20 and SEQ ID NO:22 or at least 90% sequence homology to a soluble methane monooxygenase (sMMO) selected from the group consisting of SEQ ID NO:24, SEQ ID NO:26, SEQ ID NO:28, SEQ ID NO:30, SEQ ID NO:32 and SEQ ID NO:34. In other embodiments a method for producing fatty acid esters from a methane substrate further comprises the step of recovering the fatty acid esters produced.

In certain other embodiments, the invention is directed to a method for producing 2,3-butanediol from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the host and expressing a polynucleotide ORF, under the control of suitable regulatory sequences, wherein the ORF encodes a (2R,3R)-2,3-butanediol dehydrogenase (BDH1), and (c) feeding the host microorganism of step (b) a methane substrate under suitable growth conditions, wherein host metabolizes methane to formaldehyde as set forth in step (a), wherein the formaldehyde is converted to pyruvate by means of an endogenous type I RuMP pathway or a type II serine pathway and the host metabolizes pyruvate to produce (R)-acetoin and the BDH1 catalyzes the substrate to product conversion of (R)-acetoin to 2,3-butanediol. In certain embodiments, the (2R,3R)-2,3-butanediol dehydrogenase (BDH1) has at least 90% sequence homology to a BDH1 polypeptide of SEQ ID NO:157. In other embodiments, the polynucleotide ORF comprises a nucleotide sequence of SEQ ID NO:156. In other embodiments a method for producing 2,3-butanediol from a methane substrate further comprises the step of recovering the 2,3-butanediol produced.

In certain embodiments, a methanotroph host microorganism of the invention is selected from genus consisting of *Methylobacter, Methylomicrobium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis*, and *Methyloacidophilum*. In other embodiments, the methanotroph host microorganism is selected from the phylum Verrucomicrobia. In another embodiment, the methanotroph host is *Methylococcus capsulatus*, strain Bath.

In certain other embodiments, a non-methanotroph host microorganism of the invention is a yeast microorganism or bacterial microorganism. In certain embodiments, the non-methanotroph yeast microorganism is selected from *Saccha-*

*romyces cerevisiae, Hansenuela polymorpha, Pichia pastoris* and *Kluyveromyces lactis*. In one particular embodiment, the yeast microorganism is *Pichia pastoris*.

In certain other embodiments, a non-methanotrophic bacterial microorganism of the invention is *Pseudomonas putida, Cupriavidus metallidurans* or *Rhodobacter sphaeroides*.

In other embodiments, recovering the isobutanol produced according to the methods of the invention is a process selected from distillation, liquid extraction, flash evaporation, membrane separation and phase separation.

In other embodiments, recovering the 1-butanol produced according to the methods of the invention is a process selected from distillation, liquid extraction, flash evaporation, membrane separation and phase separation.

In another embodiment, recovering the fatty alcohol produced according to the methods of the invention is a process selected from flash evaporation, membrane separation, centrifugation and phase separation.

In certain other embodiments, recovering the fatty acid ester produced according to the methods of the invention is a process selected from flash evaporation, membrane separation, centrifugation and phase separation.

In another embodiment, recovering the 2,3-butanediol produced according to the methods of the invention is a process selected from steam stripping, solvent extraction, aqueous two-phase extraction, reactive extraction and pervaporation.

In certain other embodiments, a methane substrate is provided as a dry natural gas, as a wet natural gas or as a biogas.

In other embodiments, the host microorganism is grown by a batch process, a fed-batch process or a continuous perfusion process.

In another embodiment, the fatty alcohol composition produced according to the methods of the invention comprises a carbon chain of about 5 to about 40 carbon atoms. In certain embodiments, the fatty alcohol comprises a carbon chain of 8 to 22 carbon atoms.

In another embodiment, the fatty acid ester composition produced according to the methods of the invention has a fatty acid moiety comprising a carbon chain of about 5 to about 40 carbon atoms. In one particular embodiment, the fatty acid moiety comprises a carbon chain of 8 to 22 carbon atoms.

In yet other embodiments, the fatty acid ester composition produced according to the methods of the invention has an alcohol moiety comprising a carbon chain of about 5 to about 40 carbon atoms. In one particular embodiment, the alcohol moiety comprises a chain of 8 to 22 carbon atoms.

In yet other embodiments, a non-methanotroph host microorganism of the invention is further engineered to express an exogenous methanol dehydrogenase (MDH). In certain embodiments, the MDH is a polypeptide from Enzyme Class 1.14.18.3. In other embodiments, the MDH comprises an amino acid sequence having at least 90% sequence homology to a MDH polypeptide selected from the group consisting of SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52 and SEQ ID NO:54.

In other embodiments, the invention is directed to a substantially purified isobutanol composition produced according to the methods of the invention.

In another embodiment, the invention is directed to a substantially purified 1-butanol composition produced according to the methods of the invention.

In other embodiments, the invention is directed to a substantially purified fatty alcohol composition produced according to the methods of the invention.

In another embodiment, the invention is directed to a substantially purified fatty acid ester composition produced according to the methods of the invention.

In other embodiments, the invention is directed to a substantially purified 2,3-butanediol composition produced according to the methods of the invention.

In yet other embodiments, the invention is directed to an isobutanol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce isobutanol.

In another embodiment, the invention is directed to an isobutanol producing non-methanotroph host microorganism manufactured according to the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce isobutanol.

In yet other embodiments, the invention is directed to a 1-butanol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol.

In other embodiments, the invention is directed to a 1-butanol producing non-methanotroph host microorganism manufactured according to the steps of (a) providing a non-methanotroph host microorganism which has been genetically engineered to express a methane monooxygenase (MMO), (b) introducing into the host and expressing at least one polynucleotide open reading frame (ORF), under the control of suitable regulatory sequences, wherein the at least one polynucleotide ORF encodes a polypeptide that catalyzes a reaction in a 1-butanol pathway, and (c) feeding the host of step (b) a methane substrate under suitable growth conditions, wherein the MMO polypeptide catalyzes the substrate to product conversion of methane to methanol, an endogenous methanol dehydrogenase (MDH) polypeptide catalyzes the substrate to product conversion of methanol to formaldehyde and the formaldehyde produced is converted to pyruvate through an endogenous RuMP or serine pathway, wherein the host metabolizes pyruvate to produce 1-butanol.

In another embodiment, the invention is directed to a fatty alcohol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a fatty-acyl-CoA reductase (FAR), and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol.

In other embodiments, the invention is directed to a fatty alcohol producing non-methanotroph host microorganism manufactured according to the steps of (a) providing a non-methanotroph host microorganism which has been genetically engineered to express a methane monooxygenase (MMO), (b) introducing into the host microorganism and expressing a polynucleotide open reading frame (ORF), under the control of suitable regulatory sequences, wherein the polynucleotide ORF encodes a fatty-acyl-CoA reductase (FAR), and (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous RuMP or serine pathway and the host metabolizes acetyl-CoA to produce a fatty alcohol.

In another embodiment, the invention is directed to a fatty acid ester producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a wax ester synthase (WES) and (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty acyl-CoA and alcohols to produce a fatty acid ester.

In certain other embodiments, the invention is directed to a fatty acid ester producing non-methanotroph host microorganism manufactured according to the steps of (a) providing a non-methanotroph host microorganism which has been genetically engineered to express a methane monooxygenase (MMO), (b) introducing into the host microorganism and expressing at least one polynucleotide open reading frame (ORF), under the control of suitable regulatory sequences, wherein the at least one polynucleotide ORF encodes a wax ester synthase (WES) and (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to acetyl-CoA through an endogenous RuMP or serine pathway and the host metabolizes fatty acyl-CoA and alcohols to produce a fatty acid ester.

In certain other embodiments, the invention is directed to a 2,3-butanediol producing methanotroph host microorganism manufactured according to the steps of (a) providing a methanotrophic host microorganism that metabolizes methane ($CH_4$) to methanol ($CH_3OH$) and methanol to formaldehyde ($H_2C=O$), (b) introducing into the host and expressing a polynucleotide ORF, under the control of suitable regulatory sequences, wherein the ORF encodes a (2R,3R)-2,3-butanediol dehydrogenase (BDH1), and (c) feeding the host microorganism of step (b) a methane substrate under suitable growth conditions, wherein host metabolizes methane to formaldehyde as set forth in step (a), wherein the formaldehyde is converted to pyruvate by means of an endogenous type I RuMP pathway or a type II serine pathway and the host metabolizes pyruvate to produce (R)-acetoin and the BDH1 catalyzes the substrate to product conversion of (R)-acetoin to 2,3-butanediol.

BRIEF DESCRIPTION OF THE DRAWINGS

Certain embodiments of the invention are illustrated in the drawings, in which.

DETAILED DESCRIPTION OF THE INVENTION

Figure 1:
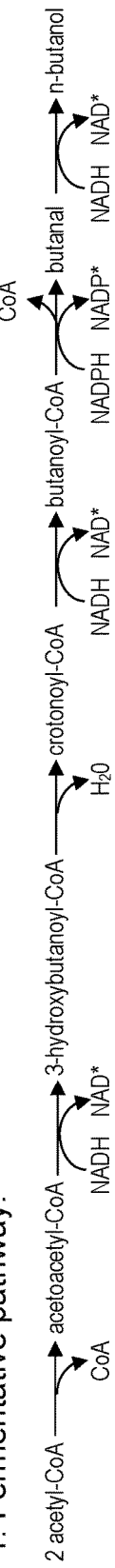
FIG. 1 depicts five pathways for the biosynthetic production of n-butanol (1-butanol) and one pathway for the biosynthetic production of isobutanol.
Figure 1:
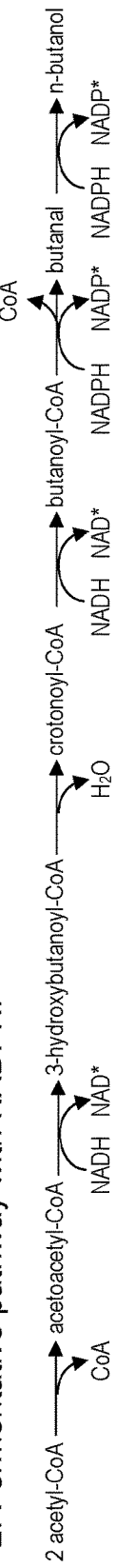
Figure 1:
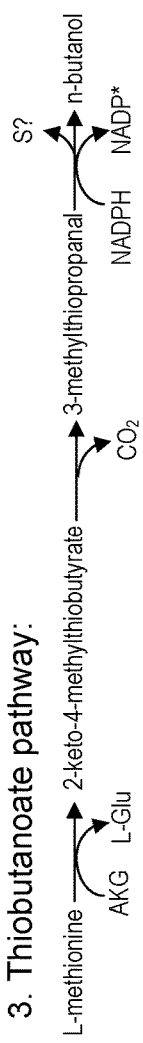
Figure 1:
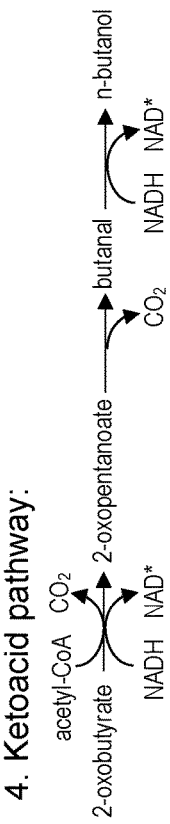
Figure 1:
Figure 1:
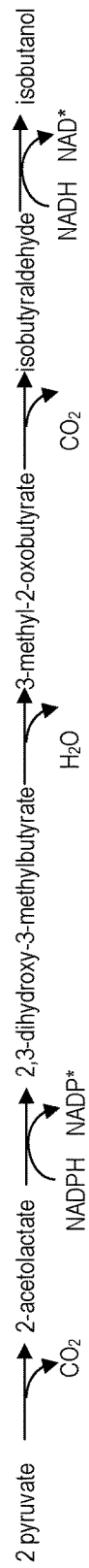

Unless defined otherwise, all technical and scientific terms used herein have the same meaning as commonly understood to one of ordinary skill in the art to which this disclosure pertains. Although methods and materials similar or equivalent to those described herein can be used in the practice of the disclosed methods and compositions, the exemplary methods, devices and materials are described herein.

In certain embodiments, the present invention is directed to host microorganisms metabolically engineered to produce multi-carbon compounds. Multi-carbon compounds such as ethanol, n-butanol, sec-butanol, isobutanol, tert-butanol, fatty (or aliphatic long chain) alcohols, fatty acid methyl esters, 2,3-butanediol and the like, are important industrial commodity chemicals with a variety of applications, including, but not limited to their use in fuels (e.g., bio-fuel, bio-diesel) and bio-based chemicals. The present invention addresses a number of commercial, industrial and environmental needs in the art related to the production of multi-carbon compounds.

As set forth herein, the metabolically engineered host microorganisms of the present invention utilize methane ($CH_4$) as their sole carbon source (i.e., the host microorganism does not require plant based feedstocks for growth and energy) and ameliorate much of the ongoing depletion of arable food source "farmland" currently being diverted to grow bio-fuel feedstocks, and as such, improve the environmental footprint of future bio-fuel, bio-diesel and bio-based chemical compositions. Furthermore, use of the metabolically engineered host microorganisms set forth in the present invention (which utilize methane as the sole carbon source) mitigate current industry practices and methods of producing multi-carbon compounds from petroleum or petroleum-derived feedstocks.

Thus, in certain embodiments of the invention, a host microorganism is genetically engineered to produce multi-carbon compounds. As is known in the art, methanotrophic organisms are able to metabolize methane as their primary source of carbon and energy, can grow aerobically or anaerobically, and require single-carbon compounds (e.g., methane, $CH_4$; methanol, $CH_3OH$ and/or formaldehyde, $H_2C=O$) to survive. In particular embodiments, a host microorganism of the invention is a methanotroph. As defined herein, a "methanotroph", a "methanotrophic" or a "methanophile" host microorganism of the invention is a "prokaryotic microorganism which can metabolize methane as its primary source of carbon and energy".

In other embodiments, the host microorganism of the invention is a non-methanotrophic microorganism genetically engineered to metabolize methane as its only source of carbon and energy. As defined herein, a "non-methanotroph" host microorganism of the invention is a host microorganism which "cannot metabolize (or utilize) methane as its sole carbon source", until the "non-methanotroph" host microorganism has been genetically modified or engineered according to the methods of the present invention. As further defined herein, a "non-methanotroph" host microorganism of the invention includes any prokaryotic and eukaryotic microbial species which comprise a complete or partial "endogenous ribulose monophosphate (RuMP) pathway, a serine pathway or a mixed RuMP/serine pathway" (e.g., see RuMP, serine and mixed (Type X) pathways described below). In certain embodiments, a "non-methanotroph" host microorganism of the invention includes prokaryotic and eukaryotic microbial species from the Domains Archaea, Bacteria and Eucarya, wherein the Domain Eucarya includes yeast, filamentous fungi, protozoa, algae or higher Protista. The terms "microbial" and "microbes" are used interchangeably with the term "microorganism".

As defined herein, the phrase "providing a methanotrophic host microorganism that metabolizes methane to methanol and metabolizes methanol to formaldehyde" refers to an "endogenous enzymatic activity encoded by one or more endogenous genes of the methanotroph host microorganism". For example, an endogenous enzyme (or polypeptide) encoded by one or more endogenous genes of a methanotroph host microorganism include a methane monooxygenase (MMO) enzyme (which metabolizes (or converts) methane to methanol) and a methanol dehydrogenase (MDH) enzyme (which metabolizes (or converts) methanol to formaldehyde). Stated another way, the phrase "providing a methanotrophic host microorganism that metabolizes methane to methanol and metabolizes methanol to formaldehyde" does not require the introduction of exogenous (or heterologous) genes encoding single-carbon (C1) oxidizing enzymes (or polypeptides), as such enzymes and the activity thereof are inherent (endogenous) attributes of a methanotrophic host microorganism of the invention.

Furthermore, as is known in the art, a "methanotrophic host microorganism" of the invention comprises endogenous genes encoding at least a Type I methanotroph RuMP pathway and/or a Type II methanotroph serine pathway. In general, Type I methanotrophs (e.g., Methylomonas, Methylomicrobium, Methylobacter, Methylocaldum, Methylosphaera) assimilate formaldehyde produced (i.e., from the oxidation of methane to methanol and methanol to formaldehyde), using the ribulose monophosphate pathway (RuMP), whereas Type II methanotrophs (e.g., Methylocystis and Methylosinus) assimilate formaldehyde produced (i.e., from the oxidation of methane to methanol and methanol to formaldehyde), using the serine pathway. Lastly, the genus Methylococcus are known to comprise a combination of characteristics of both Type I methanotroph (RuMP) pathway and Type II methanotroph (serine) pathway.

The ribulose monophosphate pathway (RuMP) was originally identified in methanotrophic bacteria, as described above. However, more recent genome sequence analysis of various microorganisms have revealed that the key enzymes of the RuMP pathway (e.g., 3-hexulose-6-phosphate (HPS), 6-phsopho-3-hexuloisomerase (PHI)) are widely distributed (i.e., endogenous) among "non-methanotrophic" bacteria and archaeal genomes (Orita et al., 2006).

As defined herein, the phrases "recombinant host microorganism", "genetically engineered host microorganism", "engineered host microorganism" and "genetically modified host microorganism" may be used interchangeably and refer to host microorganisms that have been genetically modified to (a) express one or more exogenous polynucleotides, (b) over-express one or more endogenous and/or one or more exogenous polynucleotides, such as those included in a vector, or which have an alteration in expression of an endogenous gene or (c) knock-out or down-regulate an endogenous gene. In addition, certain genes may be physically removed from the genome (e.g., knock-outs) or they may be engineered to have reduced, altered or enhanced activity.

The terms "engineer", "genetically engineer" or "genetically modify" refer to any manipulation of a microorganism that results in a detectable change in the microorganism, wherein the manipulation includes, but is not limited to, introducing non-native metabolic functionality via heterologous (exogenous) polynucleotides or removing native-functionality via polynucleotide deletions, mutations or knock-outs. The term "metabolically engineered" generally involves rational pathway design and assembly of biosynthetic genes (or ORFs), genes associated with operons, and control elements of such polynucleotides, for the production of a desired metabolite. "Metabolically engineered" may further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

As defined herein, the term "introducing", as used in phrases such as "introducing into the methanotroph host" or "introducing into the non-methanotroph host" at least one polynucleotide open reading frame (ORF) or a gene thereof or a vector thereof includes methods known in the art for introducing polynucleotides into a cell, including, but not limited to transformation (e.g., calcium chloride, electroporation), transduction, transfection, conjugation and the like.

The phrases "metabolically engineered microorganism" and "modified microorganism" are used interchangeably herein, and refer not only to the particular subject host cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The term "mutation" as used herein indicates any modification of a nucleic acid and/or polypeptide which results in an altered nucleic acid or polypeptide (i.e., relative to the wild-type nucleic acid or polypeptide sequence). Mutations include, for example, point mutations, substitutions, deletions, or insertions of single or multiple residues in a polynucleotide (or the encoded polypeptide), which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In certain embodiments, a portion of a genetically modified microorganism's genome may be replaced with one or more heterologous (exogenous) polynucleotides. In some embodiments, the mutations are naturally-occurring. In other embodiments, the mutations are the results of artificial selection pressure. In still other embodiments, the mutations in the microorganism genome are the result of genetic engineering.

The term "expression" or "expressed" with respect to a gene sequence, an ORF sequence or polynucleotide sequence, refers to transcription of the gene, ORF or polynucleotide and, as appropriate, translation of the resulting mRNA transcript to a protein. Thus, as will be clear from the context, expression of a protein results from transcription and translation of the open reading frame sequence. The level of expression of a desired product in a host microorganism may be determined on the basis of either the amount of corresponding mRNA that is present in the host, or the amount of the desired product encoded by the selected sequence. For example, mRNA transcribed from a selected sequence can be quantitated by PCR or by northern hybridization (see Sambrook et al., Molecular Cloning: A Laboratory Manual, Cold Spring Harbor Laboratory Press, 1989). Protein encoded by a selected sequence can be quantitated by various methods (e.g., by ELISA, by assaying for the biological activity of the protein, or by employing assays that are independent of such activity, such as western blotting or radioimmunoassay, using antibodies that are recognize and bind reacting the protein).

The term "endogenous", as used herein with reference to polynucleotides (and the polypeptides encoded therein), indicates polynucleotides and polypeptides that are expressed in the organism in which they originated (i.e., they are innate to the organism). In contrast, the terms "heterologous" and "exogenous" are used interchangeably, and as defined herein with reference to polynucleotides (and the polypeptides encoded therein), indicates polynucleotides and polypeptides that are expressed in an organism other than the organism from which they (i.e., the polynucleotide or polypeptide sequences) originated or where derived.

The term "feedstock" is defined as a raw material or mixture of raw materials supplied to a microorganism, or fermentation process, from which other products can be made. For example, as set forth in the present invention, a methane carbon source or a methanol carbon source or a formaldehyde carbon source, either alone or in combination, are feedstocks for a microorganism that produces a bio-fuel or bio-based chemical in a fermentation process. However, in addition to a feedstock (e.g., a methane substrate) of the invention, the fermentation media contains suitable minerals, salts, cofactors, buffers and other components, known to those skilled in the art, suitable for the growth of the cultures and promotion of the enzymatic pathways necessary for multi-carbon compound production.

The term "substrate" refers to any substance or compound that is converted, or meant to be converted, into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material (e.g., methane), but also intermediate and end product metabolites used in a pathway associated with a metabolically engineered microorganism as described herein.

The term "fermentation" or "fermentation process" is defined as a process in which a host microorganism is cultivated in a culture medium containing raw materials, such as feedstock and nutrients, wherein the microorganism converts raw materials, such as a feedstock, into products.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, including DNA, RNA, ORFs, analogs and fragments thereof.

As defined herein, the term "open reading frame" (hereinafter, "ORF") means a nucleic acid or nucleic acid sequence (whether naturally occurring, non-naturally occurring, or synthetic) comprising an uninterrupted reading frame consisting of (i) an initiation codon, (ii) a series of two (2) or more codons representing amino acids, and (iii) a termination codon, the ORF being read (or translated) in the 5' to 3' direction.

It is understood that the polynucleotides described herein include "genes" and that the nucleic acid molecules described herein include "vectors" or "plasmids". Accordingly, the term "gene", refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "promoter" refers to a nucleic acid sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "codon-optimized" as it refers to genes or coding regions of nucleic acid molecules (or ORFs) for transformation of various hosts, refers to the alteration of codons in the gene or coding regions of the nucleic acid molecules to reflect the typical codon usage of the host organism without altering the polypeptide encoded by the DNA.

The term "operon" refers to two or more genes which are transcribed as a single transcriptional unit from a common promoter. In certain embodiments, the genes, polynucleotides or ORFs comprising the operon are contiguous genes. It is understood that transcription of an entire operon can be modified (i.e., increased, decreased, or eliminated) by modifying the common promoter. Alternatively, any gene, polynucleotide or ORF, or any combination thereof in an operon can be modified to alter the function or activity of the encoded polypeptide. The modification can result in an increase or a decrease in the activity or function of the encoded polypeptide. Further, the modification can impart new activities on the encoded polypeptide.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes", that is, that replicate autonomously or can integrate into a chromosome of a host microorganism. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

The term "homolog", as used with respect to an original enzyme, polypeptide, gene or polynucleotide (or ORF encoding the same) of a first family or species, refers to distinct enzymes, genes or polynucleotides of a second family or species, which are determined by functional, structural or genomic analyses to be an enzyme, gene or polynucleotide of the second family or species, which corresponds to the original enzyme or gene of the first family or species. Most often, "homologs" will have functional, structural or genomic similarities. Techniques are known by which homologs of an enzyme, gene or polynucleotide can readily be cloned using genetic probes and PCR. Identity of cloned sequences as "homologs" can be confirmed using functional assays and/or by genomic mapping of the genes.

A polypeptide (or protein or enzyme) has "homology" or is "homologous" to a second polypeptide if the nucleic acid sequence that encodes the polypeptide has a similar sequence to the nucleic acid sequence that encodes the second polypeptide. Alternatively, a polypeptide has homology to a second polypeptide if the two proteins have "similar" amino acid sequences. Thus, the terms "homologous proteins" or "homologous polypeptides" is defined to mean that the two polypeptides have similar amino acid sequences. In certain embodiments of the invention, polynucleotides and polypeptides homologous to one or more polynucleotides and/or polypeptides set forth in Table 1 may be readily identified using methods known in the art for sequence analysis and comparison.

A homologous polynucleotide or polypeptide sequence of the invention may also be determined or identified by BLAST analysis (Basic Local Alignment Search Tool) or similar bioinformatic tools, which compare a query nucleotide or polypeptide sequence to a database of known sequences. For example, a search analysis may be done using BLAST to determine sequence identity or similarity to previously published sequences, and if the sequence has not yet been published, can give relevant insight into the function of the DNA or protein sequence.

Bioconversion of Methane to Multi-Carbon Compounds

In general, the conversion of methane ($CH_4$) to multi-carbon compounds such as isobutanol (($CH_3$)$_2$CHCH$_2$OH), 1-butanol or n-butanol ($CH_3CH_2CH_2CH_2OH$), ethanol ($CH_3CH_2OH$), fatty alcohols, fatty acid esters, 2,3-butanediol and the like, using a "methanotrophic host microorganism", requires at least the following three steps, all of which are innate (or endogenous) with respect to methanotrophic organisms: (1) a methane ($CH_4$) substrate is oxidized to methanol ($CH_3OH$) via a methane monooxygenase (MMO) (e.g., particulate methane monooxygenase (pMMO) or soluble methane monooxygenase (sMMO)), (2) the methanol ($CH_3OH$) is oxidized to formaldehyde ($H_2C=O$) via methanol dehydrogenase (MDH) and (3) the formaldehyde ($H_2C=O$) produced in step (2) above is assimilated into a central metabolism pathway (e.g., see type I (RuMP) and type II (serine) pathways described below).

In certain embodiments of the invention, a host microorganism is a methanotroph, which endogenously expresses a methane monooxygenase (MMO) enzyme and a methanol dehydrogenase (MDH) enzyme. In other embodiments of the invention, a host microorganism of the invention is a "non-methanotrophic" prokaryotic microorganism (e.g., a non-methanotrophic bacteria or archaea) or a eukaryotic microorganism (e.g., fungi and algae) engineered to utilize a methane substrate (as sole carbon source) for growth and energy. Thus, in certain embodiments of the invention, a "non-methanotrophic" microorganism is engineered to express (or over-express) an exogenous methane monooxygenase (MMO), an enzyme requisite to metabolize methane to methanol. The non-methanotroph host microorganisms of the invention comprise an endogenous methanol dehydrogenase (MDH) enzyme, which converts methanol to formaldehyde. However, in certain embodiments, the "non-methanotroph" microorganism is further engineered to express an exogenous methanol dehydrogenase (MDH) enzyme, which converts methanol to formaldehyde. The expression of the exogenous MDH enzyme in a non-methanotroph host is not a strict requirement for the utilization of the methane substrate, but it is contemplated in certain embodiments, that the introduction and expression of an exogenous MDH in a non-methanotroph host thereof may facilitate, under certain growth conditions, the production of one or more multi-carbon compounds of the invention.

As mentioned briefly above with regard to methanotrophic host organisms, there are at least two known pathways (i.e., the ribulose monophosphate (RuMP) pathway and the serine pathway; Hanson & Hanson, 1996) for the assimilation of formaldehyde into central metabolism. In the Type I methanotroph RuMP pathway, formaldehyde combines with ribulose-5-phosphate to form hexulose-6-phosphate (catalyzed via hexulose-6-phosphate synthase), the hexulose-6-phosphate is then isomerized to fructose-6-phosphate (catalyzed via hexulose phosphate isomerase), which is an intermediate of a central metabolic pathway (i.e., glycolysis pathway). In the type II methanotroph serine pathway, formaldehyde reacts with tetrahydrofolate (THF) to form methylene-THF, the methylene-THF is then transferred to L-glycine to form L-serine, and finally the L-serine is transferred to glyoxylate to form hydroxypyruvate. The hydroxypyruvate formed is subsequently converted to 2-phosphoglycerate (catalyzed via hydroxypruvate reductase), which is an central metabolism intermediate of the glycolytic pathway.

Likewise, as mentioned briefly above, an endogenous pathway, which functions similarly (or analogous) to the ribulose monophosphate (RuMP) pathway in methanotrophs is also present in "non-methanotrophic" prokaryotes (Orita et al., 2006), wherein formaldehyde is fixed with ribulose 5-phosphate to form hexulose-6-phosphate (catalyzed via hexulose-6-phosphate synthase (HPS)) and then isomerized to fructose-6-phosphate (catalyzed via hexulose phosphate isomerase (PHI)), which is an intermediate of a central metabolic pathway. Thus, in certain preferred embodiments, a "non-methanotrophic" host microorganism of the invention comprises an endogenous RuMP pathway or an endogenous pathway analogous to the RuMP pathway. As defined herein, a pathway analogous to the RuMP pathway comprises at least a gene, polynucleotide or ORF encoding an enzyme having hexulose-6-phosphate synthase (HPS) activity from enzyme class EC 4.1.2.43 and at least a gene, polynucleotide or ORF encoding a an enzyme having hexulose phosphate isomerase (PHI) activity from enzyme class 5.3.1.27.

In other embodiments, wherein a "non-methanotrophic" host microorganism genome does not encode endogenous enzymes having HPS and PHI activity, the non-methanotroph host microorganism is genetically modified to express HPS and PHI enzymes. Thus, in certain embodiments, a gene, polynucleotide or ORF encoding a hexulose-6-phosphate synthase (HPS) is provided, wherein the gene, polynucleotide or ORF encodes a HPS polypeptide of enzyme class EC 4.1.2.43. In other embodiments, a gene, polynucleotide or ORF encoding a hexulose-6-phosphate synthase (HPS) is provided, wherein the gene, polynucleotide or ORF encodes a HPS polypeptide having at least 90% sequence homology to a *M. capsulatus* (Bath) HPS polypeptide of SEQ ID NO:173. In other embodiments, a gene, polynucleotide or ORF encoding a hexulose phosphate isomerase (PHI) is provided, wherein the gene, polynucleotide or ORF encodes a PHI polypeptide of enzyme class EC 5.3.1.27. In other embodiments, a gene, polynucleotide or ORF encoding a hexulose phosphate isomerase (PHI) is provided, wherein the gene, polynucleotide or ORF encodes a *M. capsulatus* (Bath) PHI polypeptide having at least 90% sequence homology to a PHI (also referred to as a sugar isomerase (SIS) domain) polypeptide of SEQ ID NO:175.

Once the formaldehyde has been assimilated into a central metabolic pathway of the methanotroph or non-methanotroph host organism (as described above), the fourth and final step for producing multi-carbon compounds from a methane substrate as described in steps (1)-(3) above, is the introduction of one or more nucleic acids into the host microorganism, wherein the one or more nucleic acids introduced encode one or more enzymes of a relevant multi-carbon compound pathway. Independent of the compound to be produced according to the present invention (e.g., isobutanol, 1-butanol, ethanol, fatty alcohols, fatty acid methyl esters, 2,3-butanediol and the like), any multi-carbon pathway introduced into a host microorganism must utilize a central metabolic molecule (e.g., pyruvate, acetyl-CoA, methionine and oxobutyrate) previously assimilated and introduced into the metabolic pathway through steps (1)-(3) described above. Stated another way, a salient feature of the present invention is the ability of the host microorganism to utilize methane (as a sole carbon source for growth and energy) and to produce multi-carbon compounds (via engineered metabolic pathways introduced therein), without the need for additional or supplemental carbon sources such as carbohydrates.

As defined herein, a relevant "multi-carbon compound pathway", includes, but is not limited to, a 1-butanol pathway (which includes, but is not limited to, a fermentative 1-butanol pathway, a thiobutanoate pathway, a ketoacid pathway and a methylmalate pathway), an isobutanol pathway, a fatty alcohol pathway, a fatty acid methyl ester pathway and a 2,3-butanediol pathway. A "multi-carbon compound pathway" as further defined herein, may include one specific enzyme from the pathway, multiple enzymes from the pathway or all of the enzymes of the pathway. It will be understood by a person of skill in the art, that the selection of one or more specific pathway enzymes (and nucleic acids encoding the same) may be dependent on the host microorganism (e.g., certain methanotroph hosts or "non-methanotroph" hosts may endogenously encode and express one or more enzymes of a given pathway).

For example, FIG. 1 depicts five representative 1-butanol (i.e., n-butanol) pathways (pathways 1-5), wherein one or more nucleic acids encoding one or more enzymes of any of these pathways may be introduced into a methanotroph (or non-methanotroph) host microorganism and be expressed (or over-expressed) therein to yield 1-butanol. Similarly, FIG. 1 depicts an isobutanol pathway (pathway 6), wherein one or more nucleic acids encoding one or more enzymes of the isobutanol pathway may be introduced into a methanotroph (or non-methanotroph) host microorganism and expressed (or over expressed) therein to yield isobutanol. Further contemplated herein, is the introduction into a methanotroph (or non-methanotroph) host microorganism a combination of nucleic acids encoding one or more enzymes from a 1-butanol pathway and one or more enzymes from an isobutanol pathway.

As depicted in FIG. 1, at least five pathways are known to exist for converting one or more of these metabolic precursors into n-butanol (i.e., 1-butanol). The first synthesis pathway is the classical fermentative n-butanol pathway. Beginning with acetyl-CoA, this six step pathway requires three NADH and one NADHPH, but loses no carbon atoms to by-products formed. The second n-butanol synthesis pathway is the fermentative pathway, but using NADPH instead of NADH as the electron donor for the final conversion of butanal to n-butanol. The third potential n-butanol pathway is the thiobutanoate pathway, which begins with L-methionine, which is subsequently deaminated and then converted to n-butanol in two additional steps that involve loss of carbon dioxide ($CO_2$) and a sulfur (S) atom by an unknown mechanism. The fourth n-butanol pathway is the ketoacid pathway, which starting from L-threonine, n-butanol is synthesized in four steps, involving both reduction of $NAD^+$ and oxidation of NADH, while losing two $CO_2$. The fifth n-butanol synthesis pathway is the methylmalate pathway, which begins by combining pyruvate with acetyl-CoA to form citramalate (methylmalate), a reaction known to be catalyzed by LeuA in many bacteria, followed by conversion to butanoyl-CoA, which is then converted to n-butanol using the final two reactions of the fermentative pathway. Likewise, as depicted in FIG. 1, at least one isobutanol pathway is known in the art for synthesizing isobutanol from pyruvate, wherein the five-step pathway loses two carbon atoms as $CO_2$ per molecule of isobutanol synthesized.

Thus, in certain embodiments, the present invention is directed to a method for producing isobutanol from a methane substrate comprising the steps of (a) providing a methanotrophic host microorganism that metabolizes methane ($CH_4$) to methanol ($CH_3OH$) and methanol to formaldehyde ($H_2C=O$); (b) introducing into the methanotroph host and expressing at least one polynucleotide open reading frame (ORF), under the control of suitable regulatory sequences, wherein the at least one polynucleotide ORF encodes a polypeptide that catalyzes a reaction in an isobutanol pathway; (c) feeding the methanotroph host of step (b) a methane substrate under suitable growth conditions, wherein the host metabolizes methane to formaldehyde as set forth in step (a), wherein the formaldehyde is converted to pyruvate by means of an endogenous RuMP pathway or a serine pathway and the host metabolizes pyruvate to produce isobutanol, and (d) optionally recovering the isobutanol produced.

In one particular embodiment, the one or more polynucleotide ORFs introduced in step (b) encode an isobutanol pathway polypeptide thereof selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In certain embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol. In other embodiments, the ALS polypeptide comprises an amino acid sequence comprising at least 90% sequence homology to SEQ ID NO:2, the KARI polypeptide comprises an amino acid sequence comprising at least 90% sequence homology to SEQ ID NO:4, the DHAD polypeptide comprises an amino acid sequence comprising at least 90% sequence homology to SEQ ID NO:6, the KDC polypeptide comprises an amino acid sequence comprising at least 90% sequence homology to SEQ ID NO:8 and the ADH polypeptide comprises an amino acid sequence comprising at least 90% sequence homology to SEQ ID NO:10. In yet other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In certain embodiments, the ORFs encoding the complete isobutanol pathway are comprised in one operon, two operons or three operons, wherein each operon may comprise the same promoter or a different promoter, wherein the same or different promoters may be constitutive or inducible.

In certain embodiments, a methanotroph host microorganism is modified or genetically engineered to express one or more enzymes of a metabolic pathway capable of producing n-butanol, isobutanol, fatty (or aliphatic long chain) alcohols, fatty acid methyl esters and the like. In particular embodiments, a methanotroph of the invention is selected from genera consisting of *Methylobacter, Methylomicro-* bium, Methylomonas, Methylocaldum, Methylococcus, Methylosoma, Methylosarcina, Methylothermus, Methylohalobius, Methylogaea, Methylovulum, Crenothrix, Clonothrix, Methylosphaera, Methylocapsa, Methylocella, Methylosinus, Methylocystis and Methyloacidophilum. In other embodiments, the methanotroph is from the phylum Verrucomicrobia. Previously published work has shown that several species within these taxa can be genetically transformed by introducing DNA constructs on plasmid vectors (Stafford et al., 2003), or by integrating them into the bacterial chromosome (Welander & Summons, 2012). Thus, a vector construct of the invention will typically comprise the pathway genes or polynucleotide ORFs, which are initially constructed and cloned into E. coli to generate sufficient quantities of the vector, and then the vectors are subsequently transformed into the host microorganism for expression.

In other embodiments, the invention is directed to a method for producing isobutanol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host and expressing at least one polynucleotide open reading frame (ORF), under the control of suitable regulatory sequences, wherein the at least one polynucleotide ORF encodes a polypeptide that catalyzes a reaction in an isobutanol pathway; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to pyruvate through an endogenous RuMP or serine pathway and the host metabolizes pyruvate to produce isobutanol, and (d) optionally recovering the isobutanol produced. Methods for heterologous expression of pMMO genes have been described in Gou et al. (2006). Methods for heterologous expression of sMMO genes have been described in Lloyd et al. (1999). Suitable microbial hosts for heterologous expression include microorganisms that have the ability to process methanol and formaldehyde, that have multiple heterotrophic growth modes, and/or that can assemble complex membranes and metalloprotein complexes. Such organisms include methylotrophic yeasts (e.g., Pichia pastoris) as well as bacteria such as Pseudomonas putida, Cupriavidus metallidurans and Rhodobacter sphaeroides.

In certain embodiments, the one or more polynucleotide ORFs introduced in step (b) above, encode an isobutanol pathway polypeptide selected from an Enzyme Class (EC) comprising EC 2.2.1.6, EC 1.1.1.86, EC 4.2.1.9, EC 4.1.1.72 and EC 1.1.1.1. In other embodiments, the one or more polynucleotide ORFs introduced in step (b) encode an isobutanol pathway polypeptide selected from the group consisting of acetolactate synthase (ALS), ketol-acid reductoisomerase (KARI), dihydroxy-acid dehydratase (DHAD), ketoacid decarboxylase (KDC) and alcohol dehydrogenase (ADH). In yet other embodiments, the ALS polypeptide catalyzes the substrate to product conversion of pyruvate to acetolactate; the KARI polypeptide catalyzes the substrate to product conversion of acetolactate to 2,3-dihydroxyisovalerate; the DHAD polypeptide catalyzes the substrate to product conversion of 2,3-dihydroxyisovalerate to ketoisovalerate; the KDC polypeptide catalyzes the substrate to product conversion of ketoisovalerate to isobutryaldehyde and ADH polypeptide catalyzes the substrate to product conversion of isobutyraldehyde to isobutanol.

In one particular embodiment, the ALS polypeptide comprises an amino acid sequence comprising at least 90% sequence homology to SEQ ID NO:2, the KARI polypeptide comprises an amino acid sequence comprising at least 90% sequence homology to SEQ ID NO:4, the DHAD polypeptide comprises an amino acid sequence comprising at least 90% sequence homology to SEQ ID NO:6, the KDC polypeptide comprises an amino acid sequence comprising at least 90% sequence homology to SEQ ID NO:8 and the ADH polypeptide comprises an amino acid sequence comprising at least 90% sequence homology to SEQ ID NO:10. In certain other embodiments, the one or more polynucleotide ORFs introduced in step (b) encode the complete isobutanol pathway comprising an ALS polypeptide, a KARI polypeptide, a DHAD polypeptide, a KDC polypeptide and an ADH polypeptide. In another embodiment, the methane monooxygenase (MMO) is a soluble MMO of Enzyme Class EC 1.14.13.25 or a particulate MMO of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO:34).

In certain embodiments where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxal (SEQ ID NO:42), mxaR (SEQ ID NO:44), mxaA (SEQ ID NO:46), mxaC (SEQ ID NO:48), mxaK (SEQ ID NO:50), mxaL (SEQ ID NO:52) or mcaD (SEQ ID NO:54).

In other embodiments, the invention is directed to a method for producing 1-butanol from a methane substrate comprising the steps of (a) providing a methanotrophic host microorganism that metabolizes methane ($CH_4$) to methanol ($CH_3OH$) and methanol to formaldehyde ($H_2C\!=\!O$), (b) introducing into the methanotroph host and expressing at least one polynucleotide open reading frame (ORF), under the control of suitable regulatory sequences, wherein the at least one polynucleotide ORF encodes a polypeptide that catalyzes a reaction in a 1-butanol pathway; (c) feeding the methanotroph host of step (b) a methane substrate under suitable growth conditions, wherein the host metabolizes methane to formaldehyde as set forth in step (a), wherein the formaldehyde is converted to pyruvate by means of an endogenous type I RuMP pathway or a type II serine pathway and the host metabolizes pyruvate to produce 1-butanol, and (d) optionally recovering the 1-butanol produced. In certain embodiments, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-butanol pathway polypeptide selected from the group consisting of L-threonine ammonia-lyase, 2-ethylmalate synthase (or 2-isopropylmalate synthase), isopropylmalate isomerase (or 3-isopropylmalate dehydratase), 3-isopropylmalate dehydrogenase, 2-ketoacid decarboxylase (KDC) and alcohol dehydrogenase (ADH). In certain other embodiments, L-threonine ammonia-lyase catalyzes the substrate to product conversion of L-threonine to 2-oxybutanoate (2-ketobutyrate) and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butyraldehyde and the ADH catalyzes the substrate to product conversion of butyraldehyde to 1-butanol.

In certain embodiments, a L-threonine ammonia-lyase comprises an amino acid sequence having at least 90% sequence homology to SEQ ID NO:56, a 2-ethylmalate synthase comprises an amino acid sequence having at least 90% sequence homology to SEQ ID NO:58, a isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In one particular embodiment, the one or more polynucleotide ORFs introduced in step (b) encode the complete 1-butanol pathway comprising an L-threonine ammonia-lyase, a 2-ethylmalate synthase, an isopropylmalate isomerase, a 3-isopropylmalate dehydrogenase, a KDC and an ADH.

In other embodiments, the invention is directed to a method for producing 1-butanol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host and expressing at least one polynucleotide open reading frame (ORF), under the control of suitable regulatory sequences, wherein the at least one polynucleotide ORF encodes a polypeptide that catalyzes a reaction in a 1-butanol pathway; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, the formaldehyde produced is converted to pyruvate through an endogenous RuMP or serine pathway and the host metabolizes pyruvate to produce 1-butanol, and (d) optionally recovering the 1-butanol produced.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoCl subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO:34).

In certain embodiments where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxaI (SEQ ID NO:42), mxaR (SEQ ID NO:44), mxaA (SEQ ID NO:46), mxaC (SEQ ID NO:48), mxaK (SEQ ID NO:50), mxaL (SEQ ID NO:52) or mcaD (SEQ ID NO:54).

In one particular embodiment, the one or more polynucleotide ORFs introduced in step (b) encode a 1-butanol pathway polypeptide selected from an Enzyme Class (EC) comprising EC 4.3.1.19, EC 2.3.3.6, EC 4.2.1.33, EC 1.1.1.85, EC 4.1.1.72, and EC 1.1.1.1. In another embodiment, the one or more polynucleotide ORFs introduced in step (b) encode a 1-butanol pathway polypeptide selected from the group consisting of L-threonine ammonia-lyase, 2-ethylmalate synthase (or 2-isopropylmalate synthase), isopropylmalate isomerase (or 3-isopropylmalate dehydratase), 3-isopropylmalate dehydrogenase, 2-ketoacid decarboxylase (KDC) and alcohol dehydrogenase (ADH). In certain other embodiments, L-threonine ammonia-lyase catalyzes the substrate to product conversion of L-threonine to 2-oxybutanoate (2-ketobutyrate) and ammonia; the 2-ethylmalate synthase catalyzes the substrate to product conversion of 2-oxybutanoate and acetyl-CoA to 2-ethylmalate; the isopropylmalate isomerase catalyzes the substrate to product conversion of 2-ethylmalate to 3-ethylmalate; the 3-isopropylmalate dehydrogenase catalyzes the substrate to product conversion of 3-ethylmalate to 2-ketovalerate, $CO_2$ and NADH; the KDC catalyzes the substrate to product conversion of 2-ketovalerate to butyraldehyde and the ADH catalyzes the substrate to product conversion of butyraldehyde to 1-butanol.

In certain embodiments, a L-threonine ammonia-lyase comprises an amino acid sequence having at least 90% sequence homology to SEQ ID NO:56, a 2-ethylmalate synthase comprises an amino acid sequence having at least 90% sequence homology to SEQ ID NO:58, a isopropylmalate isomerase comprises an amino acid sequence having at least 90% sequence homology to SEQ ID NO:60 and SEQ ID NO:62, a 3-isopropylmalate dehydrogenase comprises an amino acid sequence having at least 90% sequence homology to SEQ ID NO:64, the KDC comprises an amino acid sequence having at least 90% sequence homology to SEQ ID NO:8 and the ADH comprises an amino acid sequence having at least 90% sequence homology to SEQ ID NO:10. In one particular embodiment, the one or more polynucleotide ORFs introduced in step (b) encode the complete 1-butanol pathway comprising an L-threonine ammonia-lyase, a 2-ethylmalate synthase, an isopropylmalate isomerase, a 3-isopropylmalate dehydrogenase, a KDC and an ADH.

In certain other embodiments, the invention is directed to a method for producing fatty alcohols from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a fatty-acyl-CoA reductase (FAR); (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol, and (d) recovering the fatty alcohol produced. In certain embodiments, the FAR polypeptide is further defined as a polypeptide from Enzyme Class EC 1.2.1.50. In yet other embodiments, the FAR polypeptide catalyzes the substrate to product conversion of fatty acetyl-CoA to a fatty alcohol. In another embodiment, a FAR polypeptide comprises an amino acid sequence having at least 90% sequence homology to SEQ ID NO:66.

In still other embodiments, the invention is directed to a method for producing a fatty alcohol from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host microorganism and expressing a polynucleotide open reading frame (ORF), under the control of suitable regulatory sequences, wherein the polynucleotide ORF encodes a fatty-acyl-CoA reductase (FAR), (c) feeding the host microorganism of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes acetyl-CoA to produce a fatty alcohol, and (d) optionally recovering the fatty alcohol produced.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoC1 subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO:34).

In certain embodiments, where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxaI (SEQ ID NO:42), mxaR (SEQ ID NO:44), mxaA (SEQ ID NO:46), mxaC (SEQ ID NO:48), mxaK (SEQ ID NO:50), mxaL (SEQ ID NO:52) or mcaD (SEQ ID NO:54).

In another embodiment, the invention is directed to a method for producing a fatty acid ester from a methane substrate comprising the steps of (a) providing a methanotrophic host microorganism that metabolizes methane ($CH_4$) to methanol ($CH_3OH$) and methanol to formaldehyde ($H_2C=O$), (b) introducing into the methanotroph host and expressing a polynucleotide open reading frame (ORF), under the control of suitable regulatory sequences, wherein the polynucleotide ORF encodes a wax ester synthase (WES); (c) feeding the methanotroph host of step (b) a methane substrate under suitable growth conditions, wherein the host metabolizes methane to formaldehyde as set forth in step (a), wherein the formaldehyde is converted to acetyl-CoA by means of an endogenous type I RuMP pathway or a type II serine pathway and the host metabolizes fatty-acyl-CoA and alcohols to produce a fatty acid ester, and (d) recovering the fatty acid ester produced. In one particular embodiment, the WES polypeptide is further defined as a polypeptide from Enzyme Class EC 2.3.1.75. In another embodiment, the WES polypeptide catalyzes the substrate to product conversion of a fatty acid to a fatty acid esters. In another embodiment, the WES polypeptide catalyzes the substrate to product conversion of fatty alcohol and acyl-CoA to fatty acid esters. In one particular embodiment, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78.

In another embodiment, the invention is directed to a method for producing a fatty acid ester from a methane substrate comprising the steps of (a) providing a "non-methanotroph" host microorganism which has been genetically engineered to express a methane monooxygenase (MMO) (and optionally a methanol dehydrogenase (MDH)) and wherein the non-methanotroph host comprises either an endogenous RuMP pathway or an endogenous serine pathway, (b) introducing into the host microorganism and expressing at least one polynucleotide open reading frame (ORF), under the control of suitable regulatory sequences, wherein the at least one polynucleotide ORF encodes a wax ester synthase; (c) feeding the host of step (b) a methane substrate under suitable growth conditions, wherein the MMO polypeptide catalyzes the substrate to product conversion of methane to methanol, an endogenous MDH polypeptide catalyzes the substrate to product conversion of methanol to formaldehyde, wherein the formaldehyde is converted to acetyl-CoA by means of an endogenous RuMP or serine pathway and the host metabolizes fatty-acyl-CoA and alcohols to produce a fatty acid ester, and (d) recovering the fatty acid ester produced.

In one particular embodiment, the WES polypeptide is further defined as a polypeptide from Enzyme Class EC 2.3.1.75. In another embodiment, the WES polypeptide catalyzes the substrate to product conversion of a fatty acid to a fatty acid ester. In another embodiment, the WES polypeptide catalyzes the substrate to product conversion of fatty alcohol and acyl-CoA to fatty acid esters. In one particular embodiment, the WES polypeptide comprises an amino acid sequence having at least 90% sequence homology to a WES polypeptide selected from SEQ ID NO:68, SEQ ID NO: 70, SEQ ID NO: 72, SEQ ID NO:74, SEQ ID NO: 76 and SEQ ID NO: 78.

In certain embodiments, the non-methanotroph host microorganism is genetically modified to express an exogenous methane monooxygenase (MMO). In one embodiment, the methane monooxygenase is a soluble MMO (sMMO) of Enzyme Class EC 1.14.13.25 or a particulate MMO (pMMO) of Enzyme Class 1.14.18.3. In other embodiments, the MMO comprises an amino acid sequence having at least 90% sequence homology to a particulate methane monooxygenase (pMMO) of operon 1 comprising pmoCl subunit 1 (SEQ ID NO:12), pmoA subunit 1 (SEQ ID NO:14), pmoB subunit 1 (SEQ ID NO: 16) or a pMMO of operon 2 comprising pmoC subunit 2 (SEQ ID NO:18), pmoA subunit 2 (SEQ ID NO:20), pmoB subunit 2 (SEQ ID NO:22). In other embodiments, the MMO comprises an amino acid sequence having at least 90% sequence homology to a soluble methane monooxygenase (sMMO) selected from mmoX (SEQ ID NO:24), mmoY (SEQ ID NO:26), mmoB (SEQ ID NO:28), mmoZ (SEQ ID NO:30), mmoD (SEQ ID NO:32) or mmoC (SEQ ID NO:34).

In certain embodiments, where an exogenous methanol dehydrogenase (MDH) is optionally provided and expressed in a host microorganism, the MDH is a polypeptide from Enzyme Class 1.14.18.3. In certain other embodiments, the MDH comprises an amino acid sequence comprising at least 90% sequence homology to mxaF (SEQ ID NO:36), mxaJ (SEQ ID NO:38), mxaG (SEQ ID NO:40), mxaI (SEQ ID NO:42), mxaR (SEQ ID NO:44), mxaA (SEQ ID NO:46), mxaC (SEQ ID NO:48), mxaK (SEQ ID NO:50), mxaL (SEQ ID NO:52) or mcaD (SEQ ID NO:54).

Figure 9:
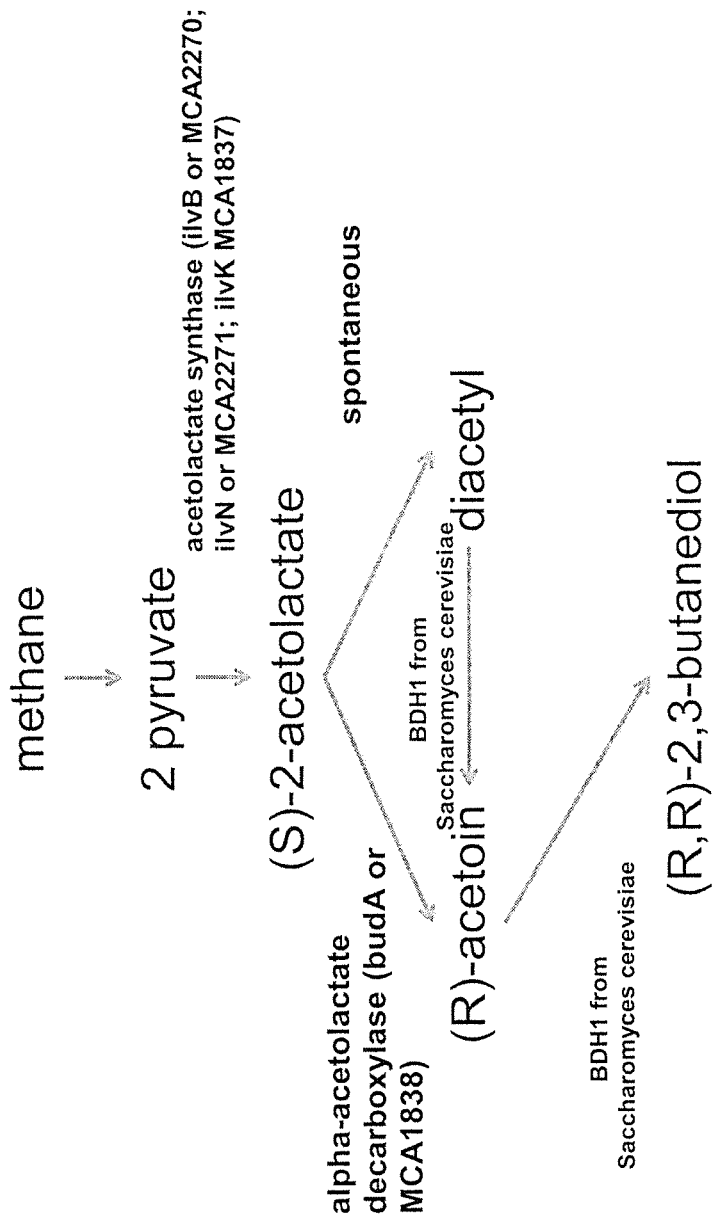
FIG. 9 shows an engineered pathway for 2,3-butanediol production from methane using a heterologously expressed BDH1 enzyme from Saccharomyces cerevisiae.

In certain other embodiments, the invention is directed to methods of producing 2,3-butanediol from a methane substrate. The compound 2,3-butanediol (a four-carbon diol) is an important intermediate for the chemical industry. At the commercial scale, 2,3-butanediol is mainly produced or generated from petroleum, where it serves as a precursor for the production of various commodity and specialty chemicals, such as the solvent methyl ethyl ketone (MEK), gamma-butyrolactone (GBL) and 1,3-butadiene. The biological production of 2,3-butanediol from methane requires engineering the native (or endogenous) metabolism of methanotrophs to take advantage of their endogenous production of (R)-acetoin (FIG. 9). The compound (R)-acetoin is produced in methanotrophs from two molecules of pyruvate, which are ultimately derived from methane. By introducing and expressing a single gene (SEQ ID NO:156) encoding a (2R,3R)-2,3-butanediol dehydrogenase (BDH1) from *Saccharomyces cerevisiae* in a suitable microbial expression host (such as *M. capsulatus* (Bath)), the (R)-acetoin is converted into 2,3-butanediol. Thus, in certain embodiments, a host microorganism of the invention is genetically modified to express an exogenous (2R,3R)-2,3-butanediol dehydrogenase (BDH1) having at least 90% sequence homology to a BDH1 polypeptide of SEQ ID NO:157.

General methods for gene synthesis and DNA cloning, as well as vector and plasmid construction, are well known in the art, and are described in a number of publications (Lipps, 2008; Peccoud, 2012; Ausubel et al., 2002). More specifically, techniques such as digestion and ligation-based cloning, as well as in vitro and in vivo recombination methods, can be used to assemble DNA fragments encoding a polypeptide that catalyzes a substrate to product conversion into a suitable vector. These methods include restriction digest cloning, sequence- and ligation-independent Cloning (SLIC) (Li & Elledge, 2012), Golden Gate cloning (Engler et al., 2009), Gibson assembly (Gibson et al., 2009), and the like (Merryman & Gibson, 2012; Wang et al., 2012). Some of these methods can be automated and miniaturized for high-throughput applications (Yehezkel et al., 2011; Ma et al., 2012).

In certain embodiments, the cloning procedures use in vitro homologous recombination, to insert DNA fragments into a vector (e.g., the In-Fusion kit from Clontech Laboratories, Inc. (Mountain View, CA)). For example, (1) the recipient vector is linearized by a restriction digest and purified; (2) PCR primers that are complementary to the fragment to be cloned and that are complementary (with 15-base pair extensions) to the ends of the linearized vector are used to amplify the insert, using high-fidelity polymerase; (3) the size of the PCR amplicon is verified by agarose gel electrophoresis; (4) the PCR product is purified by a spin-column; (5) the In-Fusion reaction is run according to the manufacturer's instructions; (6) competent *E. coli* cells are transformed with 2.5 μL of the reaction products; (7) positive transformants are selected from colonies grown on antibiotic selection medium and transferred to individual liquid cultures with the appropriate antibiotic; (8) the cells are harvested after overnight growth at 37° C. with 200 rpm shaking and (9) the plasmid DNA is extracted and analyzed for the correct insert.

The plasmid vector is chosen so that it will be capable of replicating in both an *E. coli* host (for cloning and amplification) and a methanotrophic or non-methanotrophic host microorganism (for metabolic pathway expression). The plasmid can be transferred from the *E. coli* donor cell to the recipient cell via bacterial conjugation. In addition, the vector contains a promoter sequence upstream of the one or more polynucleotide ORFs that are to be expressed. The promoter sequence can be included as part of the insert so that it can be adjusted and tested for each new construct. Broad-host-range (bhr) vectors for different gram-negative bacterial hosts have been described in the literature (Marx & Lidstrom, 2001). These vectors typically contain the following components: (1) an origin of replication that is functional in *E. coli* (colE1); (2) an oriV/IncP origin of replication for the non-*E. coli* host; (3) an oriT/IncP origin of transfer, which is needed for transferring a bacterial plasmid from a bacterial host such as *E. coli* to the recipient during bacterial conjugation; (4) a traJ' gene, which codes for a transcriptional activator that initiates production of the proteins needed for conjugative transfer; and (5) a trfA, the replication initiation protein gene of plasmid RK2 which binds to a activates oriV.

Figure 2:
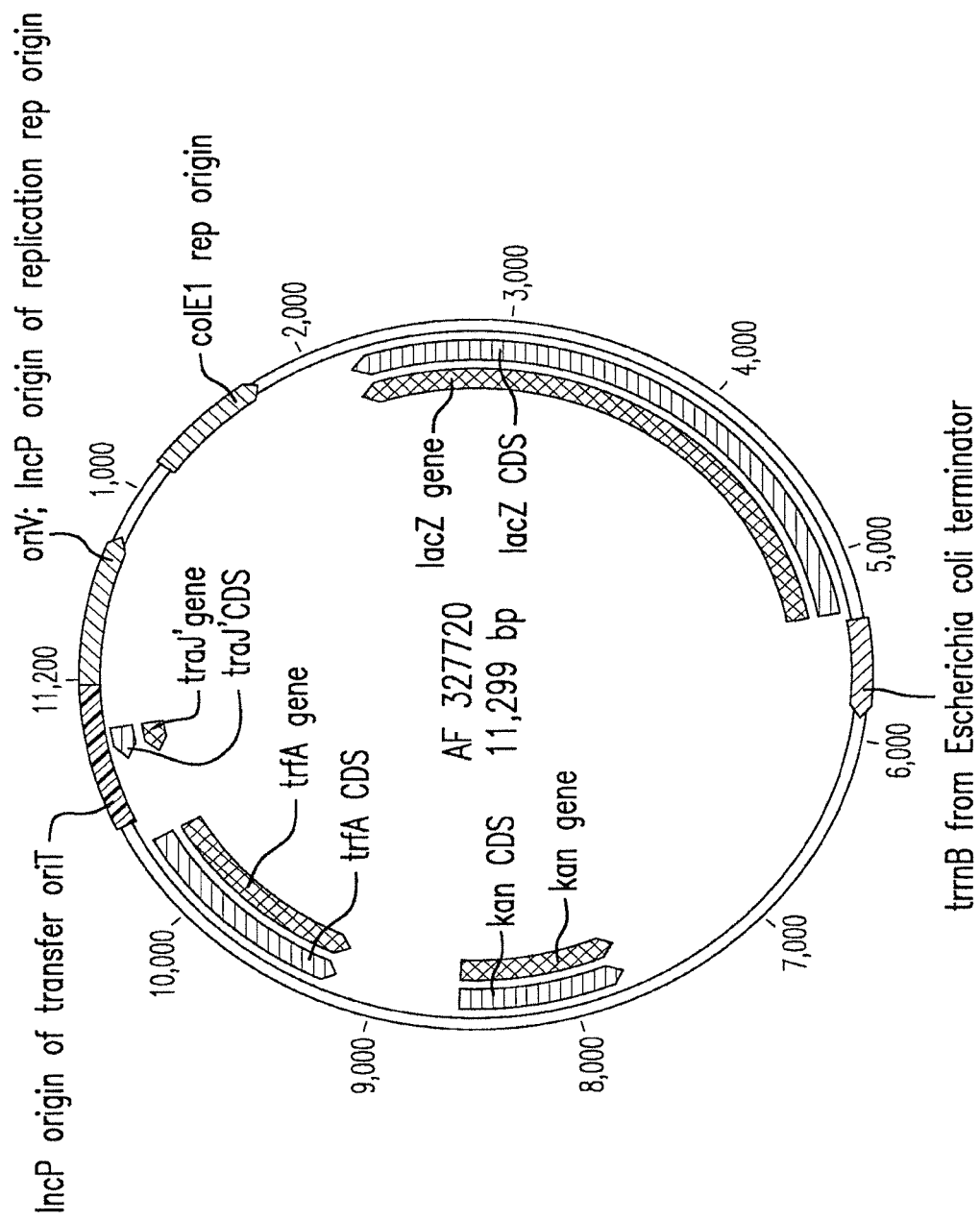
FIG. 2 depicts a vector map of the broad host range expression plasmid pCM 132. The vector map shows the following components: (1) an origin of replication that is functional in *E. coli* (colE1); (2) an oriV/IncP origin of replication for the non-*E. coli* microbial host; (3) an oriT/IncP origin of transfer, which is needed for transferring a bacterial plasmid from a bacterial host such as *E. coli* to the recipient during bacterial conjugation; (4) a traJ gene, which codes for a transcriptional activator that initiates production of the proteins needed for conjugative transfer; (5) a trfA gene, the replication initiation protein gene of plasmid RK2 which binds to and activates oriV; (6) a lacZ (beta-galactosidase) gene for identifying plasmids with DNA inserts based on colony color using indolyl-galactoside-based substrates; and (7) a kanamycin resistance gene (kan). Genes of interest are inserted into the polylinker region that lies between the rrnB transcription terminator and the 5'-end of the lacZ gene.

In one embodiment, the conjugative bhr plasmid is based on pCM132 (GenBank Accession No. AF327720, SEQ ID NO:79) (Marx & Lidstrom, 2001), which has been engineered to contain a kanamycin resistance gene for plasmid selection and a lacZ (beta-galactosidase) gene for identifying plasmids with DNA inserts based on colony color using indolyl-galactoside-based substrates. Genes (or polynucleotide ORFs thereof) of interest can be inserted into the polylinker region that lies between the rrnB transcription terminator and the 5'-end of the lacZ gene (e.g., see, FIG. 2).

Figure 3:
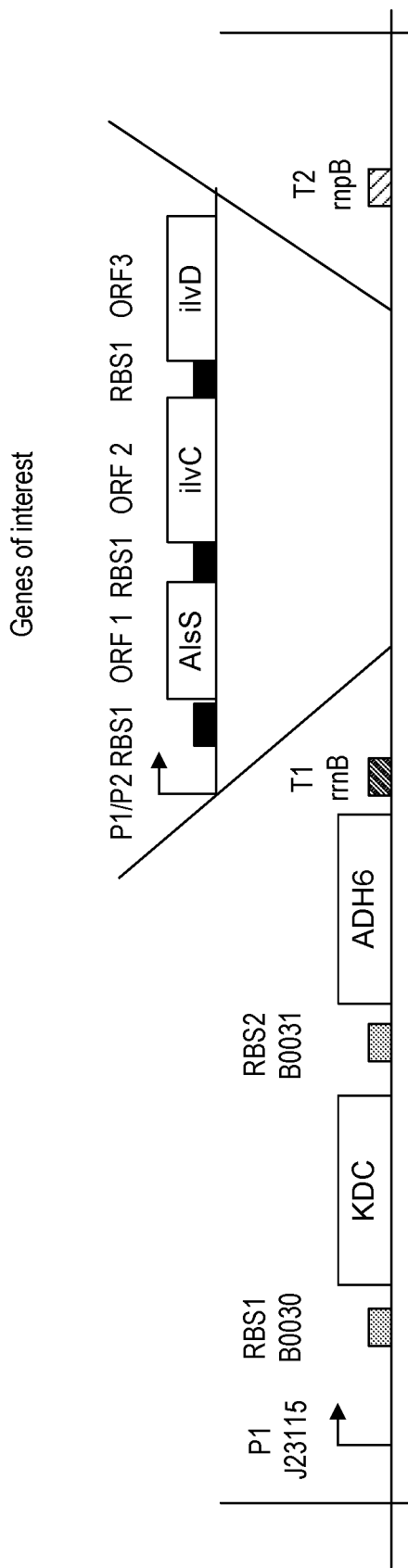
FIG. 3 shows a schematic diagram of component DNA arrangements for cloning into an expression vector.

Typical gene cassettes for expressing an engineered metabolic pathway in a host microorganism such as a methanotroph are shown in FIG. 3. The cassette comprises one or more open reading frames (ORFs) which encode the enzymes of the introduced pathway, a promoter for directing transcription of the downstream ORF(s) within the operon, ribosome binding sites for directing translation of the mRNAs encoded by the individual ORF(s), and a transcriptional terminator sequence. Due to the modular nature of the various components of the expression cassette, one can create combinatorial permutations of these arrangements by substituting different components at one or more of the positions. One can also reverse the orientation of one or more of the ORFs to determine whether any of these alternate orientations improve the product yield.

In one embodiment, the plasmids generated as part of the present invention are based on the broad-host-range expression vector pCM132 (Marx & Lidstrom, 2001). In this embodiment, the use of the Clontech (catalog no. 639647) InFusion HD Cloning System kit is one example of how to construct plasmids, but is not meant to limit or exclude other methods that are known in the art, including Gibson assembly, yeast in vivo recombination, PCR Splicing by Overlap Extension, or any combination of these with standard molecular biology techniques.

In certain embodiments of the invention, the plasmids of interest are generated in a modular fashion such that various modules, including suitable regulatory sequences, can be easily assembled or replaced as needed and are amenable to scaled-up, high-throughput assembly. The plasmids are designed to consist of multiple linear modules: a vector backbone and one or more vector inserts. The 5' and 3' ends of individual modules have overlapping sequence homology to the ends of adjacent modules within the designed plasmid. The overlapping homology between the modules allows them to be assembled into a circular plasmid using the Clontech InFusion HD Cloning System kit or other assembly method known in the art. Primers were designed to introduce homologous ends to the PCR-amplified products to facilitate assembly.

Vector backbones of the invention contain the components of the plasmid that will remain constant. In certain embodiments, the broad-host range vector pCM132 is modified to produce vector backbones for the plasmids (vectors) of the invention. The pCM132 vector, further described below in the Examples section, consists of the following components: trrnB terminator, kanamycin resistance gene, trfA, IncP oriT, IncP oriV, colE1 ori, and lacZ. This parental vector was modified to replace lacZ with a vector insert that contains promoter sequence(s) to produce plasmids pJSvec (SEQ ID NO: 80) and pMZT3 (SEQ ID NO: 81). In certain embodiments of the invention, vector backbones were PCR-amplified with the NEB Phusion master mix (M0531L) according to the manufacturer's instructions, unless specified otherwise.

The general rationale or procedure for selecting the appropriate ORFs for a given pathway was to examine a list of pathway-relevant genes as specified in the literature. Using this set of pathway-relevant genes as a target, BLAST searches were run, looking for genes in three groups: (1) similar genes found in microbial hosts that are phylogenetically close to the ones already listed in the literature, (2) similar genes found in microbes that are phylogenetically distant from the microbial host of the targeted gene, and (3) homologs that are similar to the target gene but that are found in the wild-type methanotroph or non-methanotroph organism that is to be used as the expression host. An example of the above strategy would be to target the kivD gene (encoding alpha-ketoisovalerate decarboxylase) from *Lactococcus lactis*: the first group would contain genes from species similar to *L. lactis*, including *Lactococcus* itself; the second group would be genes similar to kivD, but found in organisms phylogenetically distant from *L. lactis*; and finally the last group would include a kivD gene in a microbe of interest, specifically, *Methylococcus capsulatus* (Bath). Thus, in certain embodiments of the invention, the exemplary polynucleotide and polypeptide sequences set forth in Table 1 are used to identify similar or homologous polynucleotide, genes, ORFs and polypeptides found in microbial hosts that are (1) phylogenetically close to the ones already listed, (2) found in microbes that are phylogenetically distant from the microbial host of the targeted sequence, and (3) homologs that are similar to the target gene but that are found in the wild-type methanotroph or non-methanotroph organism that is to be used as the expression host.

For example, genes encoding similar proteins or polypeptides to those of the invention may isolated directly by using all or a portion of a nucleic acid (e.g., see Table 1, below) or a primer sequence (e.g., see Table 2, below) as DNA hybridization probes to screen libraries from any desired microorgansim using methodology well known to those skilled in the art. Specific oligonucleotide probes based upon these nucleic acid sequences can be designed and synthesized by methods known in the art (Sambrook et al., 1989; Ausubel et al., 1987). Moreover, the entire sequence can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of or the full-length of the instant sequence. The resulting amplification products can be labeled directly during amplification reactions or labeled after amplification reactions, and used as probes to isolate full-length DNA fragments under conditions of appropriate stringency.

Alternatively a nucleic acid sequence of the invention may be employed as a hybridization reagent for the identification of homologs. The basic components of a nucleic acid hybridization test include a probe, a sample suspected of containing the gene or gene fragment of interest, and a specific hybridization method. Probes are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. base. Hybridization methods are well defined and know in the art.

An important component of these engineered operons is the promoter sequence. The promoter must be chosen based on its compatibility with the transcriptional machinery of the host organism, as well as its ability to tune the desired level of gene expression (e.g., high or low). For example, one may introduce the strong pmxaF or pmmoX promoters from a methanotroph to generate high expression levels in a methanotrophic or non-methanotroph host. Alternatively, one can introduce a promoter from the Anderson promoter collection, which is a library of constitutive sigma70 bacterial promoters (http://partsregistry.org/Promoters/Catalog/Anderson; Registry of Standard Biological Parts), such as J23100 (strong) or J23115 (weak), to modulate expression of different ORFs or combinations of ORFs. Inducible promoters, whose activity is controlled by the addition of exogenous small molecule activators, such as IPTG, arabinose or salicylate, can also be used to provide temporal control of gene expression. However, regardless of the choice of promoter, its effect on host expression must be empirically tested in vivo to be certain of its effectiveness for achieving the desired level of expression.

These different combinatorial permutations of the cassette can be synthesized, cloned and expressed in the target host organism (via chemical transformation, electroporation, or conjugation of the DNA) so that the production of a multi-carbon product can be compared. The best candidate or candidates can then be further engineered to provide additional improvements in product yield by repeating the design-build-test cycle.

In one embodiment, the host microorganism for expressing the plasmid is a methanotroph, and plasmid vector(s) containing the metabolic pathway expression cassettes are readily mobilized into these organisms via conjugation. Various methods for bacterial conjugation are known in the art, and one of the most widely used methods takes advantage of a strain of *E. coli* S17-1, which has an RP4 plasmid (with the RK2 tra genes for transfer of genetic material) inserted into the chromosome for mobilizing oriT(RP4)-carrying plasmids (Simon et al. 1983; Simon, 1984).

The transfer of plasmid containing RP4-mob from *E. coli* to methanotrophs, as further described in the Examples section, was based on the conjugation methods described previously (Martin & Murrell, 1995; Ali, 2006). A 10 ml overnight *E. coli* S17-1λ, pir culture, containing RP4-mob plasmid, was collected on a 0.2 µm pore-size nitrocellulose filter (Millipore). The *E. coli* donor strain was washed twice with 50 ml NMS. A 50 ml methanotroph culture grown to mid exponential phase ($A_{540}$ of 0.2-0.5) was also collected on the same filter and washed again with 50 mL NMS medium. The filter was placed on an NMS agar plate containing 0.02% (w/v) proteose peptone and incubated for 24 hours at 30° C. with methane except for *M. capsulatus*, which was incubated at 37° C. for 24 hours.

Following incubation, the cells were washed with 10 ml NMS and collected by centrifugation (7,000×g for 10 min) before re-suspending the cells in 1 ml NMS. Aliquots (50-100 µl) of the cells were spread onto NMS plates containing selective antibiotics and incubated at the appropriate temperature. Colonies typically formed on the plates after 8-12 days. (Note: the *E. coli* S17-1λ, pir strain has chromosomally integrated conjugal transfer functions, thus allowing transfer of plasmid to occur by means of a bi-parental mating without a helper plasmid). Transconjugants can also be purified by serial cultivation in liquid medium containing the appropriate antibiotics for selection, followed by plating onto selective NMS agar plates to obtain single colonies.

In an alternative method for expressing metabolic pathway genes in a microbial host, the biosynthetic pathway genes are inserted directly into the chromosome. Methods for chromosomal modification include both non-targeted and targeted deletions and insertions. For example, non-targeted insertions can be achieved by using transposon mutagenesis to make insertion mutants or gene "knockouts" in vitro using the EZ-Tn5 <KAN-2> Insertion Kit (Epicentre). Briefly, the procedure is as follows, according to the manufacturer: Preparation: prepare 0.2 µg of recombinant DNA for the EZ-Tn5<KAN-2> insertion reaction. Day 1: perform the 2-hour in vitro EZ-Tn5<KAN-2> insertion reaction; transform competent recA-*E. coli* with 1 µl of the reaction mix and select for kanamycin-resistant transposon insertion clones on kanamycin plates overnight. Day 2: prepare DNA from kanamycin-resistant colonies, (and optionally map the EZ-Tn5 <KAN-2> Transposon insertion sites and optionally (DNA) sequence chosen clones bi-directionally using the unlabeled forward and reverse transposon-specific primers supplied in the kit.

For targeted modifications, various methods have been developed based on RecA-dependent homologous recombination (Hamilton et al., 1989; Link et al., 1997; Posfai et al., 1999). However, using antibiotic resistance markers for deletion/insertion is limited by the number of different antibiotics that can be used in a given target organism. For this reason, markerless insertion methods have been developed. For example, Yu et al. (2008) describe a deletion procedure in which expression of the λ-Red recombinase genes (gam, bet and exo) and the I-SceI endonuclease gene are controlled by tightly regulated promoters ParaB and PrhaB. Arabinose and rhamnose added to cultures to induce ParaB and PrhaB are used and depleted by the bacteria. Thus, by changing the carbon source in the medium from arabinose to rhamnose in bacteria that contain the pREDI plasmid, one can replace a targeted genomic region with a markerless deletion cassette and subsequently delete the selection markers that were introduced.

Sun et al. (2008) also describe methods for sequence-specific insertion or deletion of genes within a bacterial genome. This method permits multiple markerless insertions and scarless deletions in the targeted genome. In the Sun et al. method, a target gene can be deleted in two steps. In the first step, a linear DNA fragment is created that carries the cat (chloramphenicol resistance) gene and sacB (a levansucrase gene that confers sensitivity to sucrose). The fragment is flanked by long (500 bp) regions of DNA that are homologous to the regions that flank the targeted deletion site. The DNA fragment is electroporated into the host cell, which already contains plasmid pKD46, a vector containing the genes for λ Red recombination. Homologous recombination then directs the replacement of the targeted gene. Medium containing chloramphenicol is used to select for cells that contain the desired insertion or deletion. In the second step, a second DNA fragment that contains the desired deletion or insertion is electroporated into host cells that contain the pKD46 plasmid. By plating the resulting cells on medium containing sucrose, one can select for transformants in which the cat-sacB cassette has been replaced. These candidates are also screened for sensitivity to chloramphenicol, and the deletion can be confirmed by PCR and sequencing. By repeating the process, multiple deletions and/or insertions can be achieved. The pKD46 plasmid can then be removed by culturing the cells at 37 C. Thus, by using various genes encoding the isobutanol, butanol, fatty alcohol and fatty acid ester biosynthetic pathways, these pathways can be inserted into the genome of a methanotroph (or non-methanotroph), and unwanted genes (e.g., genes that encode for enzymes that produce competing products) can be removed.

U.S. Patent Publication No. 2006/0057726 describes using sacB gene and the pGP704 suicide vector to engineer markerless insertions into single carbon (C1) metabolizing bacteria. Yomantas et al. (2010) describes methods for markerless substitutions in the genome of the methylotrophic bacterium *Methylophilus methylotrophus*.

Several methanotroph strains were evaluated according to the present invention as potential hosts for pathway engineering. Of the well characterized methanotroph strains, *Methylosinus trichosporium* OB3b (NCIMB 11131) and *Methylococcus capsulatus* str. Bath (NCIMB 11853) were examined for their ease of transformability (via conjugation), growth rate, and suitability for industrial fermentation. Both strains can be cultivated in liquid or agar containing Nitrate Mineral Salts (NMS) medium (Whittenbury et al., 1970; Bowman, 2000). Although both strains were found to transform with approximately equal efficiency, *Methylococ-* cus capsulatus (Bath) has the advantage of growing about twice as fast as M. trichosporium (ca. 24-30 to reach saturation in shake flask growth). In addition, the ability of M. capsulatus (Bath) to grow more readily at 45° C. is an advantage in industrial cultivation, since this relatively high temperature will impede the growth of other potentially contaminating microorganisms. Furthermore, the complete genome sequence of M. capsulatus (Bath) has been published (Ward et al., 2004), and as such, manipulation of its genome via genetic engineering is readily available to one of skill in the art. Thus, in certain embodiments, M. capsulatus (Bath) is used as a model organism for further development of genetically modified host microorganisms.

Following conjugation, positive methanotroph trans-conjugants were purified on NMS agar containing the appropriate antibiotic selection (e.g., 15 µg/ml kanamycin for selecting the plasmid and counter-selecting the untransformed methanotroph host cells, and 10 µg/ml for counter-selecting the E. coli donor cells). Alternatively, transconjugants can be purified by serial cultivation in liquid medium containing the appropriate antibiotics for selection, followed by plating onto selective NMS agar plates to obtain single colonies. Colonies were used to inoculate small (5-10 ml) starter cultures in liquid NMS medium containing, for example, 15 µg/ml kanamycin in 125-ml flasks. The flasks were stoppered with tight-fitting Suba Seals to create a closed atmosphere inside the flasks. A volume of gas corresponding to 20% of the total volume of the flask and composed of 95% methane and 5% carbon dioxide was injected via a sterile syringe and 23-gauge needle into each flask. Flasks were shaken at 200 rpm and 45° C. When these cultures achieved an optical density of $A_{540}$>0.5 (after about 24 hours), a 1:100 dilution of these cells was used to inoculate 125 ml (or larger volume) cultures, and the same growth protocol was followed. Growth in shake flasks is most robust when the liquid volume is maintained at about 5-10% of the nominal volume of the flask so that good aeration of the liquid is achieved. These flasks were then used for the subsequent assays of product formation. In certain examples related to 2-KIV feeding experiments, only the ketoacid intermediate was added along with the methane and $CO_2$ at the zero time point.

After approximately 72 hours of growth, the cultures were harvested for analysis by gas chromatography. The sealed flasks were first chilled for at least 1 hour on ice, to concentrate any volatile organic compounds from the vapor phase into the liquid phase. After opening the flasks, an aliquot of the culture was diluted 1:2 with ethyl acetate in a clean 50 ml tube to extract and concentrate the isobutanol, butanol, fatty alcohols or fatty acid esters. After vortexing or shaking (and centrifugation to separate the phases), a small volume of the organic layer (approximately 1 ml) was filtered through a 0.2 µm PTFE filter, and 1 µl of the purified extract was then injected into an Agilent 7890A GC equipped with a Leap Technologies (Carrboro, NC) CombiPAL autosampler for analysis. Appropriate purified standards were included to generate a standard curve and determine the concentration of the targeted product. Each measurement included a positive control and a negative control (e.g., a wild-type sample or other appropriate background control) with each sample set. Additional details of the methods used for the specific products are given in the Examples section. Strains with the highest levels of production were designated for further scale-up in 1-10 liter fermentors.

During the analysis of the engineered host strains, unexpectedly high levels of isobutanol and butanol consumption (up to 30 mM after 72 hours of growth) was observed even in wild-type cultures of M. capsulatus (Bath), and therefore it was important to find mutant strains that can produce these products at a rate that is greater than their inherent rate of consumption. In certain embodiments of the invention, the competing alcohol dehydrogenase and alcohol oxidase activities are identified, and reduced or eliminated by gene knockouts, as described above.

For initial fermentation scale-up in the 1-10 liter range, methods similar to those described in Theisen et al. (2005) and U.S. Pat. No. 4,594,324 can be used, with specific modifications for M. capsulatus (Bath). A fermentation system such as the Sartorius-Stedim Biostat A plus system (Goettingen, Germany) can be used, or other equivalent fermentation systems and methods for methanotroph fermentation (e.g., see Jiang et al., 2010). An Applikon ADI 1030 Bio Controller and ADI 1035 BioConsole (Applikon Biotechnology Inc., Foster City, CA) can also be used for the 10 liter vessel.

The starting inoculum is created by inoculating a large colony of M. capsulatus (Bath) containing the desired plasmid from a plate culture into 10 ml of sterile NMS medium containing kanamycin, as described above. After 24 to 48 hours, when the optical density ($A_{540}$) of the culture is greater than 0.5, five starter flasks of NMS medium are inoculated at 1:100 dilution. The liquid volumes in these starter inocula can range in size from 20 ml each for a 1 liter fermentor to 200 ml each for a 10 liter fermentor (i.e., about a 10% inoculum).

After autoclaving the NMS medium in the fermentor vessel, the phosphate salts portion of the NMS medium and the kanamycin (both sterilized) are added to the vessel. The same inlet can be used to inject the starter cultures. Air is supplied as oil-free compressor air, and the methane carbon source is supplied from a pre-mixed tank (Airgas) containing 95% methane and 5% $CO_2$. The air and methane are mixed to 15-20% methane using equipment that is rated intrinsically safe or explosion proof to eliminate the possibility of sparking or static electricity, which could lead to an explosion. The gas flow rate depends on the fermentor size and culture density, but a value of 0.75 liters per minute for 10 liters is typical. The gas mixture is fed into the fermentor, and the entire culture is mixed with an impeller rotating at approximately 200 rpm for agitation, the rate of which may be increased during growth. For maintenance of the culture pH at 6.8, 0.1 M HCl or 1 M NaOH is added as needed. The temperature is maintained at 45° C. by a thermostatic jacket. The effluent gas is fed through a water-jacketed condenser to reduce liquid loss at 45° C., and vented to a fume hood.

The fermentation is monitored (via pH and dissolved oxygen probes) and controlled using Sartorius BioPAT MFCS bioprocess control software (Sartorius Corp, Bohemia, NY). A dissolved oxygen concentration below 1% saturation with air (typically 0.2-0.3%) is desirable to avoid wasting methane. Periodically, small samples of the fermentation broth are removed by sterile transfer and used to measure the optical density of the culture. These samples can also be used to monitor product formation using the methods described above and in the Examples section. Purity of the culture can also be checked by plating a small sample onto R2A agar, which allows most organisms other than methanotrophs to grow. Cultures achieve an optical density ($A_{540}$) of greater than 9 after about 48 hours. For M. capsulatus (Bath), 1 ml of culture with $A_{540}$ equal to 1 corresponds to about 0.23-0.25 mg of dry weight of biomass. When the maximum cell density or product concentration is achieved, the culture can be harvested and analyzed.

For large-scale commercial fermentation, a system based on the fermentor design employed by Norferm (Norefem, AS; Stavanger, Norway) for production of single-cell protein can be used (Bothe et al., 2002; EP 1419234; U.S. Publication No. 2009/0263877). The largest system has a total volume of 300 m$^3$ (300,000 liters) and an annual production capacity of 10,000 tons of biomass (van Laere et al., 2005). Publications such as EP 1419234, U.S. Publication No. 2009/0263877 and Villadsen (2012), and references therein, describe a loop reactor and bioprocess methods for culturing methanotrophs at the commercial scale. The advantage of this design is that nutrient gases such as methane and oxygen are supplied to the system in such a way that exposure of the cells to nutrient-depleted culture medium or to unduly high concentrations of nutrient gases is minimized.

However, when using "wet" natural gas as a nutrient feedstock, the problem of acetate and propionate toxicity (resulting from the oxidation of ethane and propane, respectively) may need to be addressed (Bothe et al., 2002; Eiteman & Altman, 2006). A genetic approach is to eliminate (knock-out) or knock-down the ethanol and propanol dehydrogenases and acetaldehyde/propionaldehyde dehydrogenases that convert the ethanol and propanol to the corresponding acids. Another approach is to introduce the genes for acetate assimilation from an organism that can use it as a carbon source, such as E. coli (Wolfe, 2005). For example, AMP-ACS (acetate:CoA ligase [AMP forming]; EC 6.2.1.1) catalyzes the conversion of acetate and ATP to an enzyme-bound acetyladenylate (acetyl-AMP) and pyrophosphate. In a subsequent step, it reacts the acetyl-AMP with CoASH (CoenzymeA-SH) to acetyl-CoA and free AMP. Similarly, AMP-ACS can activate and assimilate propionate (Wolfe, 2005). In this way, the two potentially harmful organic acids are converted into the useful intermediate, acetyl-CoA. These genes can be cloned and expressed in a methanotroph host by the methods described above.

Another aspect of the commercial production of multi-carbon compounds from methane using the present invention involves recovering and purifying the desired product from the fermentation broth. The method to be used depends on the physico-chemical properties of the product and the nature and composition of the fermentation medium and cells. For example, U.S. Pat. No. 8,101,808 describes methods for recovering C3-C6 alcohols from fermentation broth using continuous flash evaporation and phase separation processing. Thus, the biologically produced multi-carbon compounds of the invention may be isolated from the fermentation medium using methods known in the art for Acetone-butanol-ethanol (ABE) fermentations For example, solids may be removed from the fermentation medium by centrifugation, filtration, decantation, wherein the multi-carbon compounds of the invention may be isolated from the fermentation medium using methods such as distillation, azeotropic distillation, liquid-liquid extraction, adsorption, gas stripping, membrane evaporation, or pervaporation.

In certain embodiments the invention, the fermentation process produces greater than about 7% (v/v) concentration of the desired multi-carbon product in the fermentation broth, and the product is separated from the rest of the medium using membrane separation technology to achieve about a 12% or greater concentration of the product, at which point relatively small molecules (such as isobutanol) can be further purified by phase separation in an integrated system (Hickey & Slater, 1990; Neel, 1995; Hagg, 1998; Liu et al., 2011). Continuous recovery of the product from the fermentation medium has the advantage of possibly reducing the toxicity effects of the multi-carbon products.

For longer-chain alcohols, such as fatty alcohols, U.S. Pat. No. 8,268,599 describes methods for separating these components from the aqueous phase of the fermentation by bi-phasic separation, whereby the immiscibility of the product compounds with the fermentation broth allows the organic phase to be collected and removed. This separation can also reduce the toxic effects of the product on the host microbial cells.

U.S. Publication No. 2007/0251141 describes methods for recovering fatty acid methyl esters (FAMEs) from a liquid suspension by adding urea and creating a phase separation whereby the saturated and unsaturated FAMEs can be recovered separately. Membrane separation methods can also be applied to purifying fatty acid ester products such as biodiesel (Saleh, 2011).

In certain embodiments, a methane substrate of the invention is provided or obtained from a natural gas source, wherein the natural gas is "wet" natural gas or "dry" natural gas. Natural gas is referred to as "dry" natural gas when it is almost pure methane, having had most of the other commonly associated hydrocarbons removed. When other hydrocarbons are present, the natural gas is referred to as "wet". Wet natural gas typically comprises about 70-90% methane, about 0-20% ethane, propane and butane (combined total), about 0-8% $CO_2$, about 0-5% N2, about 0-5% $H_2S$ and trace amounts of oxygen, helium, argon, neon and xenon. In certain other embodiments, a methane substrate of the invention is provided or obtained from methane emissions, or methane off-gases, which are generated by a variety of natural and human-influenced processes, including anaerobic decomposition in solid waste landfills, enteric fermentation in ruminant animals, organic solids decomposition in digesters and wastewater treatment operations, and methane leakage in fossil fuel recovery, transport, and processing systems.

Table 1 below, provides exemplary polynucleotide and polypeptide sequences for implementing various embodiments of the present invention. These sequences are not meant to limit or exclude the use of other polynucleotide sequences encoding polypeptides or enzymes useful for producing multi-carbon compounds according to the present invention. For example, one of skill in the art can search gene sequence databases (or genome databases) and/or protein sequence databases (e.g., via BLAST or other sequence search algorithms) to identify homologous polynucleotides encoding one or more enzyme activities based on the reference sequences set forth in Table 1. Alternatively, a homologous polynucleotide may be isolated directly by using all or a portion of a nucleic acid sequence set forth in Table 1 (or a primer sequence set forth below in Table 2) as DNA hybridization probes to screen libraries from any desired microorgansim and/or PCR amplify a desired polynucleotide sequence using methodology well known to those skilled in the art.

TABLE 1

Exemplary Nucleic Acid and Polypeptide Sequences Described in the Invention

| Pathway or Reaction | Gene Name | Nucleic acid SEQ | Enzyme Name | Polypeptide SEQ ID | Organism |
|---|---|---|---|---|---|
| isobutanol | MCA1837 | SEQ ID NO: 1 | ALS | SEQ ID NO: 2 | *M. capsulatus*, Bath |
| isobutanol | MCA2272 | SEQ ID NO: 3 | KARI | SEQ ID NO: 4 | *M. capsulatus*, Bath |
| isobutanol | MCA2082 | SEQ ID NO: 5 | DHAD | SEQ ID NO: 6 | *M. capsulatus*, Bath |
| isobutanol | MCA0996 | SEQ ID NO: 7 | KDC | SEQ ID NO: 8 | *M. capsulatus*, Bath |
| isobutanol | YMR318C | SEQ ID NO: 9 | ADH | SEQ ID NO: 10 | *S. cerevisiae* |
| isobutanol | MtKDC | SEQ ID NO: 82 | KDC | SEQ ID NO: 162 | *M. trichosporium* |
| isobutanol | MtADH | SEQ ID NO: 83 | ADH | SEQ ID NO: 163 | *M. trichosporium* |
| isobutanol | McADH-2a | SEQ ID NO: 84 | ADH | SEQ ID NO: 164 | *M. capsulatus*, Bath |
| isobutanol | McADH-2b | SEQ ID NO: 85 | ADH | SEQ ID NO: 165 | *M. capsulatus*, Bath |
| Isobutanol | LlkivD | SEQ ID NO: 86 | KDC | SEQ ID NO: 166 | *L. lactis* |
| Isobutanol | ScPDC6 | SEQ ID NO: 87 | KDC | SEQ ID NO: 167 | *S. cerevisiae* |
| Isobutanol | ScARO10 | SEQ ID NO: 88 | KDC | SEQ ID NO: 168 | *S. cerevisiae* |
| Isobutanol | ScADH2 | SEQ ID NO: 89 | ADH | SEQ ID NO: 169 | *S. cerevisiae* |
| Isobutanol | ScPDC1 | SEQ ID NO: 90 | KDC | SEQ ID NO: 170 | *S. cerevisiae* |
| isobutanol | CaPDC | SEQ ID NO: 91 | KDC | SEQ ID NO: 171 | *C. acetobutylicum* |
| $CH_4$ to $CH_3OH$ | MCA1798 | SEQ ID NO: 11 | pmoC subunit 1 | SEQ ID NO: 12 | *M. capsulatus*, Bath |
| $CH_4$ to $CH_3OH$ | MCA1797 | SEQ ID NO: 13 | pmoA subunit 1 | SEQ ID NO: 14 | *M. capsulatus*, Bath |
| $CH_4$ to $CH_3OH$ | MCA1796 | SEQ ID NO: 15 | pmoB subunit 1 | SEQ ID NO: 16 | *M. capsulatus*, Bath |
| $CH_4$ to $CH_3OH$ | MCA2855 | SEQ ID NO: 17 | pmoC subunit 2 | SEQ ID NO: 18 | *M. capsulatus*, Bath |
| $CH_4$ to $CH_3OH$ | MCA2854 | SEQ ID NO: 19 | pmoA subunit 2 | SEQ ID NO: 20 | *M. capsulatus*, Bath |
| $CH_4$ to $CH_3OH$ | MCA2853 | SEQ ID NO: 21 | pmoB subunit 2 | SEQ ID NO: 22 | *M. capsulatus*, Bath |
| $CH_4$ to $CH_3OH$ | MCA1194 | SEQ ID NO: 23 | mmoX | SEQ ID NO: 24 | *M. capsulatus*, Bath |
| $CH_4$ to $CH_3OH$ | MCA1195 | SEQ ID NO: 25 | mmoY | SEQ ID NO: 26 | *M. capsulatus*, Bath |
| $CH_4$ to $CH_3OH$ | MCA1196 | SEQ ID NO: 27 | mmoB | SEQ ID NO: 28 | *M. capsulatus*, Bath |
| $CH_4$ to $CH_3OH$ | MCA1198 | SEQ ID NO: 29 | mmoZ | SEQ ID NO: 30 | *M. capsulatus*, Bath |
| $CH_4$ to $CH_3OH$ | MCA1199 | SEQ ID NO: 31 | mmoD | SEQ ID NO: 32 | *M. capsulatus*, Bath |
| $CH_4$ to $CH_3OH$ | MCA1200 | SEQ ID NO: 33 | mmoC | SEQ ID NO: 34 | *M. capsulatus*, Bath |
| $CH_3OH$ to $H_2CO$ | MCA0779 | SEQ ID NO: 35 | mxaF | SEQ ID NO: 36 | *M. capsulatus*, Bath |
| $CH_3OH$ to $H_2CO$ | MCA0780 | SEQ ID NO: 37 | mxaJ | SEQ ID NO: 38 | *M. capsulatus*, Bath |
| $CH_3OH$ to $H_2CO$ | MCA0781 | SEQ ID NO: 39 | mxaG | SEQ ID NO: 40 | *M. capsulatus*, Bath |
| $CH_3OH$ to $H_2CO$ | MCA0782 | SEQ ID NO: 41 | mxaI | SEQ ID NO: 42 | *M. capsulatus*, Bath |
| $CH_3OH$ to $H_2CO$ | MCA0783 | SEQ ID NO: 43 | mxaR | SEQ ID NO: 44 | *M. capsulatus*, Bath |
| $CH_3OH$ to $H_2CO$ | MCA0785 | SEQ ID NO: 45 | mxaA | SEQ ID NO: 46 | *M. capsulatus*, Bath |
| $CH_3OH$ to $H_2CO$ | MCA0786 | SEQ ID NO: 47 | mxaC | SEQ ID NO: 48 | *M. capsulatus*, Bath |
| $CH_3OH$ to $H_2CO$ | MCA0787 | SEQ ID NO: 49 | mxaK | SEQ ID NO: 50 | *M. capsulatus*, Bath |
| $CH_3OH$ to $H_2CO$ | MCA0788 | SEQ ID NO: 51 | mxaL | SEQ ID NO: 52 | *M. capsulatus*, Bath |
| $CH_3OH$ to $H_2CO$ | MCA0789 | SEQ ID NO: 53 | mxaD | SEQ ID NO: 54 | *M. capsulatus*, Bath |
| 1-butanol | MCA0354 | SEQ ID NO: 55 | Threonine-ammonia-lyase | SEQ ID NO: 56 | *M. capsulatus*, Bath |
| 1-butanol | MCA2275 | SEQ ID NO: 57 | 2-ethylmalate synthase | SEQ ID NO: 58 | *M. capsulatus*, Bath |
| 1-butanol | MCA2065 | SEQ ID NO: 59 | Isopropyl malate dehydratase, large subunit | SEQ ID NO: 60 | *M. capsulatus*, Bath |
| 1-butanol | MCA2064 | SEQ ID NO: 61 | Isopropyl malate dehydratase, small subunit | SEQ ID NO: 62 | *M. capsulatus*, Bath |
| 1-butanol | VIMSS17191 | SEQ ID NO: 160 | tdcB | SEQ ID NO: 161 | *E. coli* |
| 1-butanol | MCA0996 | SEQ ID NO: 7 | KDC | SEQ ID NO: 8 | *M. capsulatus*, Bath |
| 1-butanol | YMR318C | SEQ ID NO: 9 | ADH | SEQ ID NO: 10 | *S. cerevisiae* |
| 1-butanol | MtKDC | SEQ ID NO: 82 | KDC | SEQ ID NO: 162 | *M. trichosporium* |
| 1-butanol | MtADH | SEQ ID NO: 83 | ADH | SEQ ID NO: 163 | *M. trichosporium* |
| 1-butanol | McADH-2a | SEQ ID NO: 84 | ADH | SEQ ID NO: 164 | *M. capsulatus*, Bath |
| 1-butanol | McADH-2b | SEQ ID NO: 85 | ADH | SEQ ID NO: 165 | *M. capsulatus*, Bath |
| 1-butanol | LlkivD | SEQ ID NO: 86 | KDC | SEQ ID NO: 166 | *L. lactis* |
| 1-butanol | ScPDC6 | SEQ ID NO: 87 | KDC | SEQ ID NO: 167 | *S. cerevisiae* |
| 1-butanol | ScARO10 | SEQ ID NO: 88 | KDC | SEQ ID NO: 168 | *S. cerevisiae* |
| 1-butanol | ScADH2 | SEQ ID NO: 89 | ADH | SEQ ID NO: 169 | *S. cerevisiae* |
| 1-butanol | ScPDC1 | SEQ ID NO: 90 | KDC | SEQ ID NO: 170 | *S. cerevisiae* |
| 1-butanol | CaPDC | SEQ ID NO: 91 | KDC | SEQ ID NO: 171 | *C. acetobutylicum* |
| Fatty alcohol | FAR | SEQ ID NO: 65 | FAR | SEQ ID NO: 66 | *M. algicola* |
| Fatty acid ester | Ab-wax-dgaT | SEQ ID NO: 67 | wax-dgaT | SEQ ID NO: 68 | *A. baylyi* |
| Fatty acid ester | Psyc_0223 | SEQ ID NO: 69 | PaWES | SEQ ID NO: 70 | *P. arcticus* |
| Fatty acid ester | ROP_02100 | SEQ ID NO: 71 | RoWES1 | SEQ ID NO: 72 | *R. opacus* |
| Fatty acid ester | ROP_13050 | SEQ ID NO: 73 | RoWES2 | SEQ ID NO: 74 | *R. opacus* |
| Fatty acid ester | ROP_54550 | SEQ ID NO: 75 | RoWES3 | SEQ ID NO: 76 | *R. opacus* |
| Fatty acid ester | ROP_26950 | SEQ ID NO: 77 | RoWES4 | SEQ ID NO: 78 | *R. opacus* |
| 2,3-butanediol | YAL060W | SEQ ID NO: 156 | Bdh1 | SEQ ID NO: 157 | *S. cerevisiae* |
| RuMP | MCA3049 | SEQ ID NO: 160 | HPS | SEQ ID NO: 161 | *M. capsulatus*, Bath |
| RuMP | MCA3050 | SEQ ID NO: 162 | HPS/PHI | SEQ ID NO: 163 | *M. capsulatus*, Bath |

TABLE 2

Plasmid, Primer, Promoter and Gene Fragment Sequences Described in the Invention

| Name | Nucleic acid SEQ ID |
|---|---|
| pCM132 | SEQ ID NO: 79 |
| pJSvec | SEQ ID NO: 80 |
| pMZT3 | SEQ ID NO: 81 |
| JPS00082 | SEQ ID NO: 92 |
| JPS00031 | SEQ ID NO: 93 |
| JPS00032 | SEQ ID NO: 94 |
| GMV257 | SEQ ID NO: 95 |
| JPS00118 | SEQ ID NO: 96 |
| JPS00119 | SEQ ID NO: 97 |
| ESG00087 | SEQ ID NO: 98 |
| GMV251 | SEQ ID NO: 99 |
| rnpB | SEQ ID NO: 100 |
| JPS00161 | SEQ ID NO: 101 |
| JPS00162 | SEQ ID NO: 102 |
| JPS00163 | SEQ ID NO: 103 |
| JPS00164 | SEQ ID NO: 104 |
| JPS00172 | SEQ ID NO: 105 |
| JPS00173 | SEQ ID NO: 106 |
| JPS00174 | SEQ ID NO: 107 |
| JPS00176 | SEQ ID NO: 108 |
| JPS00177 | SEQ ID NO: 109 |
| JPS00157 | SEQ ID NO: 110 |
| JPS00178 | SEQ ID NO: 111 |
| Me-AM1 PmxaF | SEQ ID NO: 112 |
| JPS00169 | SEQ ID NO: 113 |
| GMV00251 | SEQ ID NO: 114 |
| JPS00170 | SEQ ID NO: 115 |
| JPS00171 | SEQ ID NO: 116 |
| JPS00153 | SEQ ID NO: 117 |
| JPS00151 | SEQ ID NO: 118 |
| JPS00154 | SEQ ID NO: 119 |
| JPS00183 | SEQ ID NO: 120 |
| JPS00185 | SEQ ID NO: 121 |
| J23100 | SEQ ID NO: 122 |
| J23100 hybrid | SEQ ID NO: 123 |
| J23115 | SEQ ID NO: 124 |
| GMV0233 | SEQ ID NO: 125 |
| GMV00235 | SEQ ID NO: 126 |
| GMV00433 | SEQ ID NO: 127 |
| GMV00434 | SEQ ID NO: 128 |
| GMV00435 | SEQ ID NO: 129 |
| GMV00436 | SEQ ID NO: 130 |
| GMV00437 | SEQ ID NO: 131 |
| GMV00438 | SEQ ID NO: 132 |
| GMV00439 | SEQ ID NO: 133 |
| GMV00440 | SEQ ID NO: 134 |
| GMV00441 | SEQ ID NO: 135 |
| GMV00442 | SEQ ID NO: 136 |
| ESG00084 | SEQ ID NO: 137 |
| ESG00088 | SEQ ID NO: 138 |
| pMZT37 | SEQ ID NO: 139 |
| MaFAR-g1 | SEQ ID NO: 140 |
| MaFAR-g2 | SEQ ID NO: 141 |
| MaFAR-g3 | SEQ ID NO: 142 |
| MaFAR-g4 | SEQ ID NO: 143 |
| GMV410 | SEQ ID NO: 144 |
| GMV411 | SEQ ID NO: 145 |
| GMV412 | SEQ ID NO: 146 |
| GMV413 | SEQ ID NO: 147 |
| GMV414 | SEQ ID NO: 148 |
| GMV415 | SEQ ID NO: 149 |
| GMV416 | SEQ ID NO: 150 |
| GMV417 | SEQ ID NO: 151 |
| GMV418 | SEQ ID NO: 152 |
| GMV419 | SEQ ID NO: 153 |
| GMV420 | SEQ ID NO: 154 |
| GMV421 | SEQ ID NO: 155 |
| GMV422 | SEQ ID NO: 158 |
| GMV423 | SEQ ID NO: 159 |

EXAMPLES

The present invention is further defined in the following Examples. It should be understood that these examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

Biosynthetic Production of Isobutanol from Methane

Initial experiments were performed to confirm and validate enzymatic activity of isobutanol pathway enzymes at the relatively high temperatures (i.e., 45° C.) requisite for growth of one preferred methanotroph host organism, *Methylococcus capsulatus* (Bath). Thus, in this example, the methanotroph *M. capsulatus* was engineered in the first series of experiments to overexpress two isobutanol pathway enzymes, ketoacid decarboxylase (KDC) and alcohol dehydrogenase (ADH), prior to introducing the full complement of five isobutanol pathway enzymes (Atsumi et al., 2010) into *M. capsulatus*. Following the functional validation of KDC and ADH activity in *M. capsulatus* (set forth below), the complete five-gene isobutanol pathway was introduced into *M. capsulatus*, the results of which are set forth below.

Gene Selection, Synthesis and Cloning

For the two-gene (isobutanol) pathway experiments (and for the downstream section of the five-gene isobutanol pathway set forth below), ketoacid decarboxylase (KDC) and alcohol dehydrogenase (ADH) genes were amplified by colony PCR from *Methylosinus trichosporium* (strain: OB3b, National Collection of Industrial, Food and Marine Bacteria (NCIMB) Accession No: 11131) and *Methylococcus capsulatus* (Bath). The *Methylosinus trichosporium* gene, MtKDC, encoding KDC is set forth in SEQ ID NO:82, *Methylosinus trichosporium* gene, MtADH, encoding ADH is set forth in SEQ ID NO:83. The *Methylococcus capsulatus* (Bath) gene, McKDC, encoding KDC is set forth in SEQ ID NO:7, the *Methylococcus capsulatus* (Bath) genes, McADH-2a and McADH-2b, encoding two ADH2 homologs, are set forth in SEQ ID NO:84 and SEQ ID NO:85, respectively.

Other KDC and ADH genes such as L1KIVD: *Lactococcus lactis* KDC (SEQ ID NO:86); ScPDC6: *Saccharomyces cerevisiae* PDC6 (SEQ ID NO:87); ScARO10: *S. cerevisiae* ARO10 (SEQ ID NO:88); ScADH2: *S. cerevisiae* ADH2 (SEQ ID NO:89); ScPDC1: *S. cerevisiae* PDC1 (SEQ ID NO:90); CaPDC: *Clostridium acetobutylicum* PDC (SEQ ID NO:91) were codon optimized for expression in *M. capsulatus* and de novo synthesized by GenScript (Piscataway, NJ). Various KDC and ADH combinations were cloned with a constitutive promoter (J23115) or inducible (Ptrc) promoter into plasmid pCM132 (Accession No. AF327720; SEQ ID NO:79) with the Clontech In-Fusion kit (Mountain View, CA). A gene for the ds-Red protein was used as a control. Plasmids were transformed into *E. coli* S17-1 for conjugation.

Vector Inserts

Vector inserts contain the DNA fragments that are to be carried in the plasmid. The vector inserts were designed as exchangeable parts to the vector backbone described above. In one embodiment of the 2-gene pathway example, the plasmids were designed to contain two inserts made up of *Methylococcus capsulatus* KDC (MCA0996; SEQ ID NO:7) and *Saccharomyces cerevisiae* ADH6 (YMR318C; SEQ ID NO:9) genes. Both genes were amplified from genomic DNA of their respective hosts, with the primers described above in Tables 2 and below in Table 3.

The plasmid pJS034 introduced a second terminator sequence into pGMV145. The pGMV145 vector backbone was PCR amplified with primers JPS00161 (SEQ ID

TABLE 3

Plasmid insert modules, templates and primers

| Plasmid | PCR rxn: | Vector Backbone | Insert 1 | Insert 2 | Insert3 |
|---|---|---|---|---|---|
| pJS0025 | template | pJSvec | MCA0996 (*M. capsulatus* DNA) | YMR318C (*S. cerevisiae* DNA) | — |
|  | primer 1 | JPS0082 | JPS0032 | JPS00118 | — |
|  | primer 2 | JPS0031 | GMV00257 | JPS00119 | — |
| pGMV145 | template | pMZT3 | MCA0996 (*M. capsulatus* DNA) | YMR318C (*S. cerevisiae* DNA) | — |
|  | primer 1 | JPS0082 | GMV00251 | JPS00118 | — |
|  | primer 2 | ESG00087 | GMV00257 | JPS00119 | — |
| pJS034 | template | pGMV145 | IDT gBlock synthesized rnpB DNA | — | — |
|  | primer 1 | JPS00161 | JPS00163 | — | — |
|  | primer 2 | JPS00162 | JPS00164 | — | — |
| pJS041 pJS041n | template | pJS034 | MCA1837 (*M. capsulatus* DNA) | MCA2272 (*M. capsulatus* DNA) | MCA2082 (*M. capsulatus* DNA) |
|  | primer 1 | JPS00162 | JPS00173 | JPS00176 | JPS00157 |
|  | primer 2 | JPS00172 | JPS00174 | JPS00177 | JPS00178 |
| pJS048 | template | pJS034 | IDT gBlock synthesized Me-AM1 PmxaF DNA | — | — |
|  | primer 1 | JPS00169 | JPS00170 | — | — |
|  | primer 2 | GMV251 | JPS00171 | — | — |
| pJS038 | template | pGMV145 | MCA1837 (*M. capsulatus* DNA) | — | — |
|  | primer 1 | JPS00153 | JPS00151 | — | — |
|  | primer 2 | GMV251 | JPS00154 | — | — |
| pJS042 pJS042n | template | pJS048 | pJS038 | — | — |
|  | primer 1 | JPS00162 | JPS00173 | — | — |
|  | primer 2 | JPS00172 | JPS00178 | — | — |
| pJS050 | template | pJS041n | pJS041n | — | — |
|  | primer 1 | JPS00183 | JPS00174 | — | — |
|  | primer 2 | JPS00176 | JPS00185 | — | — |

The modular parts (i.e., vector backbone and vector inserts) were PCR amplified (as listed in Table 3) with NEB Phusion master mix (New England Biolabs; Ipswich, MA) according to the manufacturer's instructions and in vitro assembled with the Clontech InFusion HD Cloning System kit (Clontech; Mountain View, CA) according to the manufacturer's instructions to generate circular plasmid listed below.

The in vitro assembled plasmids (2 µl of the InFusion reaction) were transformed into chemically competent NEB Turbo *E. coli* cells, screened by colony PCR, purified, and subsequently sequence verified.

The plasmid pJSvec (SEQ ID NO:80) served as the template for the vector backbone with an inducible promoter and consisted of the pCM132 cloning vector (SEQ ID NO:79), lacIq, and the IPTG-inducible pTrc promoter.

The plasmid pMZT3 (SEQ ID NO:81) served as the template for the vector backbone with a constitutive promoter and consisted of the pCM132 (SEQ ID NO:79) cloning vector and *E. coli* J23115 promoter (SEQ ID NO:124).

The plasmid pJS0025 was designed to express *M. capsulatus* KDC (MCA0996; SEQ ID NO:7) and *S. cerevisiae* ADH6 (YMR 318C; SEQ ID NO:9) from the inducible promoter.

The plasmid pGMV145 was designed to express *M. capsulatus* KDC (MCA0996; SEQ ID NO:7) and *S. cerevisiae* ADH6 (YMR 318C; SEQ ID NO:9) from the constitutive promoter.

NO:101)/JPS00162 (SEQ ID NO:102) and KOD mastermix. The insert contained DNA sequence for rnpB (SEQ ID NO:100) synthesized as a gBlock from Integrated DNA Technologies (Coralville, IA) and amplified with JPS00163 (SEQ ID NO:103)/JPS00164 (SEQ ID NO:104) primers.

Expression of the Full Five-Gene Pathway for Methane-to-Isobutanol Conversion

In order to synthesize isobutanol from methane (i.e., via pyruvate), without the need to exogenously supply a ketoacid intermediate, the pJS041 and pJS041n plasmids were designed to express all five isobutanol pathway genes: (1) *M. capsulatus* KDC (MCA0996; SEQ ID NO:7) and (2) *S. cerevisiae* ADH6 (YMR318C; SEQ ID NO:9) from the J23115 constitutive promoter (SEQ ID NO:124), and (3) *M. capsulatus* ilvK (MCA1837; SEQ ID NO:1), (4) *M. capsulatus* ilvC (MCA2272; SEQ ID NO:3), and (5) *M. capsulatus* ilvD (MCA2082; SEQ ID NO:5) from the J23100 constitutive promoter (see, FIG. 3). Plasmid pJS041n contains the canonical J23100 promoter sequence (5'-TTGACGGCTAGCTCAGTCCTAGGTACAGTGCTAGC-3'; SEQ ID NO:122), and plasmid pJS041 contains a modified J23100 promoter sequence (5'-TTGACGGCTAGCTCAGCCCTTGGTACAATGCTAGC-3'; SEQ ID NO:123), which represents a hybrid fusion of the J23100 and J23115 (SEQ ID NO:124) promoters that arose during the process of cloning and generating the plasmid in *E. coli* (Table 3). This mutated construct was retained and tested to see whether the promoter mutations might impart improved production of isobutanol in the microbial expression host (e.g., *M. capsulatus* (Bath)).

TABLE 4

Sequence comparison between the "hybrid" promoters in plasmids pJS041 and pJS042 and the canonical promoters J23115 and J23100

| J23115 (SEQ ID NO: 124) | TTTATAGCTAGCTCAGCC CTTGGTACAATGCTAGC |
|---|---|
| pJS041-hybrid (SEQ ID NO: 123) | TTGACGGCTAGCTCAGCC CTTGGTACAATGCTAGC |
| J23100 (SEQ ID NO: 122) | TTGACGGCTAGCTCAGTC CTAGGTACAGTGCTAGC |

The pJS048 plasmid replaced the J23100 promoter with the MxaF promoter (SEQ ID NO:112) from *Methlyobacterium extorquens* AM-1 in pJS034.

The pJS050 plasmid was designed to express five genes: *M. capsulatus* KDC (MCA0996; SEQ ID NO:7) and *S. cerevisiae* ADH6 (YMR318C; SEQ ID NO:9) from the J23115 constitutive promoter and *M. capsulatus* ilvK (MCA1837; SEQ ID NO:1), *M. capsulatus* ilvC (MCA2272; SEQ ID NO:3), and *M. capsulatus* ilvD (MCA2082; SEQ ID NO:5) from the J23115 constitutive promoter.

Conjugations

The method for conjugal transfer of RP4-mob-containing plasmids into *M. trichosporium* and *M. capsulatus* (Bath) was based on the method described previously (Martin & Murrell, 1995; Stafford et. al., 2003). Briefly, 10 ml of a 16 hour culture of *E. coli* S17-1 carrying the plasmid was collected on a sterile 47 mm, 0.2 µm pore-size, nitrocellulose filter (Millipore). The cells were washed with 50 ml NMS medium without antibiotic. A fresh 50 ml culture of the *M. trichosporium* or *M. capsulatus* (Bath) recipient grown to an optical density ($A_{540}$) of 0.2-0.4 (mid-exponential phase of growth) was collected on the same filter as the *E. coli* S17-1 host cells. The cells were washed with 50 ml NMS and the filter was placed on an NMS agar plate supplemented with 0.02% (w/v) Proteose Peptone (Difco Laboratories, Detroit, MI) and incubated for 24 hours at 30° C. (for *M. trichosporium*) or 37° C. (*M. capsulatus* (Bath)) in the presence of 20-25% methane ($CH_4$) (v/v) in air. After incubation, the cells from the conjugation plate were washed from the filter with 10 ml of NMS, pelleted by centrifugation at 7,000×g, and re-suspended in 1 ml of NMS. 150 µl aliquots were spread onto selective NMS plates containing 10 µg/ml nalidixic acid to select against *E. coli* and 15 µg/ml kanamycin for plasmid selection and incubated at 30° C. or 45° C. for *M. trichosporium* or *M. capsulatus*, respectively. The remaining cells were grown in NMS liquid containing 10 µg/ml nalidixic acid and 15 µg/ml kanamycin (Sigma, St. Louis, MO) as a secondary selection process. Cells grown in liquid selection were serially passaged three times, before spreading onto selective NMS plates for clone isolation.

*M. capsulatus* Growth Conditions

From a saturated starter culture, *M. capsulatus* (Bath) cells were diluted 1:100 into 10 ml of fresh NMS containing 15 µg/ml kanamycin in a 125-ml shake flask. For ketoacid feeding experiments, cultures were treated with 1 g/L 2-ketovalerate (CAS #1821-02-9) or 8 g/L 2-ketoisovalerate (CAS #3715-19-5) with or without the inducer, 0.1 mM isopropylthiogalactoside (IPTG). The flasks were closed with Suba-seals, injected with 20-25% $CH_4$ (v/v) in air, and incubated at 45° C. for 0-120 hours.

Extraction of Alcohols from the Growth Medium

1. Isobutanol production: The shake-flask samples were prepared for extraction by cooling them on ice for 1 hour, which ensures that the volatile organic compounds (VOC's) in the vapor phase were not lost to the atmosphere after the Suba-seal is opened.
2. If extracting from a 9-10 ml culture, all of the culture was transferred to a 50 ml tube. For samples with high isobutanol productions (e.g., pGMV 145), 10 ml of ethyl acetate was added for extraction. For samples with low isobutanol production, only 3 ml of ethyl acetate was used. Once ethyl acetate was added to the cultures, they were subjected to either vortexing (1-2 minutes) or shaking at room temperature (for 1 hour) for efficient extraction.
3. The tubes were then centrifuged at 4000 rpm for 20 minutes in an Eppendorf 5810 centrifuge equipped with an A-4-81 rotor.
4. One (1) ml of the organic layer was then filtered (0.2 µm PTFE membrane) and transferred to 2 ml glass Agilent gas chromatography vials for analysis.

GC-FID Analysis for Isobutanol

The extracted alcohol compounds were quantified with the Agilent 7890A gas chromatograph (GC) with flame ionization detector and PAL auto-sampler. An HP InnoWax capillary column (30 m, 0.32-mm internal diameter, 0.25-mm film thickness; Agilent Technologies, Santa Clara, CA) was used to separate the alcohols. The GC oven temperature was initially set at 35° C. for 1 minute and ramped at rate of 10° C./minute until 85° C. was reached and held for 1 minute. A second temperature ramp of 80° C./minute up to 240° C. was performed and held for 2 minutes. Hydrogen gas was the carrier gas used with 9.3 psi constant inlet pressure. The inlet and detector were maintained at 240° C. A 1 µl sample was injected in split injection mode with a 25:1 split ratio.

Figure 4:
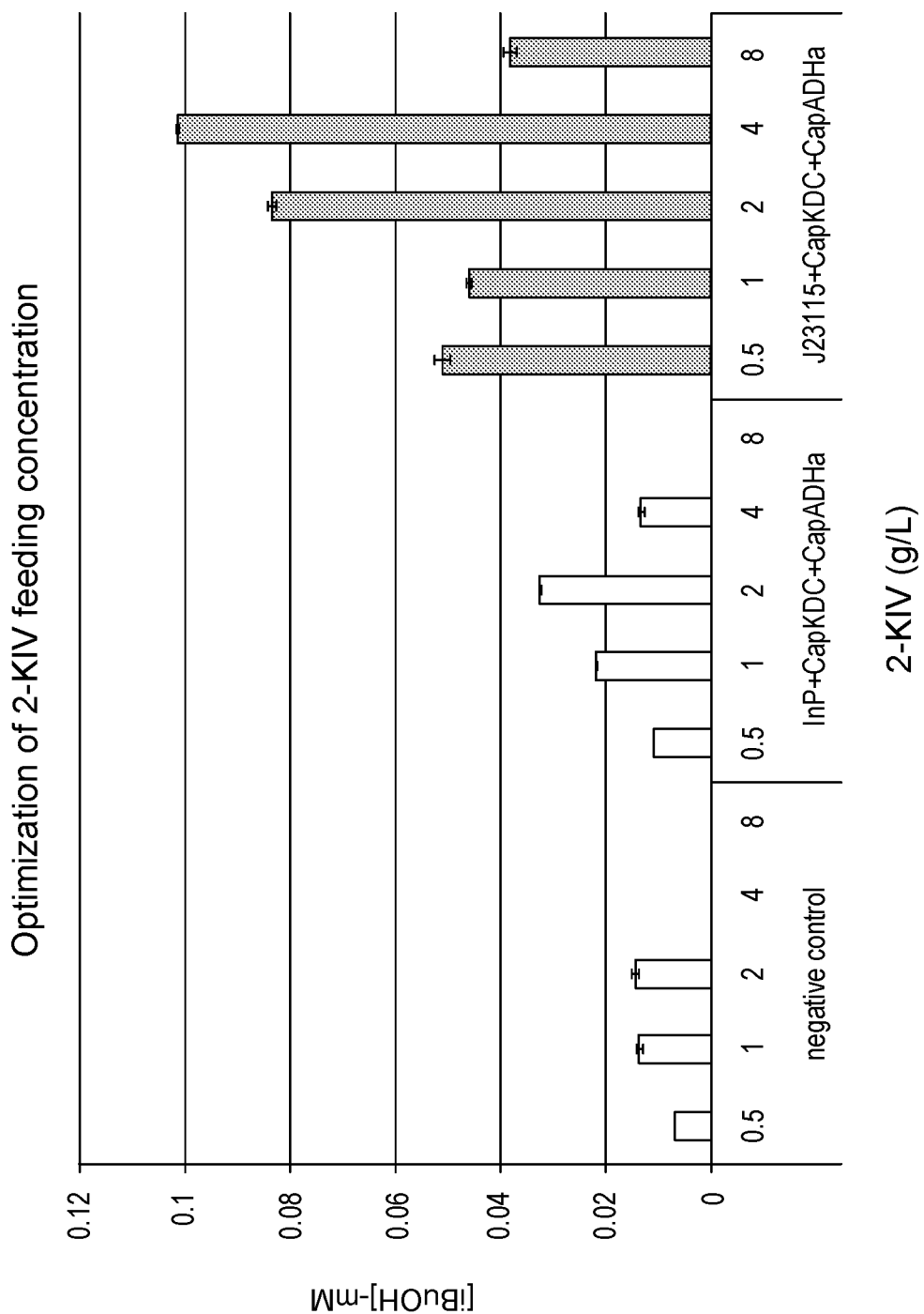
FIG. 4 shows the optimization of the 2-ketoisovalerate (2-KIV) concentration fed to various engineered host strains expressing the two-gene (isobutanol) pathway.
Figure 5:
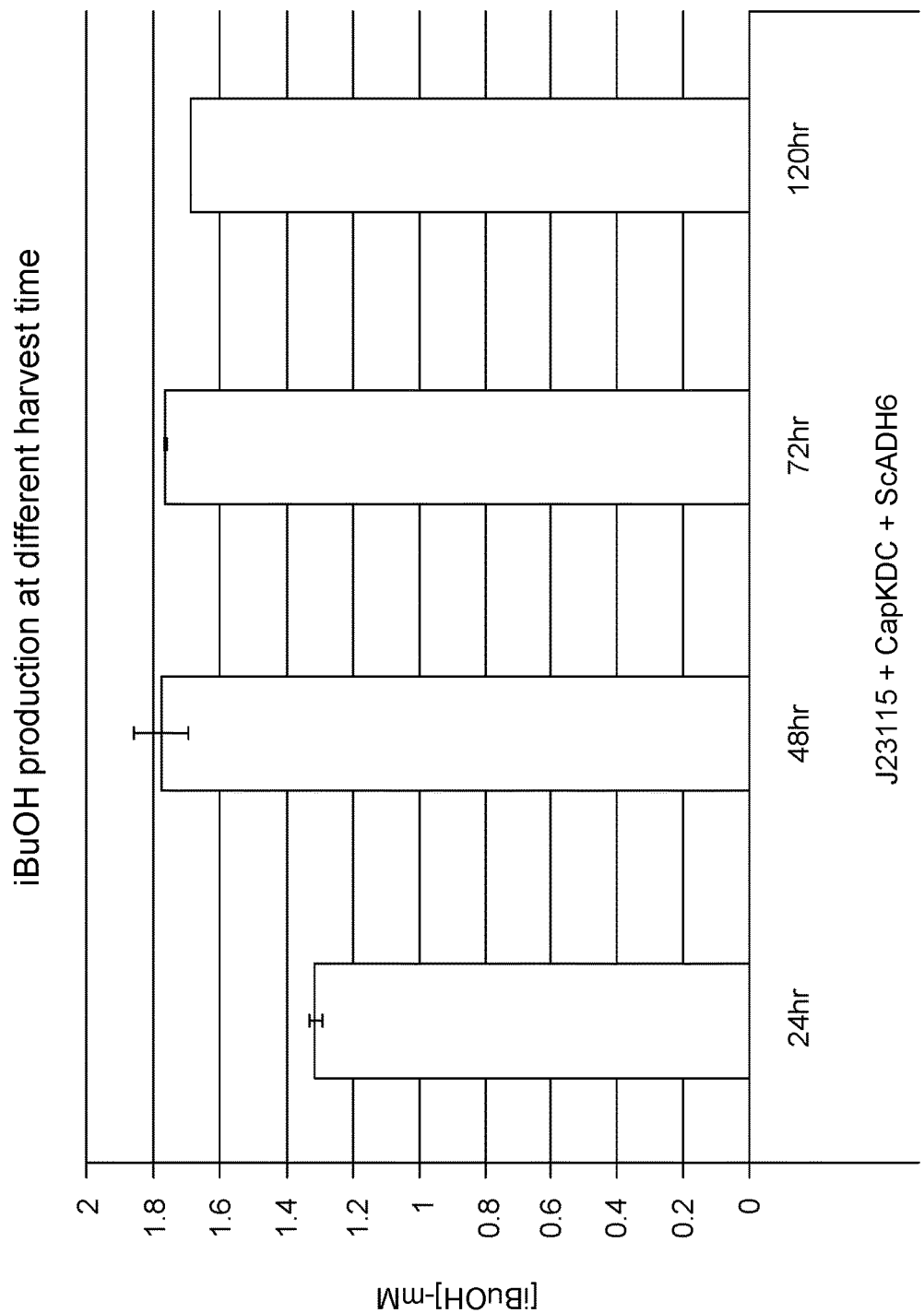
FIG. 5 shows the measured production of isobutanol in an *M. capsulatus* strain expressing plasmid pGMV145 (containing: promoter J23115, the gene for *M. capsulatus* (Bath) 2-ketoisovalerate decarboxylase (CapKDC) and the gene for S. cerevisiae alcohol dehydrogenase (ScADH6)), harvested at different time intervals after 2-KIV addition.
Figure 6:
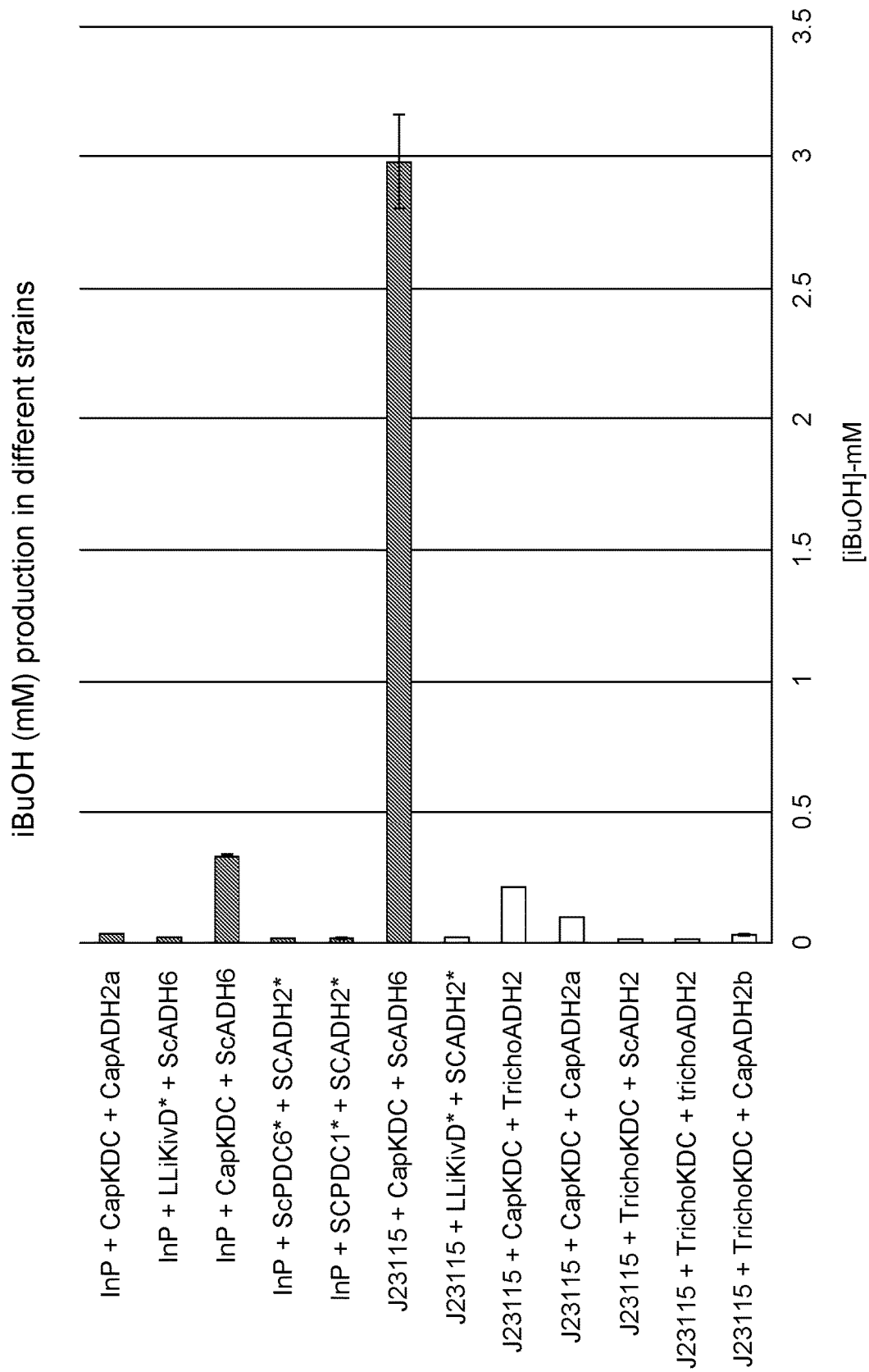
FIG. 6 is a comparison of isobutanol production after 2-KIV feeding in various engineered host strains expressing different combinations of two genes (i.e., isobutanol pathway genes) and with different promoters.

When the two-gene KDC/ADH pathway was expressed in *M. capsulatus* and the isobutanol production was measured (using exogenous 2-KIV feeding), the following results were observed. A concentration of 2-KIV greater than about 4 g/L had a toxic effect on growth, wherein a 2-KIV concentration of about 2 g/L yielded the best results (FIG. 4). Peak isobutanol production occurred about 48-72 hours after 2-KIV feeding (FIG. 5). *E. coli* promoters function in *M. capsulatus*, but not equally well. Constitutive promoters yielded better results than inducible promoters, but the optimal constitutive promoter will typically depend on the individual construct to be used. For example, J23115 was observed to work best for *M. capsulatus* KDC and *M. capsulatus* ADH (data not shown). Lastly, different host strains require slightly different concentrations of 2-KIV to maximize isobutanol production.

Figure 7:
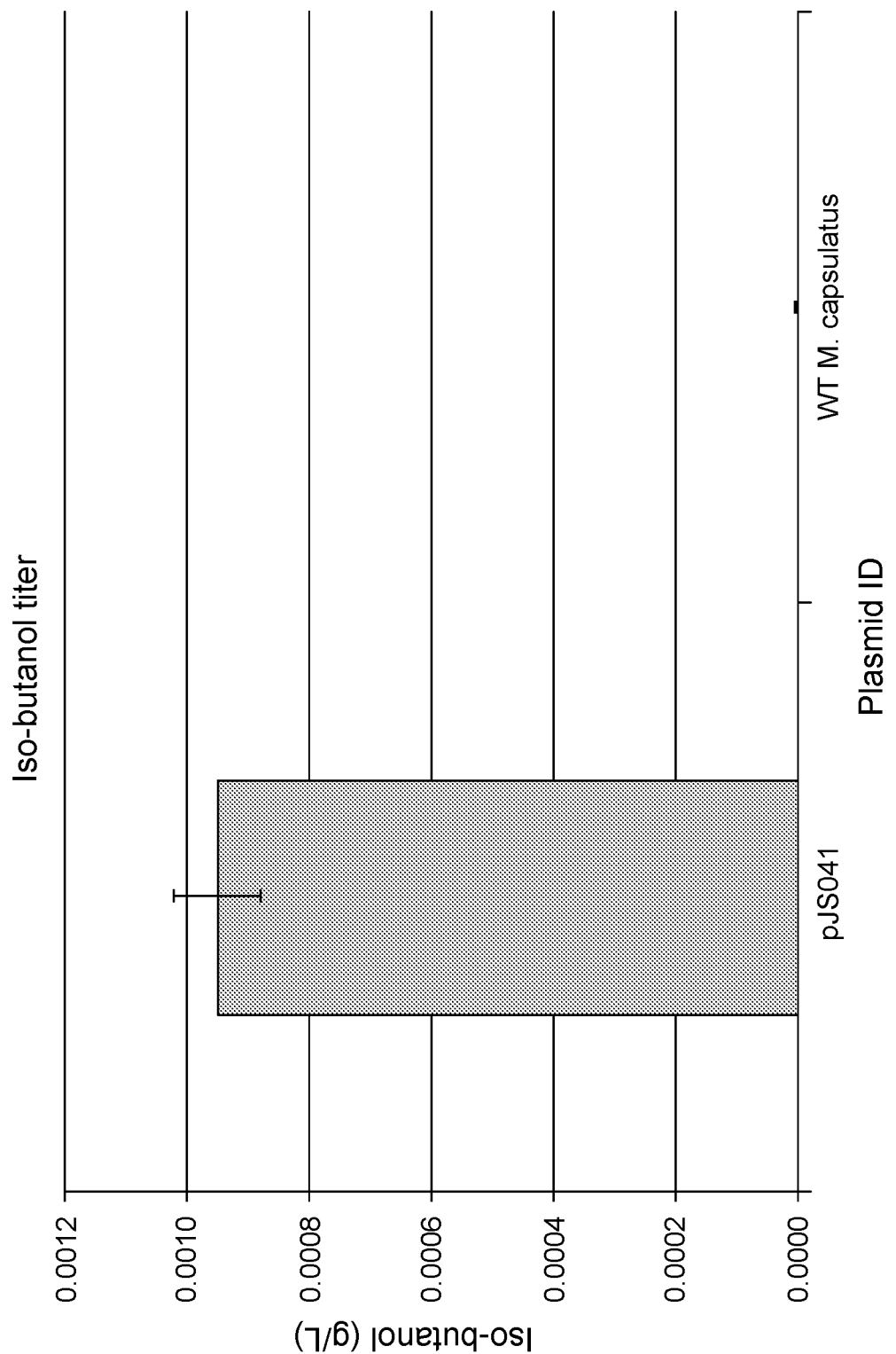
FIG. 7 compares production of isobutanol in the wild-type M. capsulatus str. Bath (no plasmid) and an engineered strain (pJS041) expressing the five-gene (isobutanol) pathway.

The best two-gene combination with a constitutive promoter (J23115; SEQ ID NO:124) was *M. capsulatus* KDC and *S. cerevisiae* ADH6 (plasmid pGMV145), wherein harvesting after 48-72 hours produced the most isobutanol (FIG. 7). The vector construct using pGMV145, having constitutive promoter J23115, a CapKDC gene (MCA0996; SEQ ID NO:7), and a ScADH6 gene (YMR318C; SEQ ID NO:9), produced the most isobutanol after 2-KIV feeding, which was about 3 mM (or about 0.22 g/L).

When the complete five-gene isobutanol pathway was introduced into a host strain, plasmid pJS041 yielded the highest levels of isobutanol production, with a measured titer of about 0.001 g/liter (FIG. 7), compared to no detectable production in the wild-type strain.

In certain embodiments, the production of isobutanol from methane substrate in a host strain (i.e., expressing the five-gene isobutanol pathway, e.g. via plasmid pJS041) is further optimized by genetic manipulations described above, as well as by cultivating the host strain in a fermentor culture with continuous $CH_4$ perfusion, instead of batch addition of $CH_4$ to the culture medium (as was done for the shake flasks experiments). In other embodiments, the production of increased isobutanol titers from methane in a host strain is further optimized via manipulations to the fermentation process (batch fed or perfusion), such as feeding additional media components as they are depleted (phosphate, nitrate, etc.) and maintaining the pH by continuously adding acid or base.

Example 2

Biosynthetic Production of 1-Butanol from Methane

A ketoacid pathway analogous to that described in Example 1, but designed to produce 1-butanol (n-butanol) is engineered in a single carbon (C1) metabolizing microbial host, such as *M. capsulatus* (Bath). In this example, L-threonine (which is ultimately generated from methane via phospoenolpyruvate) is first de-aminated to 2-ketobutyrate (2-oxobutanoate) by the action of threonine dehydratase (also referred to in the art as threonine ammonia-lyase (EC 4.3.1.19) encoded by the genes ilvA or tdcB) (Shen & Liao, 2008). The tdcB gene product has the biotechnological advantage that the enzyme is a catabolic enzyme, and is not feedback inhibited by L-valine or L-isoleucine (Guillouet et al., 1999).

In the second reaction step, the reaction catalyzed by leuA (encoding isopropylmalate synthase/2-ethylmalate synthase (EC 2.3.3.6)) combines 2-ketobutyrate, acetyl-CoA, and $H_2O$ to create (R)-2-ethylmalate. In the third reaction step, the gene product of leuC and leuD (encoding the two subunits of isopropylmalate isomerase) converts 2-ethylmalate into 3-ethylmalate. In the fourth reaction step, the gene product of leuB (encoding the enzyme 3-isopropylmalate dehydrogenase) converts 3-ethylmalate into 2-ketovalerate). At this stage, the same two enzymes used in the previous example, KDC (acting as a 2-ketovalerate decarboxylase) and ADH2 (alcohol dehydrogenase), are used to convert 2-ketovalerate into 1-butanol.

An alternate pathway (the citramalate pathway) from phosphoenolpyruvate and pyruvate to 2-ketobutyrate has also been described for making 1-butanol (Atsumi & Liao, 2008).

As described, above, the plasmids generated in this study are based on the broad-host-range pCM132 (Accession No. AF327720, SEQ ID NO:79) cloning vector described by Marx & Lidstrom (2001). In this embodiment, the use of the Clontech (catalog no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids pMZT3 (SEQ ID NO:81) and pMZT37 (SEQ ID NO:139).

Vector Inserts

Vector inserts contain DNA to be added to a vector backbone. The inserts were designed as exchangeable (modular) parts to the vector and in this example consist of *Methylococcus capsulatus* KDC (MCA0996; SEQ ID NO:7), leuA (MCA2275; SEQ ID NO:57), leuCDB (MCA2063; SEQ ID NO:63, MCA2064; SEQ ID NO:61 and MCA2065; SEQ ID NO:59), *Saccharomyces cerevisiae* ADH6 (YMR318C; SEQ ID NO:9), and *M. capsulatus* ilvA (MCA0354; SEQ ID NO:55) or *E. coli* tdcB (SEQ ID NO:160) genes. The genes were amplified from genomic DNA of their respective hosts with the primers described in Table 5.

The modular parts (vector backbone and vector insert) were PCR amplified as listed in Table 4 with NEB Phusion master mix according to the manufacturer's instructions and in vitro assembled with the Clontech InFusion HD Cloning System kit according to the manufacturer's instructions to generate circular plasmid. The in vitro assembled plasmids (2 ul of the InFusion reaction) were transformed into chemically competent NEB Turbo *E. coli* cells, screened for by colony PCR, purified, and subsequently sequence verified.

The pGMV145 plasmid was designed to express *M. capsulatus* KDC (MCA0996; SEQ ID NO:7) and *S. cerevisiae* ADH6 (YMR318C; SEQ ID NO:9) from the constitutive promoter.

The pJS034 plasmid introduced a second terminator sequence into pGMV145. The pGMV145 vector backbone was PCR amplified with primers JPS00161 (SEQ ID NO:101)/JPS00162 (SEQ ID NO:102) and KOD mastermix. The insert was rnpB DNA synthesized as a gBlock from IDT and amplified with JPS00163 (SEQ ID NO:103)/JPS00164 (SEQ ID NO:104) primers.

The pGMV165 plasmid was designed to express 3 genes: *M. capsulatus* ilvA (MCA0354; SEQ ID NO:55), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter.

The pGMV166 plasmid was designed to express 3 genes: *E. coli* tdcB (SEQ ID NO:160), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter.

The pGMV167 plasmid was designed to express 7 genes: *M. capsulatus* ilvA (MCA0354; SEQ ID NO:55), *M. capsulatus* KDC (MCA0996; SEQ ID NO:7) and *S. cerevisiae* ADH6 (YMR318C; SEQ ID NO:9) from the J23115 (SEQ ID NO:124) constitutive promoter and *M. capsulatus* leuCDB (MCA2063; SEQ ID NO:63, MCA2064; SEQ ID NO:61 and MCA2065; SEQ ID NO:59) and *M. capsulatus* leuA (MCA2275; SEQ ID NO:57) from second J23115 (SEQ ID NO:124) constitutive promoter.

The pGMV168 plasmid was designed to express 7 genes: *E. coli* tdcB (SEQ ID NO:160), *M. capsulatus* KDC (MCA0996; SEQ ID NO:7) and *S. cerevisiae* ADH6 (YMR318C; SEQ ID NO:9) from the J23115 constitutive promoter and *M. capsulatus* leuCDB (MCA2063; SEQ ID NO:63, MCA2064; SEQ ID NO:61 and MCA2065; SEQ ID NO:59) and leuA (MCA2275; SEQ ID NO:57) from a second J23115 constitutive promoter.

Host strains modified with these plasmids were grown on methane as described in the examples above, harvested, extracted, and analyzed for 1-butanol production.

TABLE 5

Insert Modules, Templates and Primers for 1-Butanol Production

| Plasmid | PCR rxn: | Vector backbone | Modules | | |
|---|---|---|---|---|---|
| | | | Insert 1 | Insert 2 | Insert3 |
| pGMV145 | template | pMZT3 | MCA0996 (*M. capsulatus* DNA) | YMR318C (*S. cerevisiae* DNA) | — |
| | primer 1 | JPS0082 | GMV00251 | JPS00118 | — |
| | primer 2 | ESG00087 | GMV00257 | JPS00119 | — |
| pJS034 | template | pGMV145 | IDT gBlock synthesized rnpB DNA | — | — |
| | primer 1 | JPS00161 | JPS00163 | — | — |
| | primer 2 | JPS00162 | JPS00164 | — | — |
| pGMV165 | template | pJS034 | pJS034 | MCA0354 (*M. capsulatus* DNA) | — |
| | primer 1 | GMV435 | GMV433 | GMV431 | — |
| | primer 2 | ESG000087 | GMV434 | GMV432 | — |
| pGMV166 | template | pJS034 | pJS034 | tdcB (*E. coli* DNA) | — |
| | primer 1 | GMV435 | GMV433 | GMV436 | — |
| | primer 2 | ESG000087 | GMV434 | GMV437 | — |
| pGMV167 | template | pGMV165 | pGMV165 | MCA2063-2065 (*M. capsulatus* DNA) | MCA2275 (*M. capsulatus* DNA) |
| | primer 1 | JPS163 | GMV235 | GMV439 | GMV441 |
| | primer 2 | GMV233 | GMV438 | GMV440 | GMV442 |
| pGMV168 | template | pGMV166 | pGMV166 | MCA2063-2065 (*M. capsulatus* DNA) | MCA2275 (*M. capsulatus* DNA) |
| | primer 1 | JPS163 | GMV235 | GMV439 | GMV441 |
| | primer 2 | GMV233 | GMV438 | GMV440 | GMV442 |

Example 3

Biosynthetic Production of Fatty Alcohols from Methane

Conversion of methane to diesel components requires engineering the native metabolism of methanotrophs. The two principal native pathways that can be engineered for increased production of diesel components are the fatty acid pathway and isoprenoid pathway. In the current example, the invention describes the use of the fatty acid pathway for synthesis of diesel (wax ester) components.

Fatty acids are an important source of energy and adenosine triphosphate (ATP) for many cellular organisms. Excess fatty acids, glucose, and other nutrients can be stored efficiently as fat. All cell membranes are built up of phospholipids, each of which contains fatty acids. Fatty acids are also used for protein modification. Fatty acid synthesis is the creation of fatty acids from acetyl-CoA and malonyl-CoA precursors through action of enzymes called fatty acid synthases. Fatty acid chain length and degree of saturation depends on the host microorganism. With regard to *M. capsulatus* (Bath), the primary fatty acids are C16 with saturated or mono unsaturated carbon chains.

The conversion of methane to diesel components requires the over-expression of specific heterologous (exogenous) enzymes within a methanotroph (or non-methanotroph) host microorganism, wherein the over-expression of specific heterologous (exogenous) enzymes can divert the flux from native fatty acid synthesis to compounds of interest. Key intermediates of the fatty acid pathway are the fatty acyl-ACP molecules. Thus, the over-expression of specific heterologous enzymes in a host microorganism divert the flux from acyl-ACP to diesel components such as fatty acids, fatty alcohols, fatty esters and derivatives thereof. Thus, in certain embodiments, a host microorganism has been engineered to over-express specific enzymes such as a fatty acyl ACP reductase (FAR), a fatty acyl CoA reductase (CAR) and wax ester synthases (WES) for diverting flux from native compounds to compounds of interest. Active expression of these enzymes results in the conversion of methane to diesel components via FARs, CARs and WES enzymes cloned and expressed in a host microorganism (e.g., *M. capsulatus* (Bath)).

A biosynthetic pathway analogous to that described in Example 1, but designed to produce fatty alcohols can be engineered in a (C1) metabolizing host microorganism, such as *M. capsulatus*. In this example, fatty acyl-CoA (which is ultimately generated from methane via pyruvate) is converted directly into fatty alcohols by the heterologous over-expression of a fatty-acyl-CoA reductase (FAR).

Construction of Methanotroph Plasmids for Fatty Alcohol Production

As described, above, the plasmids generated in this study are based on the broad-host-range pCM132 (Accession No. AF327720) cloning vector (SEQ ID NO:79) described by Marx & Lidstrom (2001). In this embodiment, the use of the Clontech (catalog no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids pMZT3 (SEQ ID NO:81) and pMZT37 (SEQ ID NO:139).

Vector Inserts

Vector inserts contain DNA to be added to the vector backbone. The inserts were designed as exchangeable (modular) parts to the vector and in this embodiment consist of the following components. In this example, the plasmids were designed to contain one insert: *Marinobacter algicola* fatty acid reductase (MaFAR; SEQ ID NO:65), also known as a fatty acyl-CoA reductase. The MaFAR gene was codon optimized and synthesized as a series of 4 gBlocks from Integrated DNA Technologies (Coralville, IA). The synthesized DNA was designed to include pivot regions to allow proper assembly by InFusion.

Assembly of the Constructs

The modular parts (vector backbone and vector insert) were PCR amplified as listed in Table 4 with NEB Phusion master mix according to the manufacturer's instructions and in vitro assembled with the Clontech InFusion HD Cloning System kit according to the manufacturer's instructions to generate circular plasmid. The in vitro assembled plasmids (2 µl of the InFusion reaction) were transformed into chemically competent NEB Turbo *E. coli* cells, screened for by colony PCR, purified, and subsequently sequence verified.

Plasmid pMZT3 (SEQ ID NO:81) served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO:137)/ESG00087 (SEQ ID NO:98).

Plasmid pMZT37 (SEQ ID NO:139) served as the template for the vector backbone with a constitutive promoter and consisted of the pCM132 cloning vector, *E. coli* J23100 promoter. The vector backbone was PCR amplified from the pMZT3 template with primers ESG00084 (SEQ ID NO:137)/ESG00088 (SEQ ID NO:138).

The pGMV147 plasmid was designed to express *M. algicola* FAR gene (SEQ ID NO:65) from the J23115 constitutive promoter (SEQ ID NO:124). The modules of this plasmid included the PCR amplified pMZT3 vector backbone and four synthesized DNA gene fragments from IDT (MaFAR-g1; SEQ ID NO:140, MaFAR-g2; SEQ ID NO:141, MaFAR-g3; SEQ ID NO:142 and MaFAR-g4; SEQ ID NO:143).

The pGMV148 plasmid was designed to express *M. algicola* FAR gene (SEQ ID NO:65) from the J23110 constitutive promoter (SEQ ID NO:122). The modules of this plasmid included the PCR amplified pMZT37 vector backbone and four synthesized DNA gene fragments from IDT (MaFAR-g1; SEQ ID NO:140, MaFAR-g2; SEQ ID NO:141, MaFAR-g3; SEQ ID NO:142 and MaFAR-g4; SEQ ID NO:143).

Figure 8:
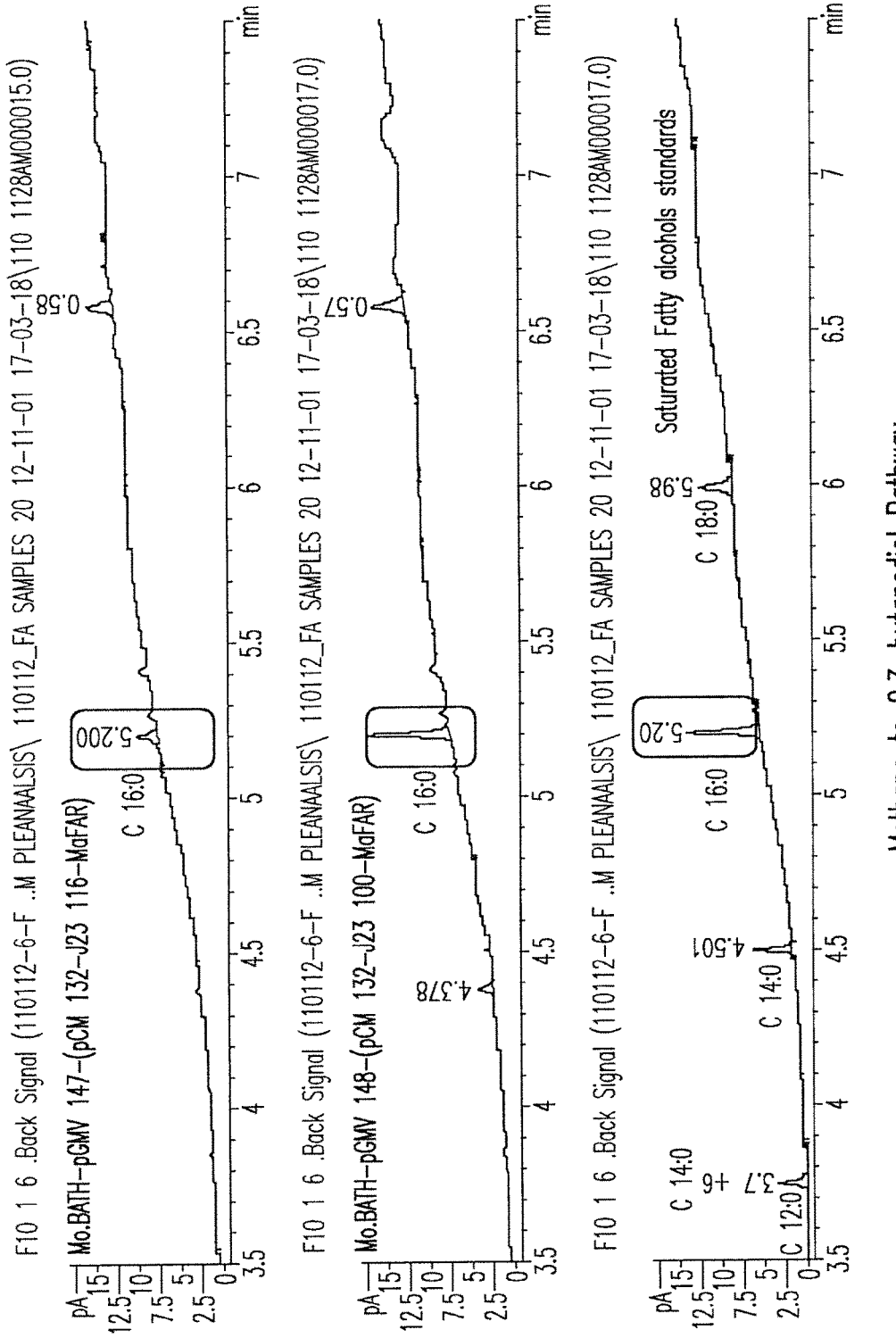
FIG. 8 is a gas chromatography (GC) analysis of fatty acid alcohol production by various engineered strains of M. capsulatus (Bath). The GC peak at about 5.2 minutes corresponds to a C16:0 fatty alcohol standard.

Gas chromatography results after various host strains were grown on methane in shake flasks, extracted, and analyzed as described above, are set forth in FIG. 8. The results indicate that the host strain containing plasmid pGMV148 produced C16:0 alcohol (a fatty alcohol) when grown on methane. The host strain containing plasmid pGMV147 produced only a trace amount of fatty alcohol.

TABLE 6

Insert Modules, Templates and Primers for Fatty Alcohol Production

| Plasmid | PCR rxn: | Vector backbone | Insert 1 | Insert 2 | Insert 3 | Insert 4 |
|---|---|---|---|---|---|---|
| pGMV147 | template | pMZT3 | MaFAR-g1 | MaFAR-g2 | MaFAR-g3 | MaFAR-g4 |
|  | primer 1 | ESG00084 | — | — | — | — |
|  | primer 2 | ESG00087 | — | — | — | — |
| pGMV148 | template | pMZT37 | MaFAR-g1 | MaFAR-g2 | MaFAR-g3 | MaFAR-g4 |
|  | primer 1 | ESG00084 | — | — | — | — |
|  | primer 2 | ESG00088 | — | — | — | — |

Example 4

Biosynthetic Production of Fatty Acid Methyl Esters from Methane

Construction of Methanotroph Plasmids for Fatty Acid Ester (Wax Ester) Production The plasmids generated in this example are based on the broad-host-range pCM132 (Accession no. AF327720, SEQ ID NO: 79) cloning vector described by Marx & Lidstrom (2001). In this embodiment, the use of the Clontech (catalogue no. 639647) InFusion HD Cloning System kit is one example of how to construct plasmids, but is not meant to limit or exclude other methods that are known in the art.

Vector Backbones

Vector backbones contain the components of the plasmid that will remain constant. The broad-host range pCM132 vector was modified to produce vector backbones for the plasmids in this study. The pCM132 vector consisted of the following components: trrnB terminator, kanamycin resistance gene, trfA, IncP oriT, IncP oriV, colE1 ori, and lacZ. This parental vector was modified to replace lacZ with a vector insert that contains promoter sequence to produce plasmids and pMZT3 and pMZT37.

Vector Inserts

Vector inserts contain DNA to be added to a vector backbone. The inserts were designed as exchangeable (modular) parts to the vector and in this embodiment consist of a wax ester synthase (WES) derived from *Acinetobacter* sp. ADP1 (SEQ ID NO:67), *Psychrobacter arcticum* 273-4 (SEQ ID NO:69) or *Rhodococcus opcaus* B4 (SEQ ID NO:71, SEQ ID NO:73, SEQ ID NO:75 or SEQ ID NO:77). The WES genes were codon-optimized and synthesized by GenScript.

Assembly of the Constructs

The modular parts (vector backbone and vector insert) were PCR amplified as listed in Table 7 with NEB Phusion master mix according to the manufacturer's instructions and in vitro assembled with the Clontech InFusion HD Cloning System kit according to the manufacturer's instructions to generate circular plasmid. The in vitro assembled plasmids (2 ul of the InFusion reaction) were transformed into chemically competent NEB Turbo *E. coli* cells, screened for by colony PCR, purified, and subsequently sequence verified.

Plasmid pMZT3 (SEQ ID NO:81) served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO:137)/ESG00087 (SEQ ID NO:98).

Plasmid pMZT37 (SEQ ID NO:139) served as the template for the vector backbone with a constitutive promoter and consisted of the pCM132 cloning vector, *E. coli* J23100 promoter. The vector backbone was PCR amplified from the pMZT3 template with primers ESG00084 (SEQ ID NO:137)/ESG00088 (SEQ ID NO:138).

The pGMV153 plasmid was designed to express *Acinetobacter* sp. ADP1 WES gene (wax-dgaT; SEQ ID NO:67) from the J23115 constitutive promoter. The modules of this plasmid included the PCR amplified pMZT3 vector backbone and the codon-optimized synthesized gene.

The pGMV154 plasmid was designed to express *Psychrobacter arcticum* 273-4 WES gene (Psyc_0223; SEQ ID NO:69) from the J23115 constitutive promoter. The modules of this plasmid included the PCR amplified pMZT3 vector backbone and the codon-optimized synthesized gene.

The pGMV155 plasmid was designed to express *Rhodococcus opcaus* B4 WES gene (ROP_02100; SEQ ID NO:71) from the J23115 constitutive promoter. The modules of this plasmid included the PCR amplified pMZT3 vector backbone and the codon-optimized synthesized gene.

The pGMV156 plasmid was designed to express *Rhodococcus opcaus* B4 WES gene (ROP_13050; SEQ ID NO:73) from the J23115 constitutive promoter. The modules of this plasmid included the PCR amplified pMZT3 vector backbone and the codon-optimized synthesized gene.

The pGMV157 plasmid was designed to express *Rhodococcus opcaus* B4 WS gene (ROP_26950; SEQ ID NO:77) from the J23115 constitutive promoter. The modules of this plasmid included the PCR amplified pMZT3 vector backbone and the codon-optimized synthesized gene.

The pGMV158 plasmid was designed to express *Rhodococcus opcaus* B4 WES gene (ROP_54550; SEQ ID NO:75) from the J23115 constitutive promoter. The modules of this plasmid included the PCR amplified pMZT3 vector backbone and the codon-optimized synthesized gene.

The pGMV159 plasmid was designed to express *Acinetobacter* sp. ADP1 WES gene (wax-dgaT; SEQ ID NO:67) from the J23100 constitutive promoter. The modules of this plasmid included the PCR amplified pMZT3 vector backbone and the codon-optimized synthesized gene.

The pGMV160 plasmid was designed to express *Psychrobacter arcticum* 273-4 WES gene (Psyc_0223; SEQ ID NO:69) from the J23100 constitutive promoter. The modules of this plasmid included the PCR amplified pMZT3 vector backbone and the codon-optimized synthesized gene.

The pGMV161 plasmid was designed to express *Rhodococcus opcaus* B4 WES gene (ROP_02100; SEQ ID NO:71) from the J23100 constitutive promoter. The modules of this plasmid included the PCR amplified pMZT3 vector backbone and the codon-optimized synthesized gene.

The pGMV162 plasmid was designed to express *Rhodococcus opcaus* B4 WES gene (ROP_13050; SEQ ID NO:73) from the J23100 constitutive promoter. The modules of this plasmid included the PCR amplified pMZT3 vector backbone and the codon-optimized synthesized gene.

The pGMV163 plasmid was designed to express *Rhodococcus opcaus* B4 WES gene (ROP_26950; SEQ ID NO:77) from the J23100 constitutive promoter. The modules of this plasmid included the PCR amplified pMZT3 vector backbone and the codon-optimized synthesized gene.

The pGMV164 plasmid was designed to express *Rhodococcus opcaus* B4 WES gene (ROP_54550; SEQ ID NO:75) from the J23100 constitutive promoter. The modules of this plasmid included the PCR amplified pMZT3 vector backbone and the codon-optimized synthesized gene.

Strains modified with these plasmids are grown on methane as described in the examples above, harvested, extracted, and analyzed for fatty acid ester production.

TABLE 7

Insert Modules, Templates and Primers for Fatty Acid Ester Production

| Plasmid | PCR rxn: | Vector backbone | Insert |
|---|---|---|---|
| pGMV153 | template | pMZT3 | pUC57-AbWS (WS-dgaT) |
|  | primer 1 | ESG00084 | GMV410 |
|  | primer 2 | ESG00087 | GMV416 |
| pGMV154 | template | pMZT3 | pUC57-PaWS (Psyc_0223) |
|  | primer 1 | ESG00084 | GMV411 |
|  | primer 2 | ESG00087 | GMV417 |
| pGMV155 | template | pMZT3 | pUC57-RoWS (ROP_02100) |
|  | primer 1 | ESG00084 | GMV412 |
|  | primer 2 | ESG00087 | GMV418 |
| pGMV156 | template | pMZT3 | pUC57-RoWS (ROP_13050) |
|  | primer 1 | ESG00084 | GMV413 |
|  | primer 2 | ESG00087 | GMV419 |
| pGMV157 | template | pMZT3 | pUC57-RoWS (ROP_26950) |
|  | primer 1 | ESG00084 | GMV414 |
|  | primer 2 | ESG00087 | GMV420 |
| pGMV158 | template | pMZT3 | pUC57-RoWS (ROP_54550) |
|  | primer 1 | ESG00084 | GMV415 |
|  | primer 2 | ESG00087 | GMV421 |
| pGMV159 | template | pMZT37 | pUC57-AbWS (WS-dgaT) |
|  | primer 1 | ESG00084 | GMV410 |
|  | primer 2 | ESG00088 | GMV416 |
| pGMV160 | template | pMZT37 | pUC57-PaWS (Psyc_0223) |
|  | primer 1 | ESG00084 | GMV411 |
|  | primer 2 | ESG00088 | GMV417 |
| pGMV161 | template | pMZT37 | pUC57-RoWS (ROP_02100) |
|  | primer 1 | ESG00084 | GMV412 |
|  | primer 2 | ESG00088 | GMV418 |
| pGMV162 | template | pMZT37 | pUC57-RoWS (ROP_13050) |
|  | primer 1 | ESG00084 | GMV413 |
|  | primer 2 | ESG00088 | GMV419 |
| pGMV163 | template | pMZT37 | pUC57-RoWS (ROP_26950) |
|  | primer 1 | ESG00084 | GMV414 |
|  | primer 2 | ESG00088 | GMV420 |
| pGMV164 | template | pMZT37 | pUC57-RoWS (ROP_54550) |
|  | primer 1 | ESG00084 | GMV415 |
|  | primer 2 | ESG00088 | GMV421 |

Example 5

Biosynthetic Production of 2,3-Butanediol from Methane

The four-carbon (C4) diol 2,3-butanediol is an important intermediate for the chemical industry. At the commercial scale, it is mostly generated from petroleum. It serves as a precursor for the production of various commodity and specialty chemicals, such as the solvent methyl ethyl ketone (MEK), gamma-butyrolactone (GBL), and 1,3-butadiene. The potential production of these downstream commercial products amounts to about 32 million tons per year, with a value of about $43 billion (Köpke et al., 2011).

Biological production of 2,3-butanediol from methane requires engineering the native (or endogenous) metabolism of methanotrophs to take advantage of their endogenous production of (R)-acetoin (FIG. 9). (R)-acetoin is produced in methanotrophs from two molecules of pyruvate, which are ultimately derived from methane. By introducing and expressing the gene (SEQ ID NO:156) encoding (2R,3R)-

2,3-butanediol dehydrogenase (BDH1) from *Saccharomyces cerevisiae* in a suitable microbial expression host (such as *M. capsulatus* (Bath)), (R)-acetoin is converted into 2,3-butanediol.

Construction of Methanotroph Plasmids for 2,3-Butanediol Production

As described, above, the plasmids generated in this study are based on the broad-host-range pCM132 (Accession no. AF327720, SEQ ID NO: 79) cloning vector described by Marx & Lidstrom (2001). In this embodiment, the use of the Clontech (catalogue 639647) InFusion HD Cloning System kit is one example of how to construct plasmids, but is not meant to limit or exclude other methods that are known in the art. Sequences for the ORF and PCR primers are presented below in Table 1.

Vector Backbones

Vector backbones contain the components of the plasmid that will remain constant. The broad-host range pCM132 vector was modified to produce vector backbones for the plasmids in this example. The pCM132 vector consists of the following components: trrnB terminator, kanamycin resistance gene, trfA, IncP oriT, IncP oriV, colE1 ori, and lacZ. This parental vector has been modified to replace lacZ with a vector insert that contains promoter sequence to produce plasmid pMZT3, which was used for this example.

Vector Inserts

Vector inserts contain DNA to be added to the vector backbone. The inserts were designed as exchangeable (modular) parts to the vector, and in this embodiment consists of the components listed in Table 1 and Table 8. In this example, the plasmids were designed to contain one insert: *Saccharomyces cerevisiae* (R, R)-butanediol dehydrogenase (Standard name: Bdh1p (EC 1.1.1.4); SEQ ID NO:156; Systematic gene name: YAL060W).

The BDH1 gene (SEQ ID NO:156) was codon optimized and synthesized by Integrated DNA Technologies (Coralville, IA).

Assembly of the Constructs

The modular parts (vector backbone and vector insert) were PCR amplified as listed in Table 8 with NEB Phusion master mix according to the manufacturer's instructions and in vitro assembled with the Clontech InFusion HD Cloning System kit according to the manufacturer's instructions to generate circular plasmid. The in vitro assembled plasmids (2 µl of the InFusion reaction) were transformed into chemically competent NEB Turbo *E. coli* cells, screened for by colony PCR, purified, and subsequently sequence verified.

Plasmid pMZT3 served as the template for the vector backbone with a constitutive promoter and consisted of the pCM132 cloning vector, *E. coli* J23115 promoter. The vector backbone was PCR amplified from the pMZT3 template with primers ESG00084 (SEQ ID NO:137)/ESG00087 (SEQ ID NO:98).

The pGMV111 plasmid was designed to express the *S. cerevisiae* BDH1 gene (SEQ ID NO:156) from the J23115 constitutive promoter. The modules of this plasmid included the PCR amplified pMZT3 vector backbone and the ScBDH1 insert amplified from the shuttle vector pUC57-ScBDH1 template using primers GMV268 (SEQ ID NO:158)/GMV271 (SEQ ID NO:159). The plasmid was conjugated from *E. coli* donor strain S17-1 into the *M. capsulatus* (Bath) recipient as described above Example 1. The transconjugant strain was purified by repeated rounds of antibiotic selection using kanamycin and naladixic acid to remove the parent cells, as described in Example 1 above.

Cells expressing the pGMV111 plasmid were cultivated in liquid NMS medium in sealed shake flasks in the presence of 20% methane at 45° C. as described above in Example 1, for about 72 hours with 200 rpm shaking. For UPLC analysis, proteins and other debris were separated from the 2,3-butanediol in the growth medium using 2% (wt/vol.) 5-sulfosalicylic acid and centrifugation as described in Köpke et al. (2011). Extracted samples can be analyzed using a BioRad (Hercules, CA) Fast Acid column on a Waters (Milford, MA) Acquity H-class UPLC equipped with a #2414 Refractive Index Detector. Other conditions are as follows: the mobile phase is 5 mM $H_2SO_4$, the flow rate is 0.4 ml/min, the column is maintained at 40 C, and the product is detected at 410 nm.

Methods for the processing of biologically produced 1,3-propanediol and 2,3-butanediol are further described by Xiu & Zeng, 2008.

For GC analysis, the 2,3-butanediol can be extracted from the culture medium with ethyl acetate, as described in Xiao et al., (2012). The extracted sample is analyzed on an Agilent (Santa Clara, CA) 7890A GC equipped with a Leap Technologies CombiPAL autosampler and a flame ionization detector. Either an Agilent HP-INNOWax or HP-5MS GC column can be used to separate the components according to the method of Xiao et al. (2012). Alternatively, the samples can be analyzed on a Waters Acquity H-Class UPLC equipped with a Waters 2414 Refractive Index detector using a method similar to that of Köpke et al. (2011). A BioRad (Hercules, CA) Fast Acid Column operated at 40° C. with a flow rate of 0.4 ml/minute and a 5 mM $H_2SO_4$ mobile phase can be used to perform the separation. Samples for either GC or UPLC can be quantitated against a series of known concentrations of purified (D-(−)-, L-(+)-, and meso-) 2,3-butanediol standards (Sigma, St. Louis, MO).

At the industrial fermentation scale, the 2,3-butanediol product can be extracted from the fermentation medium using one of the following methods: steam stripping, solvent extraction, aqueous two-phase extraction, reactive extraction, and pervaporation. These methods are described in Xiu & Zeng (2008).

TABLE 8

| Plasmid | PCR reaction: | Vector backbone | Insert |
|---|---|---|---|
| pGMV111 | template | pMZT3 | pUC57-ScBDH1 |
| | primer 1 | ESG00084 | GMV268 |
| | primer 2 | ESG00087 | GMV271 |

Modules

Following is a list of citations for application.

U.S. Pat. No. 4,594,324
U.S. Pat. No. 4,982,023
U.S. Pat. No. 6,576,449
U.S. Pat. No. 6,660,507
U.S. Pat. No. 6,767,744
U.S. Pat. No. 6,818,424
U.S. Pat. No. 6,969,595
U.S. Pat. No. 7,026,464
U.S. Pat. No. 7,851,188
U.S. Pat. No. 7,910,342
U.S. Pat. No. 7,943,362
U.S. Pat. No. 7,977,084
U.S. Pat. No. 7,993,889
U.S. Pat. No. 8,017,375
U.S. Pat. No. 8,030,021
U.S. Pat. No. 8,101,808

U.S. Pat. No. 8,158,404
U.S. Pat. No. 8,232,089
U.S. Pat. No. 8,263,373
U.S. Pat. No. 8,268,599
U.S. Pat. No. 8,283,143
U.S. Pat. No. 8,349,587
U.S. Publication No. 2006/0057726
U.S. Publication No. 2007/0251141
U.S. Publication No. 2009/0263877
U.S. Publication No. 2010/0274033
U.S. Publication No. 2011/0301388
U.S. Publication No. 2012/0009640
European Patent No. EP 1419234
European Patent No. EP 1328639
European Patent No. EP 1416808
European Patent No. EP 1625204
European Patent No. EP 1694854
European Patent No. EP 2464722
European Patent No. EP 306466
European Patent No. EP 418187
PCT Publication No. WO 2001/60974
Alayon et al., "Catalytic Conversion of Methane to Methanol Using Cu-Zeolites", Chimia, 66:668-674, 2012.
Ali, H., "Development of Genetic Tools in Methanotrophs and the Molecular Regulation of Methane Monooxygenase", Ph.D. Thesis, Univ. of Warwick, Coventry, U.K., 2006.
Anthony, C. and Williams, P., "The structure and mechanism of methanol dehydrogenase", Biochim. Biophys. Acta., 1647:18-23, 2003.
Arakawa et al., "Catalysis research of relevance to carbon management: progress, challenges, and opportunities", Chem. Rev., 101:953-996, 2001.
Atsumi, S. et al., "Engineering the isobutanol biosynthetic pathway in Escherichia coli by comparison of three aldehyde reductase/alcohol dehydrogenase genes", Appl. Microbiol. Biotechnology, 85:651-657, 2010.
Ausubel et al., "Current Protocols in Molecular Biology", pub. by Greene Publishing Assoc. and Wiley-Interscience, 1987.
Ausubel, F. M., Brent, R., Kingston, R E., Moore, D. D., Seidman, J. G., Smith, J. A., and Struhl, K., eds., Short Protocols in Molecular Biology, Fifth Edition. Wiley, 2002.
Avalos et al., "Compartmentalization of Metabolic Pathways in Yeast Mitochondria Improves the Production of Branched-Chain Alcohols", Nature Biotechnology, Advanced Online Publication, Feb. 17, 2013, pages 1-7, doi:10.1038/nbt.2509.
Bothe et al., "Heterotrophic bacteria growing in association with Methylococcus capsulatus (Bath) in a single cell protein production process", Appl. Microbiol. Biotechnol., 59:33-39, 2002.
Bothe, H., Jensen, K. M., Mergel, A., Larsen, J., Jorgensen, C., Bothe, H. and Jorgensen, L., "Heterotrophic bacteria growing in association with Methylococcus capsulatus (Bath) in a single cell protein production process", Appl. Microbiol. Biotechnol. 59:33-39, 2002.
Bowman, J., "The methanotrophs-the families Methylococcaceae and Methylocystaceae", In: The Prokaryotes (Dworkin, M., ed.). Springer Verlag, New York, 2000 (http://link.springer-ny. com/link/service/books/10125).
Chistoserdova et al., "A genomic view of methane oxidation by aerobic bacteria and anaerobic archaea", Genome Biol., 6:208, 2005.
Chistoserdova et al., "The Expanding World of Methylotrophic Metabolism", Annu. Rev. Microbiol., 63:477-499, 2009.
Chistoserdova, L., "Modularity of methylotrophy, revisited", Environ. Microbiol., 13:2603-2622, 2011.
Culpepper, M. A. and Rosenzweig, A. C., "Architecture and active site of particulate methane monooxygenase", Crit. Rev. Biochem. Mol. Biol., 47:483-492, 2012.
Dunfield et al., "Methane oxidation by an extremely acidophilic bacterium of the phylum Verrucomicrobia", Nature 450:879-882, 2007.
Dunfield et al., "Methylocella silvestris sp. nov., a novel methanotroph isolated from an acidic forest cambisol" Int. J. Syst. Evol. Microbiol., 53:1231-1239, 2003.
Eiteman, M. A. and Altman, E., "Overcoming acetate in Escherichia coli recombinant protein fermentations", Trends Biotechnol. 24:53-536, 2006.
Engler et al., "Golden Gate Shuffling: A One-Pot DNA Shuffling Method Based on Type IIs Restriction Enzymes", PLoS One 4:e5553, 2009.
Gellissen et al., "New yeast expression platforms based on methylotrophic Hansenula polymorpha and Pichia pastoris and on dimorphic Arxula adeninivorans and Yarrowia hpolytica—a comparison", FEMS Yeast Res., 5:1079-1096, 2005.
Gibson et al., "Enzymatic assembly of DNA molecules up to several hundred kilobases", Nature Methods 6: 343-345, 2009.
Gou et al., "Functional expression of the particulate methane mono-oxygenase gene in recombinant Rhodococcus erythropolis", FEMS Microbiol. Lett. 263:136-141, 2006.
Guillouet et al., "Expression of the Escherichia coli Catabolic Threonine Dehydratase in Corynebacterium glutamicum and Its Effect on Isoleucine Production", Appl. Environ. Microbiol. 65:3100-3107, 1999.
Hägg, M. B., "Membranes in Chemical Processing—A Review of Applications and Novel Developments, Separation and Purification Methods", Separ. Purif. Meth. 27:51-168, 1998.
Hakemian A. S. and Rosenzweig, A. C, "The biochemistry of methane oxidation", Annu. Rev. Biochem. 76:223-241, 2007.
Hamilton, C. M., Aldea, M., Washburn, B. K., Babitzke, P. & Kushner, S. R., "New method for generating deletions and gene replacements in E. coli", J Bacteriol. 171:4617-4622, 1989.
Hanson, R. S. and Hanson, T. E., "Methanotrophic bacteria", Microbiol. Rev., 60:439-471, 1996.
Hickey, P. J. and Slater, C. S., "The selective recovery of alcohols from fermentation broths by pervaporation', Separ. Purif. Meth. 19:93-115, 1990.
Jaeger, W. K. and Egelkraut, T. M., "Biofuel Economics in a Setting of Multiple Objectives and Unintended Consequences", Renewable and Sustainable Energy Reviews, 15(9):4320, 2011.
Jang, Y. S. et al., "Enhanced Butanol Production Obtained by Reinforcing the Direct Butanol-Forming Route in Clostridium acetobutylicum", mBio, 3(5):1-9, 2012.
Jiang, H., Chen, Y., Jiang, P., Zhang, C., Smith, T. J., Xing, X.-H. and Murrell, J. C., "Methanotrophs: Multifunctional bacteria with promising applications in environmental bioengineering", Biochem. Eng. J. 49:277-288, 2010.
Kidnay et al., "Fundamentals of Natural Gas Processing", Second Edition, 2011 (Dekker Mechanical Engineering). CRC Press, Boca Raton.

Kim, S., Baek, S. H. and Hahn, J. S., "Cellulosic ethanol production using a yeast consortium displaying a minicellulosome and beta-glucosidase", *Microb Cell Fact.*, 12(1):14, 2013.

Kopke et.al., "2,3-Butanediol Production by Acetogenic Bacteria, an Alternative Route to Chemical Synthesis, Using Industrial Waste Gas", *Appl. Environ. Microbiol.*, 77:5467-5475, 2011.

Li, M. Z. and Elledge, S. J., "SLIC: a method for sequence- and ligation-independent cloning", *Methods Mol. Biol.* 852:51-59, 2012.

Link, A. J., Phillips, D. and Church, G. M., "Methods for generating precise deletions and insertions in the genome wild-type *Escherichia coli*: applications to open reading frame characterization", *J. Bacteriol.* 179:6228-6237, 1997.

Lipps, G., ed. "Plasmids: Current Research and Future Trends", *Caister Academic Press*, Norfolk, England, U. K., 2008.

Liu, G., Hou D., Wei, W., Xiangli, F. and Jin, W., "Pervaporation separation of butanol-water mixtures using polydimethylsiloxane/ceramic composite membrane', *Chin. J. Chem. Eng.* 19:40-44, 2011.

Lloyd et al., "Heterologous expression of soluble methane monooxygenase genes in methanotrophs containing only particulate methane monooxygenase", *Arch. Microbiol.* 171:364-370, 1999.

Ma et al., "DNA synthesis, assembly and applications in synthetic biology", *Curr. Opin. Chem. Biol.* 16:1-8, 2012.

Martin, H. and Murrell, J. C., "Methane monooxygenase mutants of *Methylosinus trichosporium* constructed by marker-exchange mutagenesis", *FEMS Microbiol. Lett.* 127:243-248, 1995.

Marx, C. J. & Lidstrom, M. E., "Development of improved versatile broad-host-range vectors for use in methylotrophs and other Gram-negative bacteria", *Microbiology* 147:2065-2075, 2001.

Merryman, C. and Gibson, D. G., "Methods and applications for assembling large DNA constructs", *Metabol. Eng.* 14: 196-204, 2012.

Murrel et al., "Molecular biology and regulation of methane monooxygenase", *Arch. Microbiol.*, 173:325-332, 2000.

Neel, J., "Pervaporation" In: Membrane Science and Technology, 1995 (Noble, R. D. & Stern, S. A., eds.) Elsevier Science, Amsterdam, The Netherlands.

Orita et al., "The Ribulose Monophosphate Pathway Substitutes for the Missing Pentose Phosphate Pathway in the Archaeon *Thermococcus kodakaraensis*", *J. Bacteriology*, 188(13):4698-4704, 2006.

Peccoud, J., ed. "Gene Synthesis: Methods and Protocols" (*Methods in Molecular Biology*, Vol. 852). Humana Press, New York, 2012.

Phillips, R. B., Jameel, H, and Chang, H. M., "Integration of pulp and paper technology with bioethanol production", *Biotechnol Biofuels*, 6(1):13, 2013.

Posfai, G., Kolisnychenko, V., Bereczki, Z. and Blattner, F. R., "Markerless gene replacement in *Escherichia coli* stimulated by a double-strand break in the chromosome", *Nucleic Acids Res.* 27:4409-4415, 1999.

Rosenzweig, A. C. and Ragsdale, S. W. "Methods in Methane Metabolism", *Part B: Methanotrophy. Methods Enzymol.*, 495:1-309, 2011(b).

Rosenzweig, A. C. and Ragsdale, S. W., "Methods in Methane Metabolism", *Part A. Methods Enzymol.*, 494:1-373, 2011(a).

Rudolf, A., Karhumaa, K. and Hahn-Hagerdal, B., "Ethanol Production from Traditional and Emerging Raw Materials", *Yeast Biotechnology: Diversity and Applications*, Chapter 23, pages 489-513, 2009.

Saka, S. and Kusdiana, D., "Biodiesel fuel from rapeseed oil as prepared in supercritical methanol", *Fuel*, 80:225, 2001.

Saleh, J., "A Membrane Separation Process for Biodiesel Purification', *Ph.D. Thesis*, 2011, University of Ottawa, Canada.

Sambrook et al., Molecular Cloning: A Laboratory Manual, Cold Spring Harbor Laboratory Press, 1989.

Sambrook, J., Fritsch, E. F. and Maniatis, T., "Molecular Cloning: A Laboratory Manual"; Cold Spring Harbor Laboratory Press, Cold Spring Harbor, 1989.

Schrader et al., "Methanol-based industrial biotechnology: current status and future perspectives of methylotrophic bacteria", *Trends Biotechnol.*, 27:107-115, 2009.

Semrau et al., "Facultative methanotrophy: false leads, true results, and suggestions for future research", *FEMS Microbiol. Lett.*, 323:1-12, 2011.

Shen, C. R. and Liao, J. C., "Metabolic engineering of *Echerichia coli* for 1-butanol and 1-propanol production via the keto-acid pathways", *Metab. Eng.* 10:312-320, 2008.

Silhavy, et al., "Experiments with Gene Fusions", Cold Spring Harbor Laboratory, Cold Spring Harbor, N. Y. 1984, Simon R. "High frequency mobilization of Gram-negative bacterial replicons by the in vitro constructed Tn5-mob transposons", *Mol. Gen. Genet.* 196:413-420, 1984.

Simon, R., Priefer, U. and Puhler, A. "A Broad Host Range Mobilization System for In Vivo Genetic Engineering: Transposon Mutagenesis in Gram Negative Bacteria", *Nature Biotechnology* 1:784-791, 1983.

Stafford et al., "rpoN, mmoR and mmoG, genes involved in regulating the expression of soluble methane monooxygenase in *Methylosinus trichosporium* OB3b", *Microbiol.* 149:1771-1784, 2003.

Stanley, S. H. and Dalton, H., "Role of ribulose-1,5-biphosphate carboxylase/oxygenase in *Methylococcus capsulatus*", *J. Gen. Microbiol.*, 128:2927-2935, 1982.

Sun, W., Wang, S. and Curtis III, R., "Highly efficient method for introducing successive multiple scarless gene deletions and markerless gene insertions into the *Yersinia pestis* chromosome", *Appl. Environ. Microbiol.* 74:4241-4245, 2008.

Theisen et al., "Regulation of methane oxidation in the facultative methanotroph *Methylocella silvestris* BL2", *Mol. Microbiol.* 58:682-692, 2005.

Tinberg, C. E. and Lippard, S. J., "Dioxygen activation in soluble methane monooxygenase", *Acc. Chem. Res.*, 44:280-288, 2007.

Trotsenko, Y. A. and Murrell, J. C., "Metabolic Aspects of Aerobic Obligate Methanotrophy", *Adv. Appl. Microbiol.*, 63:183-229, 2008.

U.S. Department of the Interior, U. S. Geological Survey World Petroleum Assessment, 2000, U. S. Geological Survey Digital Data Series-DDS-60 (URL: http://pubs.usgs.gov/dds/dds-060/)

van Laere, V., van Batenburg, O. & Huizing, H. J., "InnoFisk1: Feasibility study into a new concept for sustainable aquaculture on board of a ship", *Innovation Network Rural Areas and Agricultural Systems*, 2005.

Veazey, M. W., "*GTL Tech Converts Methane to Ethylene without Fischer Tropsch*", Rigzone. Apr. 10, 2012 (http://www.rigzone.com/news/article.asp?a_id=116784)

Wang et al., "Available methods for assembling expression cassettes for synthetic biology", *Appl. Microbiol. Biotechnol.* 93:1853-1863, 2012.

Ward, N., Larsen, Ø., Sakwa, J., et al., *PLoS Biol.* 2:e303, 2004.

Welander, P. V. and Summons, R E., "Discovery, taxonomic distribution, and phenotypic characterization of a gene required for 3-methylhopanoid production", *Proc. Natl. Acad. Sci.*, 109:12905-12910, 2012.

Whittenbury, R., Phillips, K. C. and Wilkinson, J. F., "Enrichment, isolation and some properties of methane-utilizing bacteria", *J. Gen. Microbiol.* 61:205-218, 1970.

Wolfe, A. J., "The acetate switch", *Microbiol. Mol. Biol. Rev.* 69:12-50, 2005.

Wright, C. K. and Wimberly, M. C., "Recent Land Use Change in the Western Corn Belt Threatens Grasslands and Wetlands", *Proceedings of the National Academy of Sciences—Early Edition*, February 19, pg. 1-6, 2013; DOI: 10.1073/pnas.1215404110.

Xiao et al., "Thermophilic fermentation of acetoin and 2,3-butanediol by a novel *Geobacillus* strain", *Biotechnol. for Biofuels* 5:88, 2012.

Xingye et al., "In vitro Reconstitution and Steady-State analysis of the Fatty Acid Synthase from *Escherichia coli*", *Proceedings of the National Academy of Sciences*, 10(8):18643-18648, 2011.

Xiu, Z.-L. and Zeng, A.-P., "Present state and perspective of downstream processing of biologically produced 1,3-propanediol and 2,3-butanediol", *Appl. Microbiol. Biotechnol.* 78:917-926, 2008.

Yangkai et al., "De novo Biosynthesis of Biodiesel by *Escherichia coli* in Optimized Fed-Batch Cultivation", *PLoS ONE*, 6(5):1-7, 2011.

Yehezkel et al., "Computer-aided high-throughput cloning of bacteria in liquid medium", *Biotechniques* 50:124-127, 2011.

Yomantas, Y. A., Tokmakova, I. L., Gorshkova, N. V., Abalakina, E. G., Kazakova, S. M., Gak, E. R. and Mashko, S. V., "Aromatic amino acid auxotrophs constructed by recombinant marker exchange in *Methylophilus methylotrophus* AS1 cells expressing the aroP-encoded transporter of *Escherichia coli*", *Appl. Environ. Microbiol.* 76:75-83, 2010.

Yu, B. J., Kang, K. H., Lee, J. H., Sung, B. H., Kim, M. S. and Kim, S. C., "Rapid and efficient construction of markerless deletions in the *Escherichia coli* genome", *Nucleic Acids Res.* 36:e84, 2008.

Yurimoto, H., Katoh, N. and Sakai, Y., "Assimilation, dissimilation, and detoxification of formaldehyde, a central metabolic intermediate of methylotrophic metabolism", *Chem Rec.*, 5:367-375, 2005.

Yurimoto, H., Katoh, N. and Sakai, Y., "Genomic organization and biochemistry of the ribulose monophosphate pathway and its application in biotechnology", *Appl Microbiol Biotechnol.*, 84:407-416, 2009.

---

What is claimed is:

1. A genetically modified methanotroph comprising a heterologous polynucleotide encoding for an alcohol dehydrogenase (ADH), wherein the alcohol dehydrogenase can catalyze the conversion of isobutyraldehyde to isobutanol and comprises an amino acid sequence having at least 90% sequence homology to SEQ ID NO: 10, and wherein said methanotroph is capable of converting formaldehyde to pyruvate through a type I RuMP pathway or a type II serine pathway.

2. The methanotroph of claim 1, wherein the methanotroph further comprises a heterologous polynucleotide encoding a ketoacid decarboxylase (KDC), wherein the ketoacid decarboxylase can catalyze the conversion of ketoisovalerate to isobutryaldehyde.

3. The methanotroph of claim 2, wherein the methanotroph further comprises a heterologous polynucleotide encoding an acetolactate synthase (ALS), a heterologous polynucleotide encoding a ketol-acid reductoisomerase (KARI), and a heterologous polynucleotide encoding a dihydroxy-acid dehydratase (DHAD); wherein the acetolactate synthase can catalyze the conversion of pyruvate to acetolactate, wherein the ketol-acid reductoisomerase can catalyze the conversion of acetolactate to 2,3-dihydroxyisovalerate, and wherein the dihydroxy-acid dehydratase can catalyze the conversion of 2,3-dihydroxyisovalerate to ketoisovalerate.

4. The methanotroph of claim 3, wherein the methanotroph further comprises a heterologous polynucleotide encoding a ketoacid decarboxylase (KDC), wherein the ketoacid decarboxylase can catalyze the conversion of ketoisovalerate to isobutryaldehyde.

5. The methanotroph of claim 4, wherein the ketoacid decarboxylase (KDC) comprises an amino acid sequence having at least 90% sequence homology to SEQ ID NO: 8.

6. The methanotroph of claim 1, wherein the methanotroph further comprises a heterologous polynucleotide encoding acetolactate synthase (ALS), a heterologous polynucleotide encoding a ketol-acid reductoisomerase (KARI), heterologous polynucleotide encoding a dihydroxy-acid dehydratase (DHAD), and a heterologous polynucleotide encoding a ketoacid decarboxylase (KDC); wherein the acetolactate synthase can catalyze the conversion of pyruvate to acetolactate and comprises an amino acid sequence having at least 90% sequence homology to SEQ ID NO: 2, wherein the ketol-acid reductoisomerase can catalyze the conversion of acetolactate to 2,3-dihydroxyisovalerate and comprises an amino acid sequence having at least 90% sequence homology to SEQ ID NO: 4, wherein the dihydroxy-acid dehydratase can catalyze the conversion of 2,3-dihydroxyisovalerate to ketoisovalerate and comprises an amino acid sequence having at least 90% sequence homology to SEQ ID NO: 6, and wherein the ketoacid decarboxylase can catalyze the conversion of ketoisovalerate to isobutryaldehyde and comprises an amino acid sequence having at least 90% sequence homology to SEQ ID NO: 8.

7. The methanotroph of claim 1, wherein the methanotroph further comprises a polynucleotide sequence encoding for the alcohol dehydrogenase (ADH) and a promoter, wherein said promoter can direct the expression of the alcohol dehydrogenase in the methanotroph.

8. The methanotroph of claim 2, wherein the methanotroph further comprises a polynucleotide sequence encoding for the ketoacid decarboxylase (KDC), the alcohol dehydrogenase (ADH), and a promoter, wherein said promoter can direct the expression of the ketoacid decarboxylase and the alcohol dehydrogenase (ADH) in the methanotroph.

9. The methanotroph of claim 3, wherein the methanotroph further comprises a polynucleotide sequence encoding for the acetolactate synthase (ALS), the ketol-acid reductoisomerase (KARI), the dihydroxy-acid dehydratase (DHAD), the ketoacid decarboxylase (KDC), the alcohol dehydrogenase (ADH) and a promoter, wherein said promoter can direct the expression of the acetolactate synthase (ALS), the ketol-acid reductoisomerase (KARI), the dihydroxy-acid dehydratase (DHAD), the ketoacid decarboxylase (KDC), and the alcohol dehydrogenase (ADH) in a methanotroph.

10. The methanotroph of claim 9, wherein said promoter is constitutive.

11. The methanotroph of claim 9, wherein said promoter is inducible.

12. The methanotroph of claim 1, wherein said methanotroph is from the genus *Methylobacter, Methylomicrobium, Methylomonas, Methylocaldum, Methylococcus, Methylosoma, Methylosarcina, Methylothermus, Methylohalobius, Methylogaea, Methylovulum, Crenothrix,* Clonothrix, *Methylosphaera, Methylocapsa, Methylocella, Methylosinus, Methylocystis,* or Methyloacidophilum.

13. The methanotroph of claim 1, wherein said methanotroph is from the genus *Methylococcus*.

14. The methanotroph of claim 1, wherein said methanotroph is from the species *Methylococcus capsulatus*.

15. The methanotroph of claim 1, wherein said methanotroph is from the strain *Methylococcus capsulatus* strain Bath.

16. A method of making a multi-carbon compound comprising:
    (a) contacting a genetically modified methanotroph with a multi-carbon product precursor comprising a heterologous polynucleotide encoding for an alcohol dehydrogenase (ADH), wherein the ADH can catalyze the conversion of isobutyraldehyde to isobutanol and comprises an amino acid sequence having at least 90% sequence homology to SEQ ID NO: 10, and wherein said methanotroph is capable of converting formaldehyde to pyruvate through a type I RuMP pathway or a type II serine pathway; and (b) growing said methanotroph in conditions to produce a multi-carbon compound.

17. The method of claim 15 wherein said precursor is methane.

18. The method of claim 16 wherein said multi-carbon compound is isobutanol.

19. The method of claim 16 wherein said multi-carbon product is 1-butanol.

* * * * *